United States Patent [19]
Kumazawa et al.

[11] Patent Number: 5,028,254
[45] Date of Patent: Jul. 2, 1991

[54] AZOLE DERIVATIVES AND AGRICULTURAL AND HORTICULTURAL CHEMICAL COMPOSITION CONTAINING THE SAME

[75] Inventors: Satoru Kumazawa; Susumu Shimizu; Hiroyuki Enari; Atsushi Ito, all of Iwaki; Susumu Ikeda, Naka; Nobuo Sato; Toshihide Saishoji, both of Iwaki, all of Japan

[73] Assignee: Kureha Kagaku Kogyo Kabushiki Kaisha, Tokyo, Japan

[21] Appl. No.: 514,170

[22] Filed: Apr. 24, 1990

Related U.S. Application Data

[62] Division of Ser. No. 115,084, Oct. 30, 1987, Pat. No. 4,938,792.

[30] Foreign Application Priority Data

Nov. 10, 1986 [JP] Japan ............................... 61-265559
Jun. 30, 1987 [JP] Japan ............................... 62-161126
Oct. 27, 1987 [JP] Japan ............................... 62-271227

[51] Int. Cl.$^5$ .................... A01N 43/50; C07D 233/60
[52] U.S. Cl. .......................................... 71/92; 71/76; 514/399; 548/341
[58] Field of Search ................... 514/399; 548/341; 71/76, 92

[56] References Cited

U.S. PATENT DOCUMENTS 4,684,396  8/1987  Clough et al. ..................... 548/341

Primary Examiner—Mary C. Lee
Assistant Examiner—Patricia L. Morris
Attorney, Agent, or Firm—Nixon & Vanderhye

[57] ABSTRACT

Disclosed herein are an azole derivative represented by the formula (I):

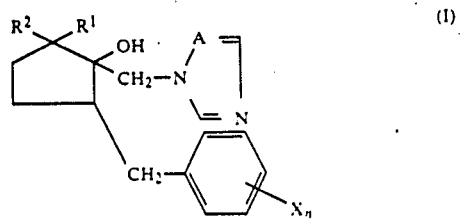

wherein $R^1$ and $R^2$ respectively represent a ($C_1$-$C_5$) alkyl group or a hydrogen atom; X represents a halogen atom, a ($C_1$-$C_5$) alkyl group or a phenyl group; n represents an integer of from 0 to 2 and A represents a nitrogen atom or a CH, provided that $R^1$ is not a hydrogen atom when $R^2$ is a hydrogen atom, a process for producing the azole derivative represented by the formula (I), and an agricultural and horticultural composition containing the azole derivative represented by the formula (I).

4 Claims, 76 Drawing Sheets

AZOLE DERIVATIVES AND AGRICULTURAL AND HORTICULTURAL CHEMICAL COMPOSITION CONTAINING THE SAME

This is a division of application Ser. No. 07/115,084, filed Oct. 30, 1987 now U.S. Pat. No. 4,938,792 issued July 3, 1990.

BACKGROUND OF THE INVENTION

The present invention relates to an azole derivative having a plant diseases controlling activity and plant growth regulating activity, a process for producing the azole derivative and an agricultural and horticultural composition containing the azole derivative as an active ingredient. More in detail, the present invention relates to 1) an azole derivative represented by the formula (I):

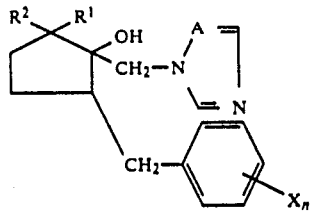

wherein $R^1$ and $R^2$ respectively represent a ($C_1$-$C_5$) alkyl group or a hydrogen atom; X represents a halogen atom, a ($C_1$-$C_5$) alkyl group or a phenyl group; n represents an integer of from 0 to 2 and A represents a nitrogen atom or a CH, provided that $R^1$ is not a hydrogen atom when $R^2$ is a hydrogen atom, 2) a process for producing the azole derivative represented by the formula (I), which process comprises the steps of a) (i) reacting an alkyl ester of 2-oxocyclopentanecarboxylic acid with a substituted benzyl halide and reacting the thus obtained alkyl ester of 1-(substituted benzyl)-2-oxocyclopentanecarboxylic acid with a($C_1$-$C_5$)alkyl halide, (ii) reacting an alkyl ester of 3-($C_1$-$C_5$ alkyl)-2-oxocyclopentanecarboxylic acid with a substituted benzyl halide, or (iii) reacting 1-(substituted benzyl)-3-($C_1$-$C_5$ alkyl)-2-oxocyclopentanecarboxylic acid with a ($C_1$-$C_5$)alkyl halide, thereby obtaining an ester derivative of cyclopentanecarboxylic acid represented by the formula (V):

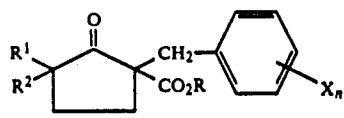

wherein $R^1$ and $R^2$ respectively represent a ($C_1$-$C_5$)alkyl group or a hydrogen atom; R represents a ($C_1$-$C_5$)alkyl group; X represents a halogen atom, a($C_1$-$C_5$)alkyl group or a phenyl group and n represents an integer of from 0 to 2, provided that $R^1$ is not a hydrogen atom when $R^2$ is a hydrogen atom, b) subjecting the thus obtained ester derivative of cyclopentanecarboxylic acid to hydrolytic decarboxylation, thereby obtaining a cyclopentanone derivative represented by the formula (IV):

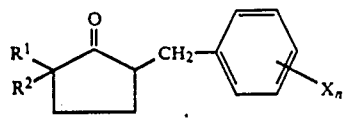

wherein $R^1$, $R^2$, X and n respectively represent the same defined as above, c) subjecting the thus obtained cyclopentanone derivative to an oxirane reaction while using sulfonium ylide or oxosulfonium ylide or subjecting a methylenecyclopentane derivative obtained from the thus obtained cyclopentanone derivative by Wittig reaction and represented by the formula (III):

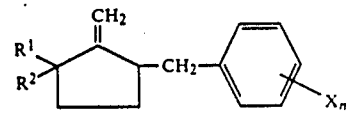

wherein $R^1$, $R^2$, X and n respectively represent the same defined as above, into epoxidation, thereby converting the cyclopentanone derivative into an oxirane derivative represented by the formula (II):

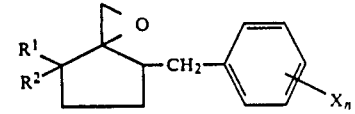

wherein $R^1$, $R^2$, X and n respectively represent the same defined as above, and then d) reacting the thus obtained oxirane derivative with an 1,2,4-triazole or an imidazole represented by the formula (VI):

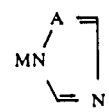

wherein M represents a hydrogen atom or an alkali metal atom and A represents a nitrogen atom or a —CH=, thereby obtaining the azole derivative represented by the formula (I):

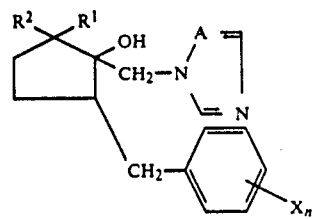

wherein $R^1$ and $R^2$ respectively represent a($C_1$-$C_5$)alkyl group or a hydrogen atom; X represents a halogen atom, a($C_1$-$C_5$)alkyl group or a phenyl group; n represents an integer of from 0 to 2 and A represents a nitrogen atom or a CH, provided that $R^1$ is not a hydrogen atom when $R^2$ is a hydrogen atom, and 3) an agricultural and horticultural composition having a fungicidal activity and a plant growth regulating activity, which comprises an effective amount of the azole derivative represented by the formula (I).

The damage of the crops due to various plant diseases is enormous, and also, a problem due to the environmental pollution by the chemicals for controlling these plant diseases has arisen.

Accordingly, an offer of an agricultural and horticultural chemical which has a controlling effect against the plant diseases, is low in toxicity to men, beasts, birds and fishes and is low in phytotoxicity to useful plants, that is, an agricultural and horticultural chemical which is high in safety on handling, small in influence to the environment and has an excellent controlling effect against plant diseases in a broad range has been demanded.

In order to fulfill such a demand, the following agricultural and horticultural fungicides have hitherto been proposed.

(1) Compounds of triazoles or imidazoles represented by the following formula:

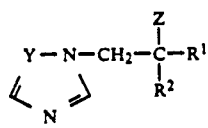

wherein $R^1$ represents a —CH=CH—X, a —C≡C—X or a —CH$_2$—CH$_2$—X (wherein X is a hydrogen atom, an alkyl group, a hydroxyalkyl group, an alkoxyalkyl group, a cycloalkyl group, a substituted aryl group which may be substituted, an aralkyl group which may be substituted, an aryloxyalkyl group which may be substituted or a heterocyclic group which may be substituted); $R^2$ represents an alkyl group, a cycloalkyl group or an aryl group which may be substituted; Z represents a chlorine atom, a cyano group or a —OR$^3$ (wherein R$^3$ is a hydrogen atom, an acetyl group, an alkyl group, an alkenyl group or an aralkyl group) and Y represents a nitrogen atom or a CH, an acid addition salt thereof and a metal complex thereof [refer to Japanese Patent application Laid-Open(KOKAI) No. 57-114577 (1982) corresponding to U.S. Pat. No. 4,507,140 and European Patent No. 52424.].

(2) Compounds of triazoles or imidazoles represented by the following formula:

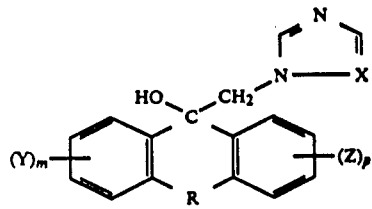

wherein R represents a cross-linking group: —(CH$_2$)$_n$— (wherein n is 0, 1 or 2), a cross-linking group: a —CH=CH—, and —O—, and —s—, and —NH— or a —C(=O)—; X represents a nitrogen atom or a CH; Y and Z may be the same or different from each other and respectively represents a halogen atom, an alkyl group, an alkoxy group, a haloalkoxy group, a haloalkyl group, a nitro group, a phenyl group or a phenoxy group, and m and p respectively represent 0, 1, 2 or 3, an acid thereof, a metal complex thereof and functional derivatives thereof [refer to Japanese Patent application Laid Open No. 57-126479 (1982) corresponding to European Patent No. 52425].

(3) Derivatives of 1-hydroxyethylazole, represented by the following formula:

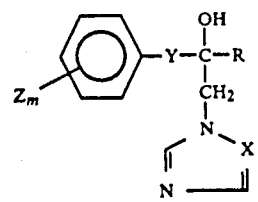

wherein R represents an alkyl group, a cycloalkyl group which may be substituted or a phenyl group which may be substituted, X represents a nitrogen atom or a CH; Y represents a —OCH$_2$—, a —CH$_2$—CH$_2$— or a —CH=CH—; Z represents a halogen atom, an alkyl group, a cycloalkyl group, an alkoxy group, an alkylthio group, a halogenoalkyl group, an alkoxy group, an alkylthio group, a halogenoalkyl group, a halogenoalkoxy group, a halogenoalkylthio group, phenyl group which may be substituted, a phenoxy group which may be substituted or phenylalkyl group which may be substituted or a phenylalkoxy group which may be substituted and m represents 0, 1, 2 or 3, an acid addition salt thereof and a metal complex thereof [refer to Japanese Patent application Laid-Open (KOKAI) No. 57-16868 (1982) corresponding to U.S. Pat. No. 4,532,341 and European Patent No. 40345].

(4) Cycloaliphatic alcoholic compounds represented by the following formula:

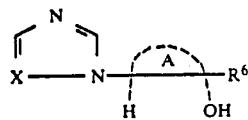

wherein $R^6$ represents an unsubstituted phenyl group or a phenyl group substituted by from 1 to 5 groups selected from the group consisting of halogen atom(s), amino group(s), nitro group(s), cyano group(s), phenyl group(s), halogenophenyl group(s), (C$_1$-C$_{10}$)alkyl group(s), halogeno (C$_1$-C$_{10}$)alkyl group(s), (C$_1$-C$_{10}$)alkylthio group(s), (C$_1$-C$_{10}$)alkylenedioxy group(s), (C$_1$-C$_{10}$)alkylamino group(s) and di(C$_1$-C$_{10}$)alkylamino groups; X represents a nitrogen atom or a methine group; a ring A is a cylcopentane ring, a cyclohexane ring, a cycloheptane ring, an indane ring, a tetrahydronaphthalene ring or a benzocyclopeptane ring, each of the respective rings not having been substituted or having been substituted in the benzene ring thereof by from one to four of the above-mentioned substituents [refer to Japanese Patent application Laid-Open (KOKAI) No. 58-189171 (1983) corresponding to U.S. Pat. No. 4,503,062 and European Pat. No. 94146].

(5) Triazole compounds or imidazole compounds represented by the following formula:

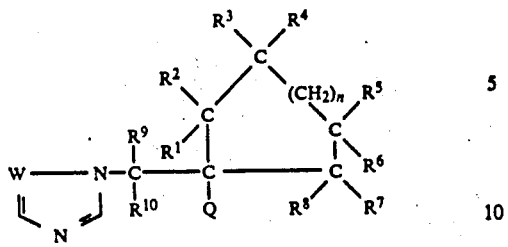

wherein W is a CH or a nitrogen atom; Q is a substituted or unsubstituted aryl group, particularly a substituted or unsubstituted phenyl group, a substituted or unsubstituted aralkyl, or a substituted or unsubstituted alkyl group; $R^1$, $R^2$, $R^3$, $R^4$, $R^5$, $R^6$, $R^7$ and $R^8$ may be the same or different from each other and respectively represent a hydrogen atom, a hydroxy group, an alkyl group, a cycloalkyl group, a substituted or unsubstituted aralkyl group, a substituted or unsubstituted phenyl group, or any of the pairs of $R^1$ and $R^2$, $R^3$ and $R^4$, $R^5$ and $R^6$ or $R^7$ and $R^8$ represents a carbonyl group (C=O) together with the adjacent ring-carbon atom; $R^9$ and $R^{10}$ may be the same or different from each other and represent respectively a hydrogen atom, an alkyl group, a cycloalkyl group, a substituted or unsubstituted aralkyl group or a substituted or unsubstituted phenyl group and n is 0 or 1, a stereoisomer thereof, an acid addition salt thereof and a metal complex thereof [refer to Japanese Patent application Laid-Open (KOKAI) No. 60-214674 (1985) corresponding to European Patent No. 153797].

As a result of the studies of some of the present inventor for providing an agricultural and horticultural fungicide which is high in safety on handling, is small in influence to the environment and shows an excellent controlling effect against the plant diseases of a broad range, they have found an azole derivative represented by the following formula:

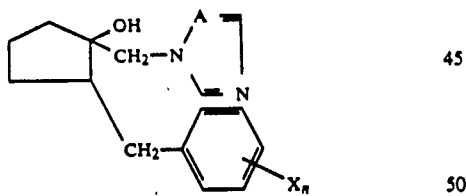

wherein X represent respectively a halogen atom, an alkyl group, a haloalkyl group, a phenyl group, a cyano group or a nitro group; n represents an integer of from 0 to 5 and A represents a nitrogen atom or a CH, provided that X may be the same or different from each other when n is 1 to 5 [refer to Japanese Patent application Laid-Open (KOKAI) No. 620149667 (1987) corresponding to U.S. Pat. application No. 06/903,992].

The present inventors have further studied a synthesis of many azole derivatives and an examination on the utility thereof in order to obtain an agricultural and horticultural fungicide which is low in toxicity to men and beasts, is high in safety on handling and shows an excellent controlling effect against plant diseases of a broad range, and as a result it has been found that an azole derivative represented by the formula (I):

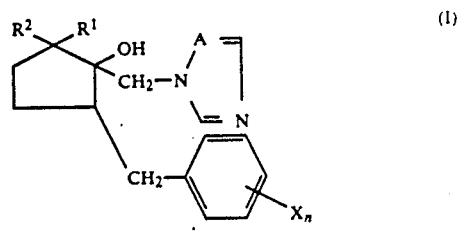

wherein $R^1$ and $R^2$ respectively represent a ($C_1$-$C_5$)alkyl group or a hydrogen atom; X represents a halogen atom, a($C_1$-$C_5$)alkyl group or a phenyl group; n represents an integer of from 0 to 2 and A represents a nitrogen atom or a CH, provided that $R^1$ is not a hydrogen atom when $R^2$ is a hydrogen atom, not only has the afore-mentioned specific properties but also can be effectively applied as a plant growth regulating agent, and on the basis of their finding, the present invention have been attained.

Namely, the object of the present invention is to provide with an azole derivative having the utility as the active ingredient of the agricultural and horticultural composition having a plant diseases controlling activity and a plant growth regulating activity, a process for producing the azole derivative, and an agricultural and horticultural composition which contains, as an active ingredient, the azole derivative which shows an excellent controlling effect on the plant diseases in a broad range and at the same time, shows a plant growth regulating effect, is low in toxicity and is excellent in safety on handling.

SUMMARY OF THE INVENTION

In a first aspect of the present invention, there is provided an azole derivative represented by the formula (I):

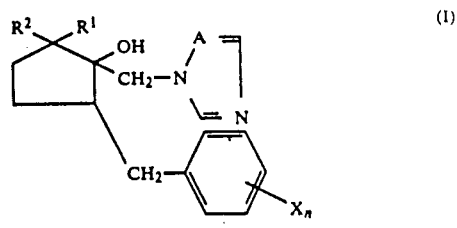

wherein $R^1$ and $R^2$ respectively represents a ($C_1$-$C_5$)alkyl group or a hydrogen atom; X represents a halogen atom, a ($C_1$-$C_5$)alkyl group or a phenyl group; n represents an integer of from 0 to 2 and A represents a nitrogen atom or a CH, provided that $R^1$ is not a hydrogen atom when $R^2$ is a hydrogen atom.

In a second aspect of the present invention, there is provided a process for producing an azole derivative represented by the formula (I):

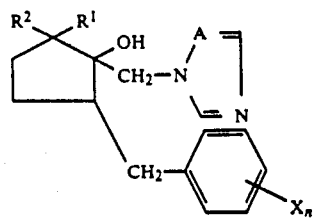

wherein $R^1$ and $R^2$ respectively represent a ($C_1$-$C_5$)alkyl group or a hydrogen atom; X represents a halogen atom, a ($C_1$-$C_5$)alkyl group or a phenyl group; n represents an integer of from 0 to 2 and A represents a nitrogen atom or a CH, provided that $R^1$ is not a hydrogen atom when $R^2$ is a hydrogen atom, which process comprises the steps of a) (i) reacting an alkyl ester of 2-oxocyclopentanecarboxylic acid with a substituted benzyl halide and reacting the thus obtained alkyl ester of 1-(substituted benzyl)-2-oxocyclopentanecarboxylic acid with a ($C_1$-$C_5$)alkyl halide, (ii) reacting an alkyl ester of 3-($C_1$-$C_5$ alkyl)-2-oxocyclopentanecarboxylic acid with a substituted benzyl halide or (iii) reacting 1-(substituted benzyl)-3-($C_1$-$C_5$ alkyl)-2-oxocyclopentanecarboxylic acid with a ($C_1$-$C_5$)alkyl halide, thereby obtaining an ester derivative of cyclopentanecarboxylic acid represented by the formula (V):

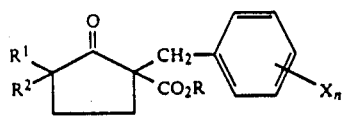

wherein $R^1$ and $R^2$ respectively represent a ($C_1$-$C_5$)alkyl group or a hydrogen atom; R represents a ($C_1$-$C_5$)alkyl group; X represents a halogen atom, a ($C_1$-$C_5$)alkyl group or a phenyl group and n represents an integer of from 0 to 2, provided that $R^1$ is not a hydrogen atom when $R^2$ is a hydrogen atom, b) subjecting the thus obtained ester derivative of cyclopentanecarboxylic acid to hydrolytic decarboxylation, thereby obtaining a cyclopentanone derivative represented by the formula (IV):

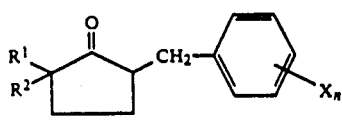

wherein $R^1$, $R^2$, X and n respectively represent the same defined as above, c) subjecting the thus obtained cyclopentanone derivative to an oxirane reaction while using sulfonium ylide or oxosulfonium ylide, or subjecting a methylenecyclopentane derivative obtained from the thus obtained cyclopentanone derivative by Wittig reaction and represented by the formula (III):

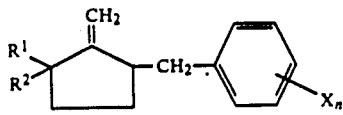

wherein $R^1$, $R^2$, X and n respectively represent the same defined as above, to epoxidation, thereby converting the cyclopentanone derivative into an oxirane derivative represented by the formula (II):

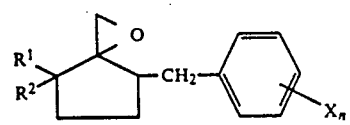

wherein $R^1$, $R^2$, X and n respectively represent the same defined as above, and then d) reacting the thus obtained oxirane derivative with a 1,2,4-triazole or an imidazole represented by the formula (VI):

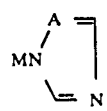

wherein M represents a hydrogen atom or an alkali metal atom and A represents a nitrogen atom or a CH.

In a third aspect of the present invention, there is provided an agricultural and horticultural composition having a fungicidal activity and a plant growth regulating activity, which comprises, as an active ingredient, an azole derivative represented by the formula (I):

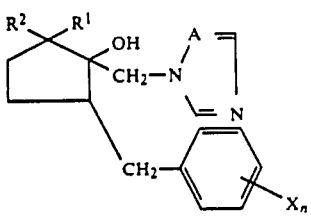

wherein $R^1$ and $R^2$ respectively represent a ($C_1$-$C_5$)alkyl group or a hydrogen atom; X represents a halogen atom, a ($C_1$-$C_5$)alkyl group or a phenyl group; n represents an integer of from 0 to 2 and A represents a nitrogen atom or a CH, provided that $R^1$ is not a hydrogen atom when $R^2$ is a hydrogen atom.

In a fourth aspect of the present invention, there is provided an oxirane derivative for producing an azole derivative represented by the formula (I), which is represented by the formula (II):

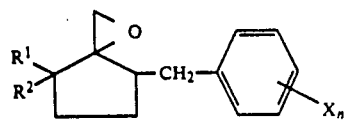

wherein $R^1$ and $R^2$ respectively represent a ($C_1$-$C_5$)alkyl group or a hydrogen atom; X represents a halogen atom, a ($C_1$-$C_5$)alkyl group or a phenyl group and n represents an integer of from 0 to 2, provided that $R^1$ is not a hydrogen atom when $R^2$ is a hydrogen atom.

In a fifth aspect of the present invention, there is provided a methylenecyclopentane derivative for producing an azole derivative represented by the formula (I), which is represented by the formula (III):

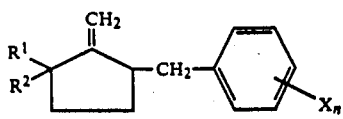
(III)

wherein $R^1$ and $R^2$ respectively represent a ($C_1$-$C_5$)alkyl group or a hydrogen atom; X represents a halogen atom, a ($C_1$-$C_5$)alkyl group or a phenyl group and n represents an integer of from 0 to 2, provided that $R^1$ is not a hydrogen atom when $R^2$ is a hydrogen atom.

In a sixth aspect of the present invention, there is provided a cyclopentanone derivative for producing an azole derivative represented by the formula (I), which is represented by the formula (IV):

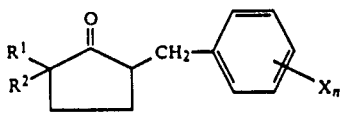
(IV)

wherein $R^1$ and $R^2$ respectively represent a ($C_1$-$C_5$)alkyl group o a hydrogen atom; X represents a halogen atom, a ($C_1$-$C_5$)alkyl group or a phenyl group and n represents an integer of from 0 to 2, provided that $R^1$ is not a hydrogen atom when $R^2$ is a hydrogen atom.

In a seventh aspect of the present invention, there is provided an ester derivative of a cyclopentanecarboxylic acid for producing an azole derivative represented by the formula (I), which is represented by the formula (V):

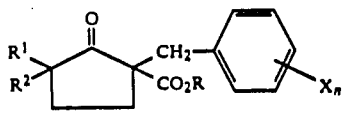
(V)

wherein $R^1$ and $R^2$ respectively represent a ($C_1$-$C_5$)alkyl group or a hydrogen atom; R represents a ($C_1$-$C_5$)alkyl group; X represents a halogen atom, a ($C_1$-$C_5$)alkyl group or a phenyl group and n represents an integer of from 0 to 2, provided that $R^1$ is not a hydrogen atom when $R^2$ is a hydrogen atom.

BRIEF EXPLANATION OF DRAWINGS

Of the attached drawings, FIG. 1 shows the infrared absorption spectrum of the compound No. 1 in Table 1, FIGS. 4 to 76 show the respective infrared absorption spectra of the respective compounds Nos. 4 to 76 in Table 1.

Figure 1:
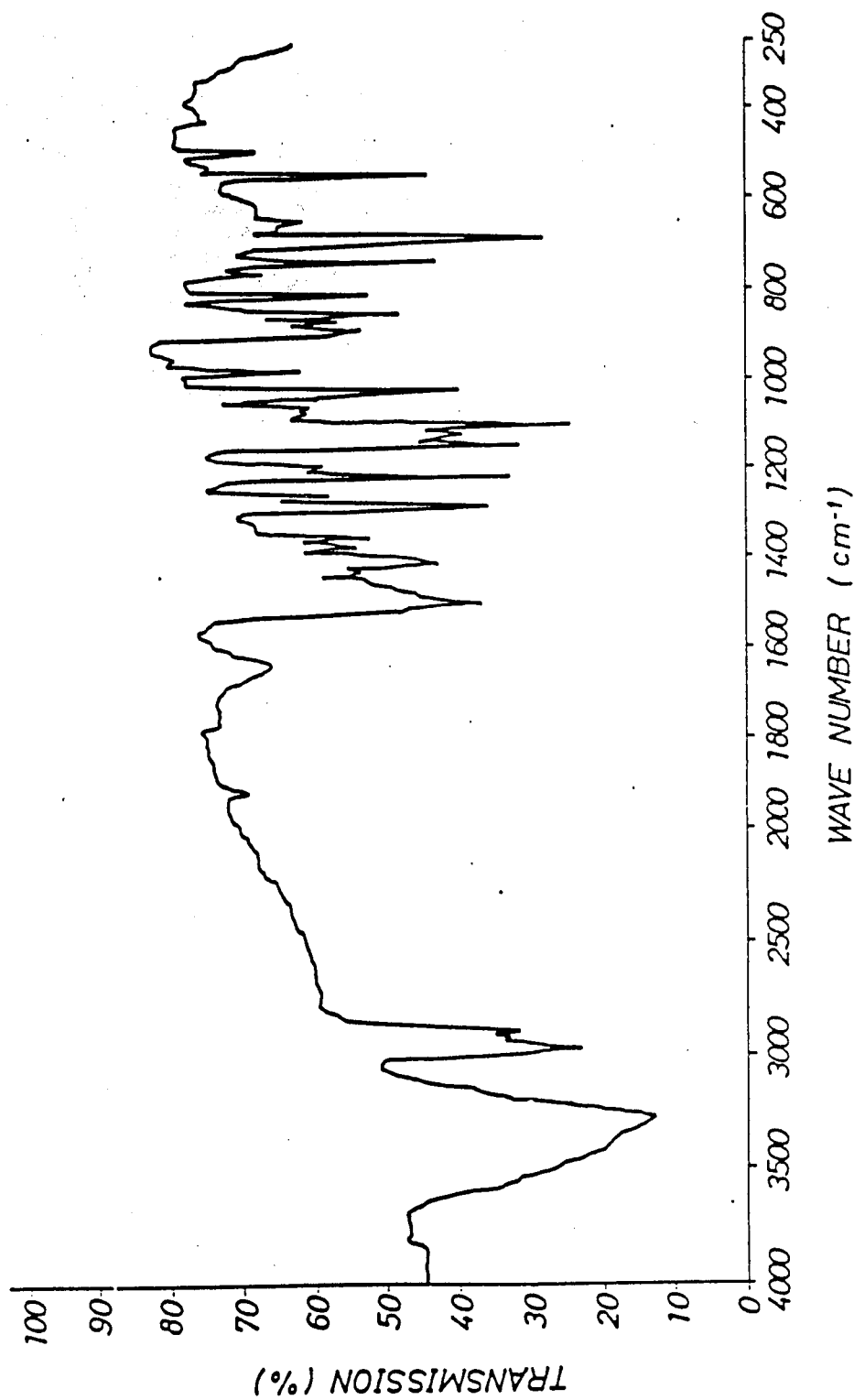
FIGS. 1 to 76 show the infrared absorption spectra of the azole derivatives according to that present invention shown in Table 1. Namely.
Figure 2:
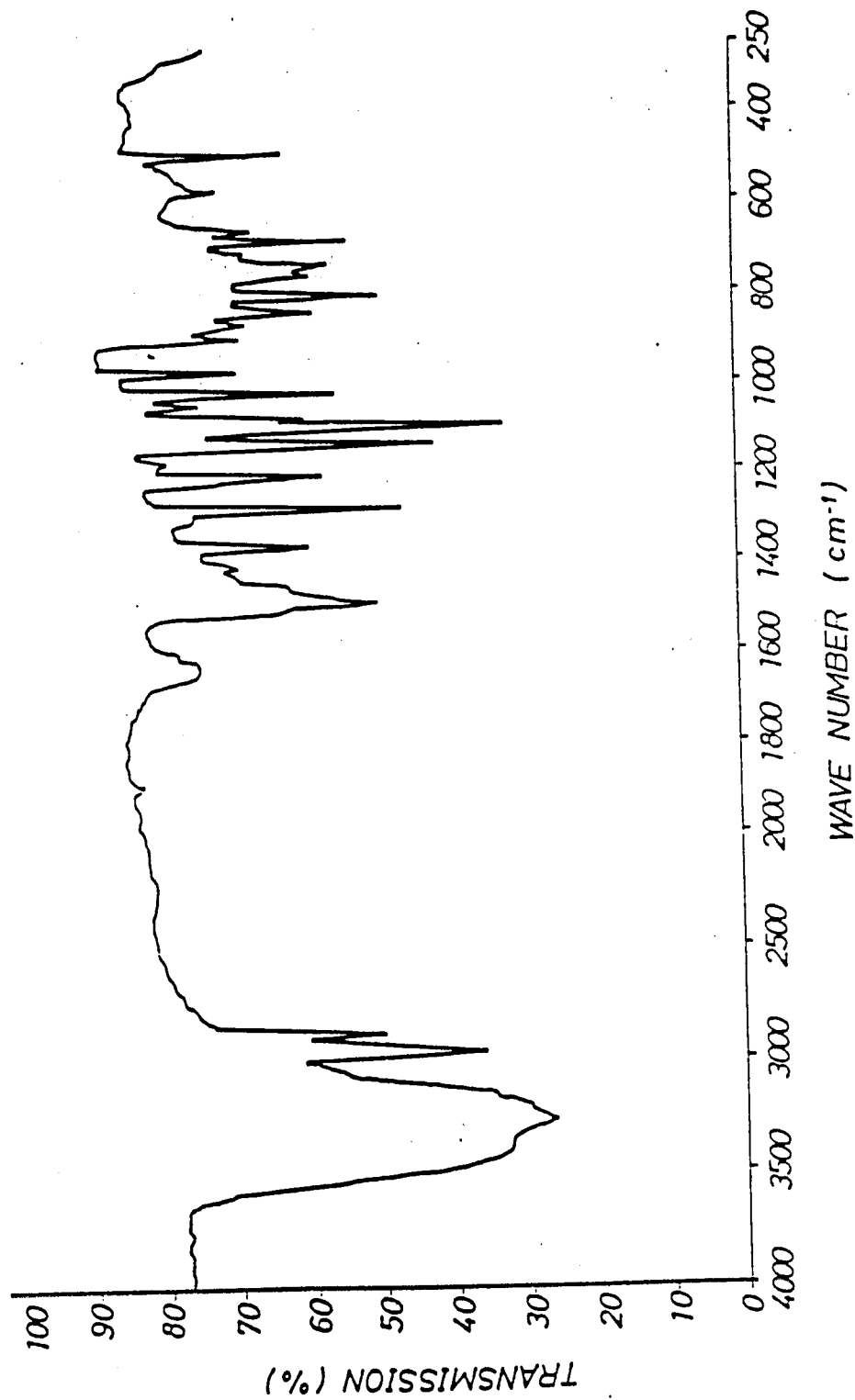
FIG. 2 shows the infrared absorption spectrum of the compound No. 2 in Table 1.
Figure 3:
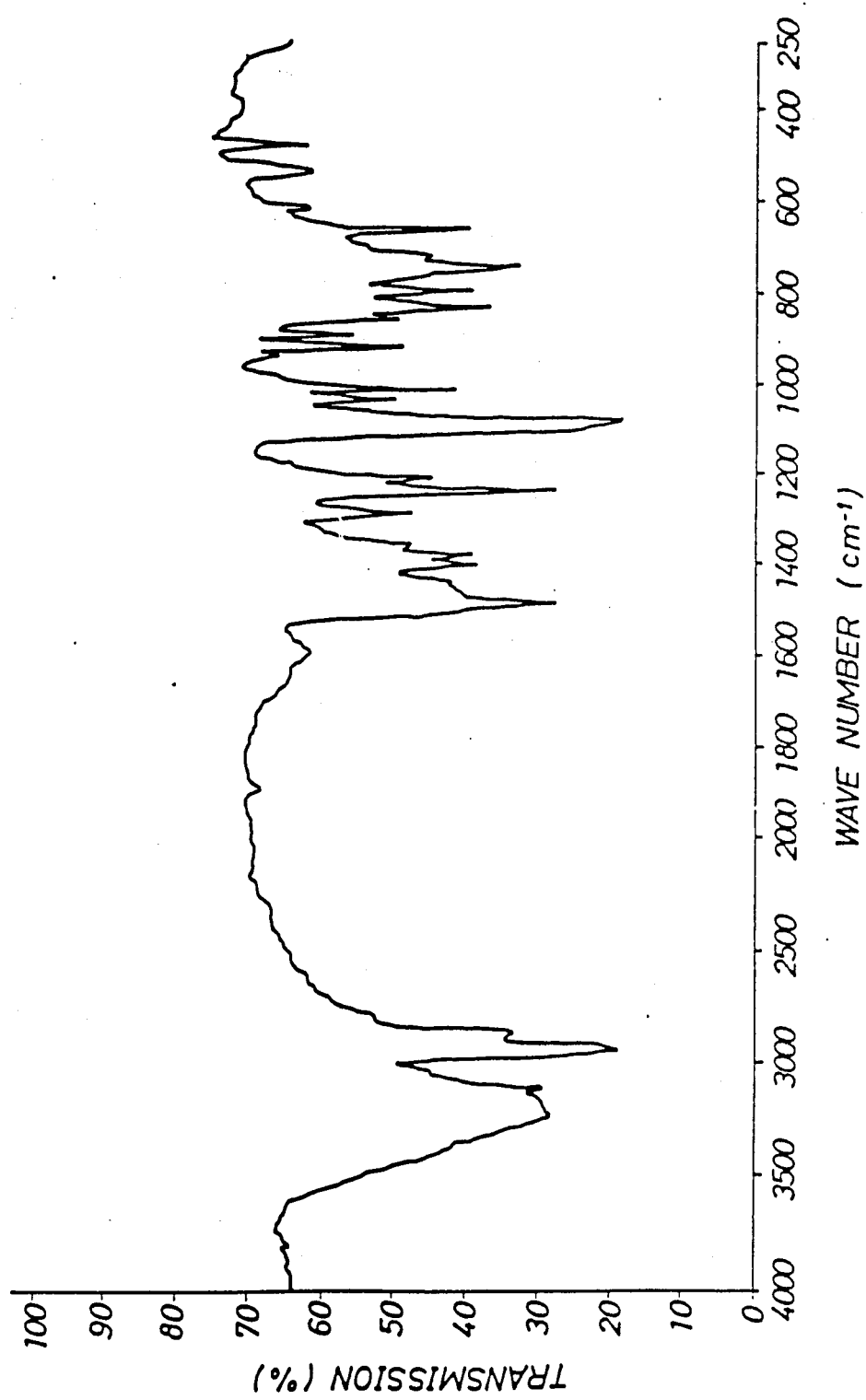
FIG. 3 shows the infrared absorption spectrum of the compound No. 3 in Table 1.
Figure 4:
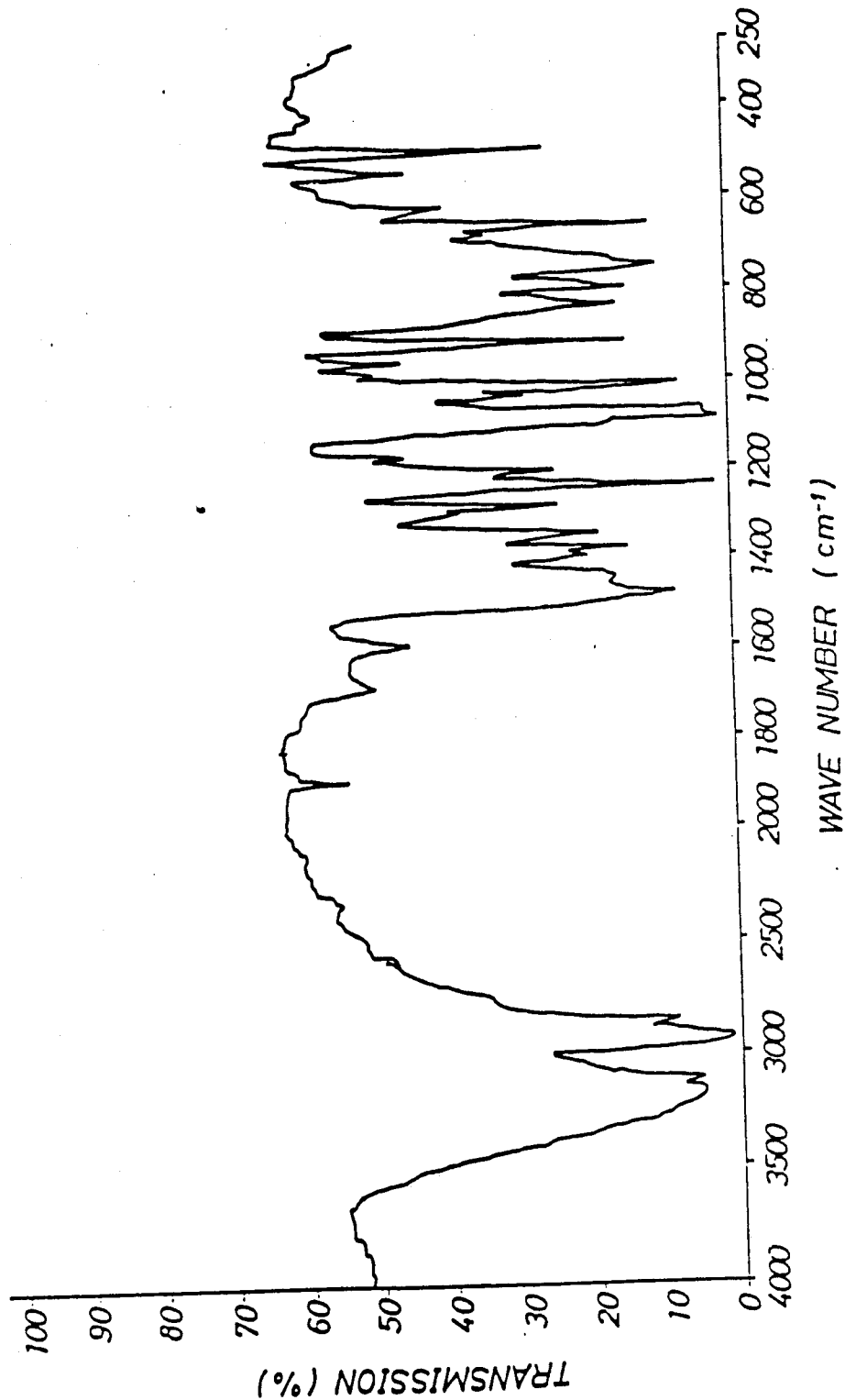
Figure 5:
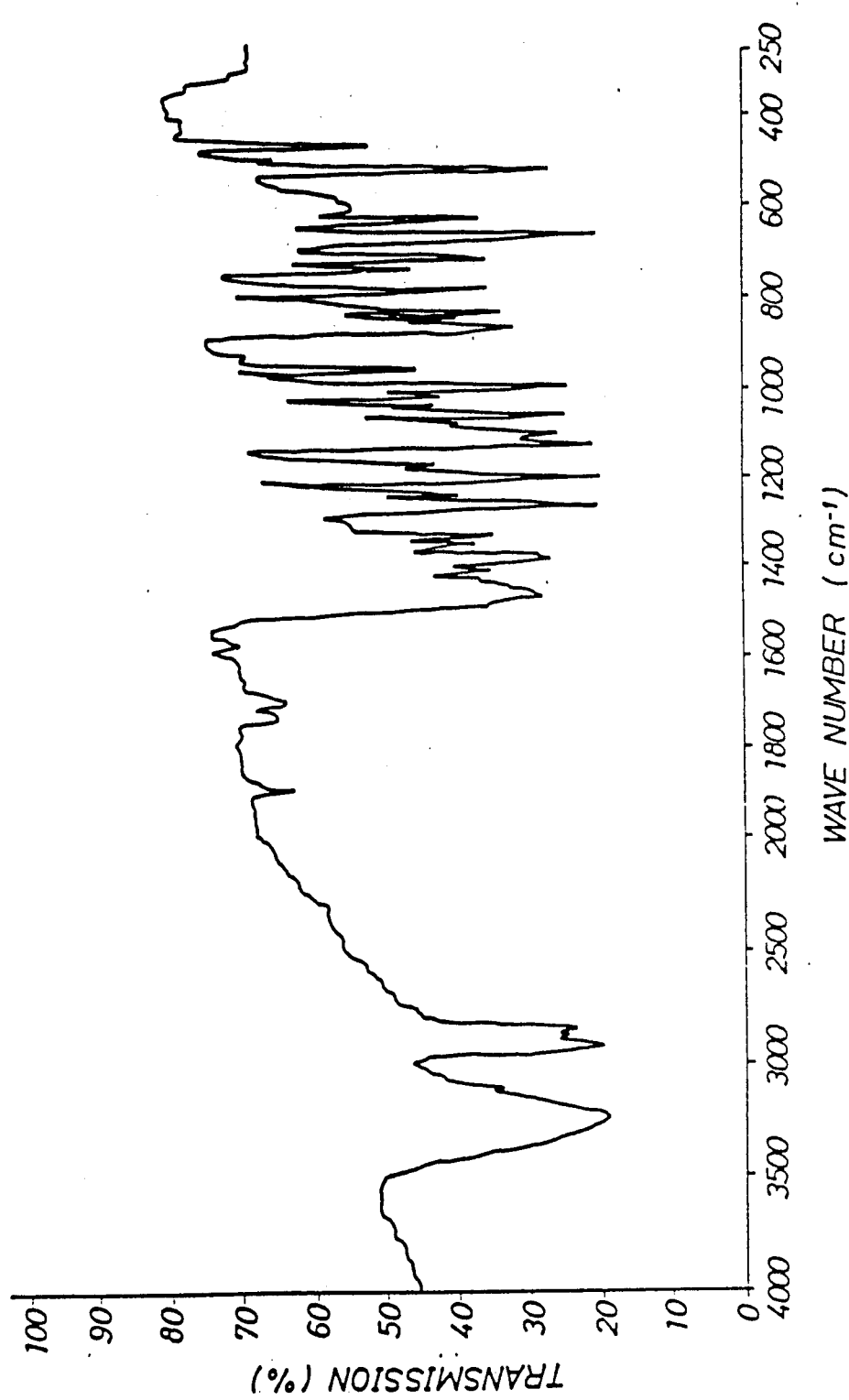
Figure 6:
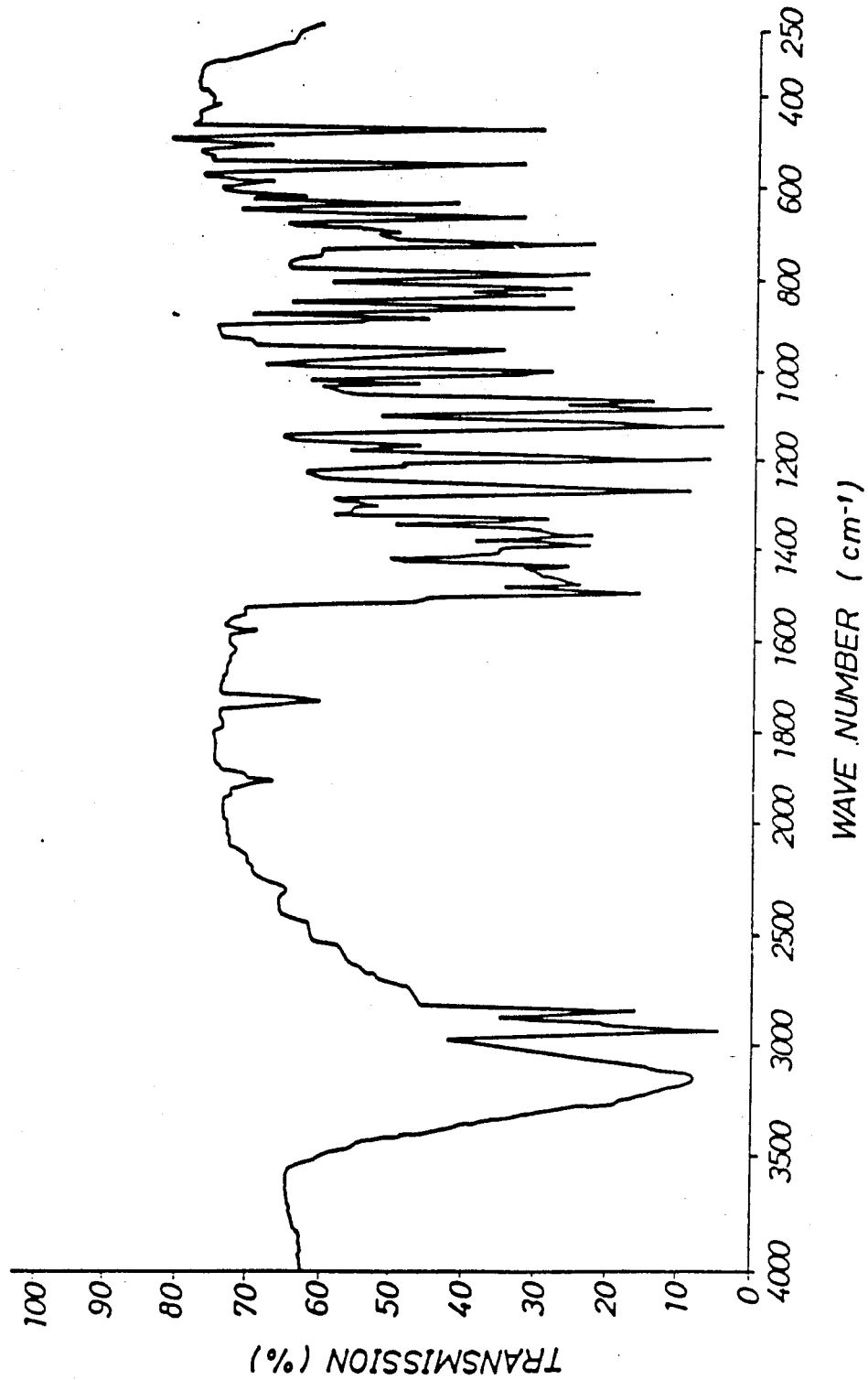
Figure 7:
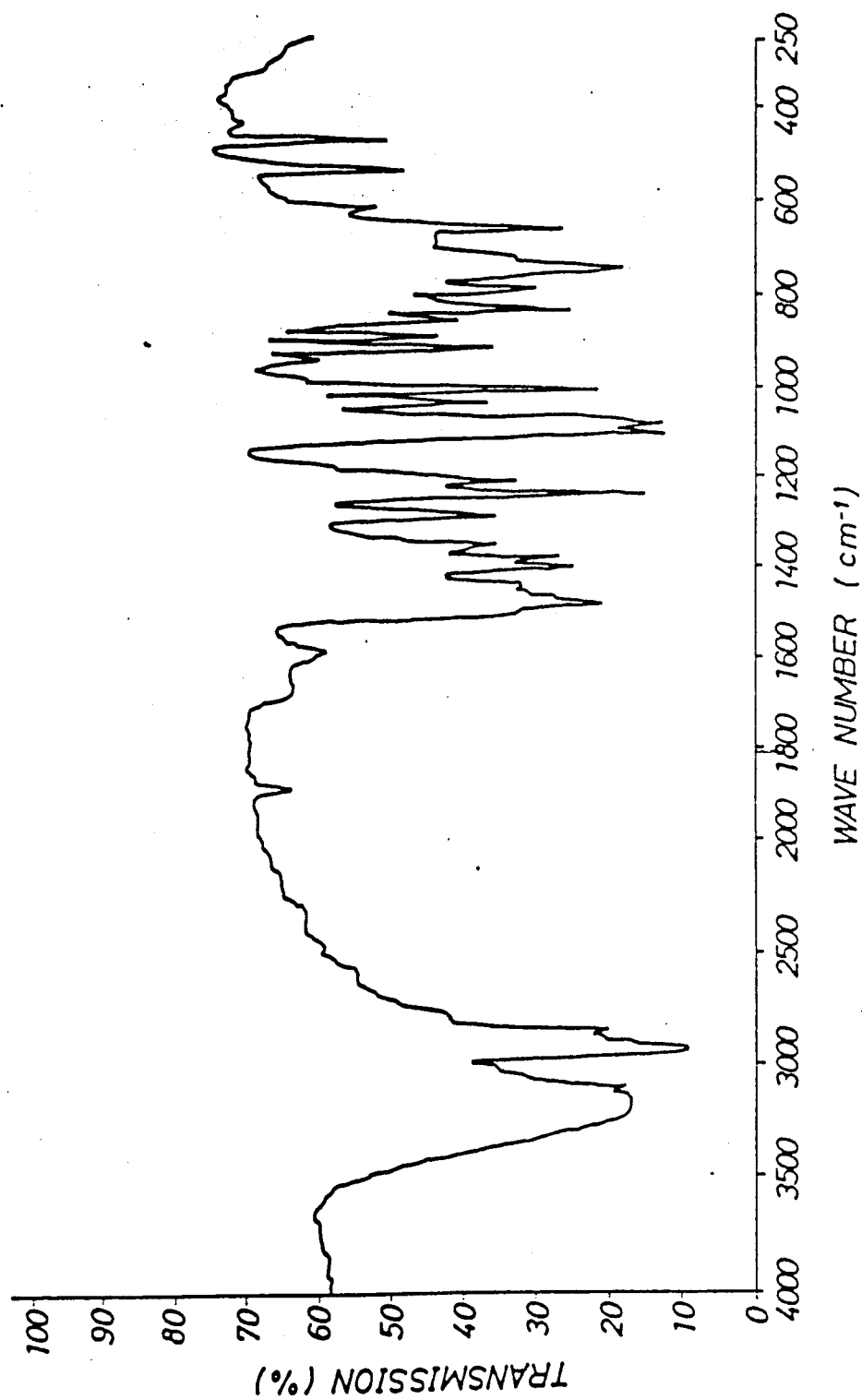
Figure 8:
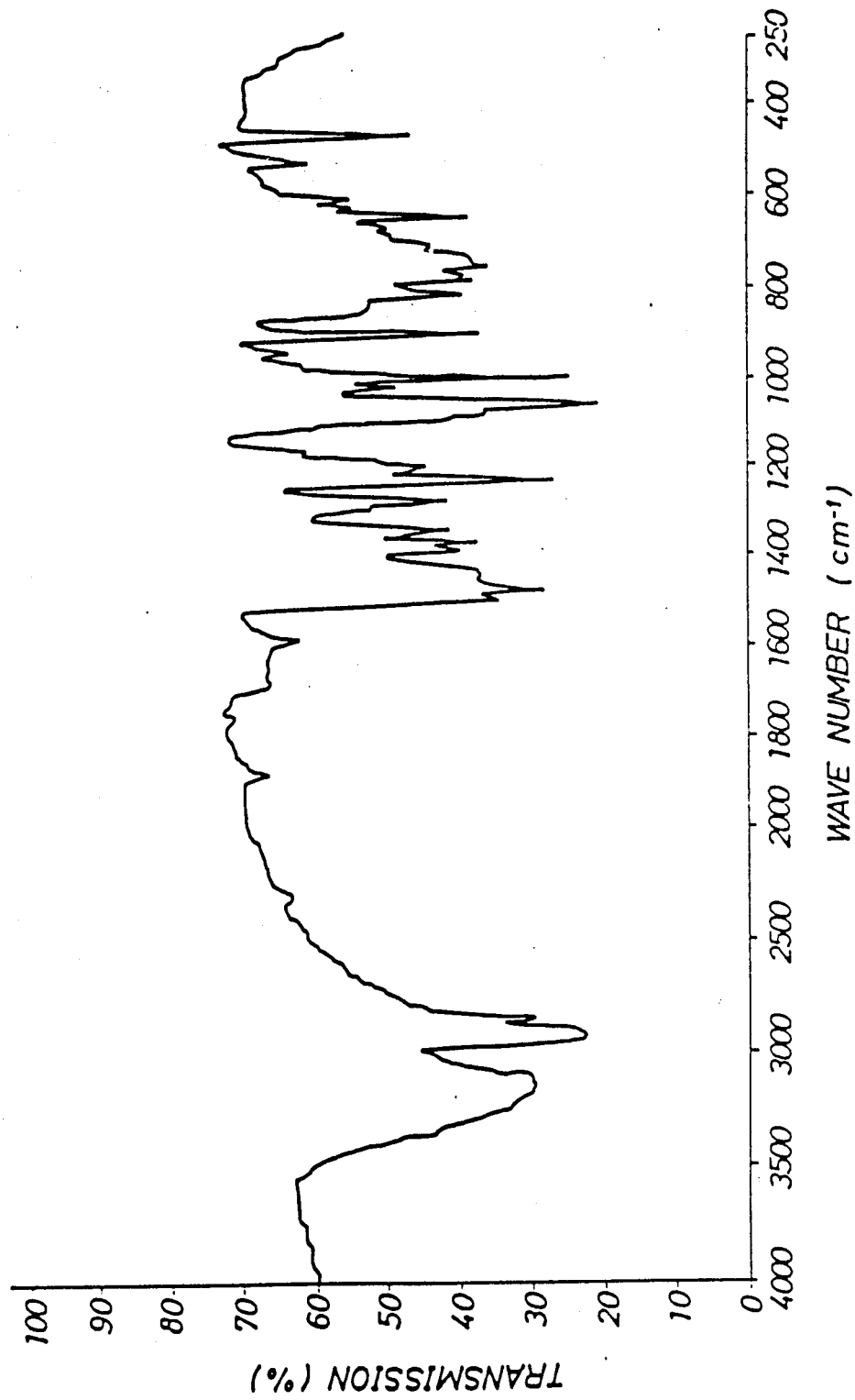
Figure 9:
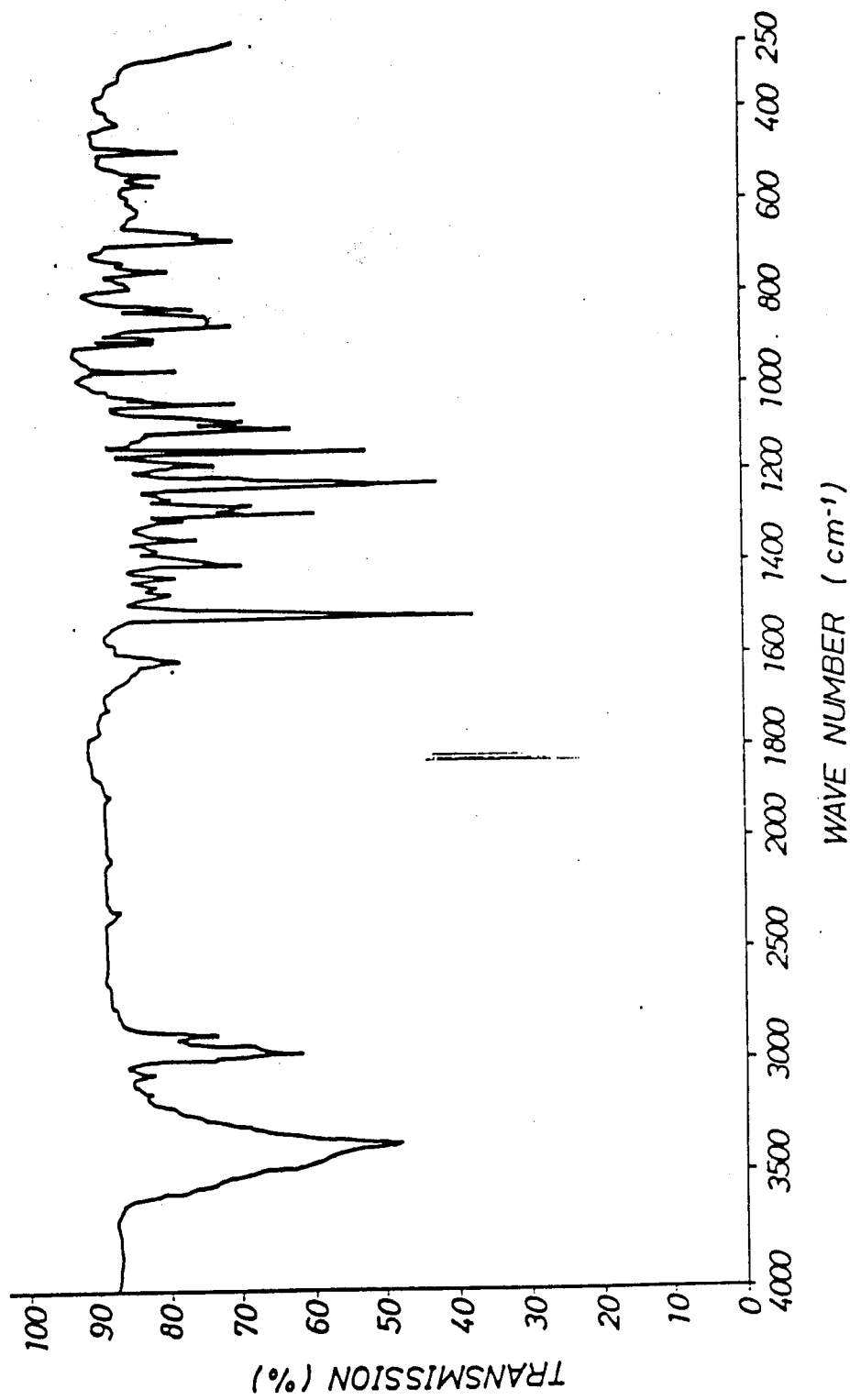
Figure 10:
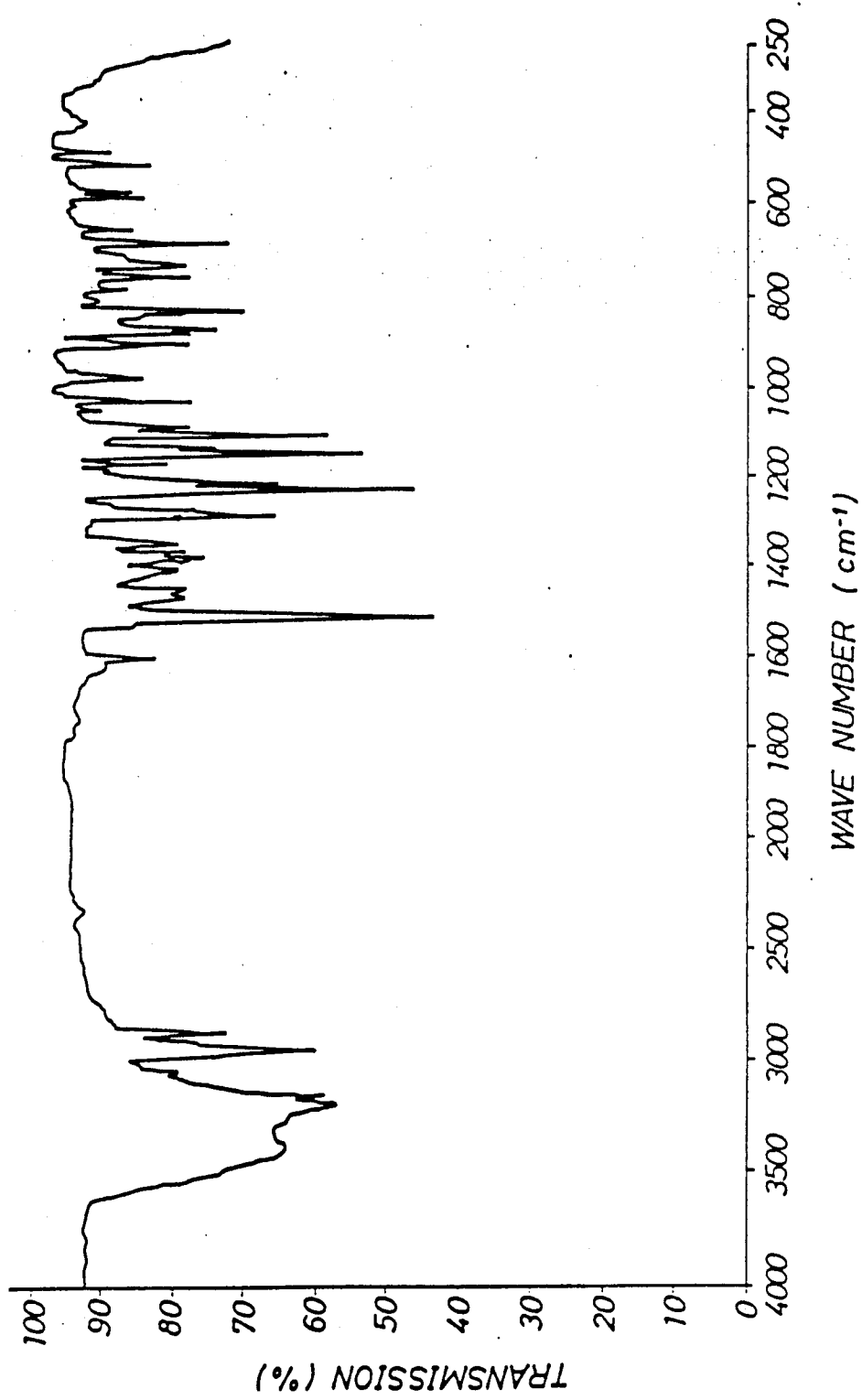
Figure 11:
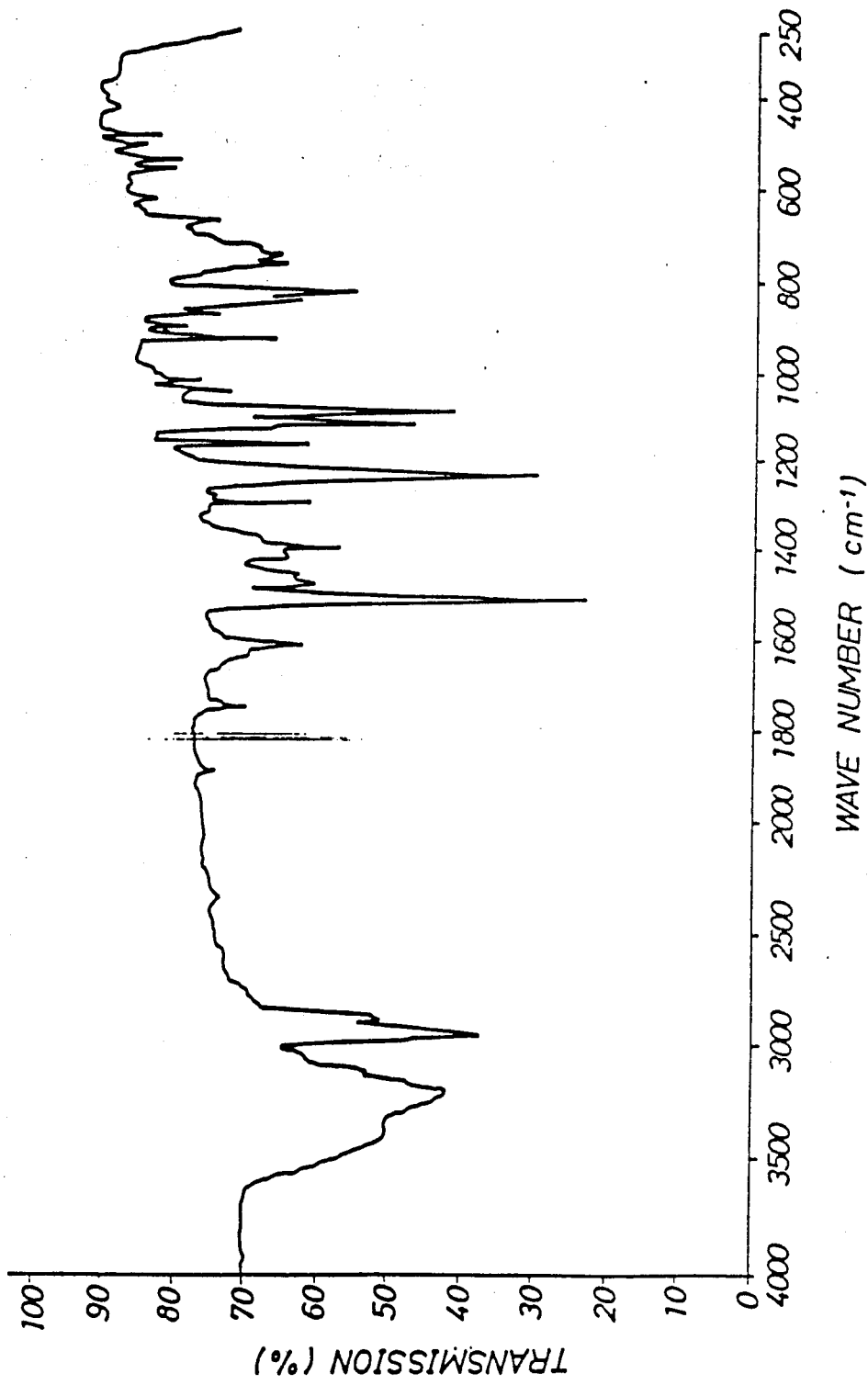
Figure 12:
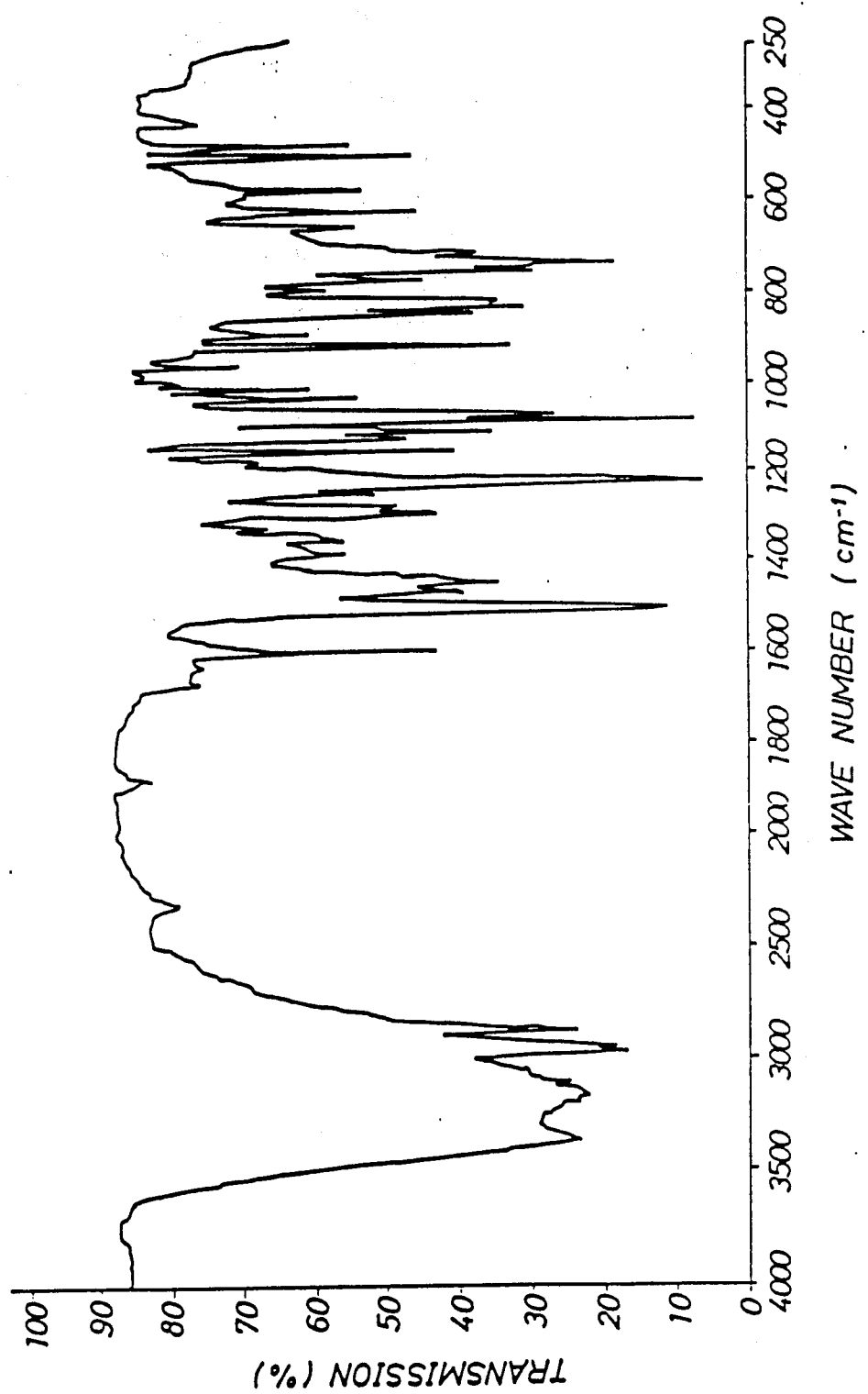
Figure 13:
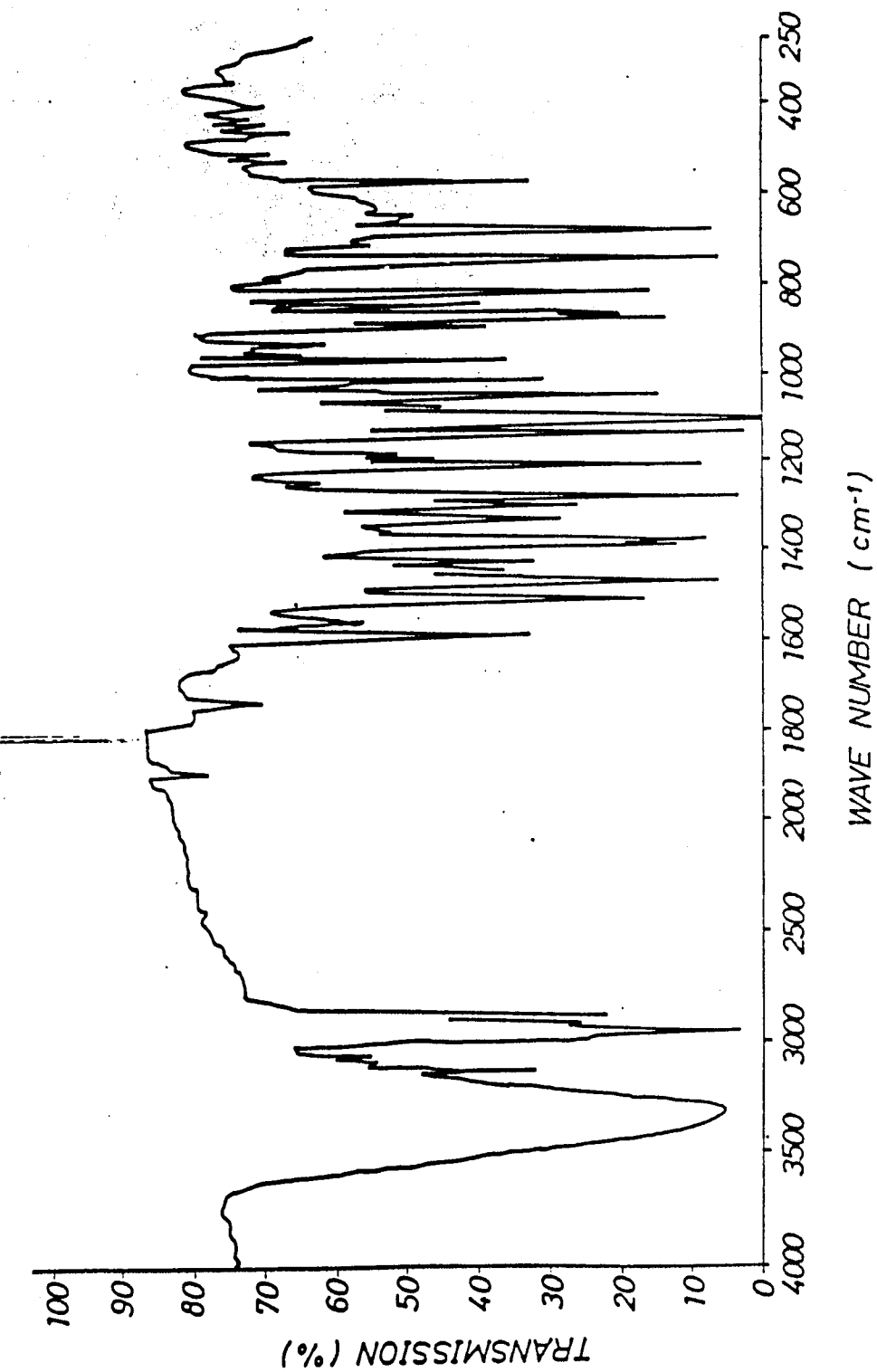
Figure 14:
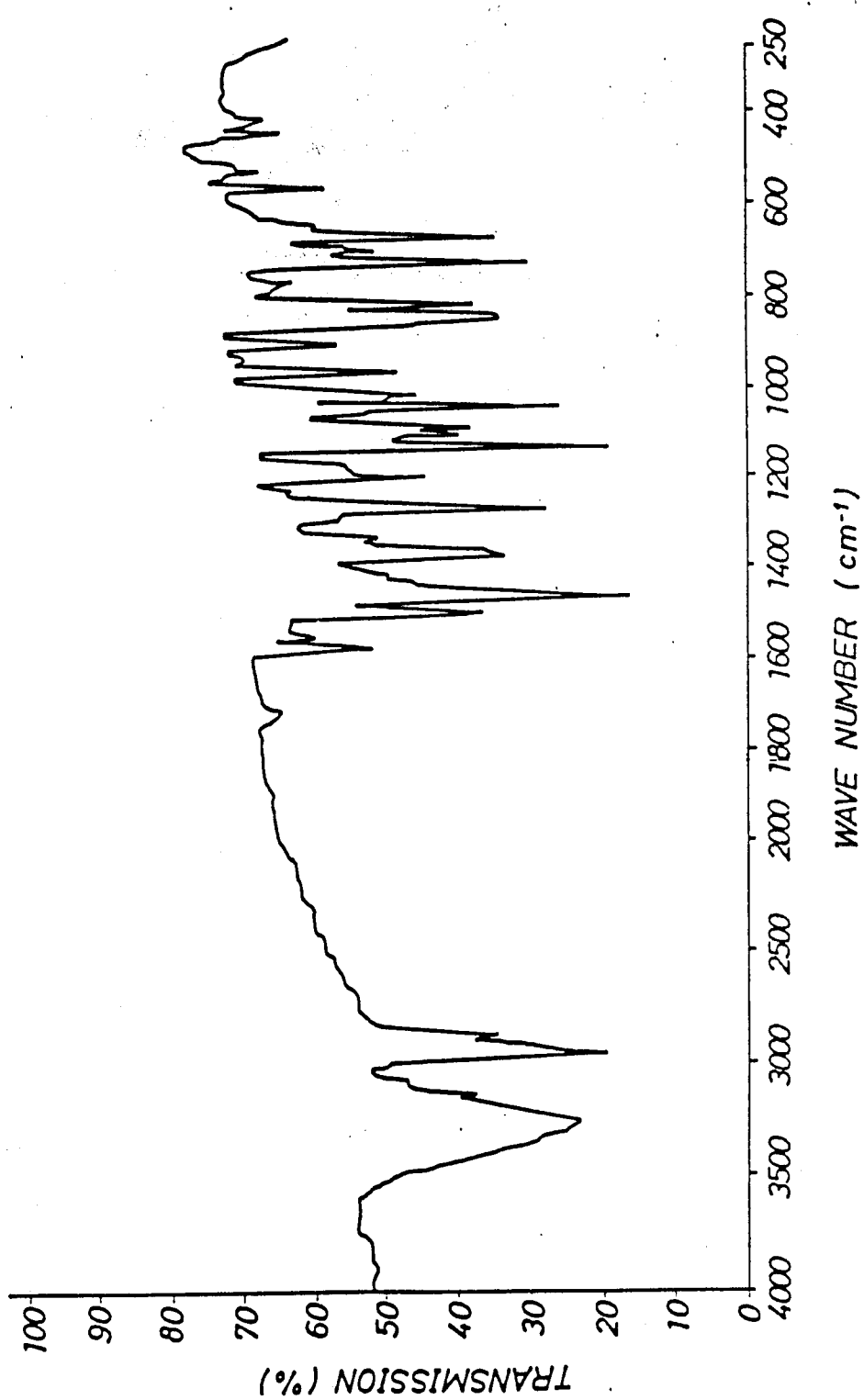
Figure 15:
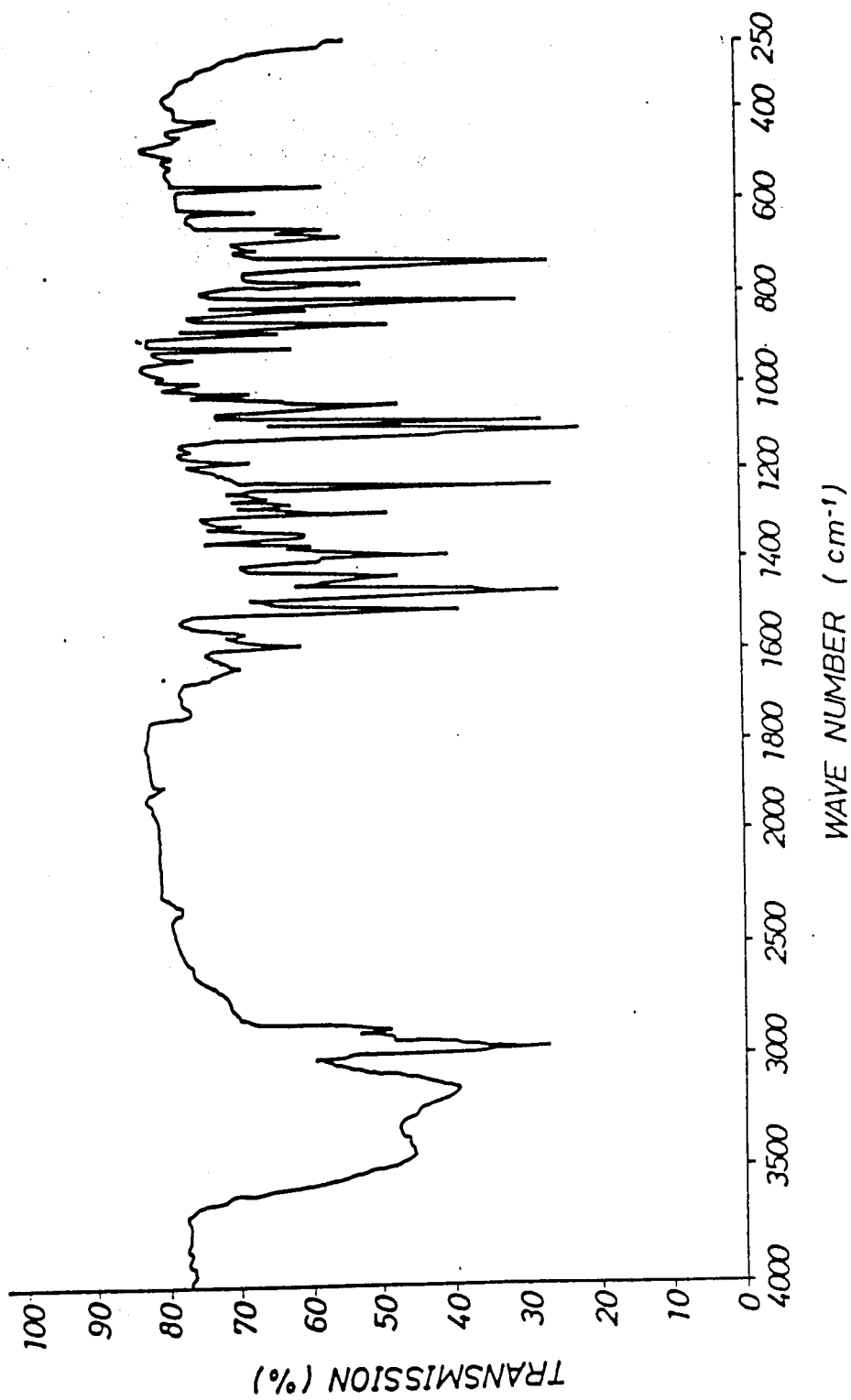
Figure 16:
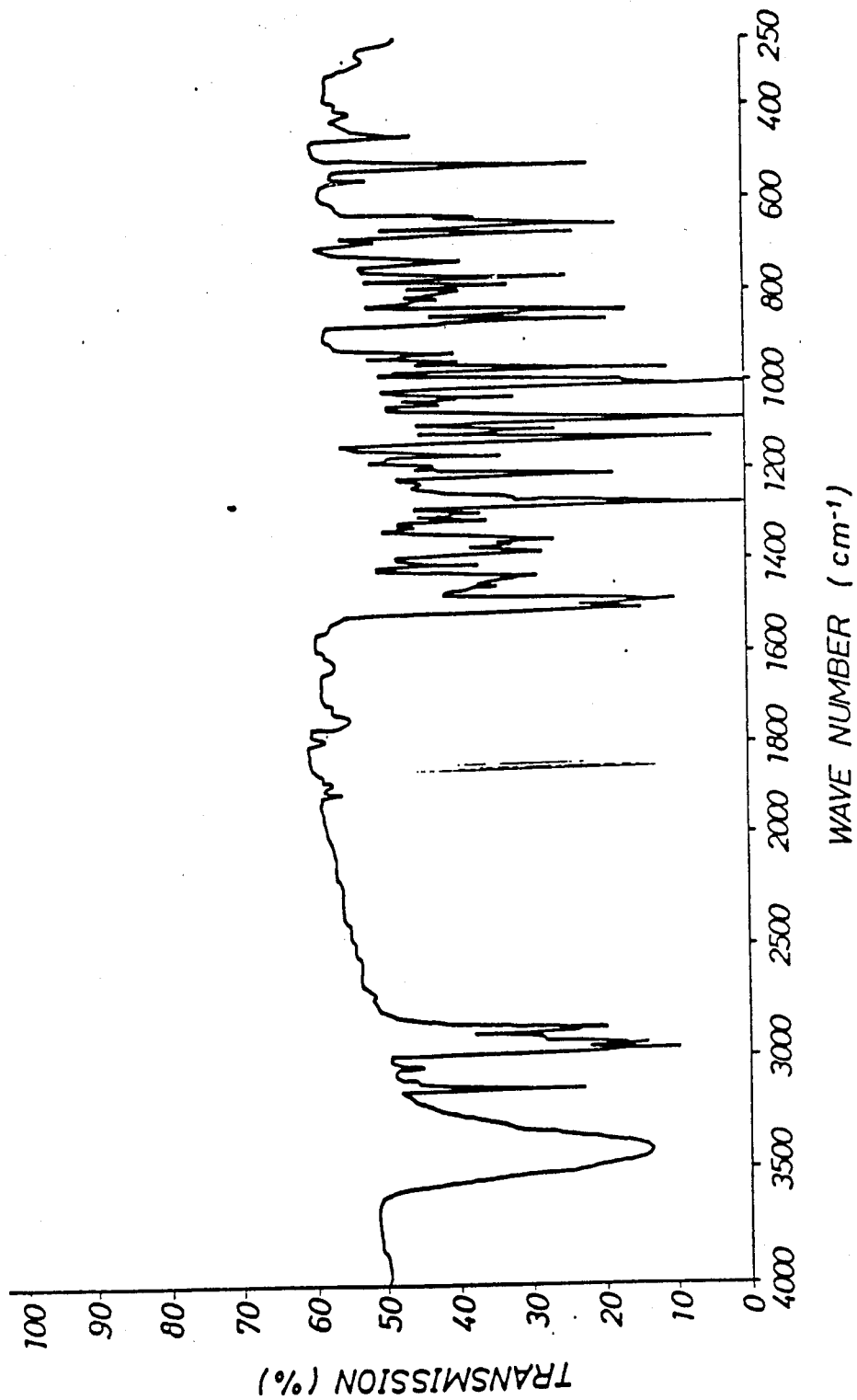
Figure 17:
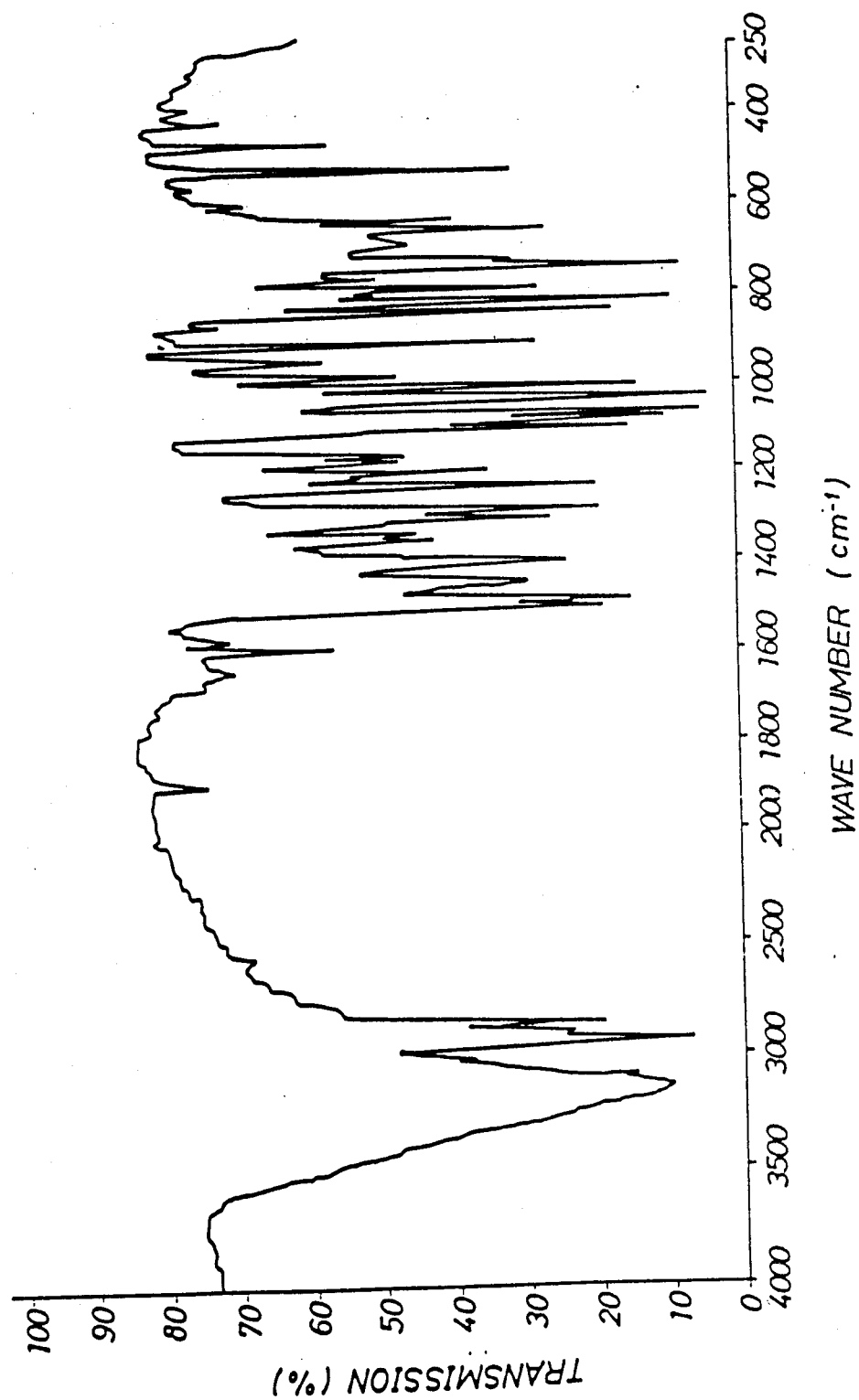
Figure 18:
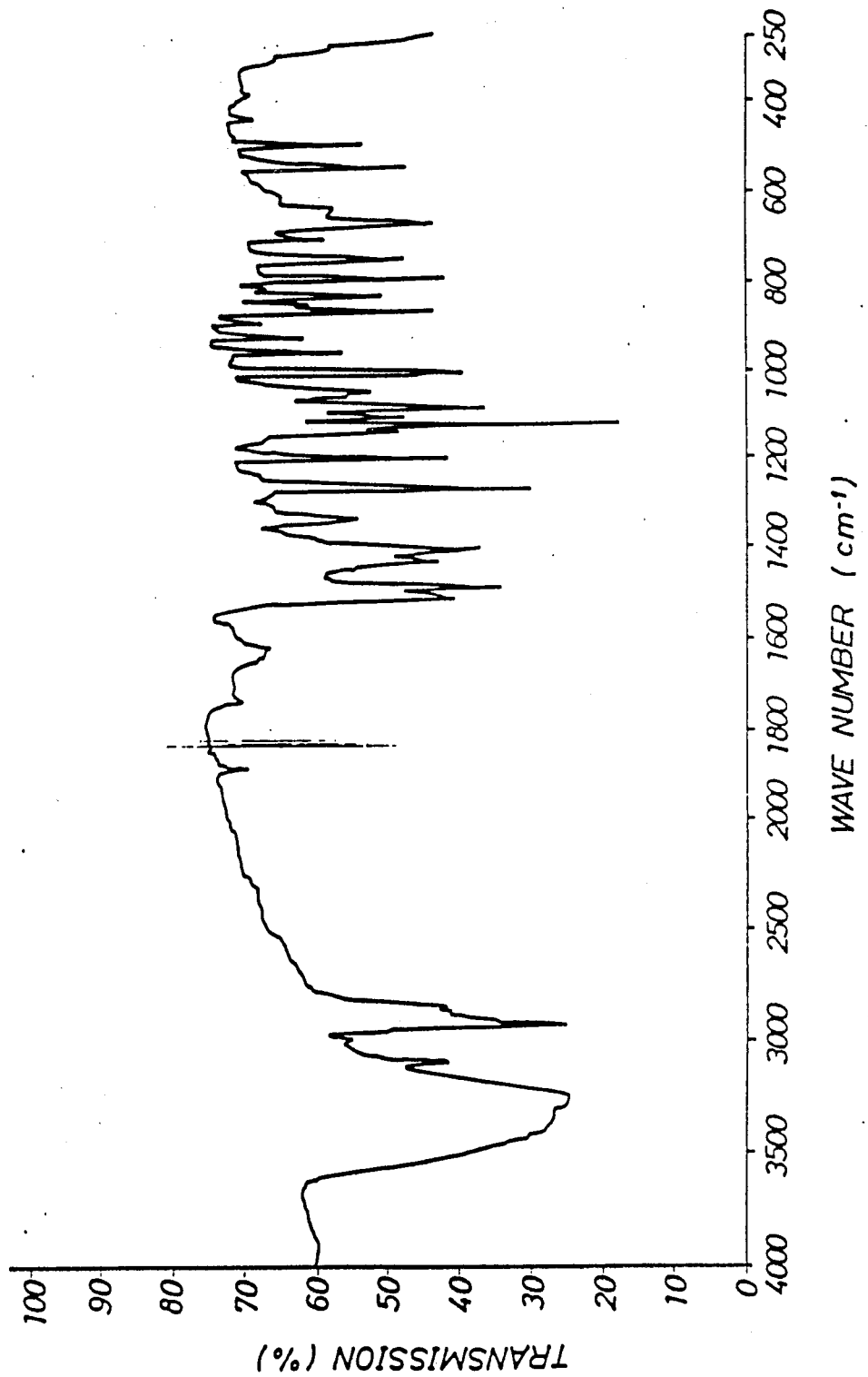
Figure 19:
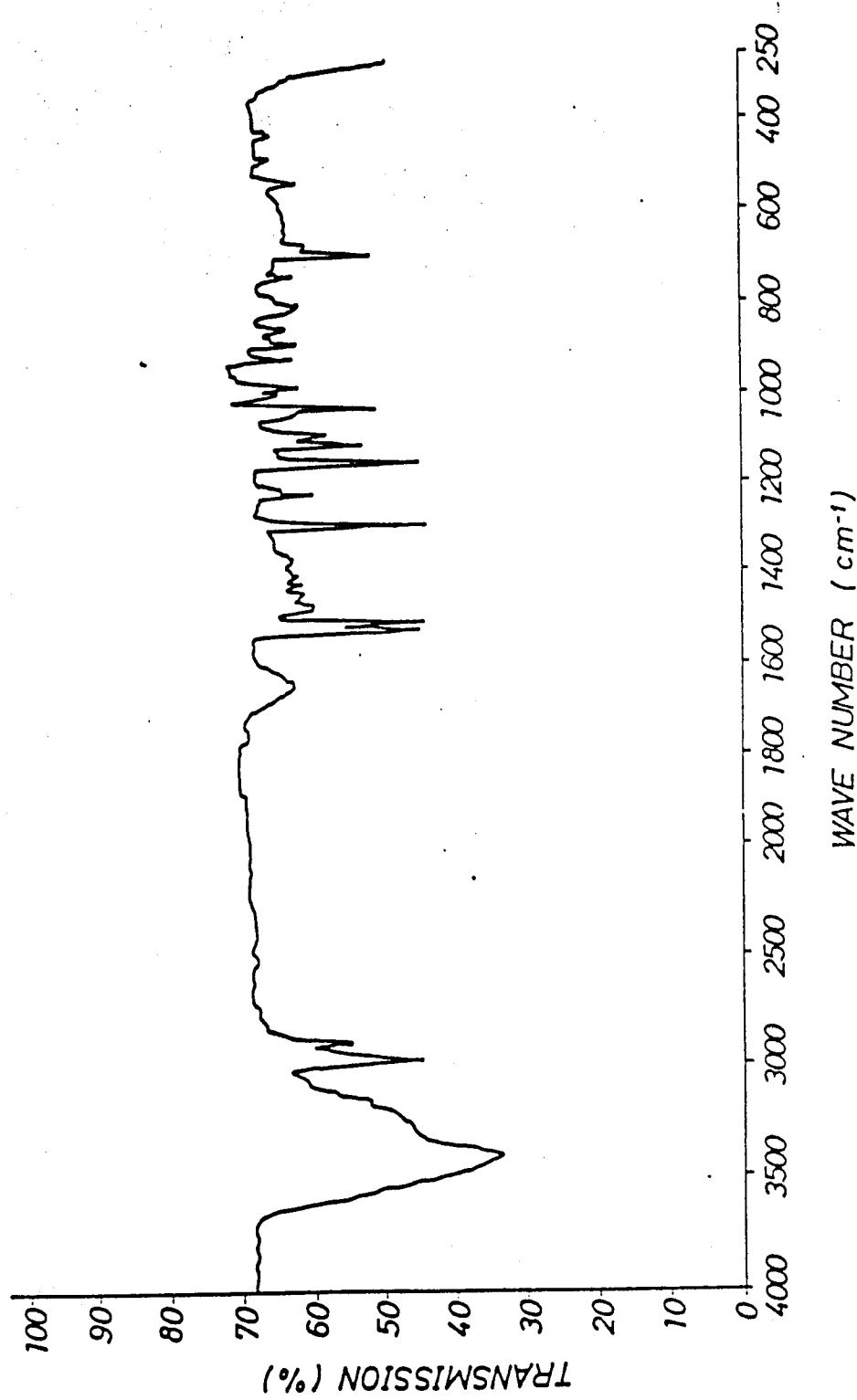
Figure 20:
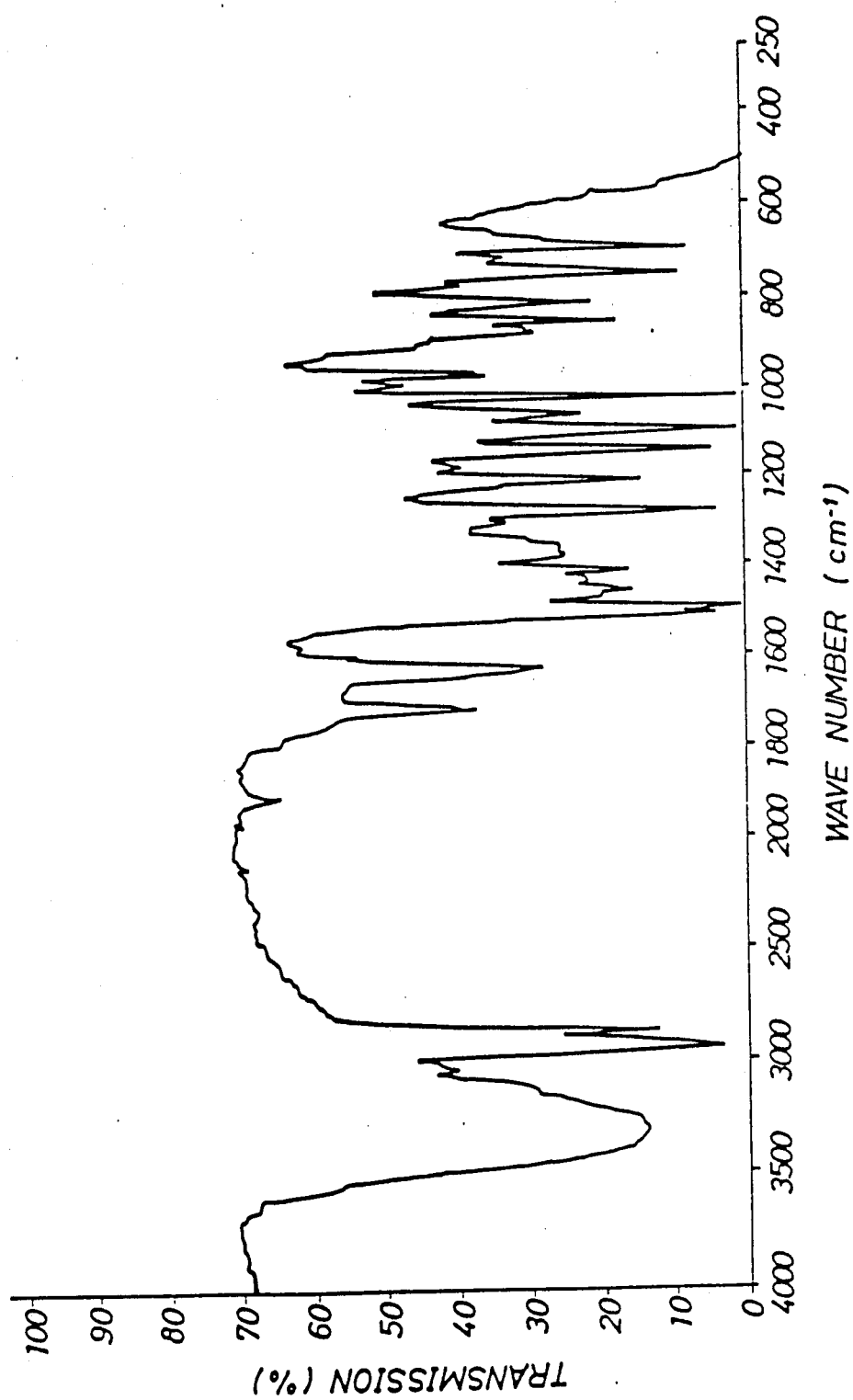
Figure 21:
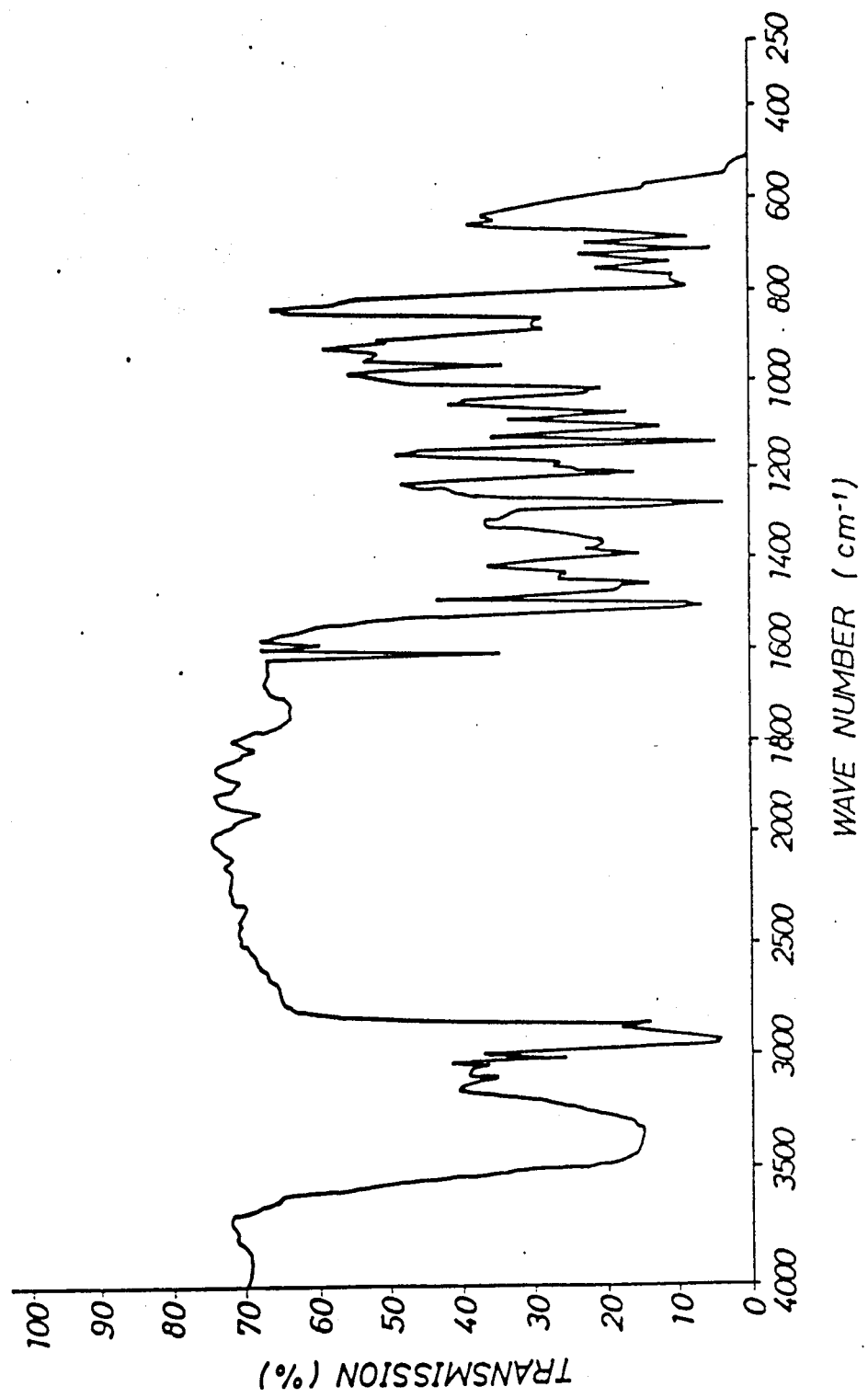
Figure 22:
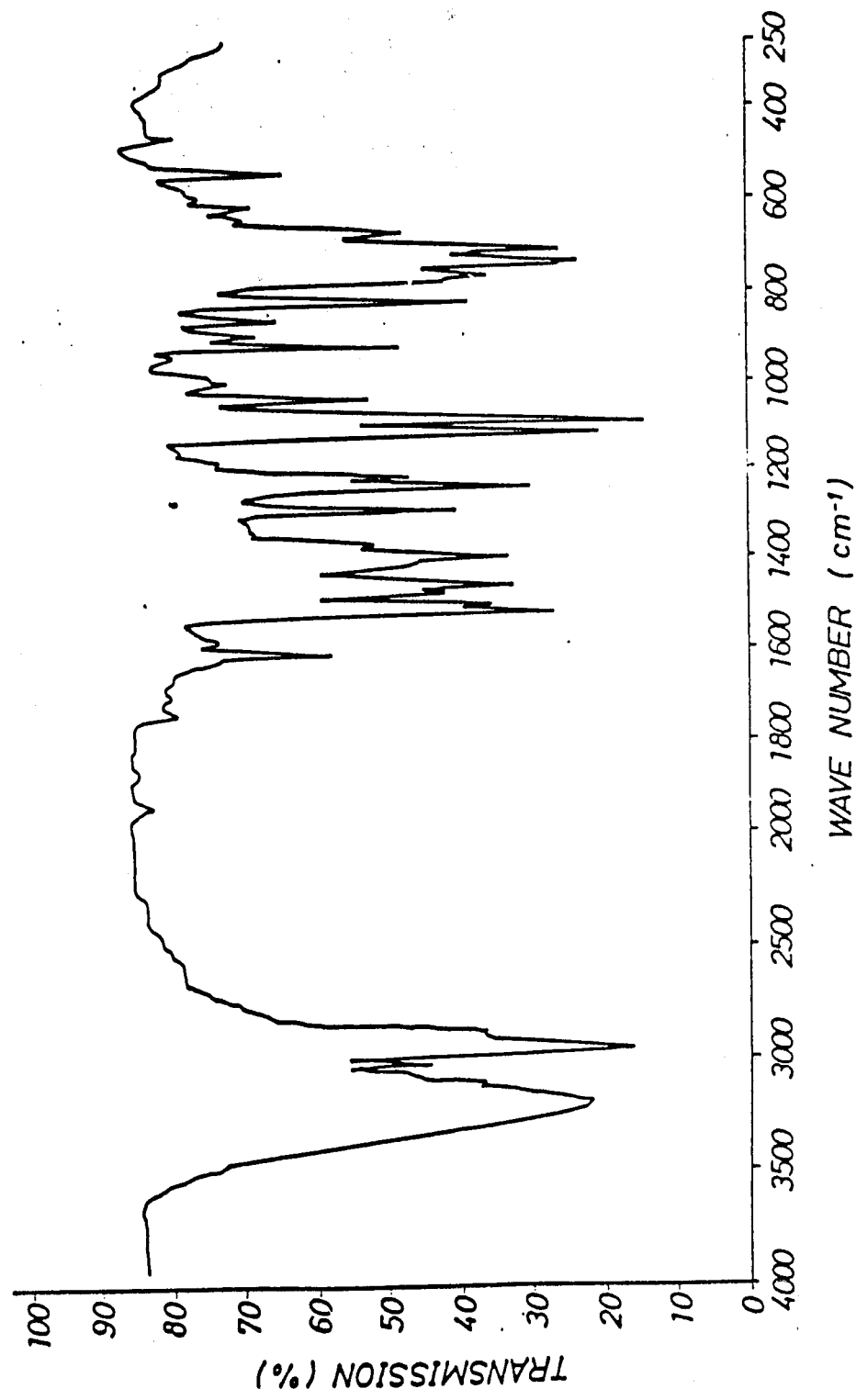
Figure 23:
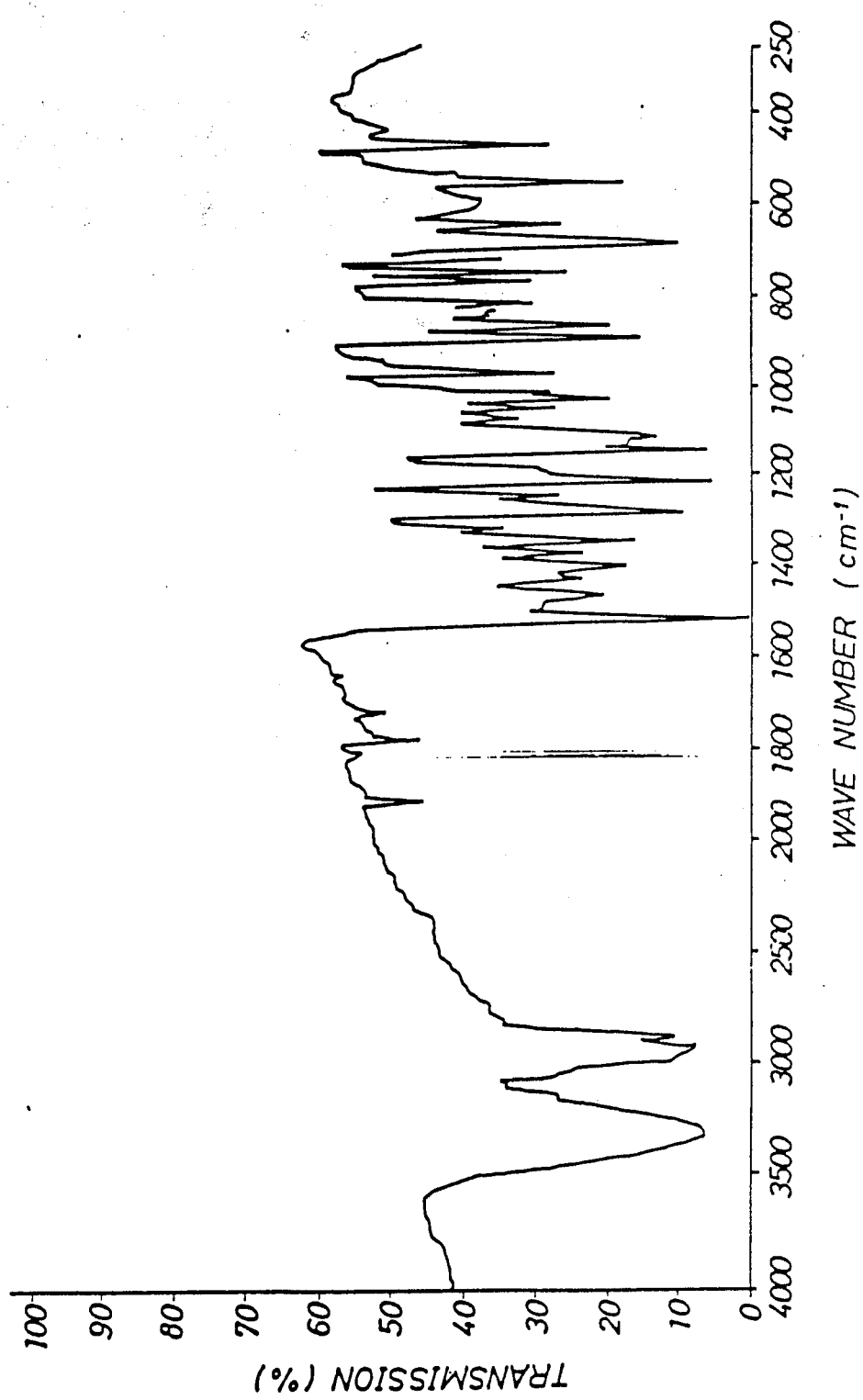
Figure 24:
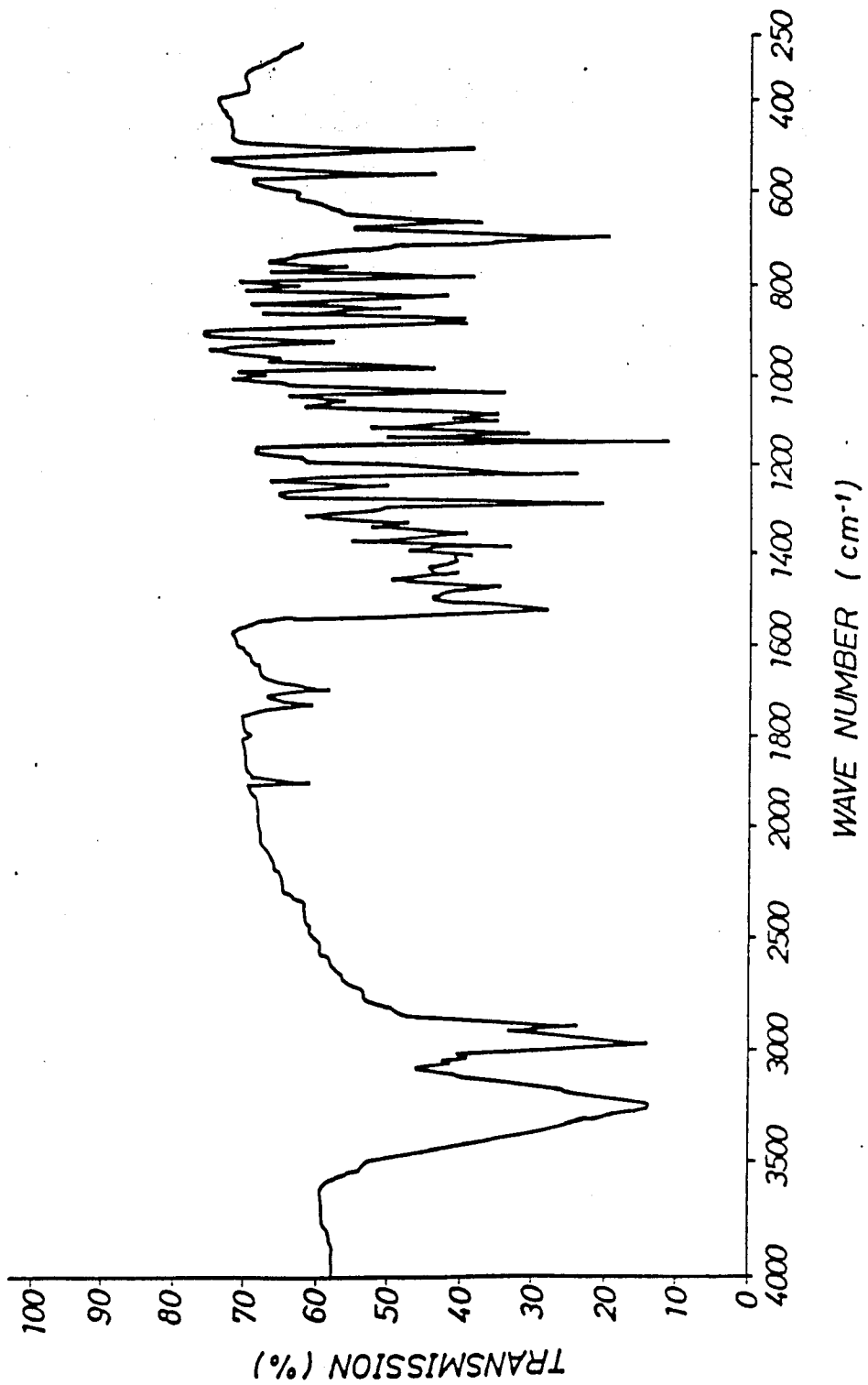
Figure 25:
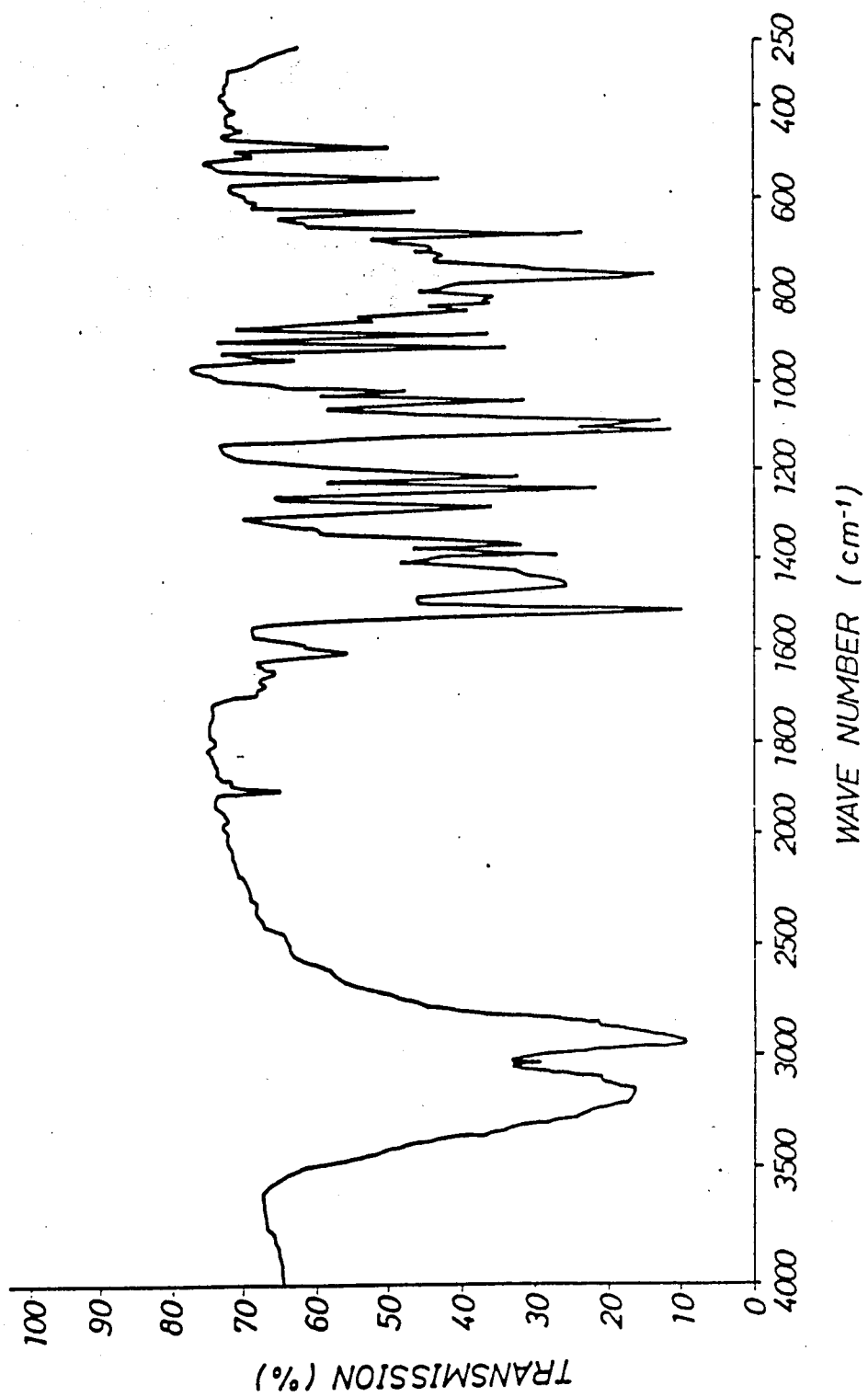
Figure 26:
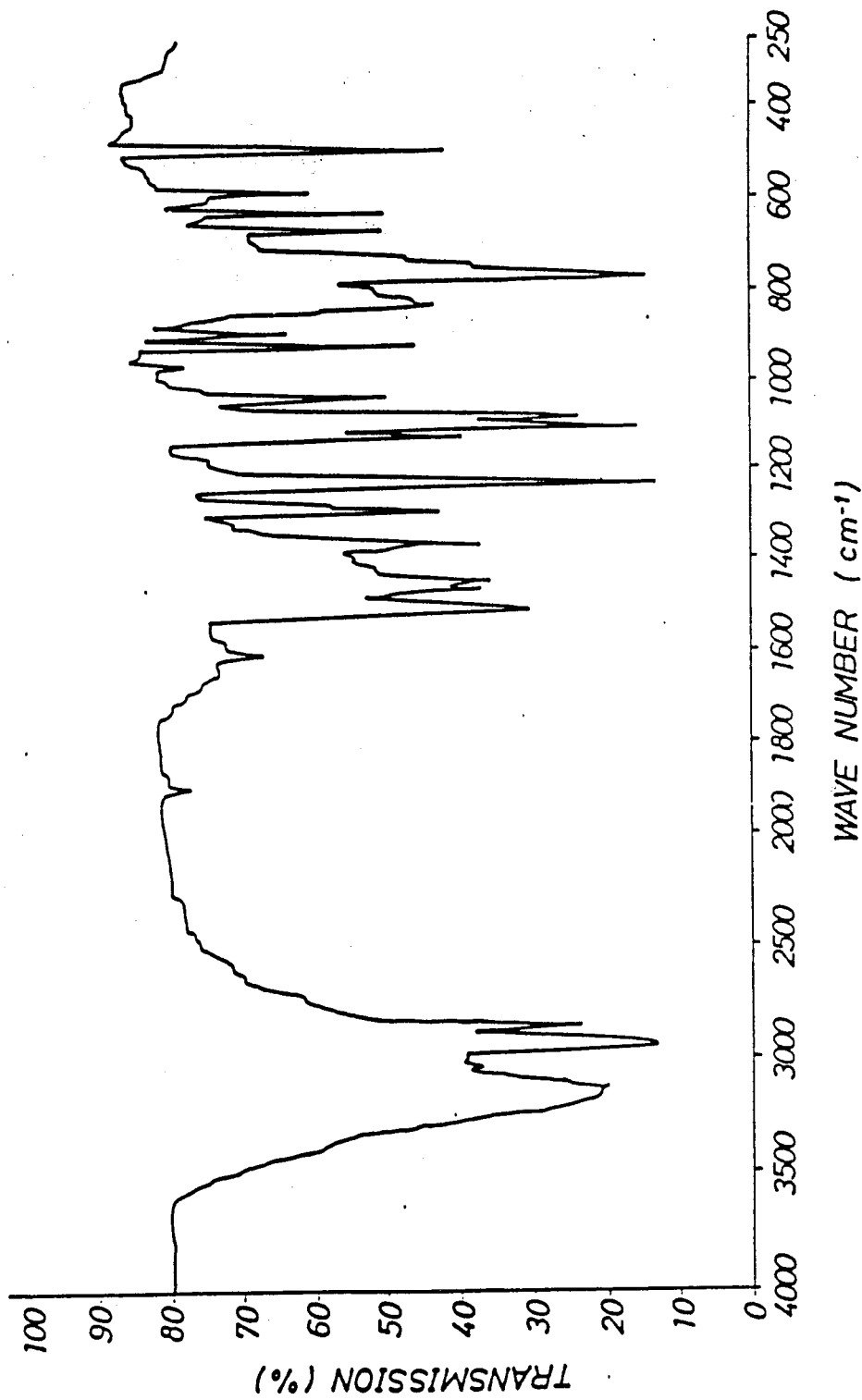
Figure 27:
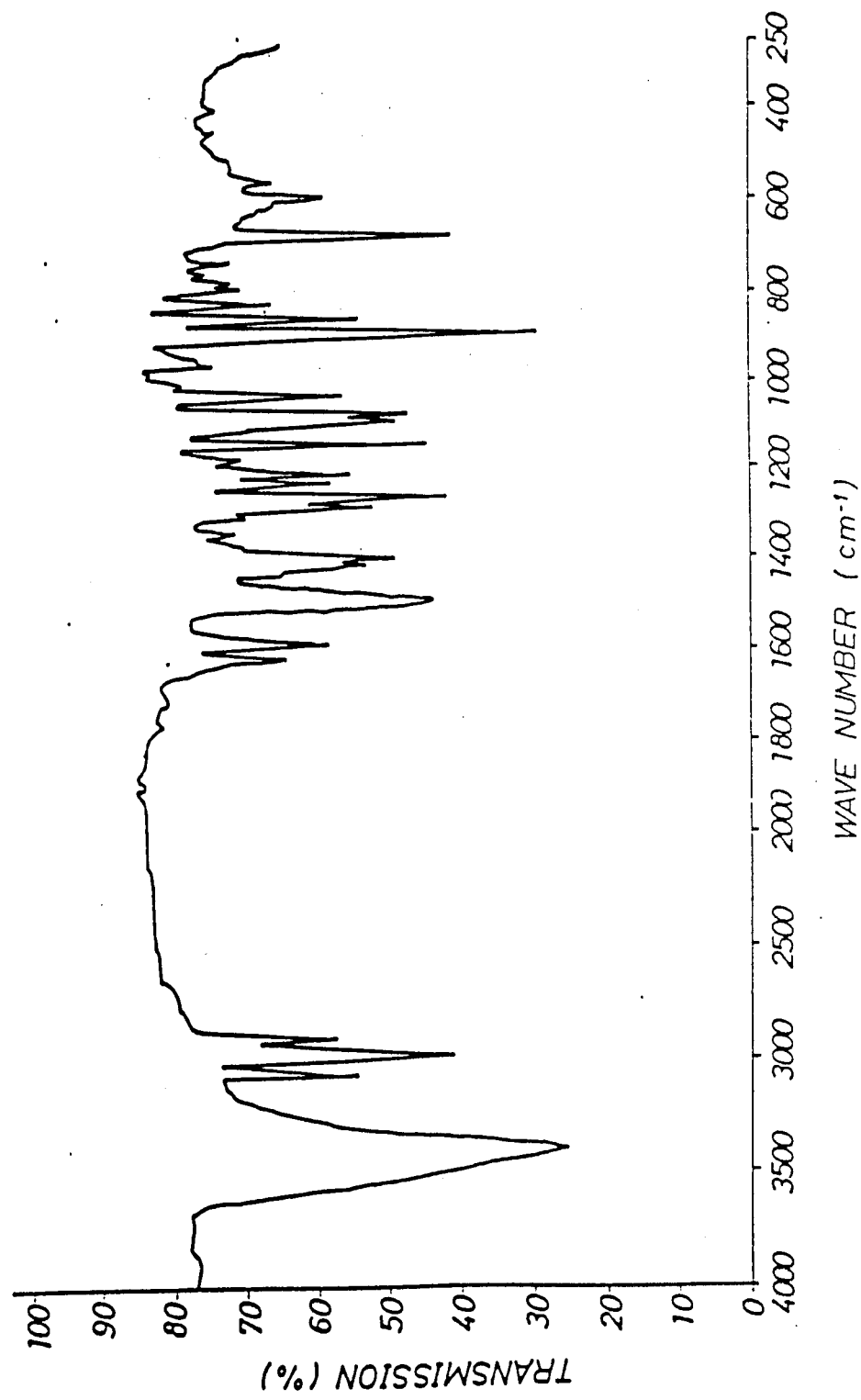
Figure 28:
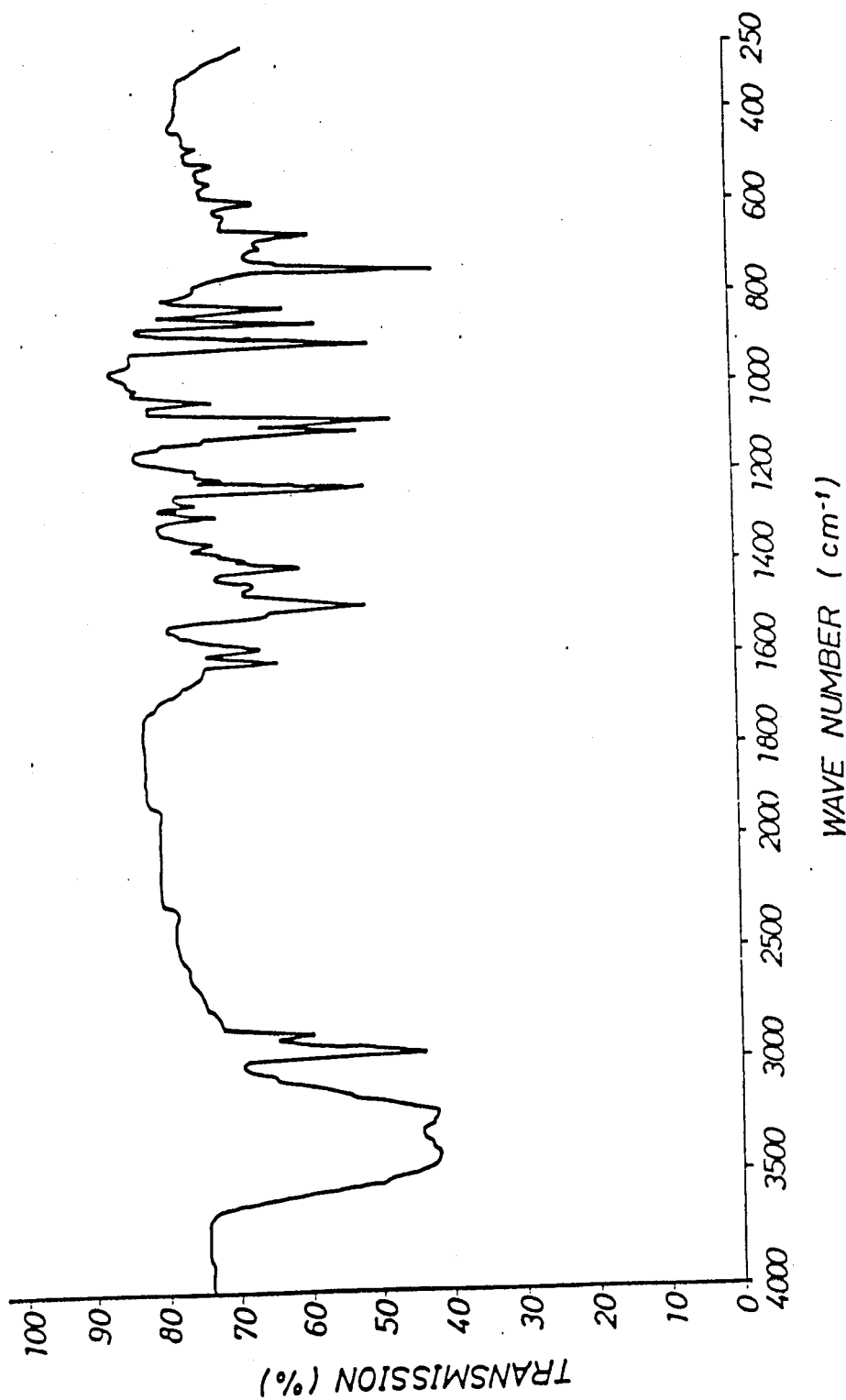
Figure 29:
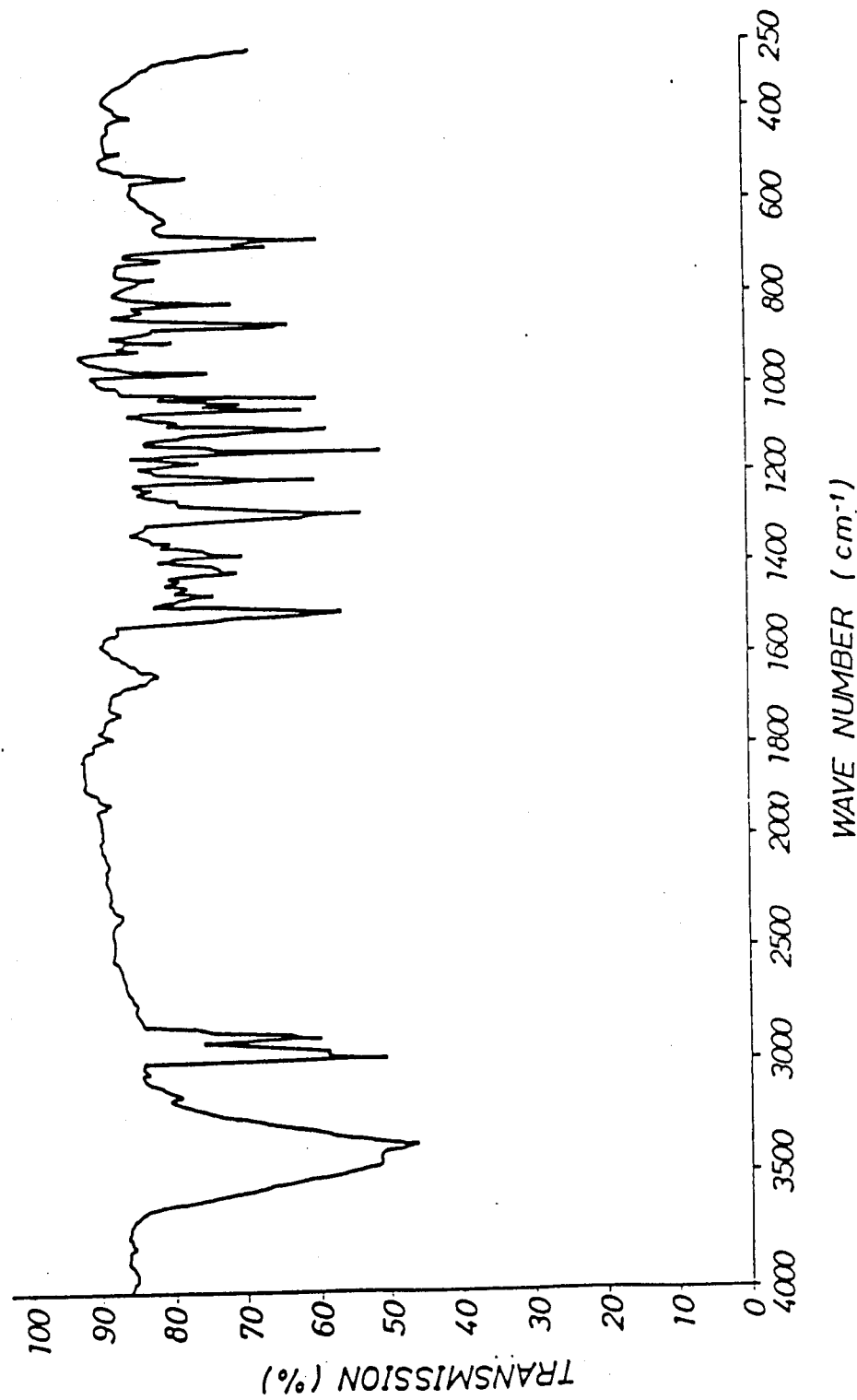
Figure 30:
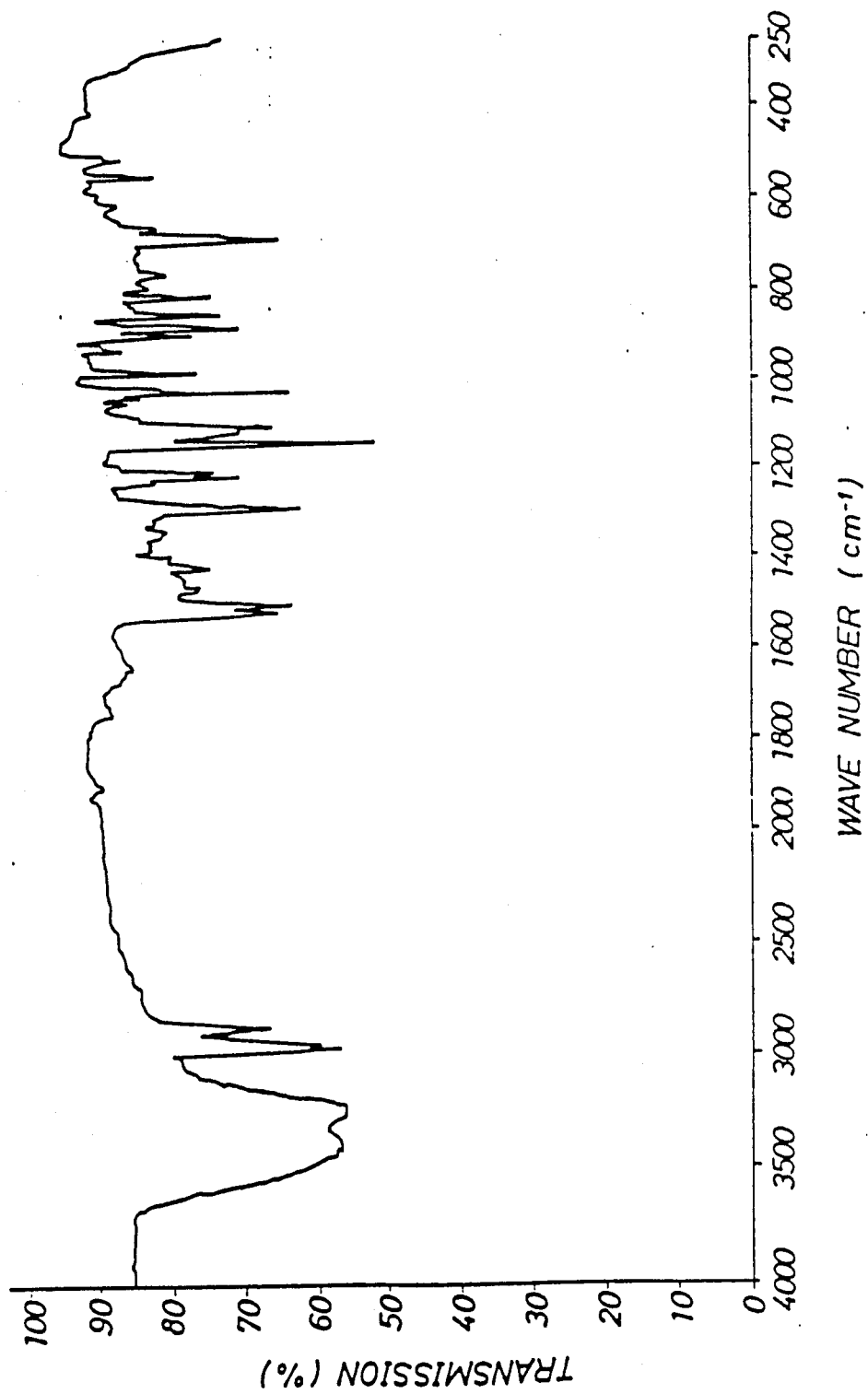
Figure 31:
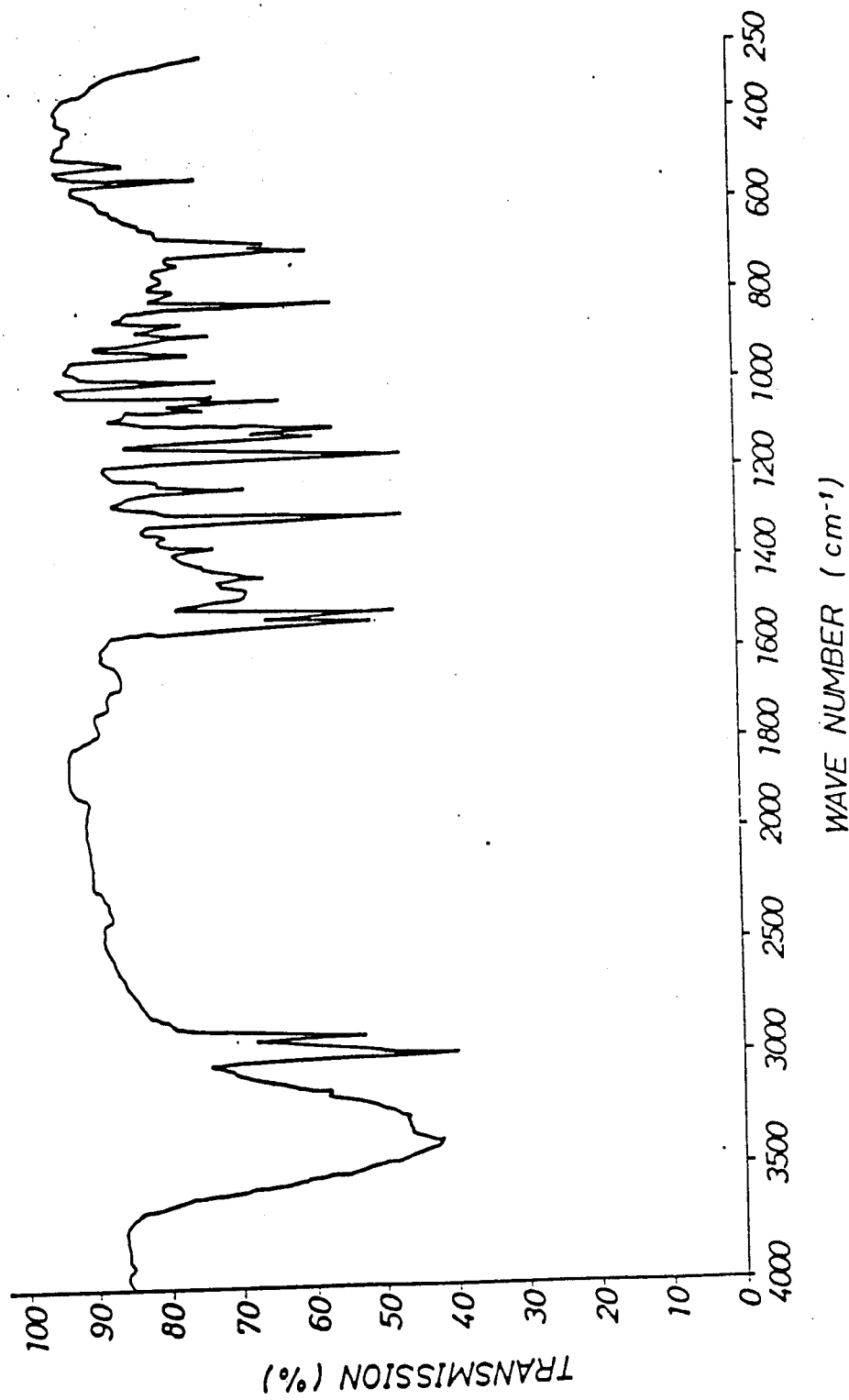
Figure 32:
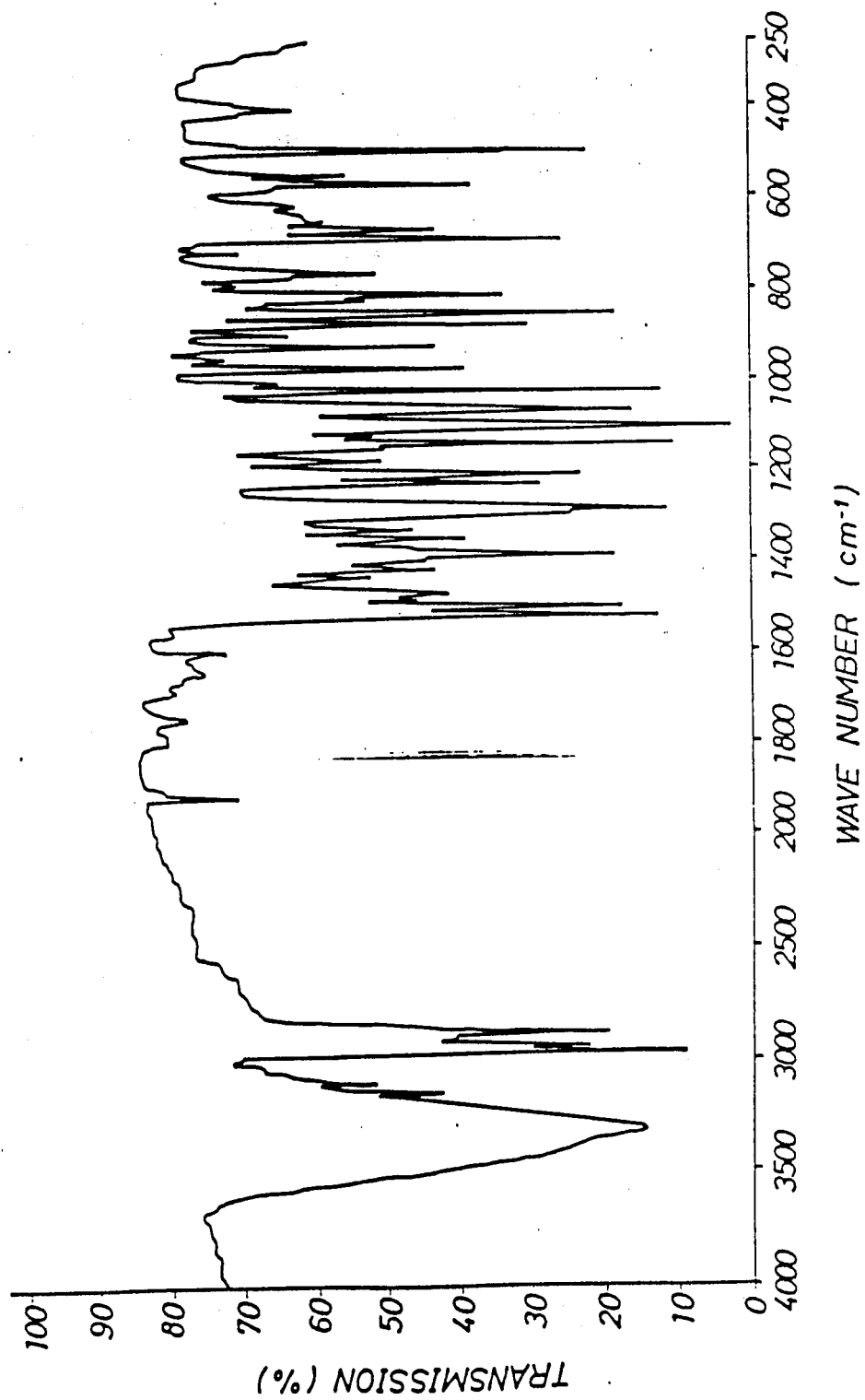
Figure 33:
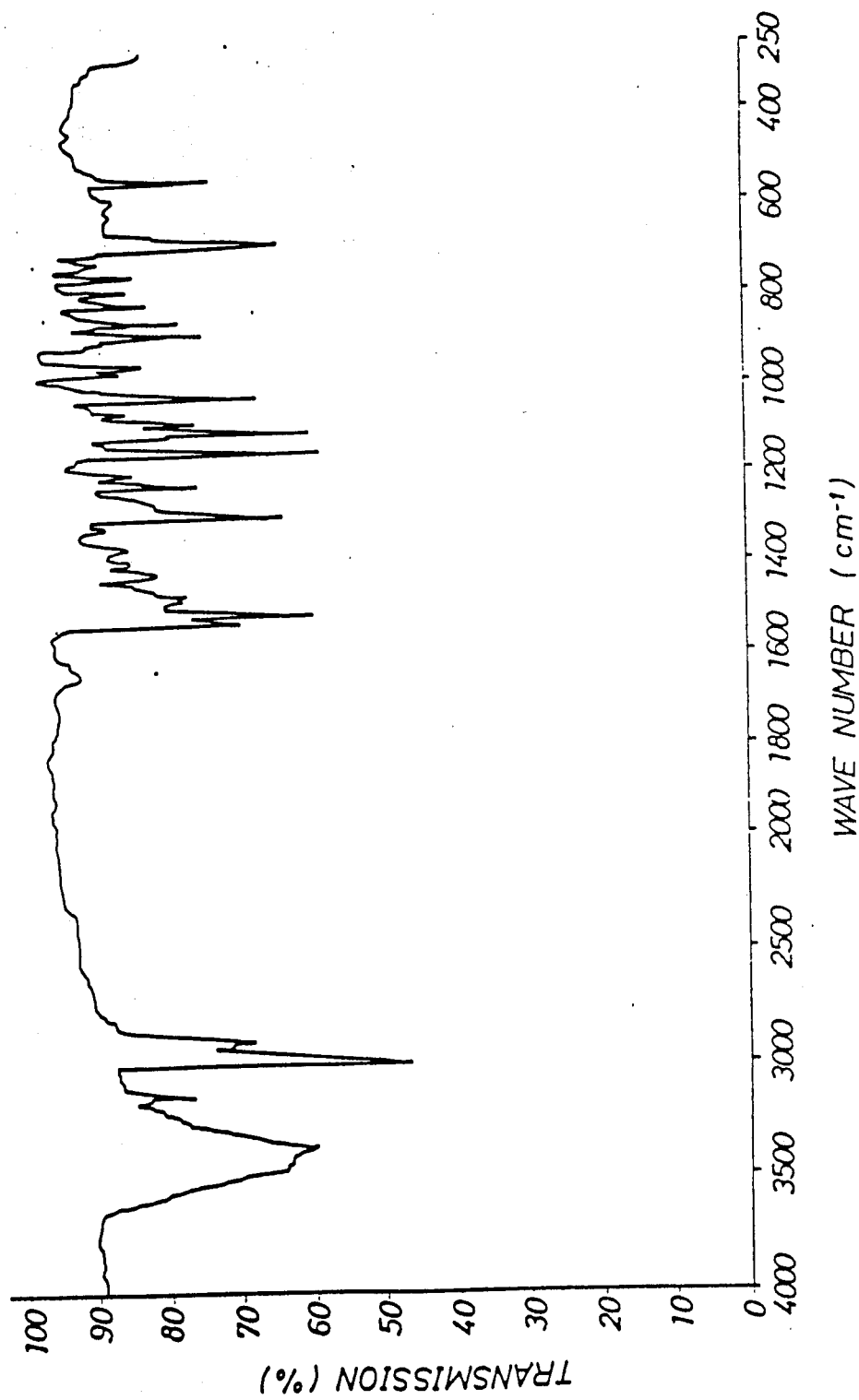
Figure 34:
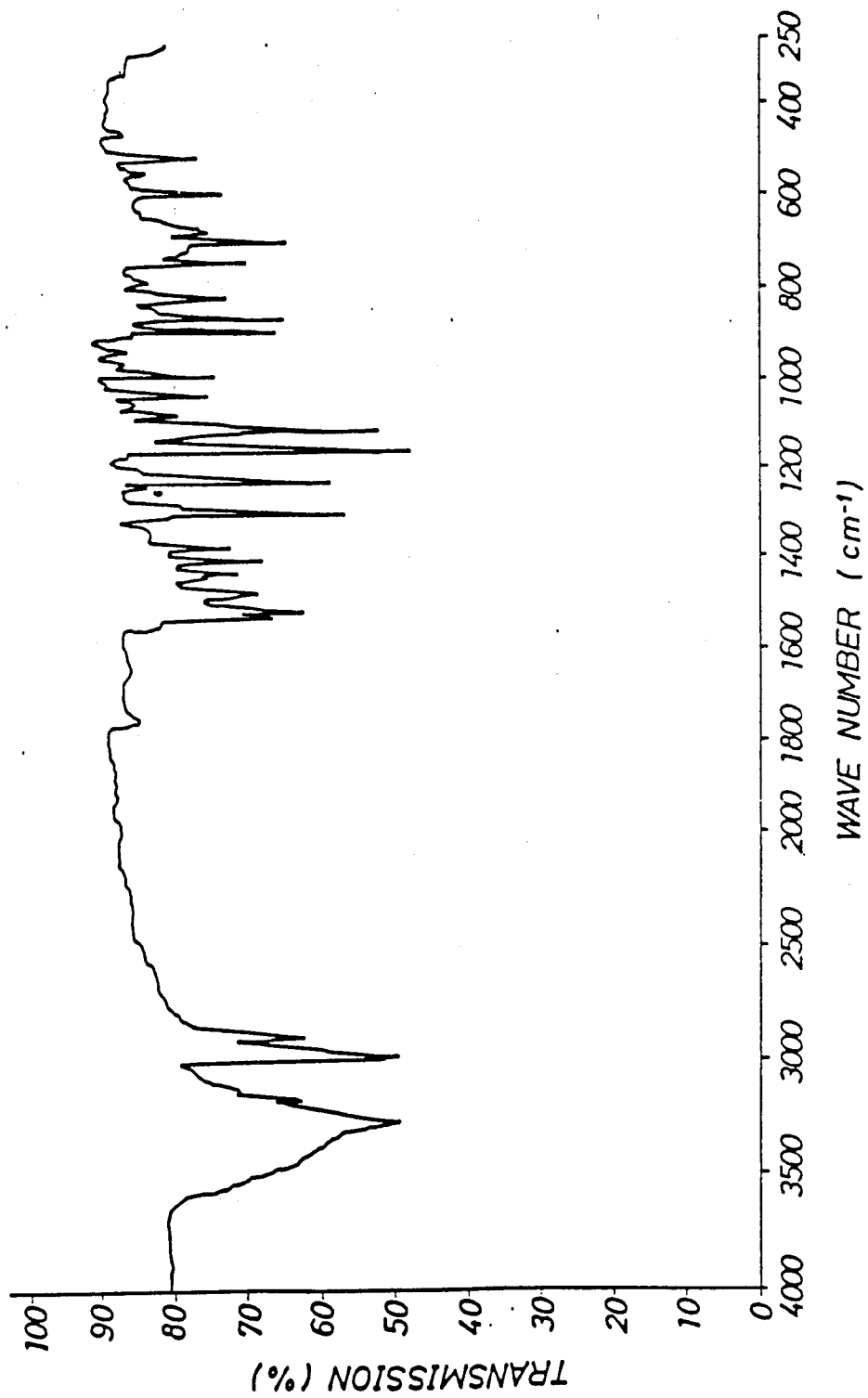
Figure 35:
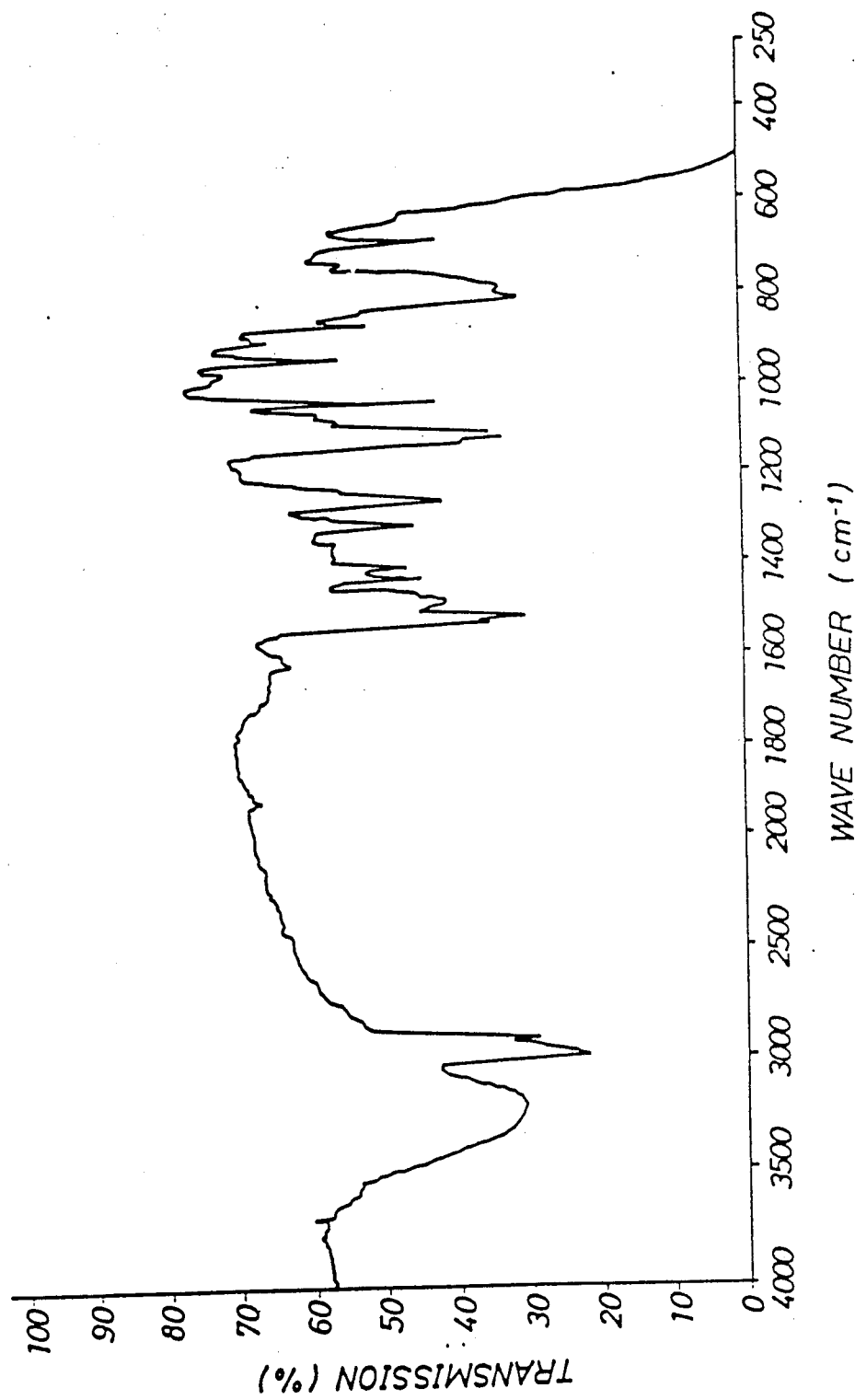
Figure 36:
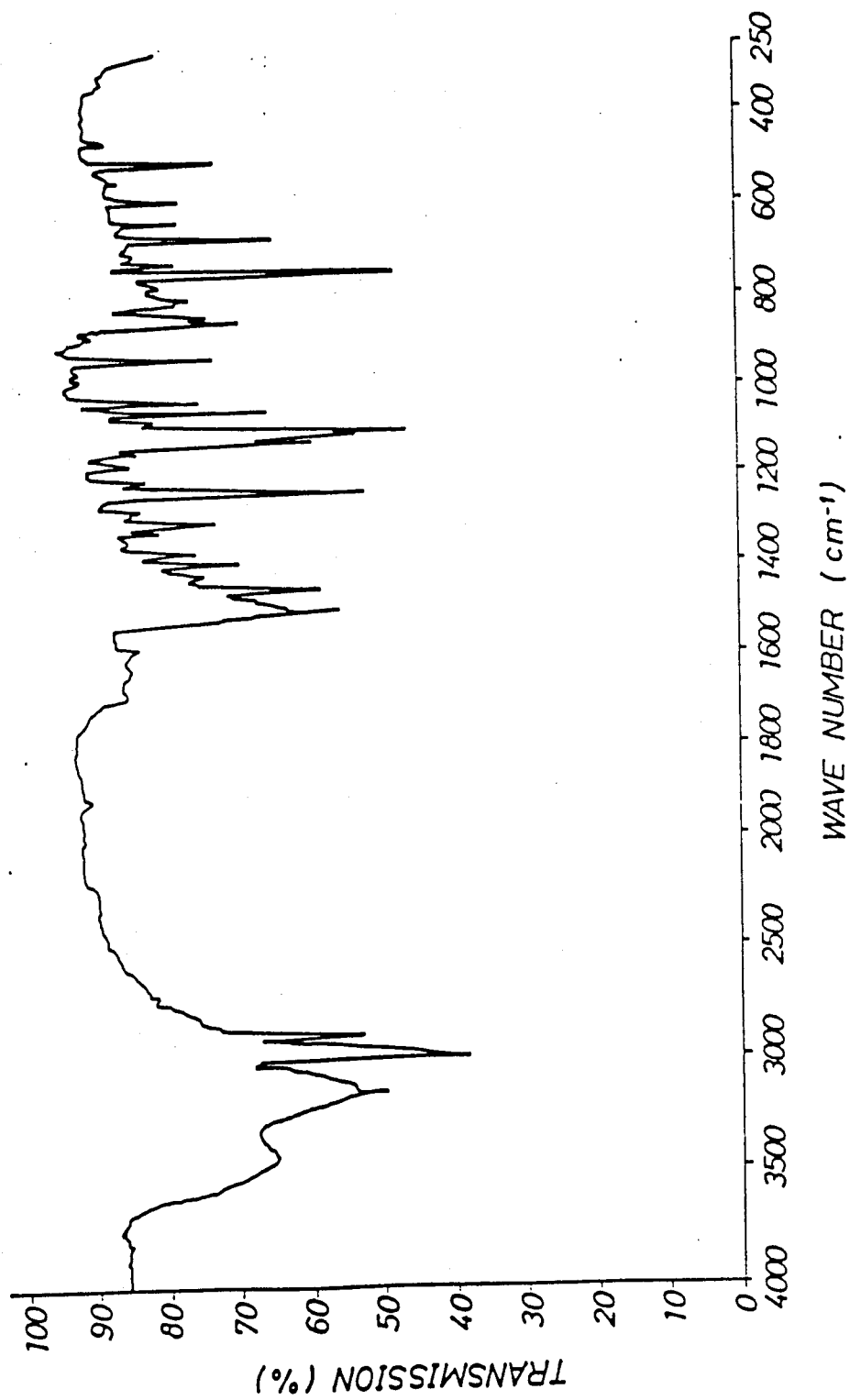
Figure 37:
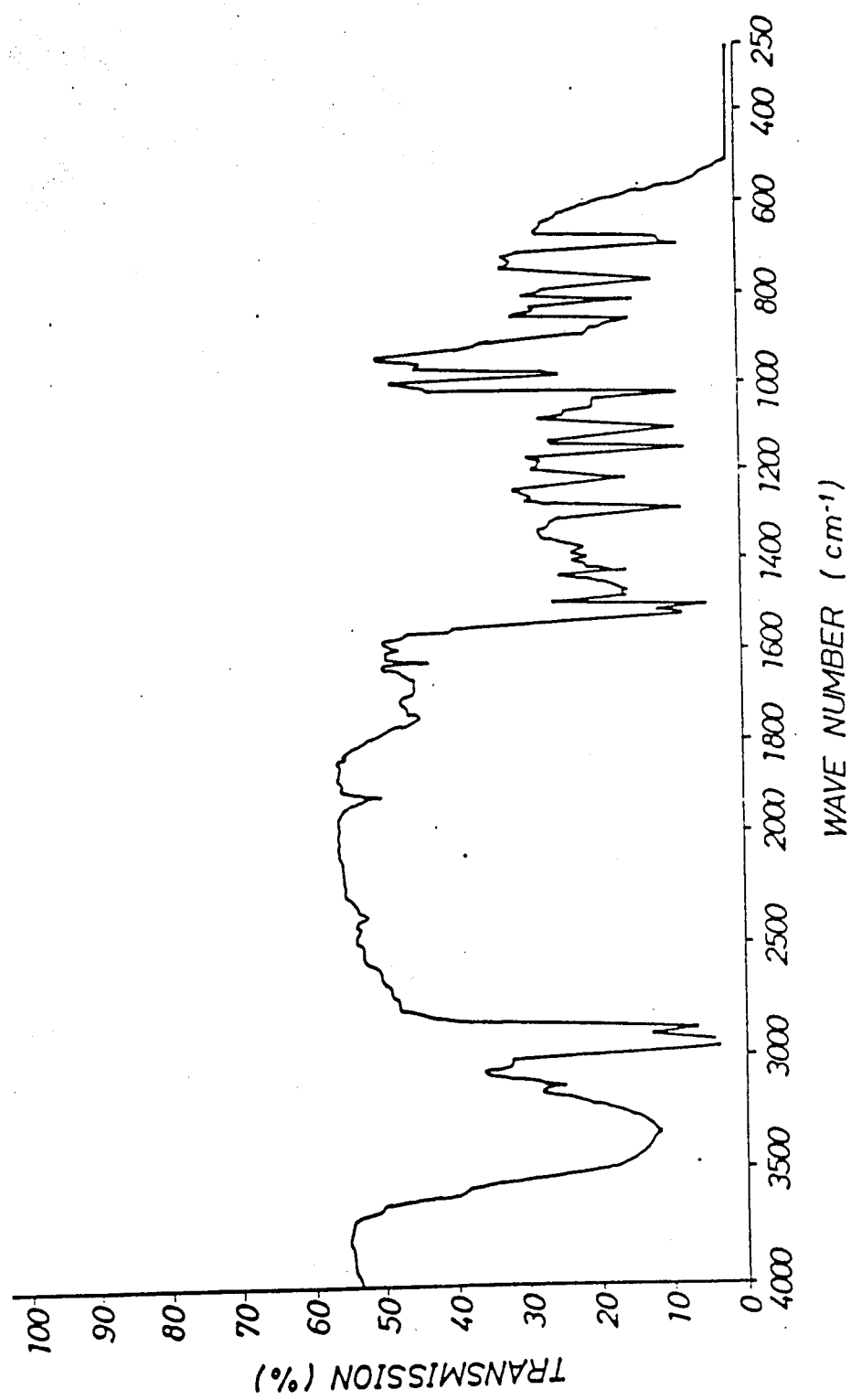
Figure 38:
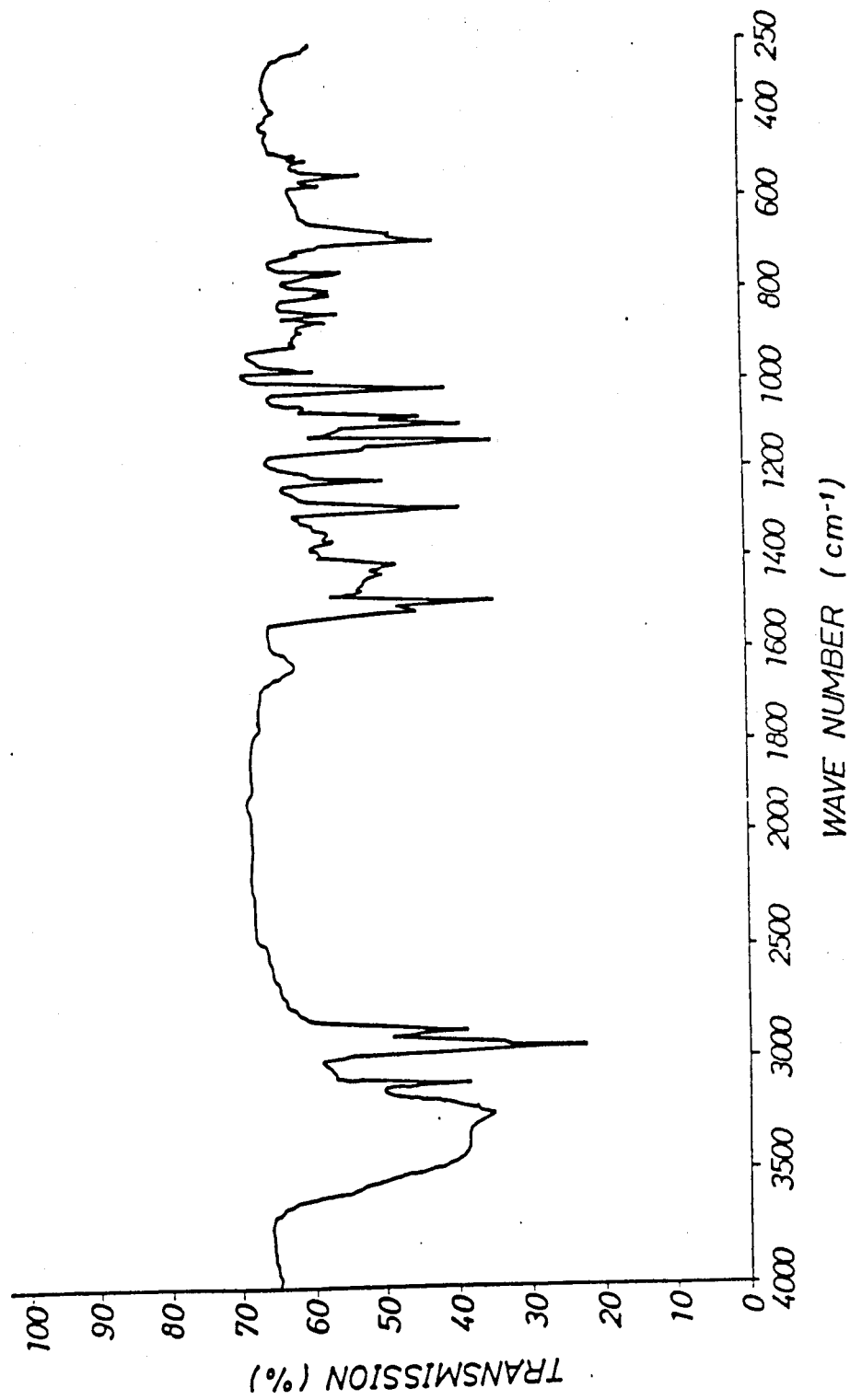
Figure 39:
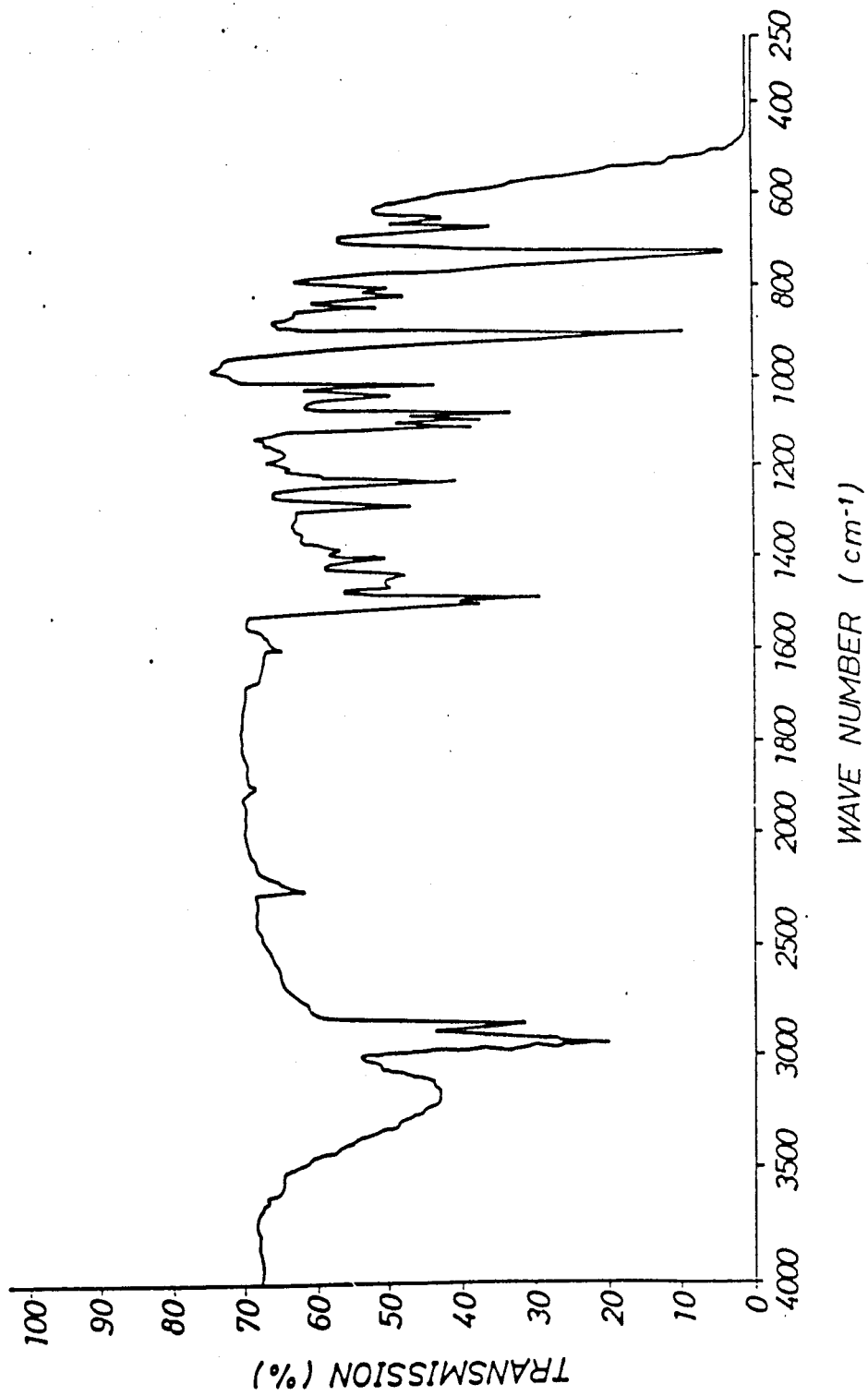
Figure 40:
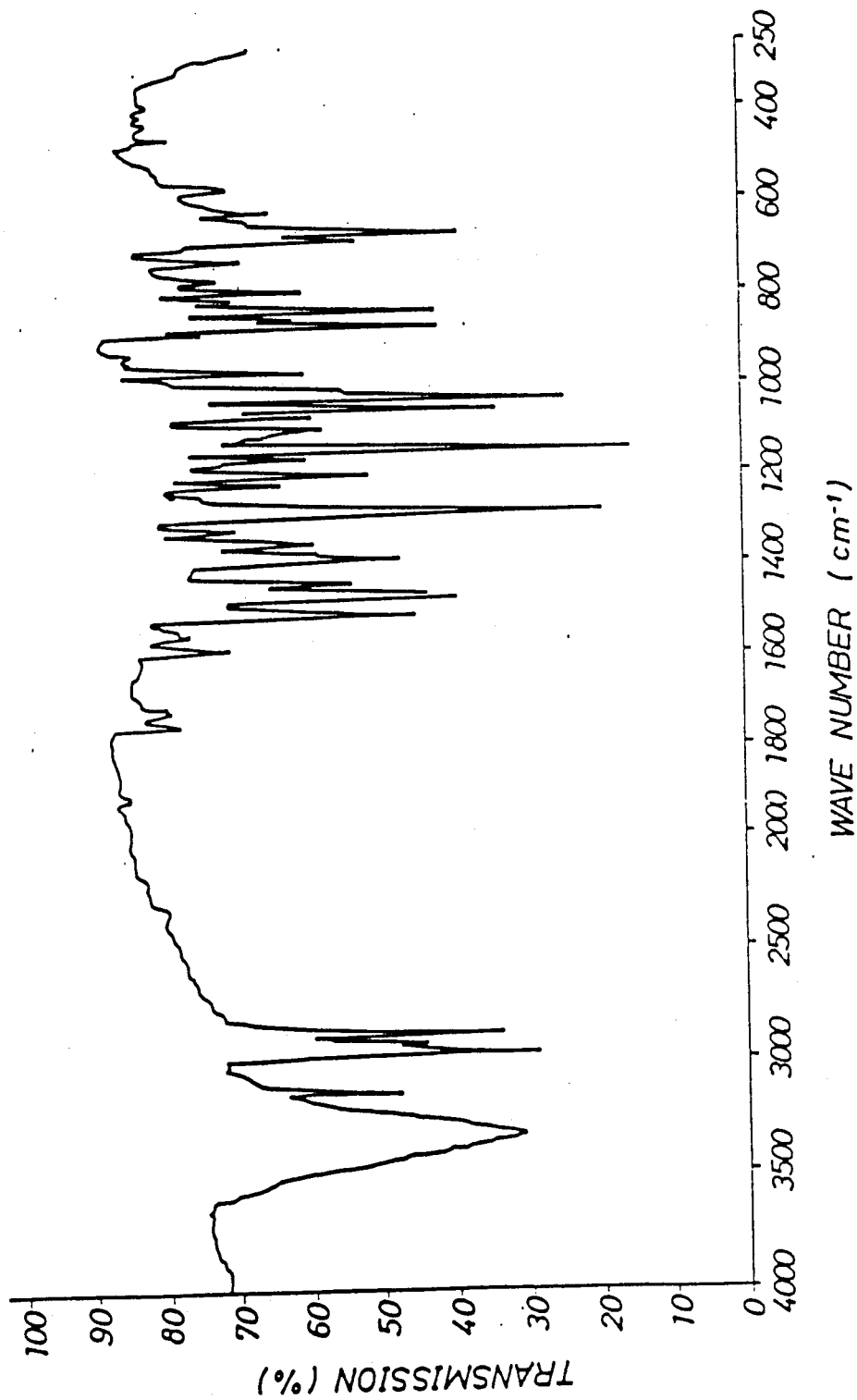
Figure 41:
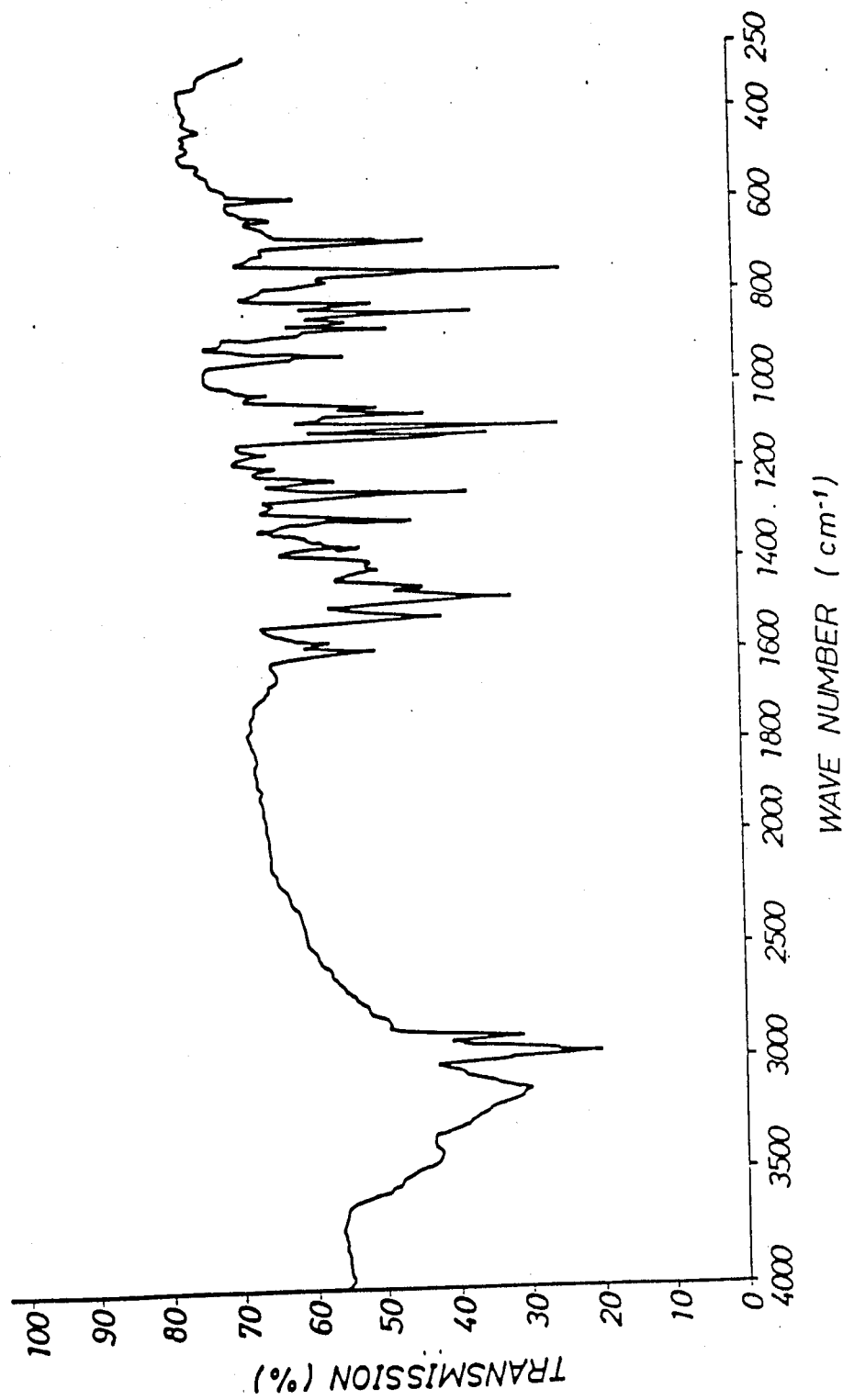
Figure 42:
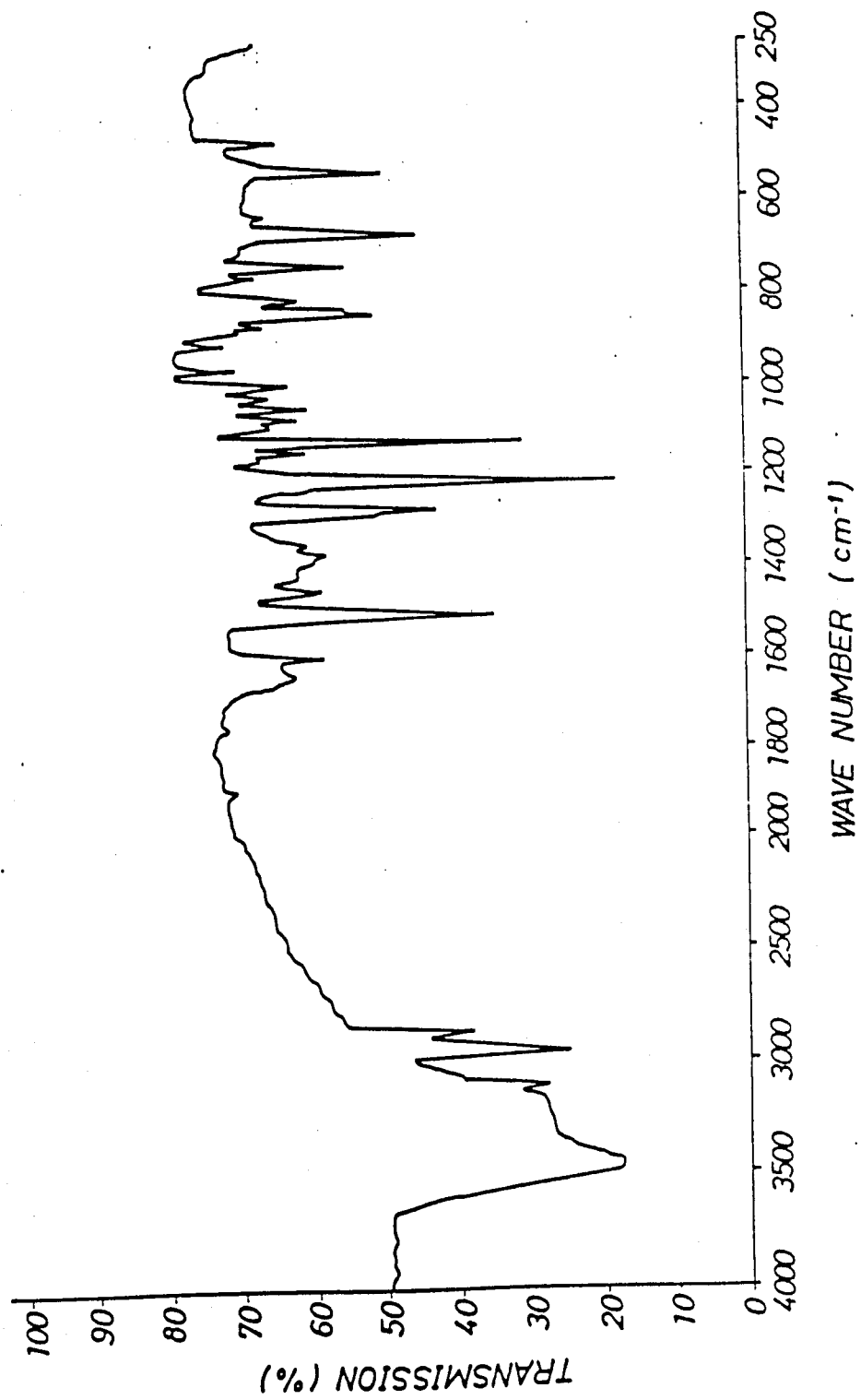
Figure 43:
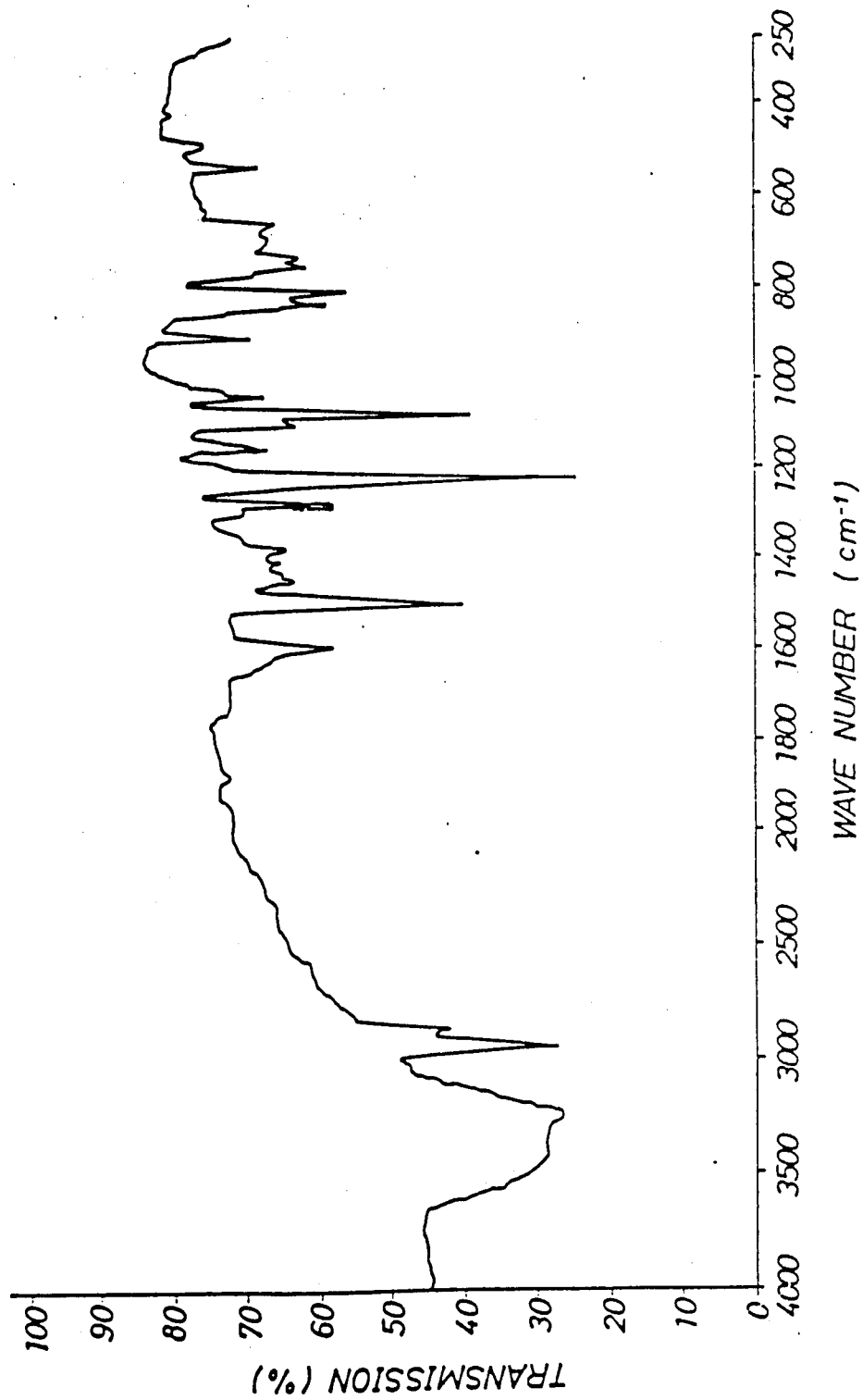
Figure 44:
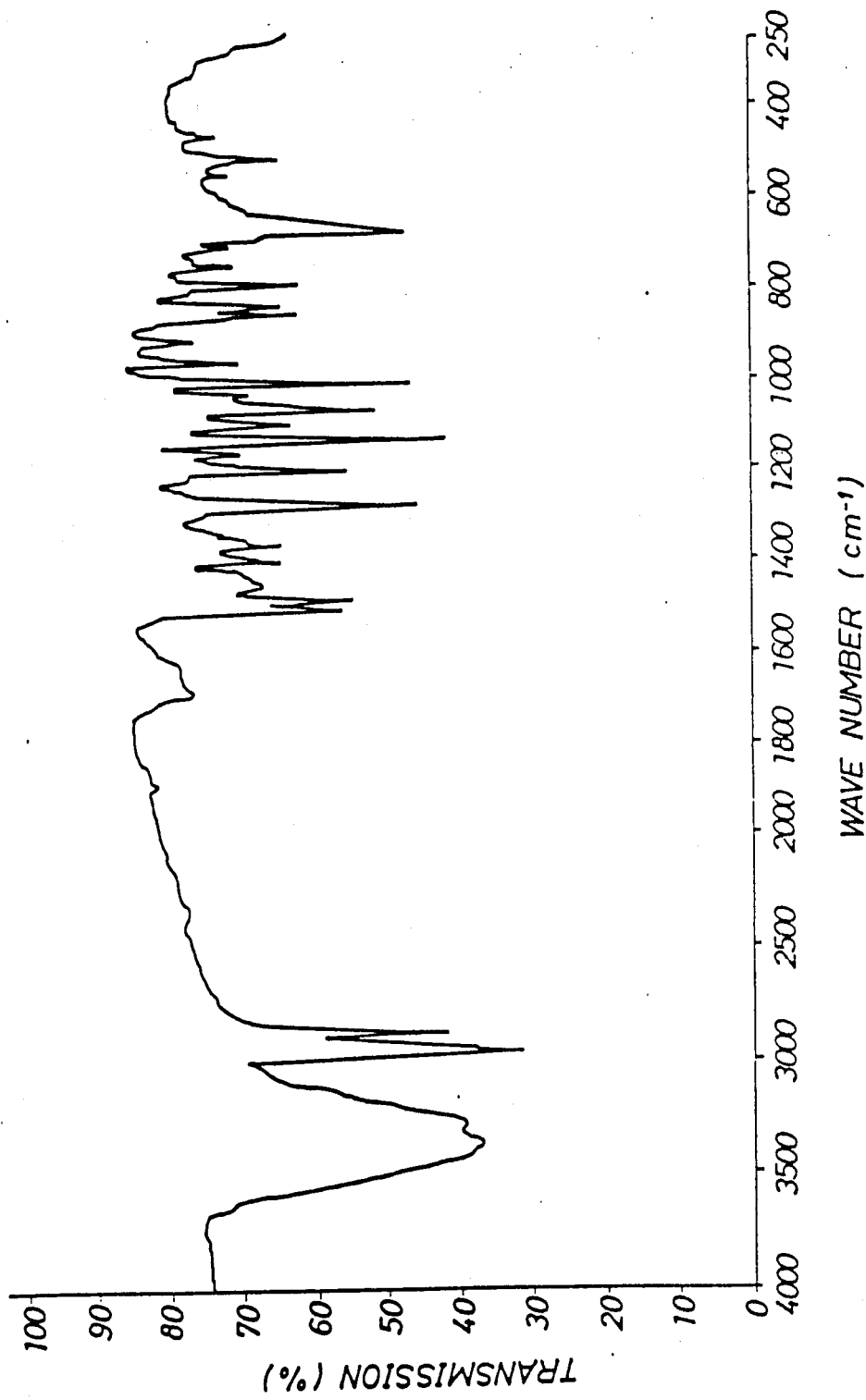
Figure 45:
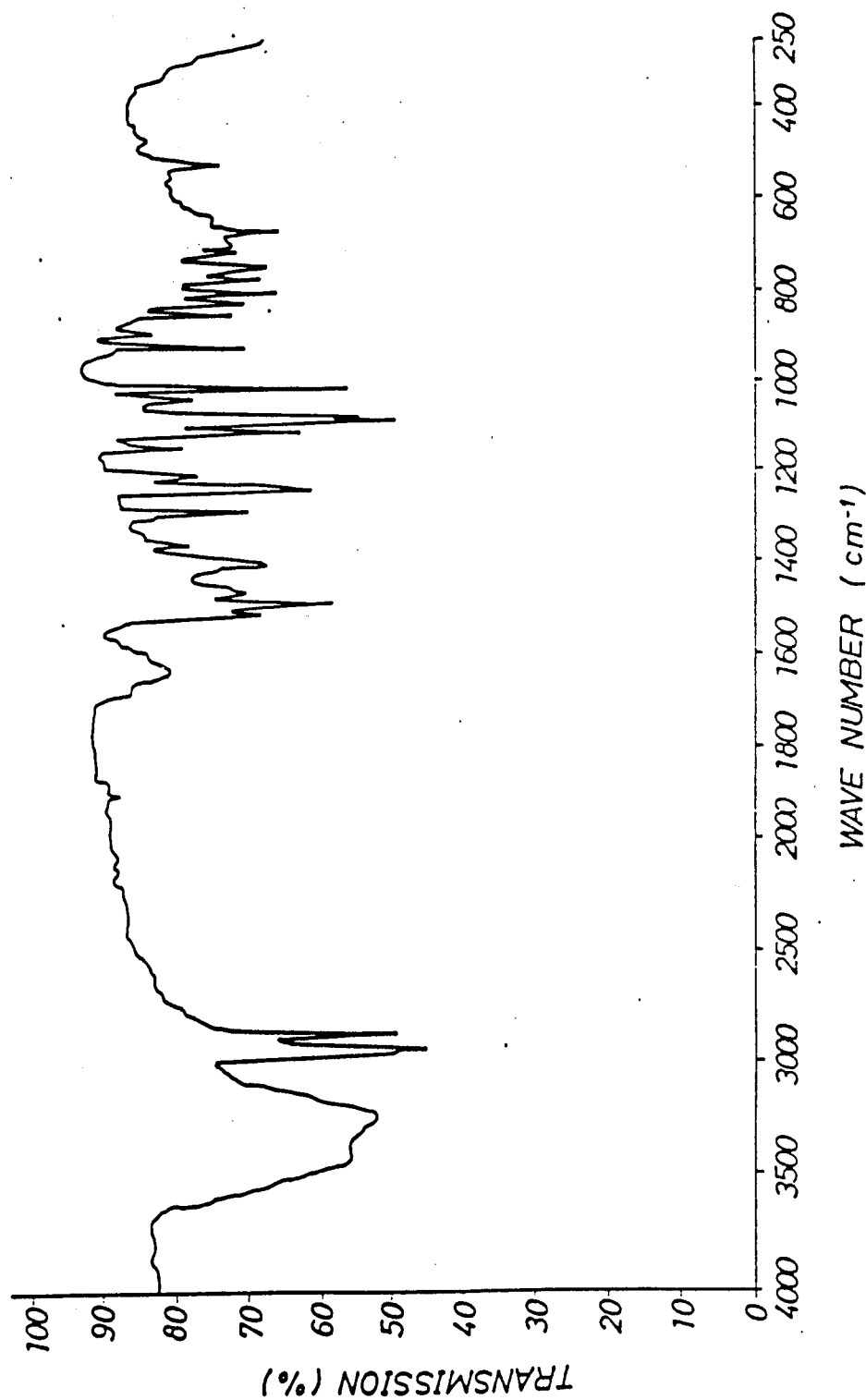
Figure 46:
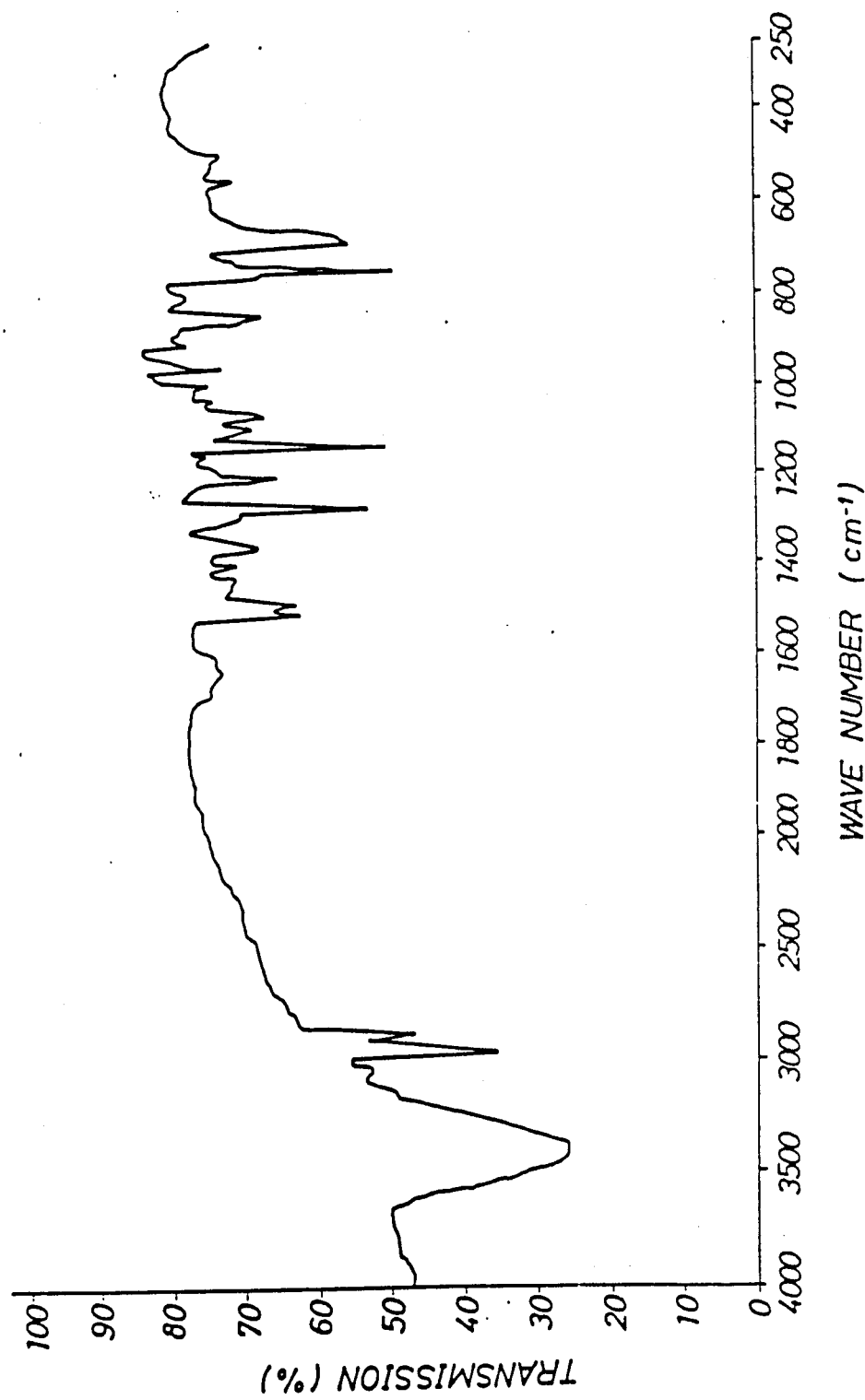
Figure 47:
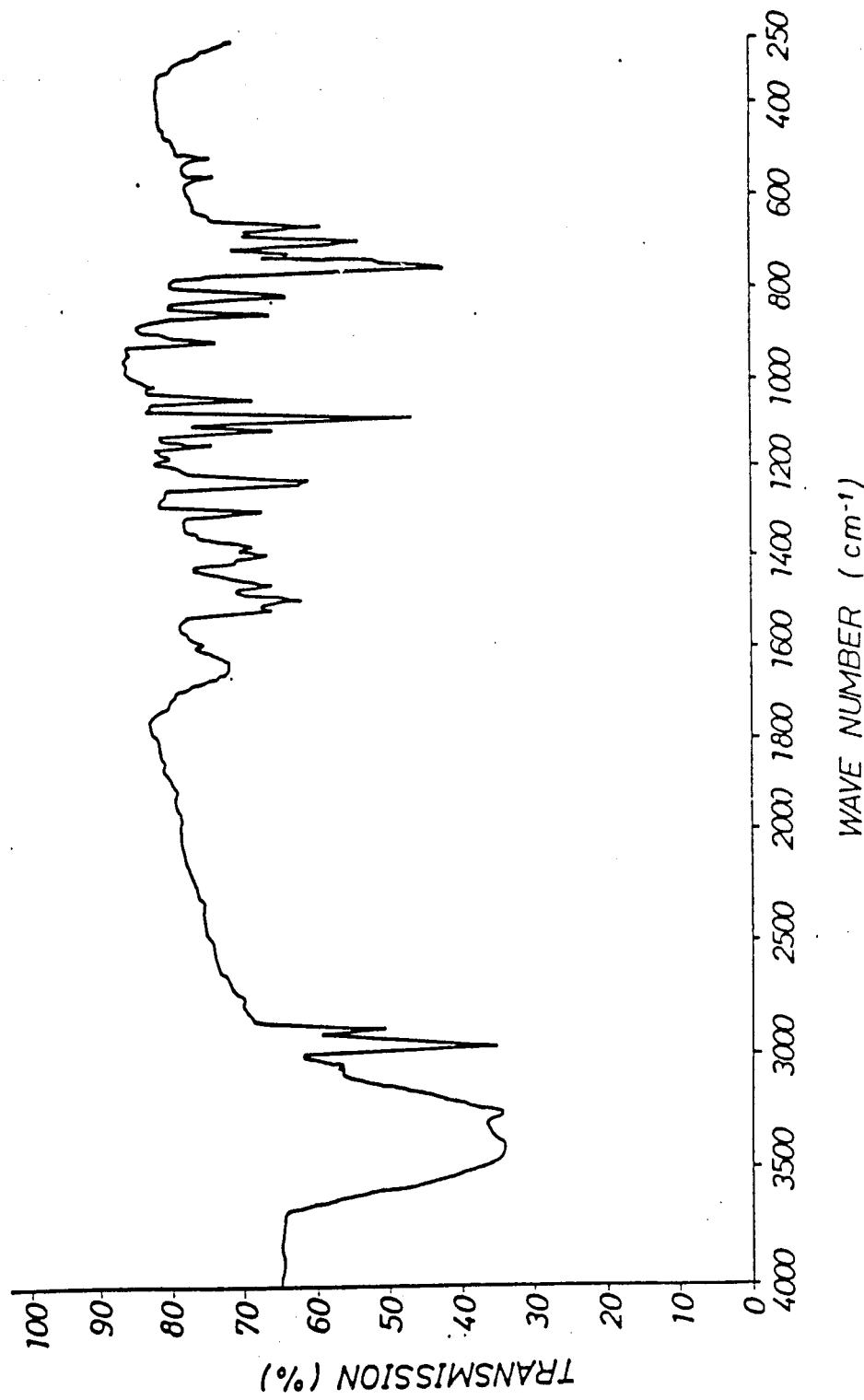
Figure 48:
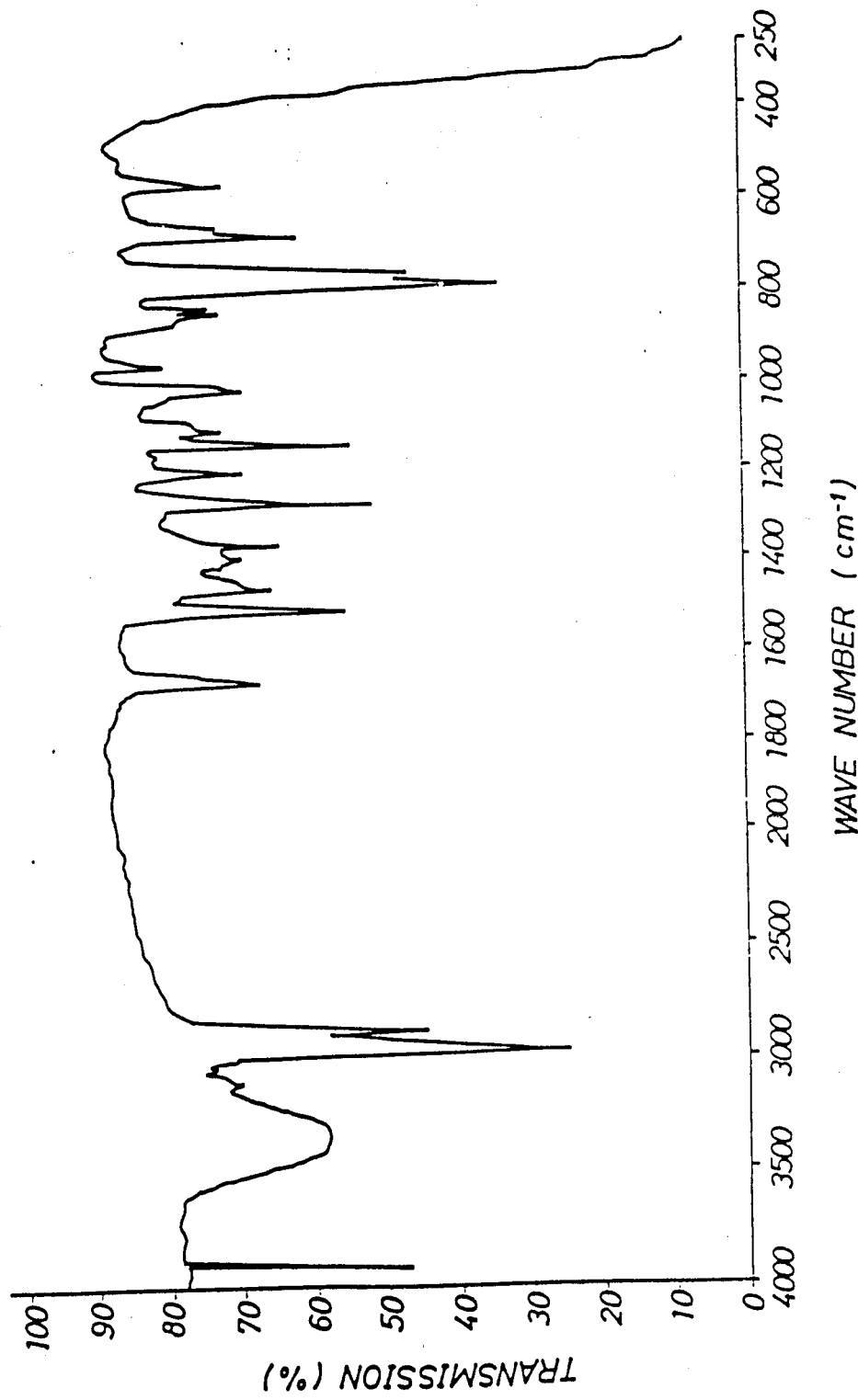
Figure 49:
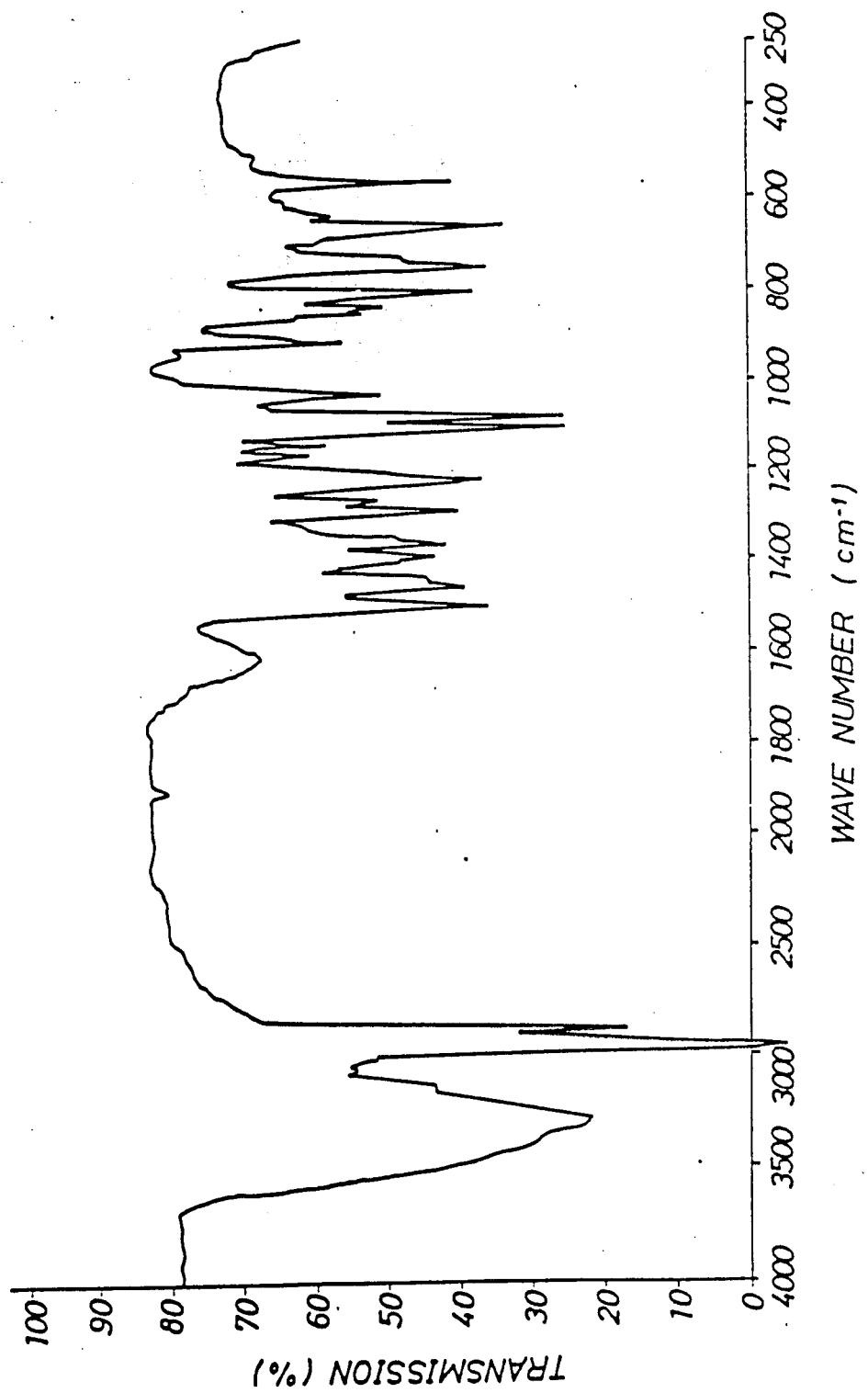
Figure 50:
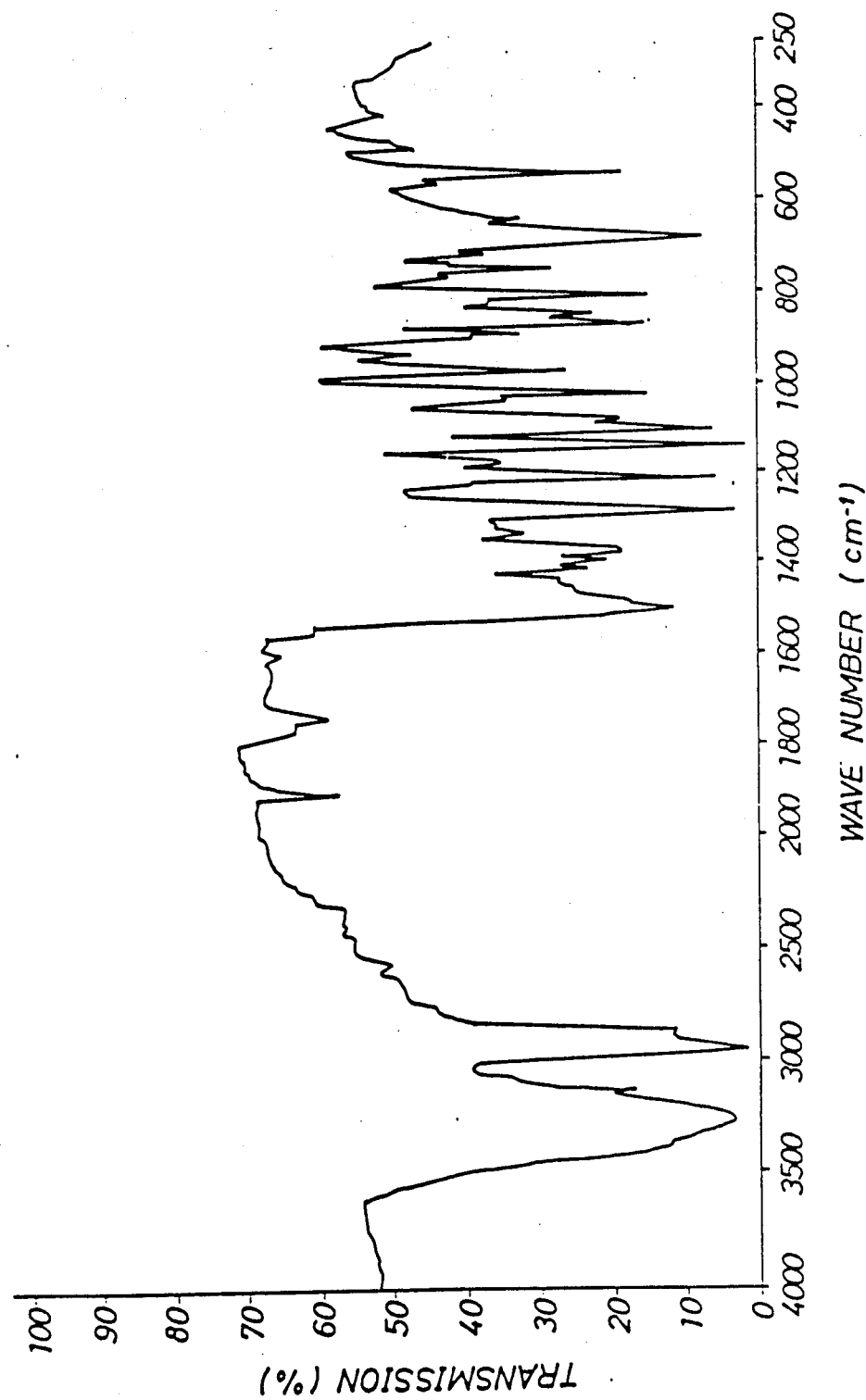
Figure 51:
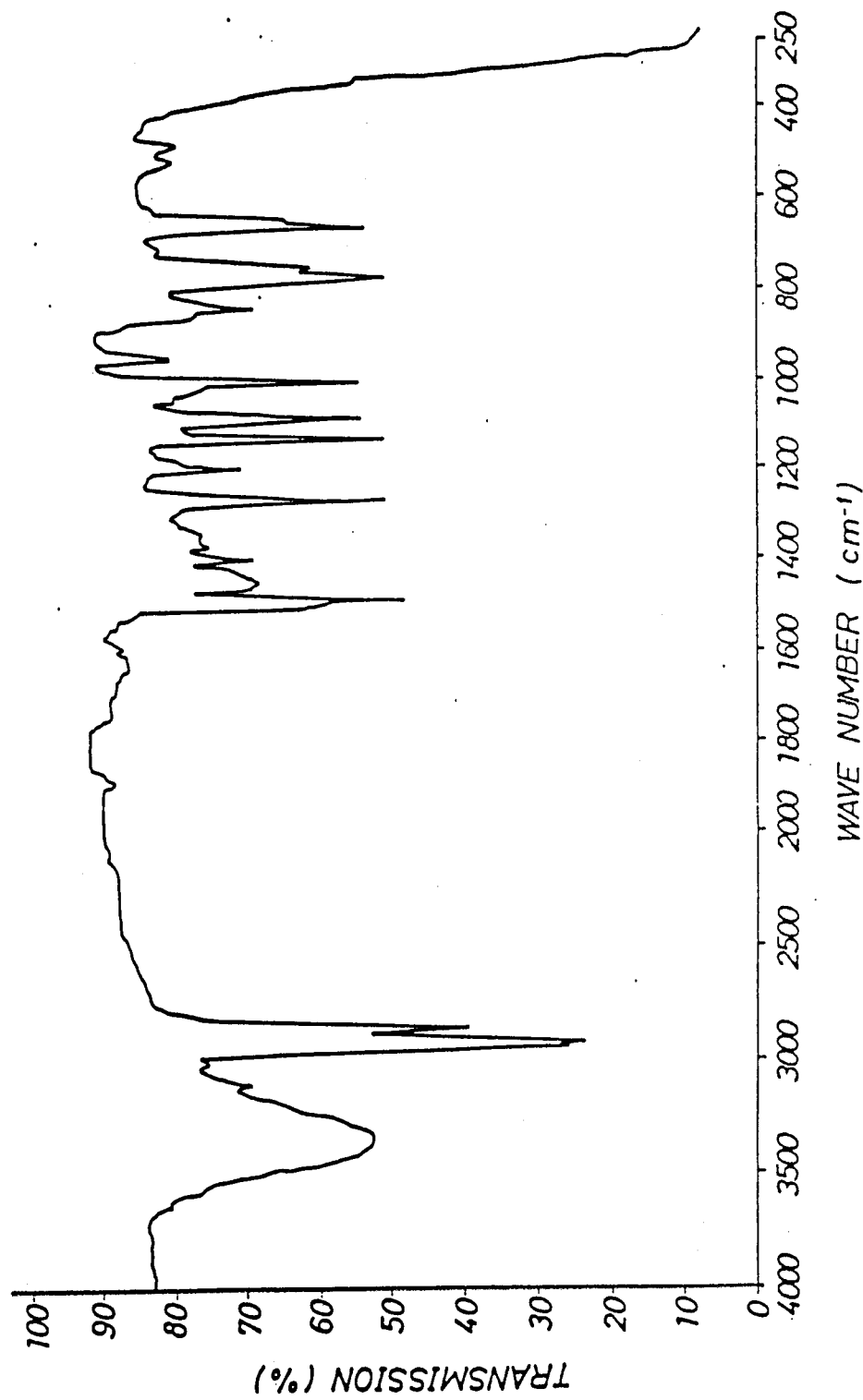
Figure 52:
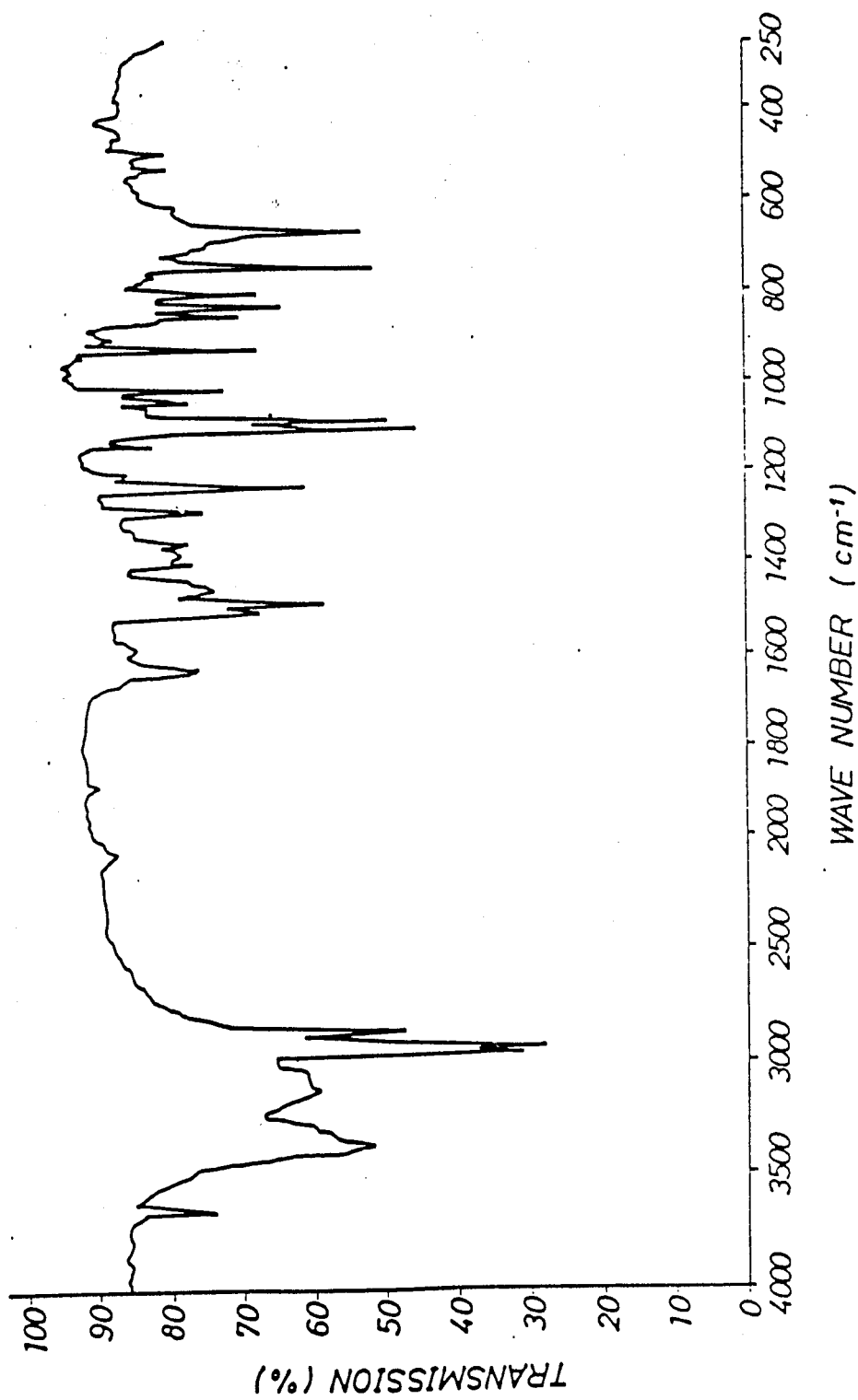
Figure 53:
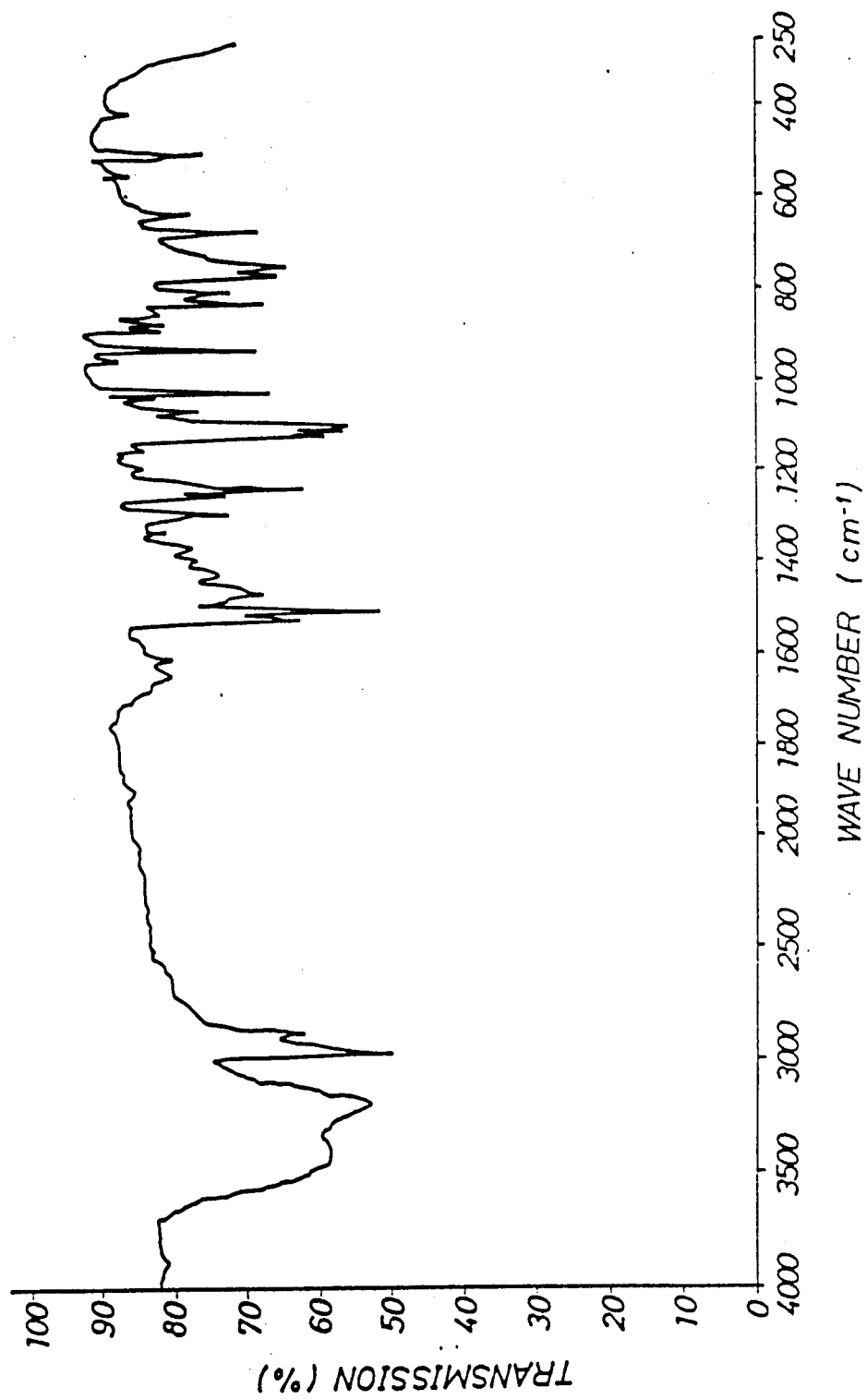
Figure 54:
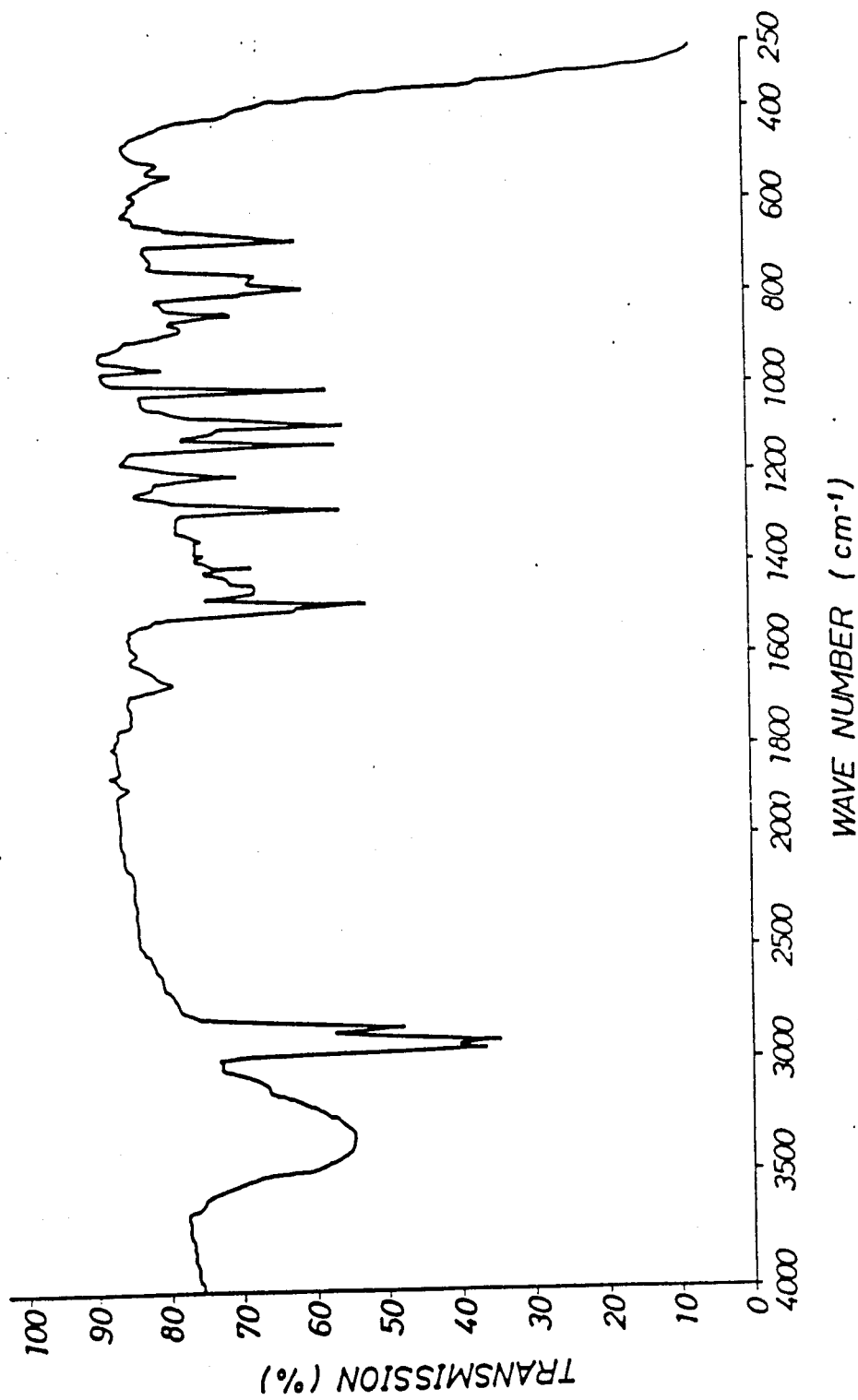
Figure 55:
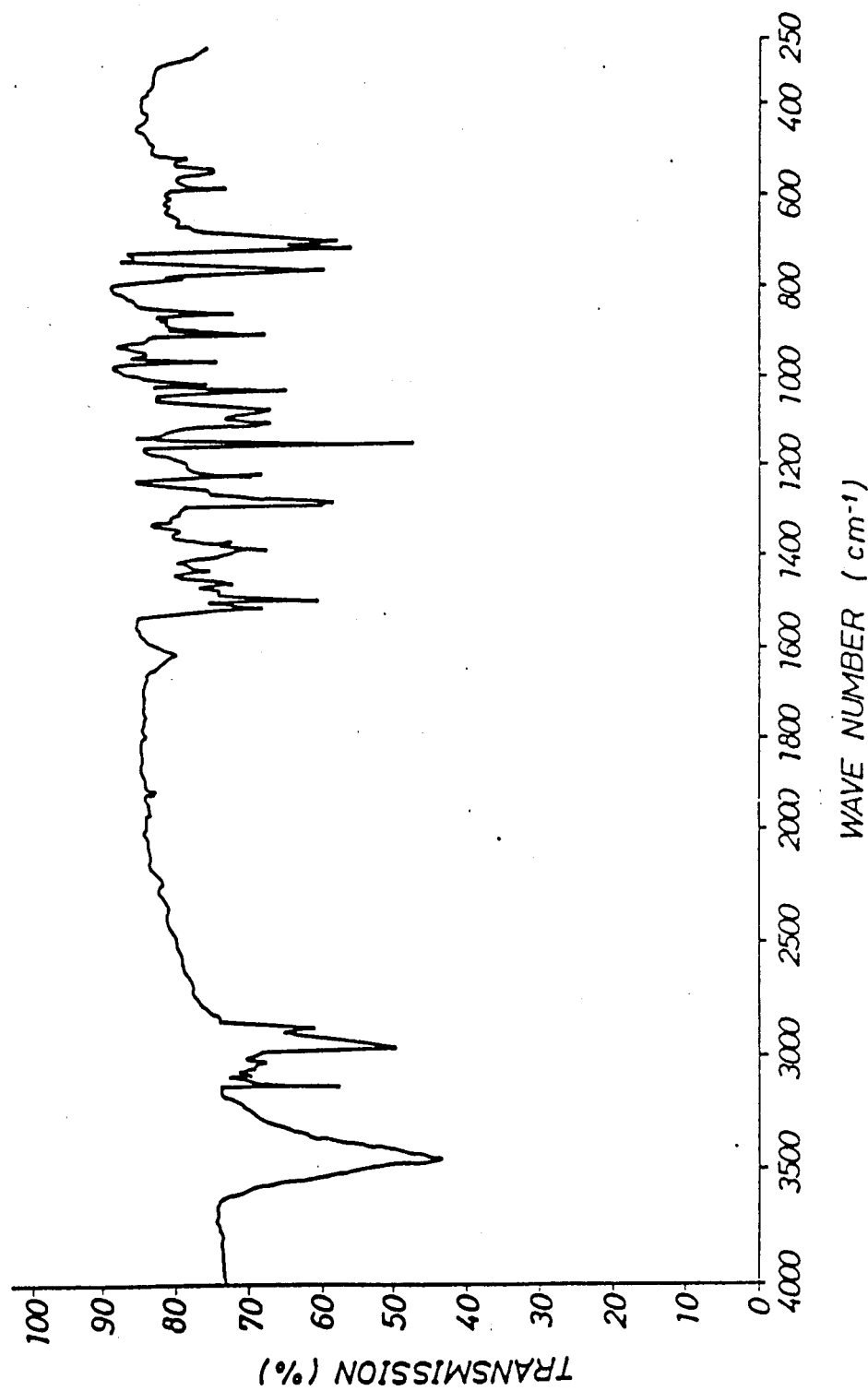
Figure 56:
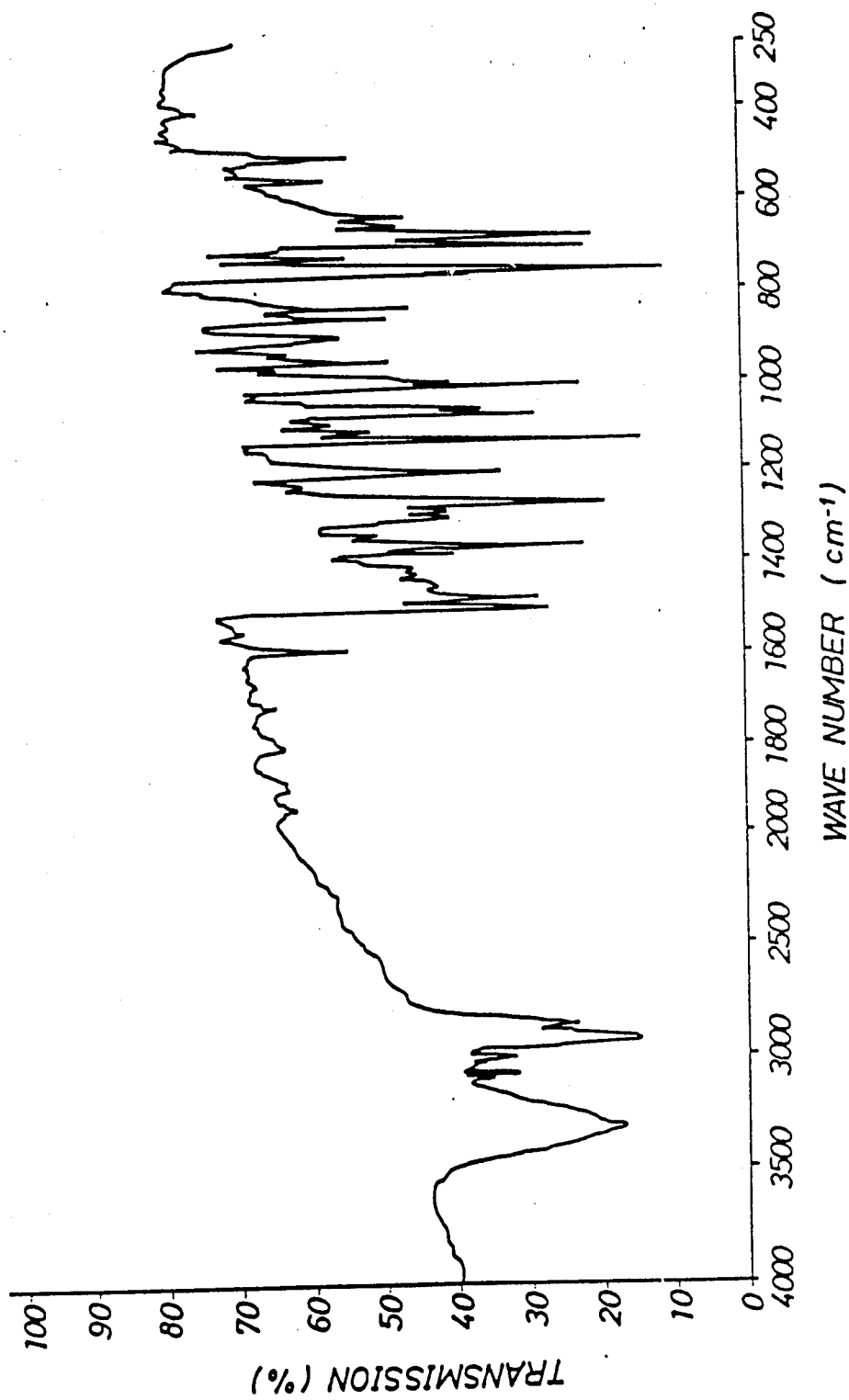
Figure 57:
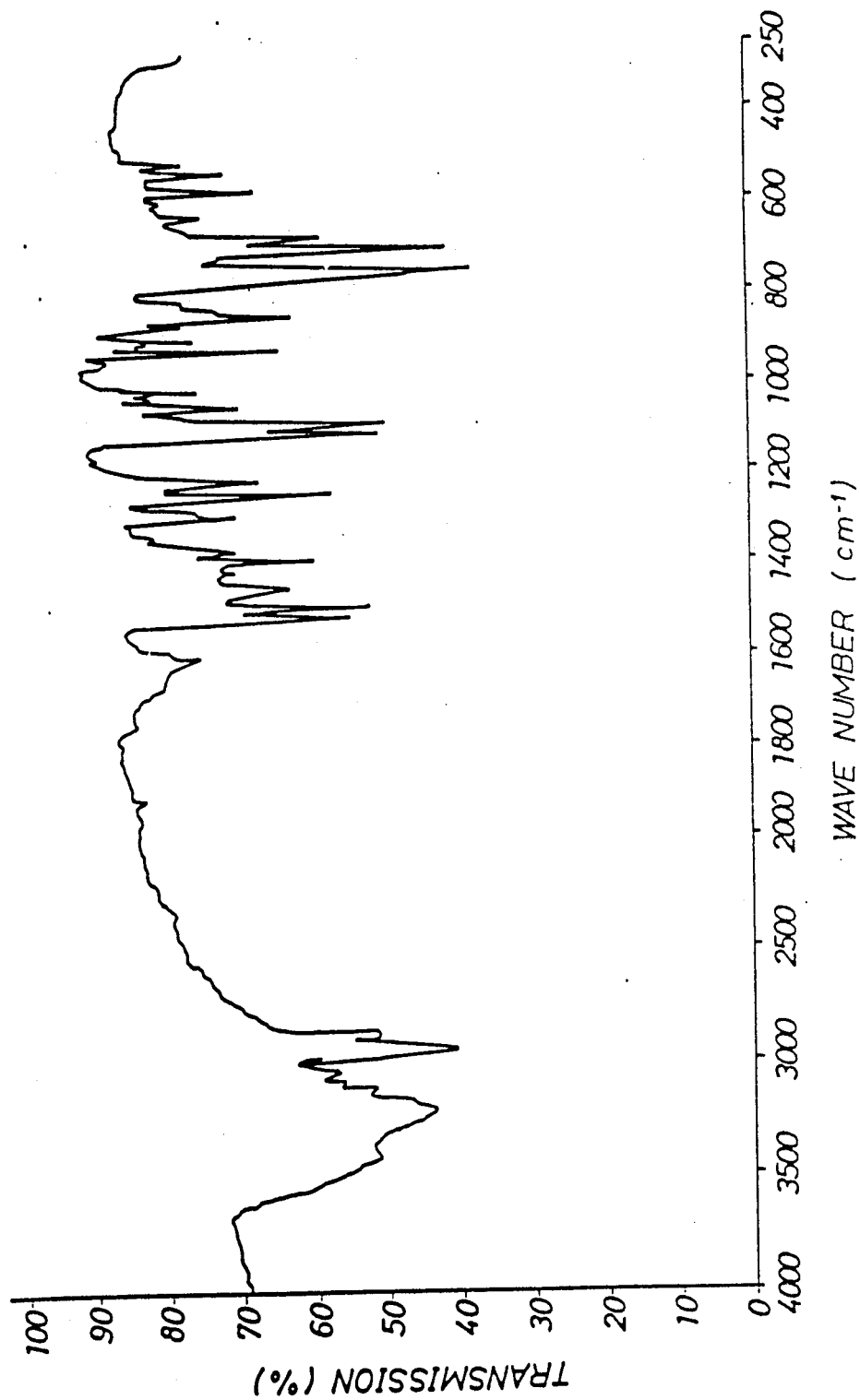
Figure 58:
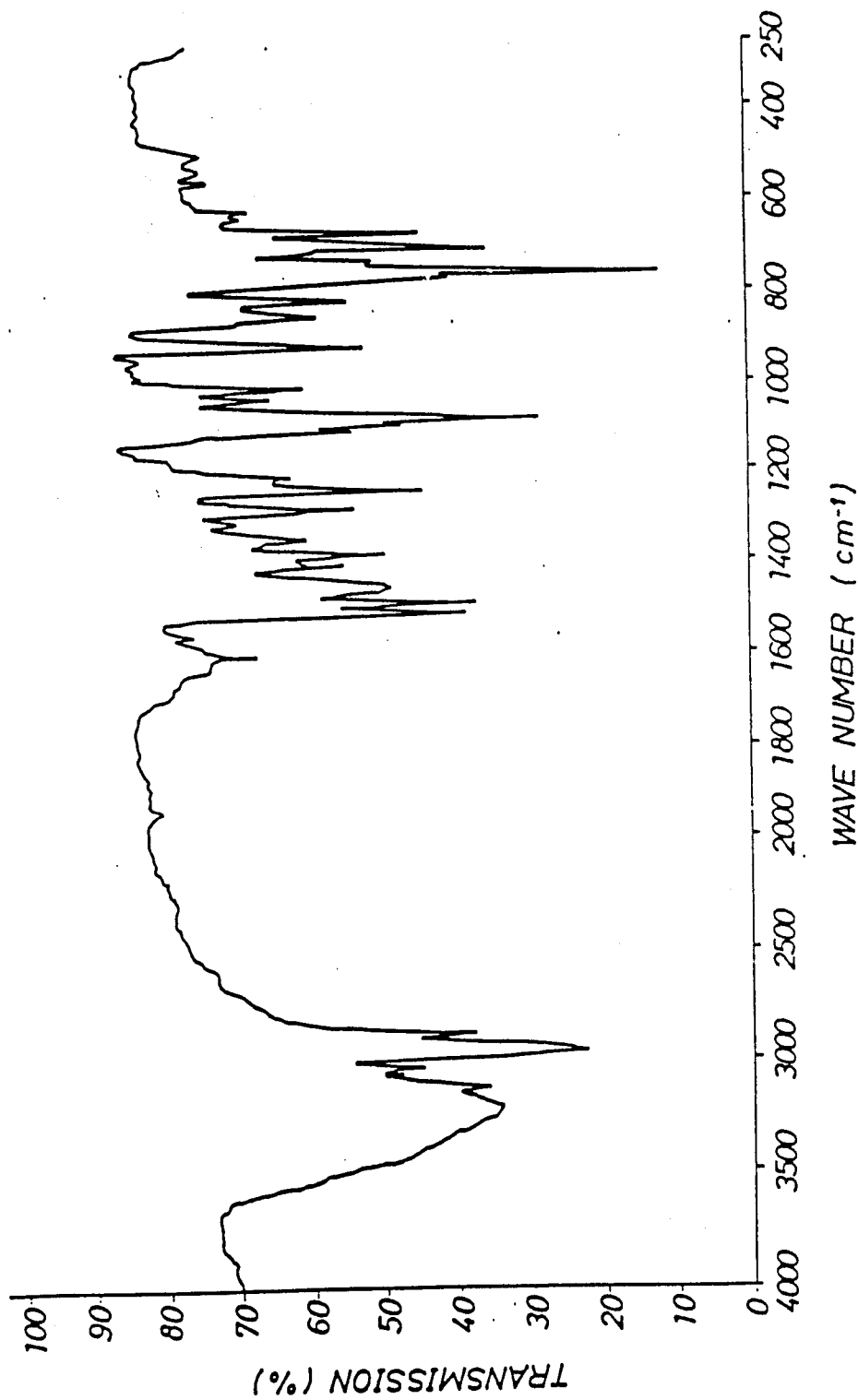
Figure 59:
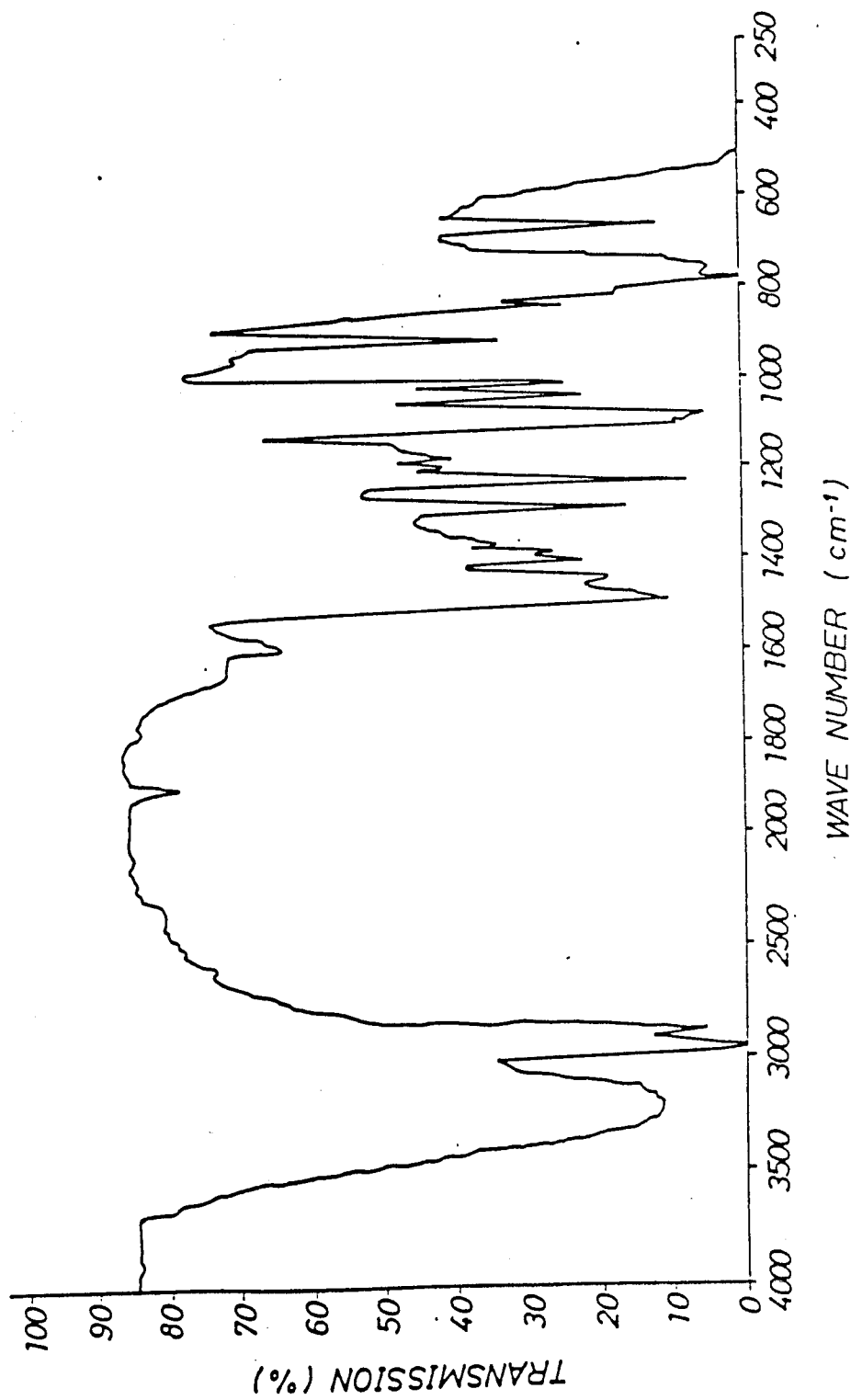
Figure 60:
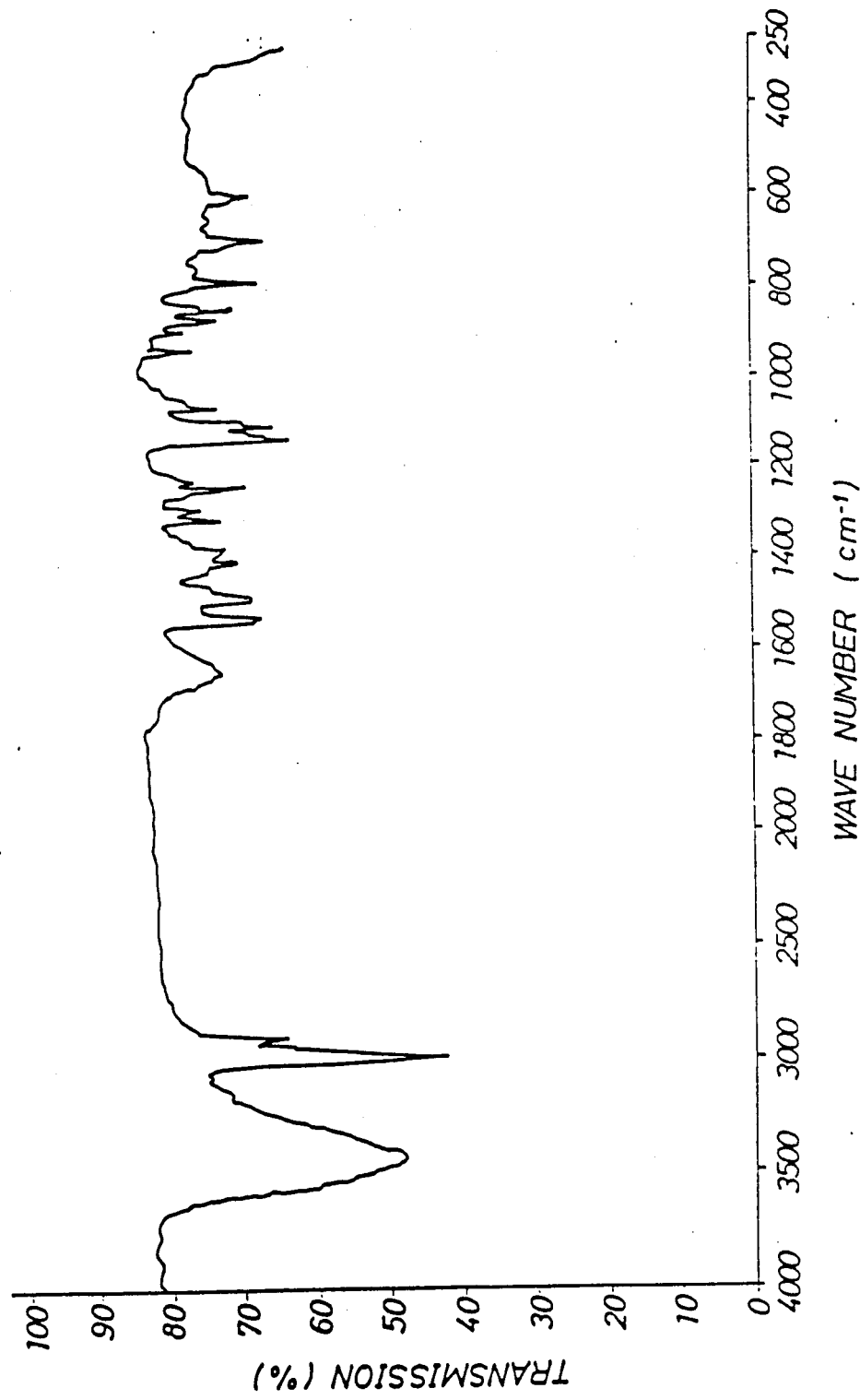
Figure 61:
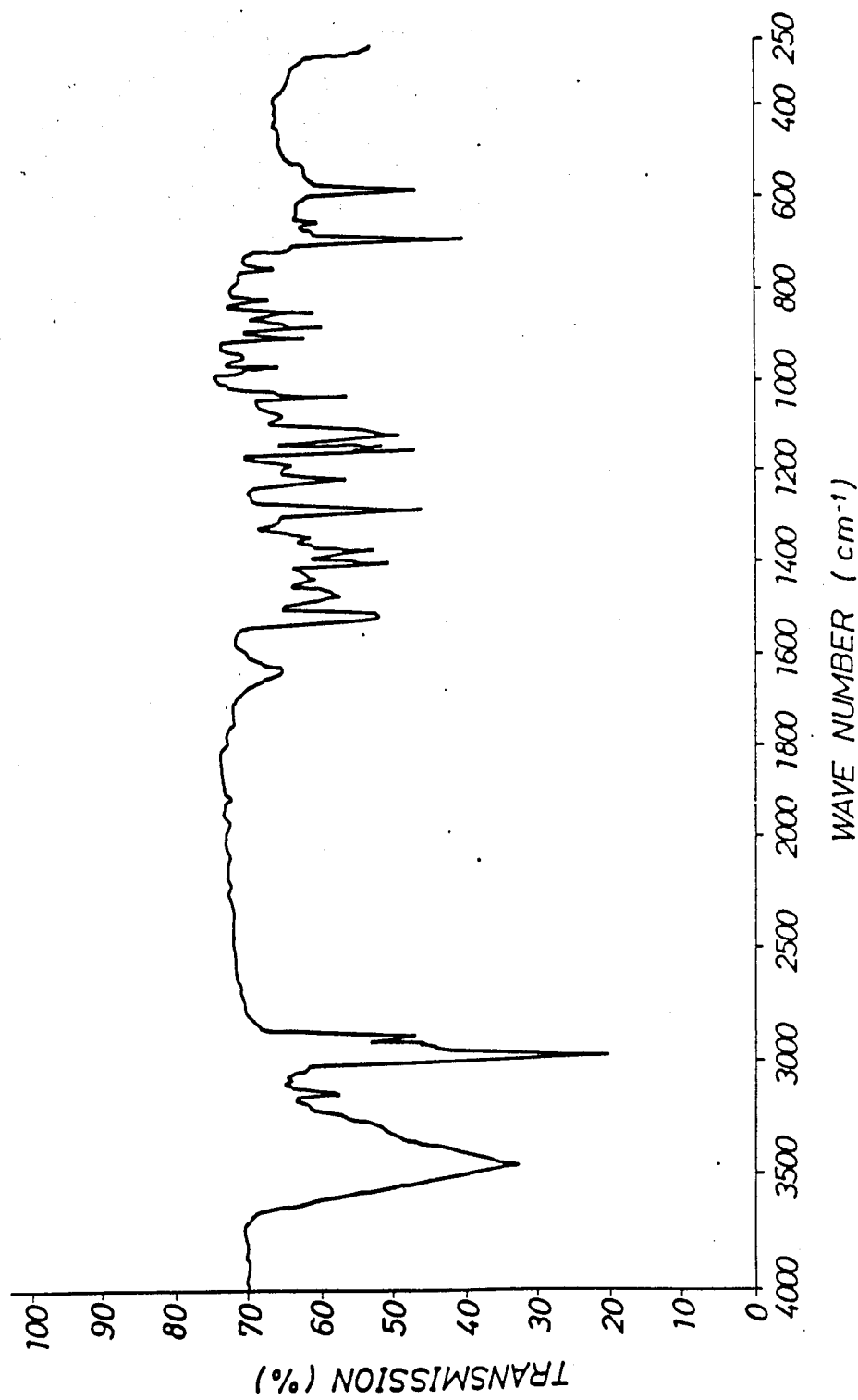
Figure 62:
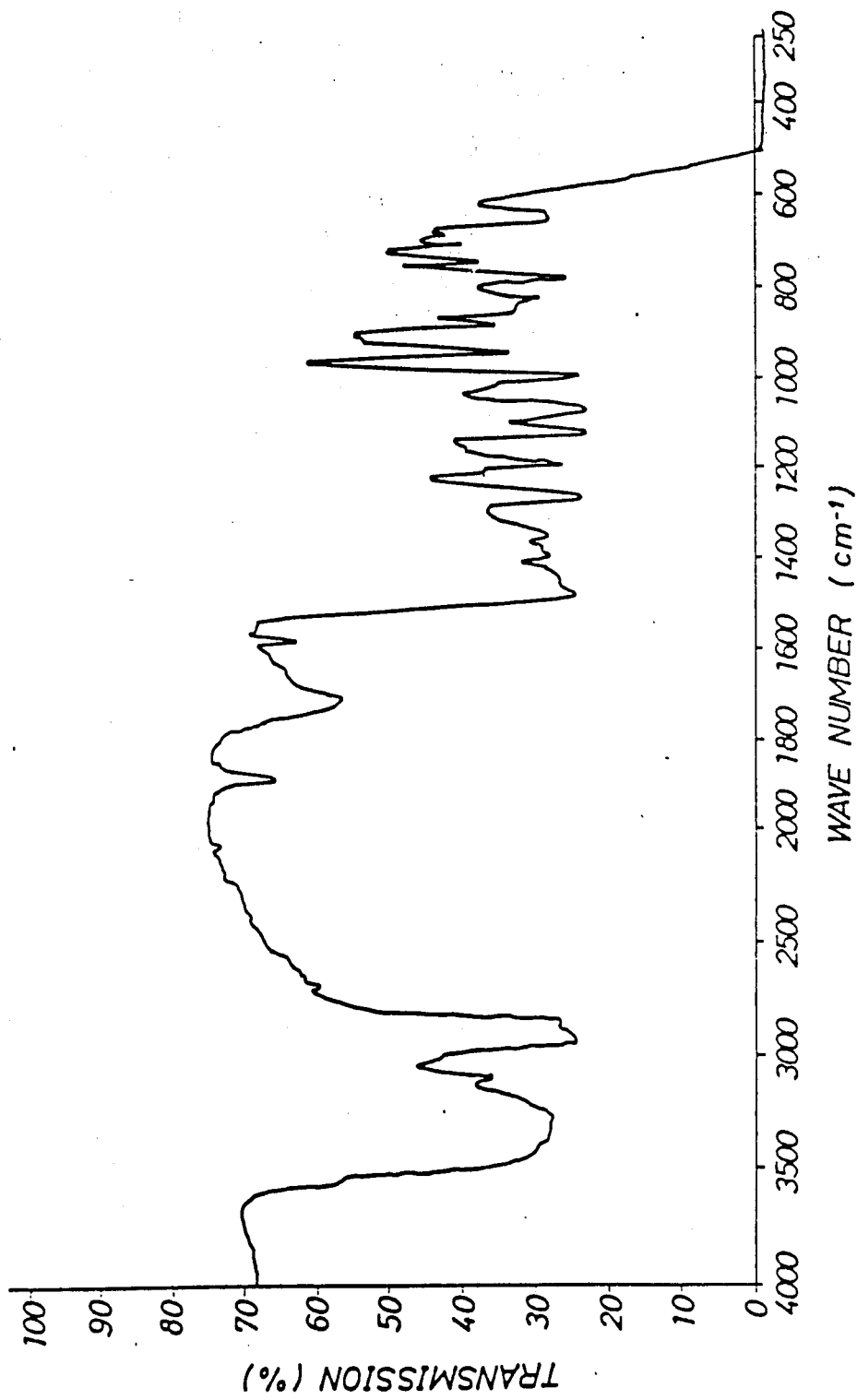
Figure 63:
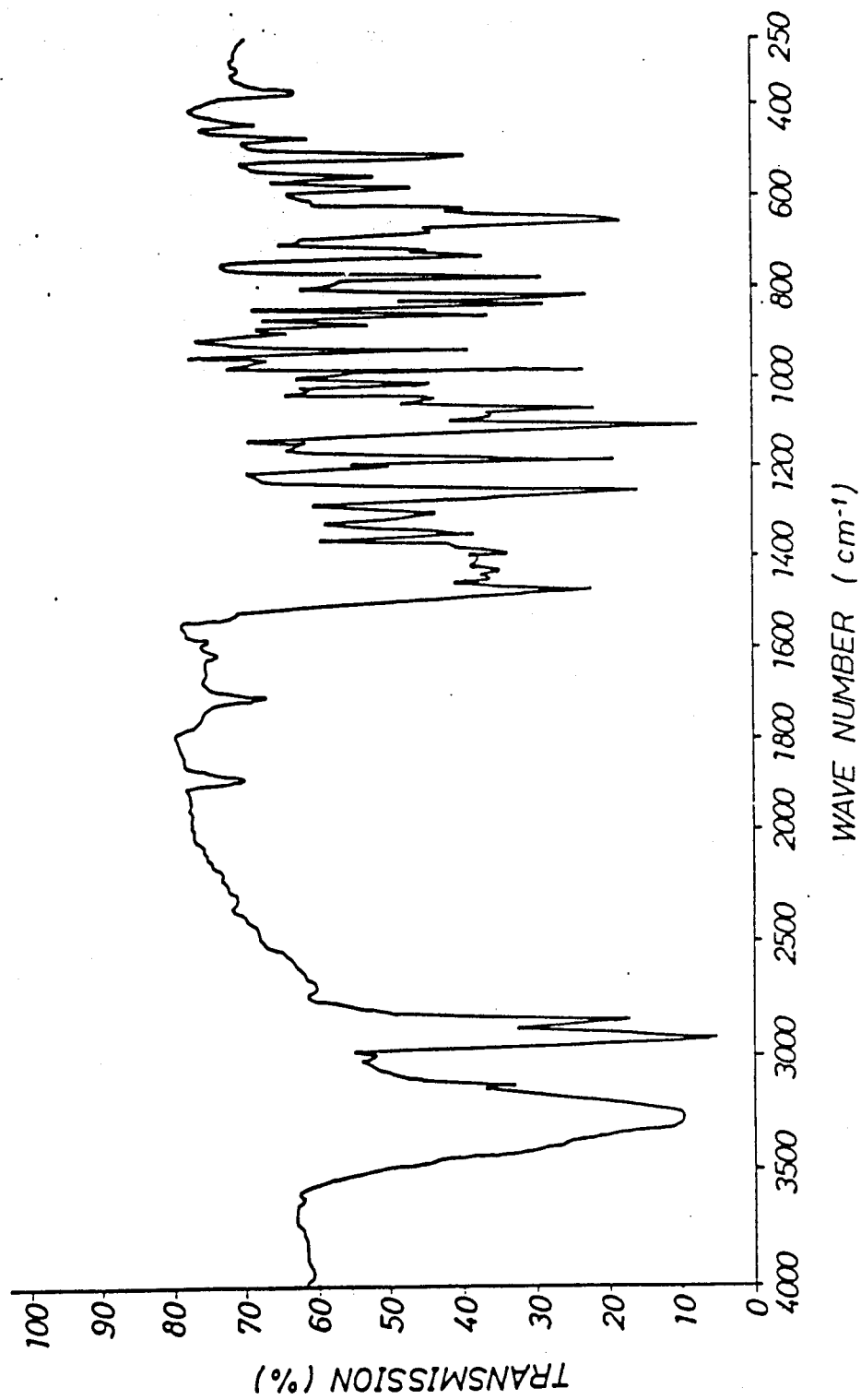
Figure 64:
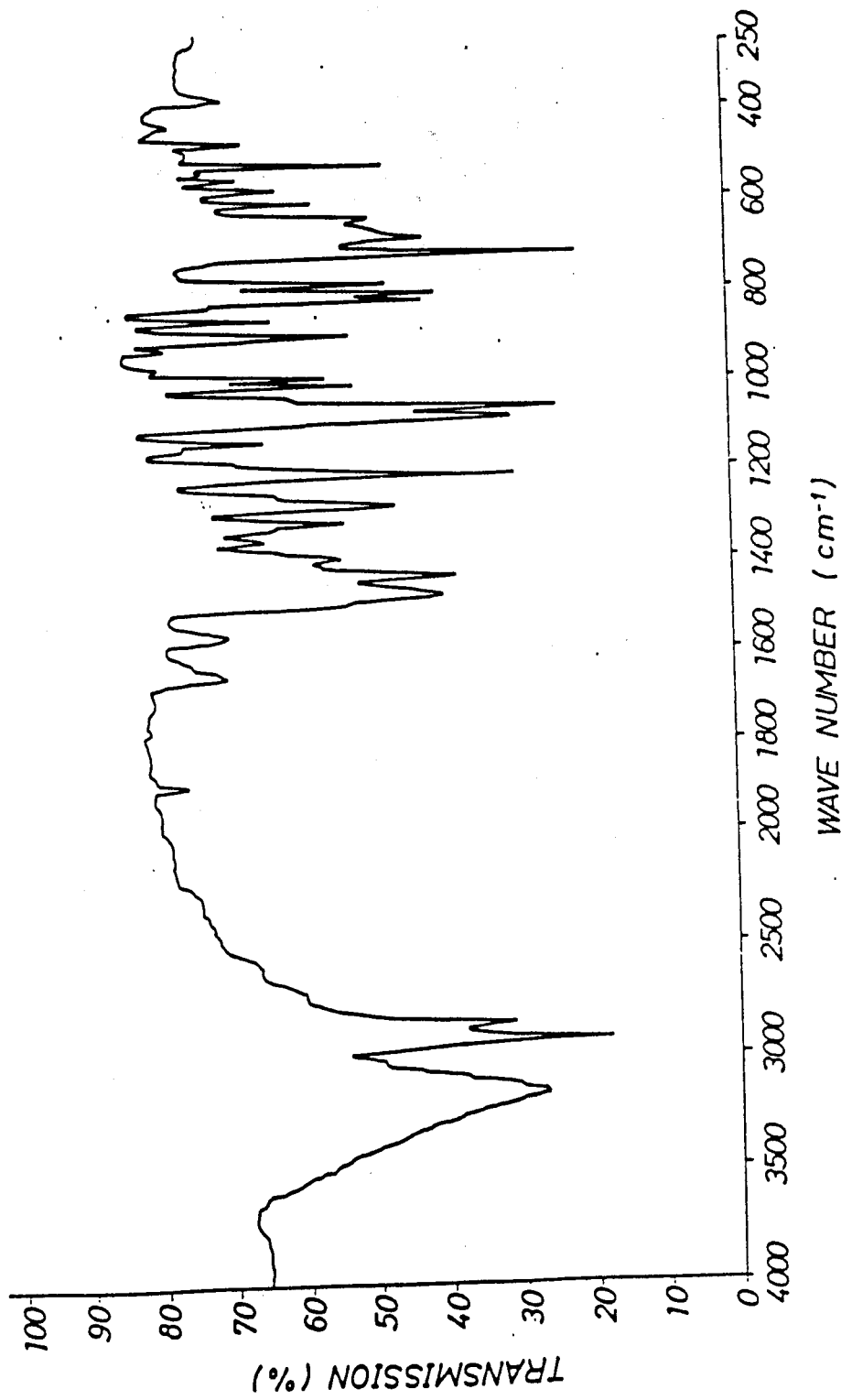
Figure 65:
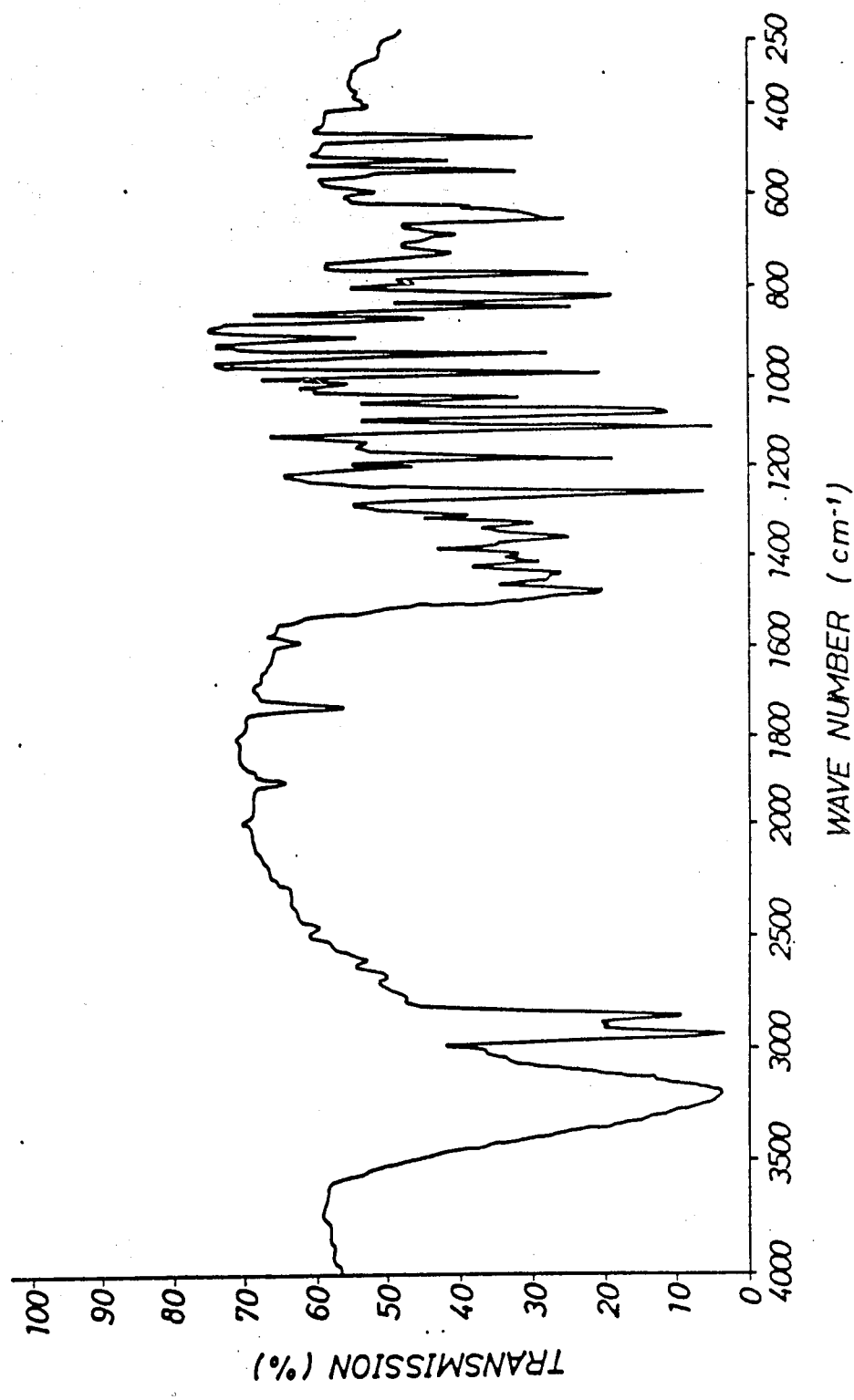
Figure 66:
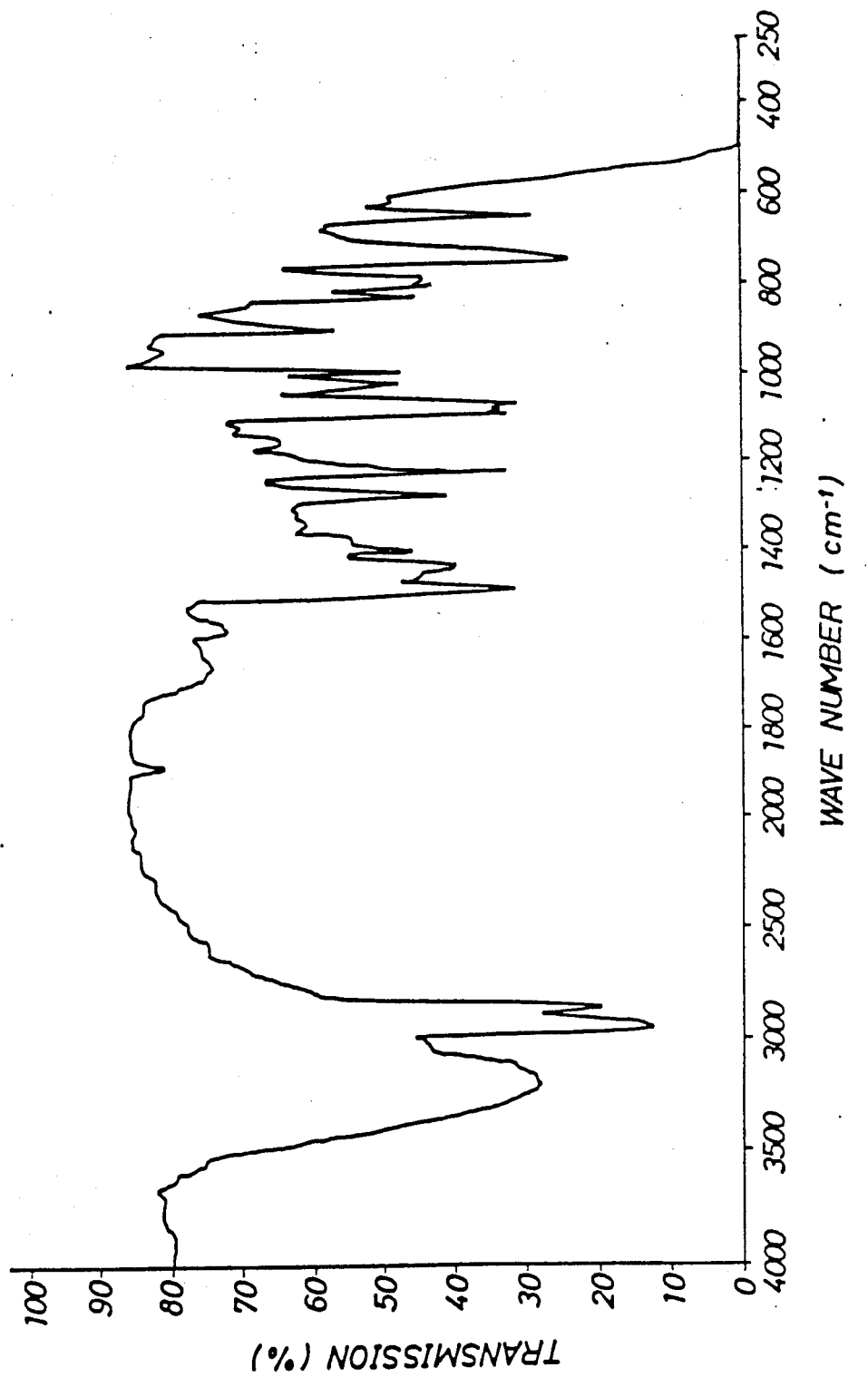
Figure 67:
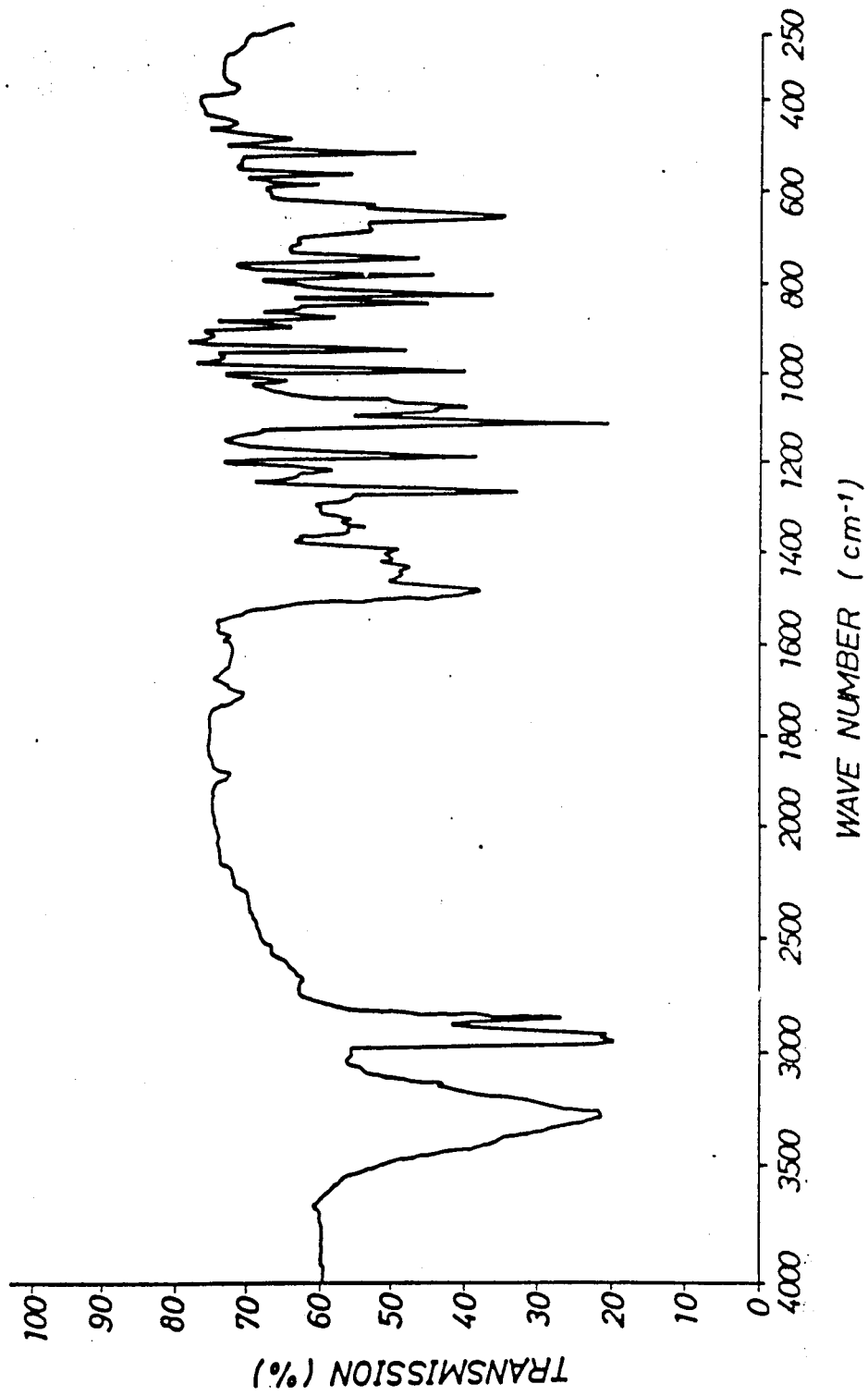
Figure 68:
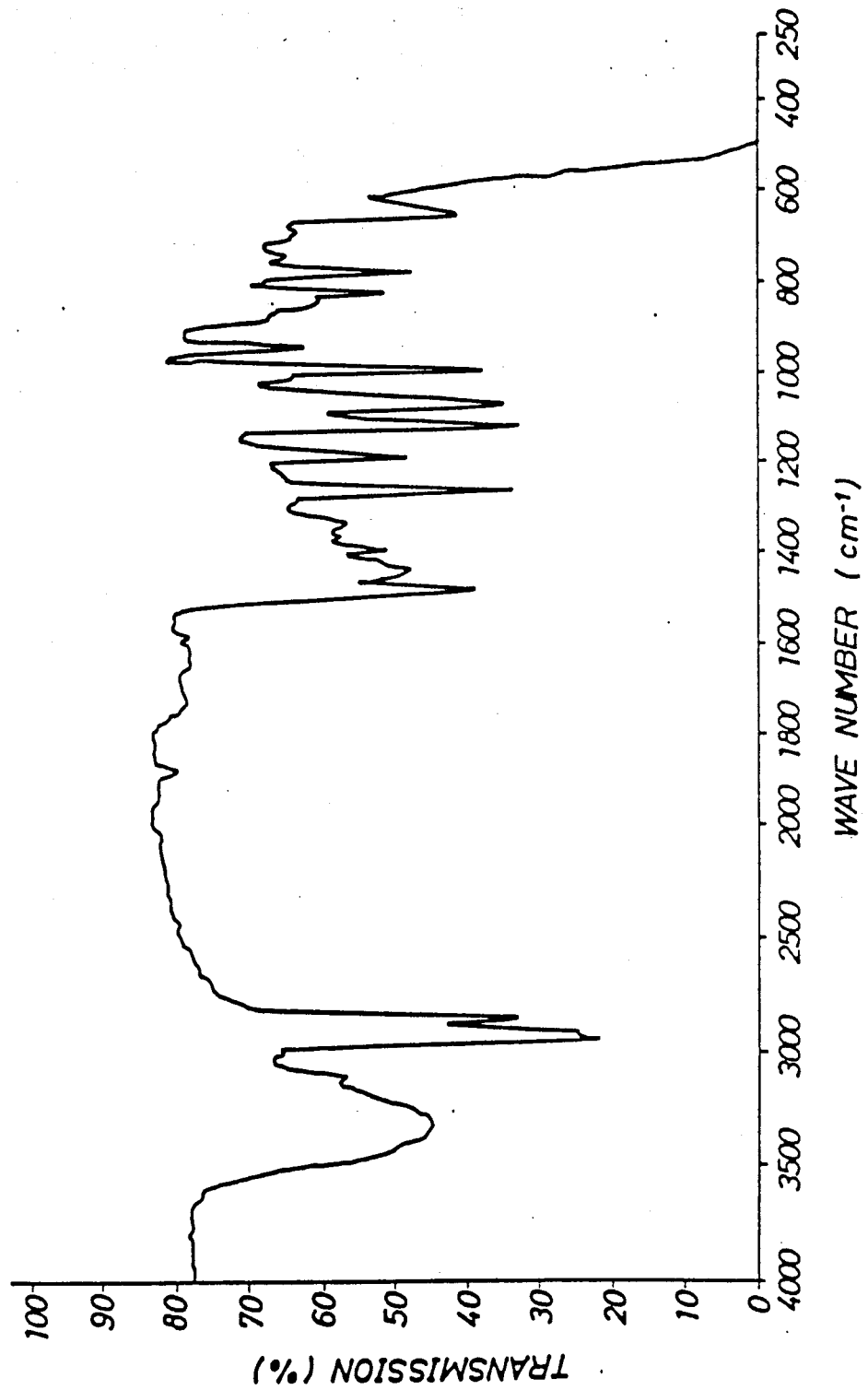
Figure 69:
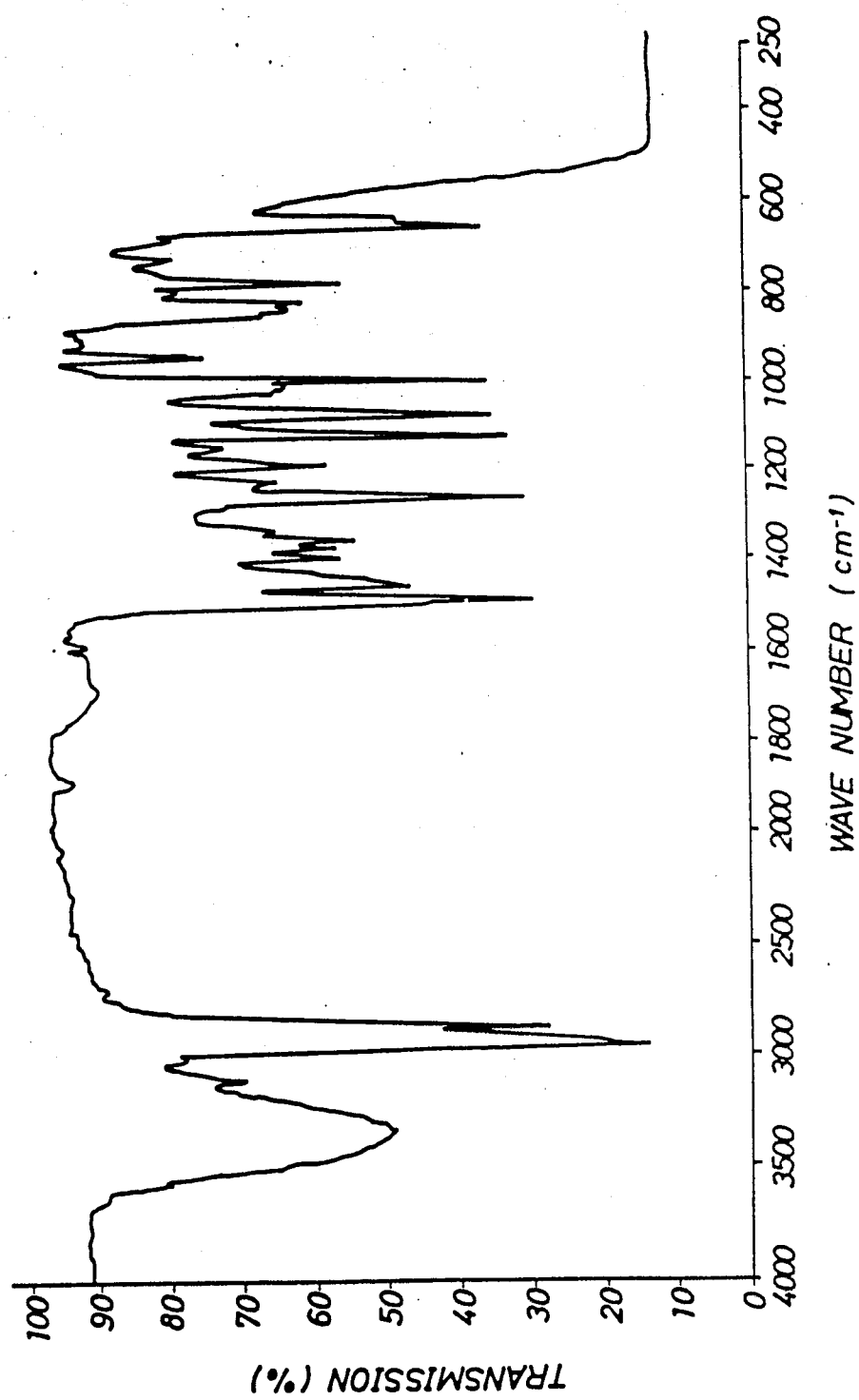
Figure 70:
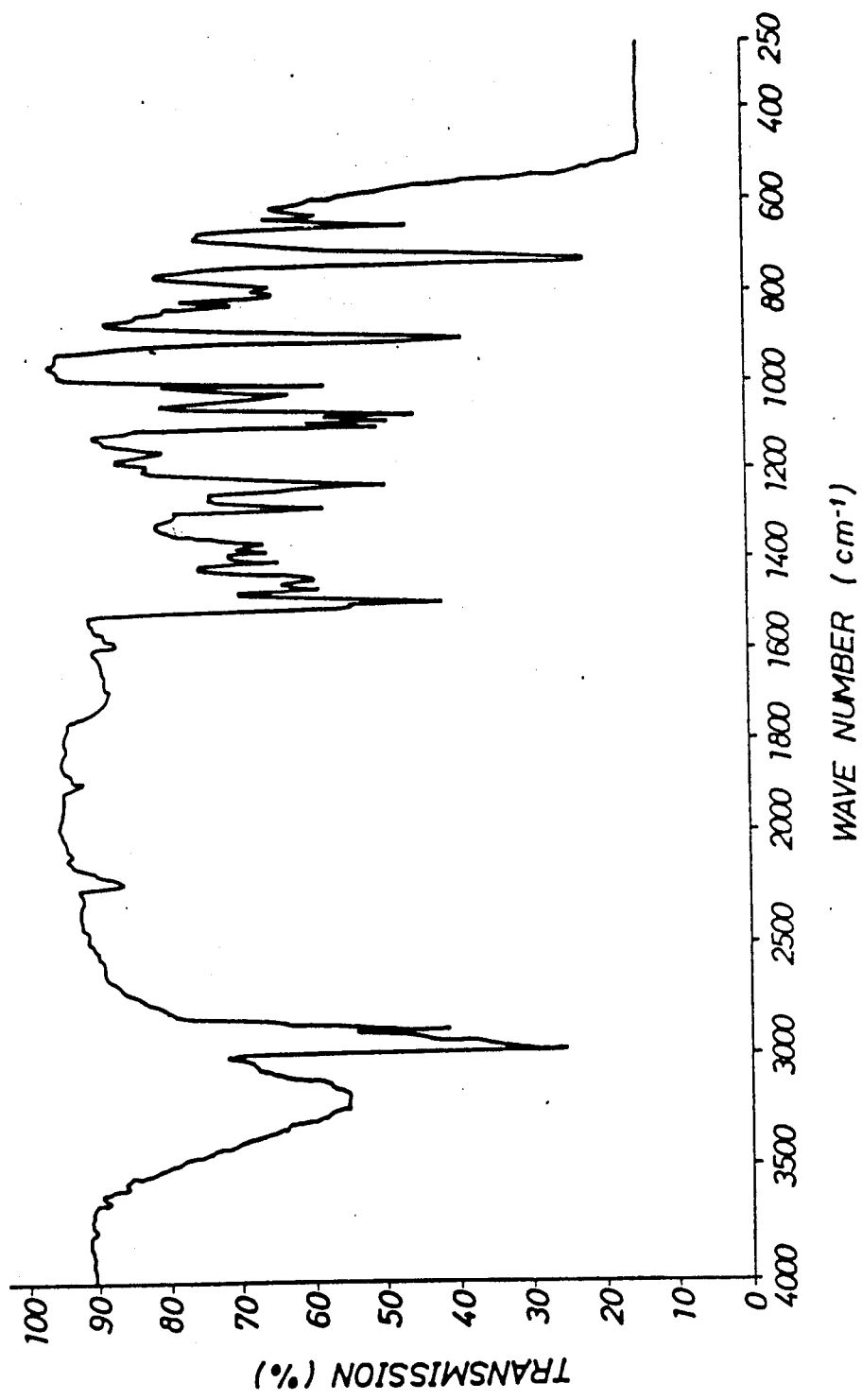
Figure 71:
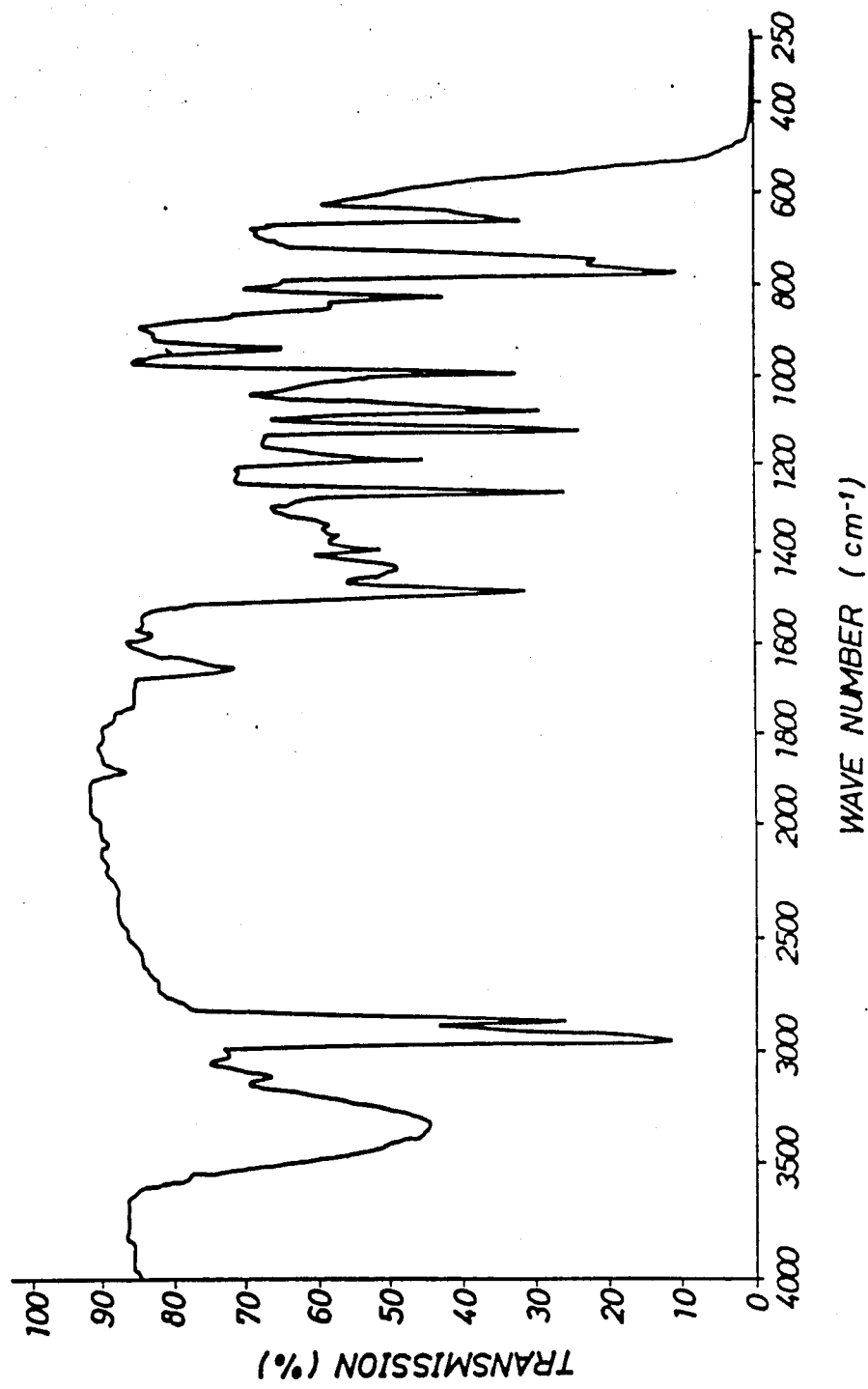
Figure 72:
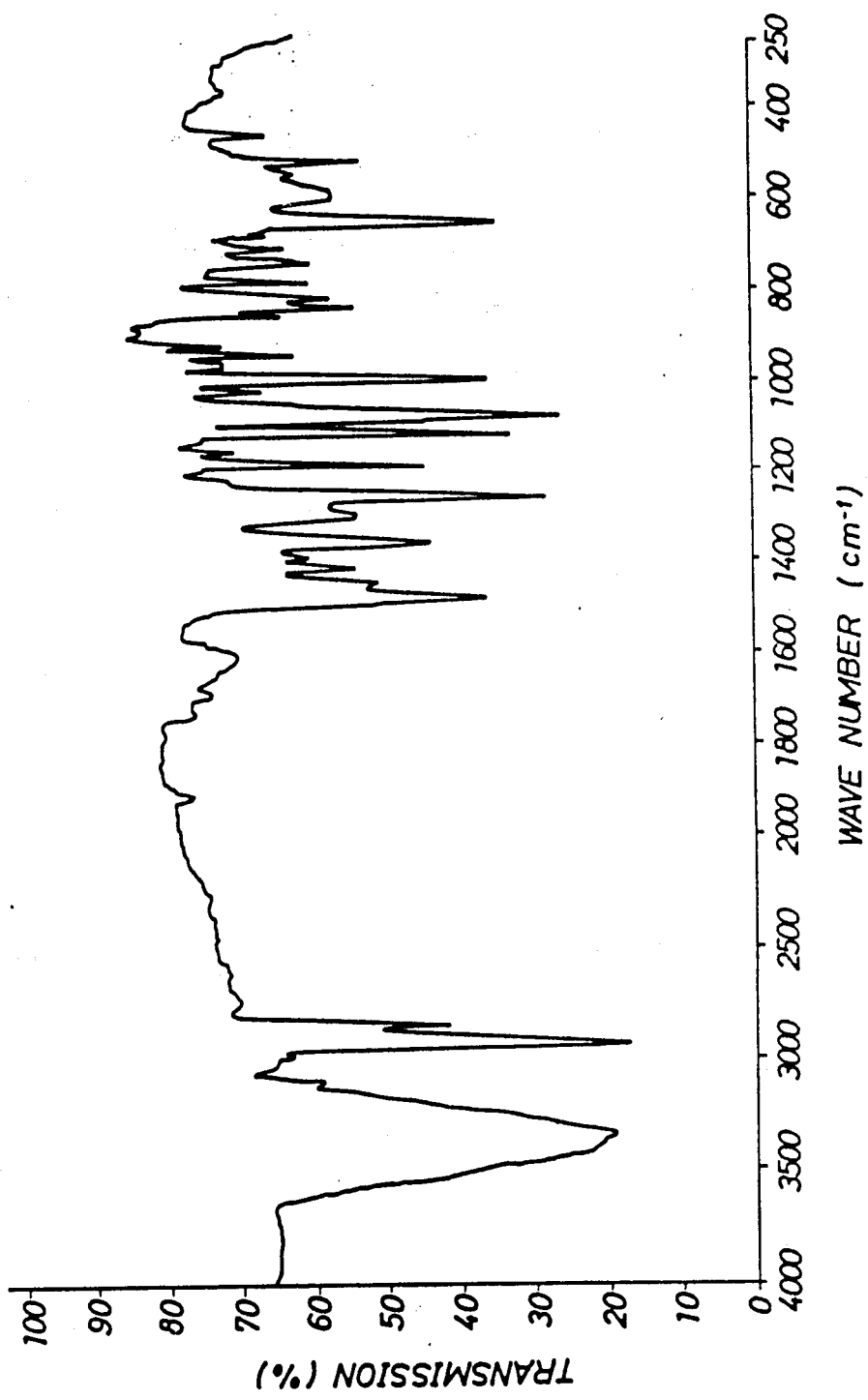
Figure 73:
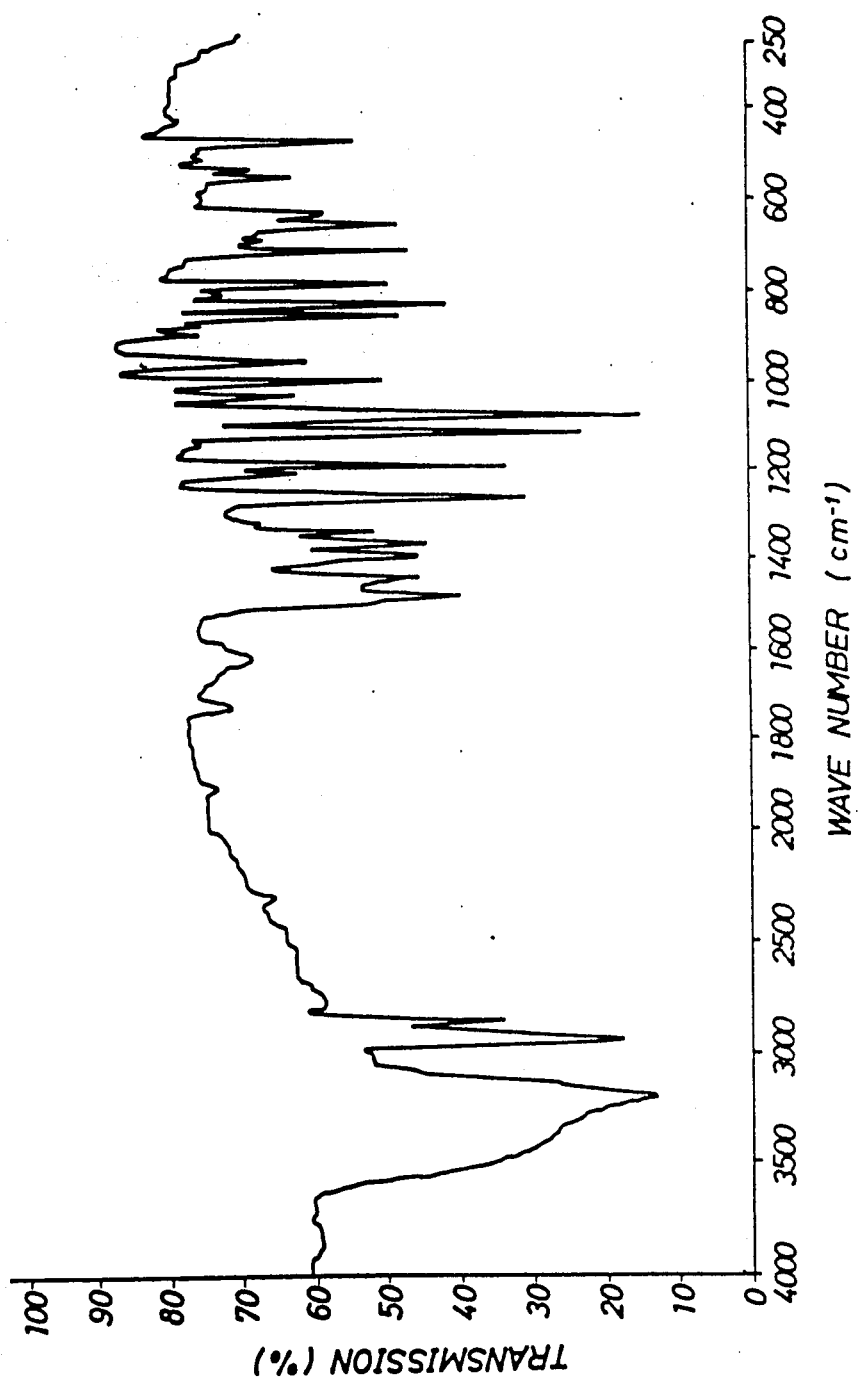
Figure 74:
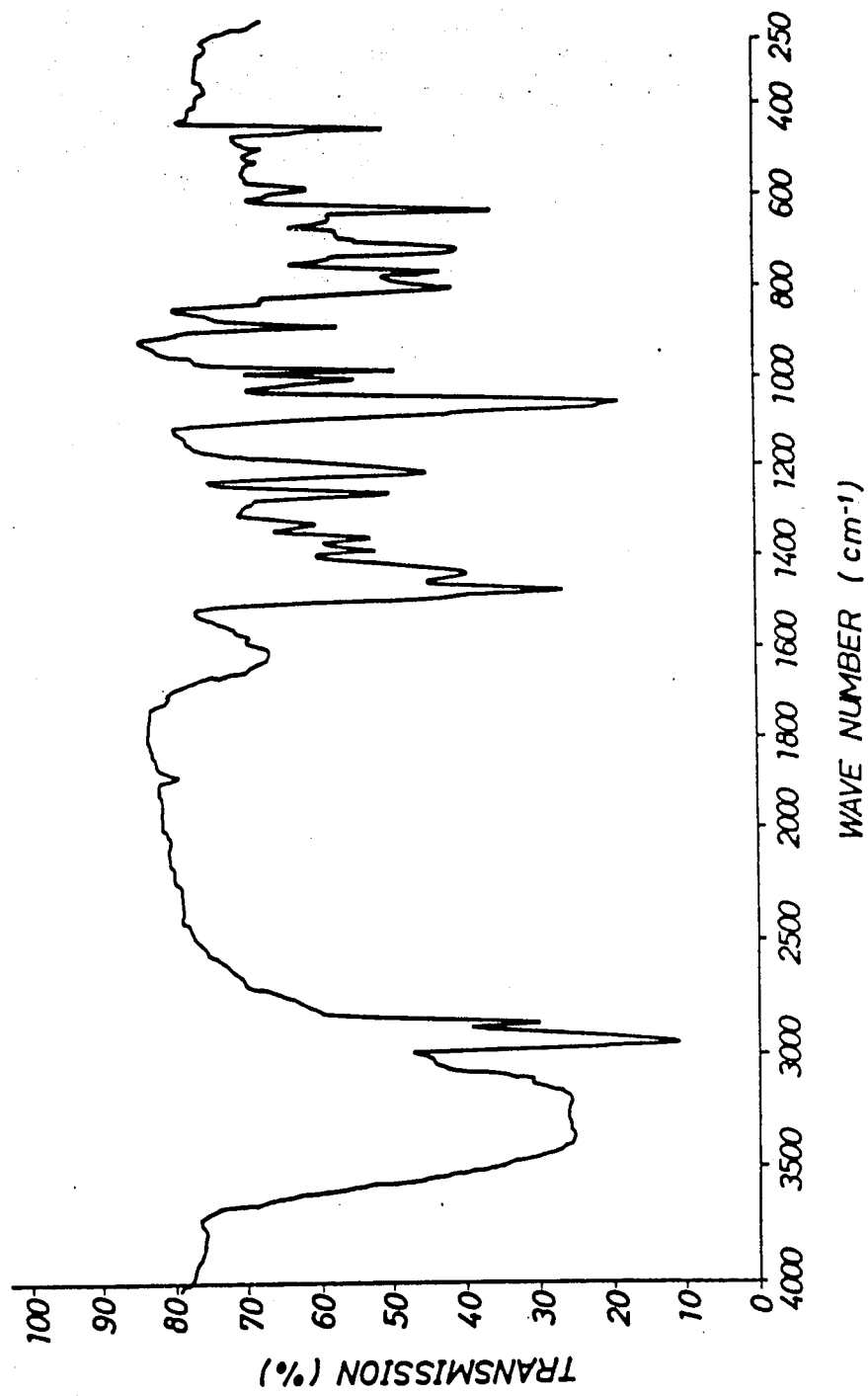
Figure 75:
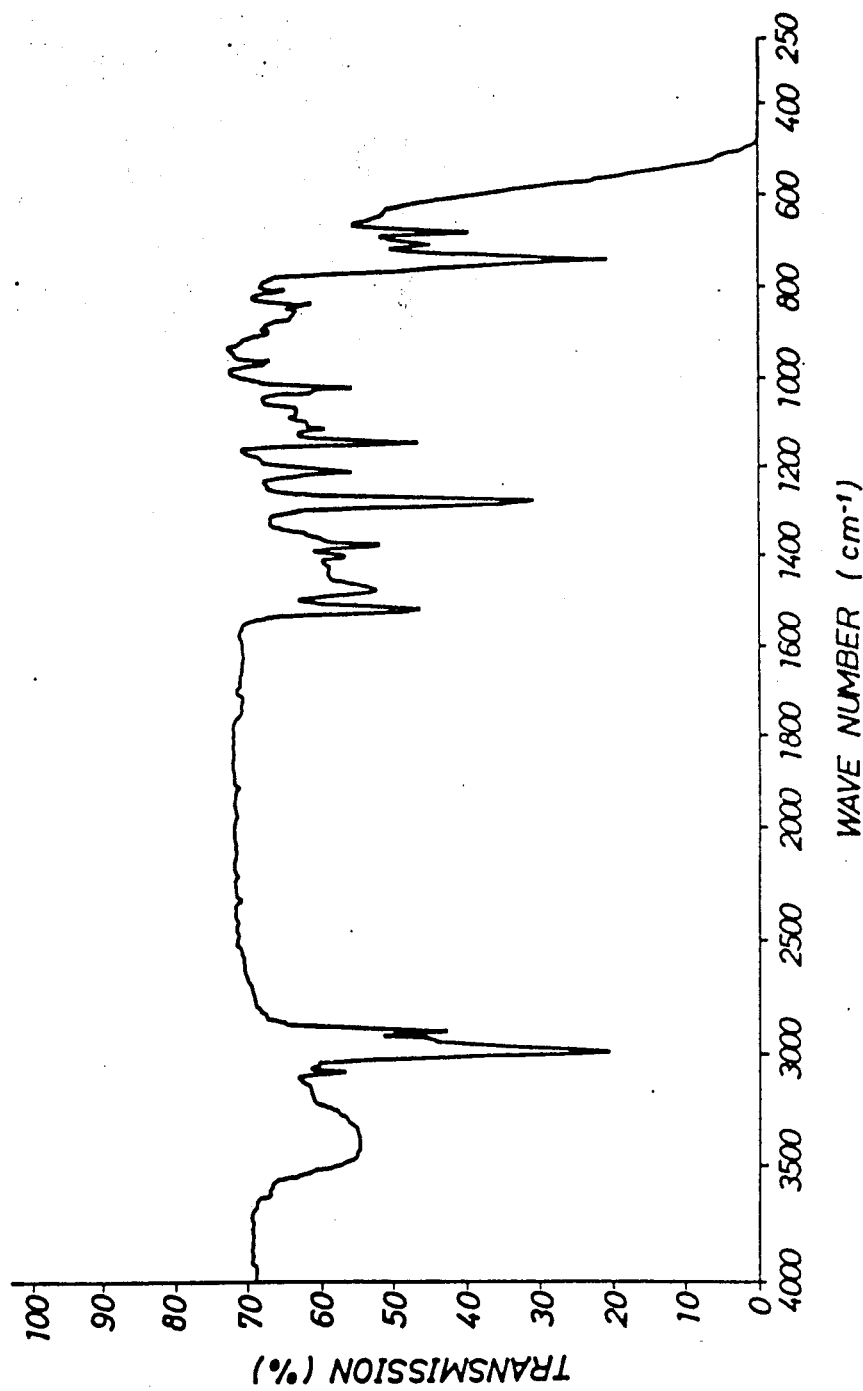

The heart of the present invention lies in a novel azole derivative represented by the formula (I):

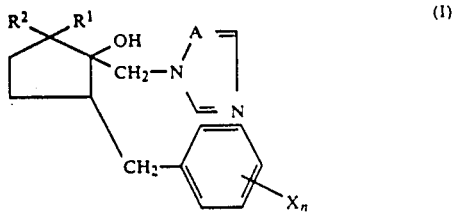
(I)

wherein $R^1$ and $R^2$ respectively represent a ($C_1$-$C_5$)alkyl group or a hydrogen atom; X represents a halogen atom, a ($C_1$-$C_5$)alkyl group or a phenyl group; n represents an integer of from 0 to 2 and A represents a nitrogen atom or a CH, provided that $R^1$ is not a hydrogen atom when $R^2$ is a hydrogen atom, a process for producing the azole derivative represented by the formula (I), each of the compounds used as the intermediates, namely an oxirane derivative represented by the formula (II), a methylenecyclopentane derivative represented by the formula (III), a cyclopentanone derivative represented by the formula (IV) and an ester derivative of cyclopentanecarboxylic acid represented by the formula (V), and an agricultural and horticultural composition containing the azole derivative represented by the formula (I) as an active ingredient and having fungicidal activity and plant growth regulating activity.

The physical and chemical properties of the azole derivative represented by the formula (I) and each of the intermediates for producing the above-mentioned azole derivative are shown in Tables 1 to 5.

Besides, every one of these intermediates is a novel compound.

TABLE I

Azole derivatives

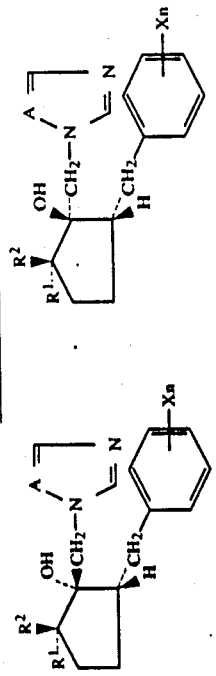

(I-A)          (I-B)

| Compound No. | Indication in Formulation (I) | | | | Indication of Stereo-isomer | Melting point (°C.) | NMR Spectral data (CDCl₃, δppm) |
|---|---|---|---|---|---|---|---|
| | R¹ | R² | Xₙ | A | | | |
| 1 | CH₃ | CH₃ | 4-Cl | N | A-type | 113–114 | 0.60(s,3H), 1.00(s,3H), 1.07–1.90(m,5H), 2.33(bs,2H), 3.53(s,1H), 4.13(s,2H), 6.80–7.23(m,4H), 7.83(s,1H), 8.02(s,1H) |
| 2 | CH₃ | CH₃ | 4-Cl | N | B-type | 90–92 | 0.82(s,3H), 1.00(s,3H), 1.23–1.93(m,4H), 2.07–2.48(m,2H), 2.85–3.07(m,1H), 3.90(s,1H), 4.37(s,2H), 7.03(d,2H,J=8), 7.25(d,2H,J=8), 7.97(s,1H), 8.27(s,1H) |
| 3 | CH₃ | CH₃ | 4-Cl | CH | A-type | 133–134 | 0.80(s,3H), 1.03(s,3H), 1.13–2.93(m,8H), 3.97(s,1H), 7.02(s,2H), 6.80–7.33(m,4H), 7.60(s,1H) |
| 4 | CH₃ | CH₃ | 4-Cl | CH | B-type | 133–134 | 0.83(s,3H), 1.03(s,3H), 1.13–3.13(m,8H), 4.03(s,1H), 6.70–7.23(m,6H), 7.63(s,1H) |
| 5 | CH₃ | CH₃ | 4-Br | N | A-type | 129–130 | 0.63(s,3H), 1.00(s,3H), 1.13–1.93(m,5H), 2.33(bs,2H), 3.60(s,1H), 4.20(s,2H), 6.93–7.50(m,4H), 7.97(s,1H), 8.17(s,1H) |
| 6 | CH₃ | CH₃ | 4-Br | N | B-type | 134–135 | 0.77(s,3H), 0.97(s,3H), 1.20–3.03(m,7H), 3.80(s,1H), 4.33(s,2H), 6.87–7.47(m,4H), 7.93(s,1H), 8.20(s,1H) |
| 7 | CH₃ | CH₃ | 4-Br | CH | A-type | 149–150 | 0.80(s,3H), 1.03(s,3H), 1.13–2.53(m,8H), 4.00(s,2H), 6.80–7.50(m,6H), 7.63(s,1H) |
| 8 | CH₃ | CH₃ | 4-Br | CH | B-type | 134–135 | 0.83(s,3H), 1.03(s,3H), 1.17–2.97(m,8H), 4.03(s,2H), 6.70–7.40(m,6H), 7.57(s,1H) |
| 9 | CH₃ | CH₃ | 4-F | N | A-type | 135–136 | 0.67(s,3H), 1.03(s,3H), 1.17–2.42(m,4H), 2.50(bs,3H), 3.63(s,1H), 4.24(s,2H), 6.73–7.33(m,4H), 7.93(s,1H), 8.13(s,1H) |
| 10 | CH₃ | CH₃ | 4-F | N | B-type | 134–135 | 0.80(s,3H), 1.02(s,3H), 1.27–3.10(m,7H), 3.90(m,1H), 4.37(s,2H), 6.73–7.27(m,4H), 7.97(s,1H), 8.27(s,1H) |
| 11 | CH₃ | CH₃ | 4-F | CH | A-type | 131–133 | 0.83(s,3H), 1.07(s,3H), 0.90–2.00(m,5H), 2.25(bs,2H), 2.57(bs,1H), 4.03(s,2H), 6.73–7.27(m,6H), 7.67(s,1H) |
| 12 | CH₃ | CH₃ | 4-F | CH | B-type | 104–106 | 0.87(s,3H), 1.03(s,3H), 1.17–3.03(m,8H), 4.10(s,2H), 6.70–7.27(m,6H), 7.73(bs,1H) |
| 13 | CH₃ | CH₃ | 2,4-Cl₂ | N | A-type | 126–127 | 0.56(s,3H), 1.01(s,3H), 0.79–2.79(m,5H), 2.66(bs,2H), 3.97(s,1H), 4.27(s,2H), 7.20(s,2H), 7.28(bs,1H), 7.92(s,1H), 8.12(s,1H) |
| 14 | CH₃ | CH₃ | 2,4-Cl₂ | N | B-type | 108–110 | 0.80(s,3H), 1.02(s,3H), 1.25–1.88(m,4H), 2.33–3.03(m,2H), 3.75(s,1H), 4.37(s,2H), 7.08–7.37(m,3H), 7.93(s,1H), 8.23(s,1H) |
| 15 | CH₃ | CH₃ | 2,4-Cl₂ | CH | A-type | 131–132 | 0.70(s,3H), 1.03(s,3H), 1.16–2.65(m,5H), 2.53(bs,2H), 2.72(bs,1H), 4.01(s,2H), 6.99(s,1H), 7.03(bs,1H), 7.24(s,1H), 7.58(s,1H) |
| 16 | CH₃ | H | 4-Cl | N | A-type | 100–102 | 0.74(d,3H,J=6), 1.00–2.27(m,6H), 2.49(d,2H,J=6.4), 3.07(s,1H), 4.20(d,2H,J=8.4), 7.03(d,2H,J=8.4), 7.22(d,2H,J=8.4), 7.95(s,1H), 8.08(s,1H) |
| 17 | CH₃ | H | 4-Cl | CH | A-type | 118–119 | 0.85(d,3H,J=5.8), 1.07–2.23(m,6H), 2.51(bd,2H,J=6.4), 3.34(bs,1H), 3.95(s,2H), 6.95(s,1H), 6.98(d,2H,J=8), 7.01(s,1H), 7.18(d,2H,J=8), 7.48(s,1H) |
| 18 | H | CH₃ | 4-Cl | N | A-type | 75–76 | 0.99(d,3H,J=6.4), 1.28–2.24(m,6H), 2.28–2.58(m,2H), 3.60(s,1H), 3.99(d,1H,J=14) |

TABLE 1-continued

Azole derivatives

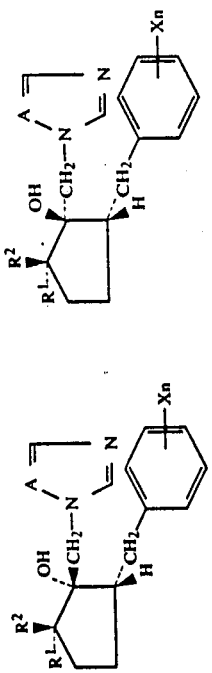

(I-A)             (I-B)

| Compound No. | Indication in Formulation (I) R¹ | R² | X_n | A | Indication of Stereo-isomer | Melting point (°C.) | NMR Spectral data (CDCl₃, δppm) |
|---|---|---|---|---|---|---|---|
| 19 | H | CH₃ | 4-Cl | N | B-type | 79~81 | 4.39(d,1H,J=14), 6.97(d,2H,J=9), 8.00(s,1H), 8.18(s,1H), 7.24(d,2H,J=9) |
| 20 | CH₃ | H | 4-Cl | N | B-type | Oily material | 0.80(d,3H,J=6.4), 0.99~2.56(m,7H), 2.73~3.39(m,1H), 3.90(bs,1H), 4.11(d,1H,J=14), 4.38(d,1H,J=14), 7.04(d,2H,J=9.4), 7.26(d,2H,J=9.4), 7.92(s,1H), 8.22(s,1H) |
| 21 | CH₃ | CH₃ | H | N | A-type | Oily material | 0.88(d,3H,J=6.6), 1.05~2.45(m,7H), 2.62~2.92(m,1H), 3.85~4.25(b,1H,OH), 4.31(s,2H), 6.98(d,2H,J=8.8), 7.22(d,2H,J=8.8), 7.95(s,1H), 8.26(s,1H) |
| 22 | CH₃ | CH₃ | H | CH | A-type | 128~130 | 0.63(s,3H), 1.03(s,3H), 1.13~2.83(m,7H), 3.57(s,1H), 4.23(s,2H), 7.23(s,5H), 8.00(s,1H), 8.17(s,1H) |
| 23 | CH₃ | CH₃ | 4-CH₃ | N | A-type | 123~124 | 0.77(s,3H), 1.03(s,3H), 1.10~2.17(m,5H), 1.97(s,1H), 2.17~2.50(m,2H), 3.97(s,2H), 6.87~7.33(m,7H), 7.57(s,1H) |
| 24 | CH₃ | CH₃ | 4-CH₃ | N | B-type | 114~115 | 0.57(s,3H), 1.02(s,3H), 1.10~2.57(m,8H), 2.27(s,3H), 4.20(s,2H), 7.02(s,4H), 7.95(s,1H), 8.13(s,1H) |
| 25 | CH₃ | CH₃ | 4-CH₃ | CH | A-type | 132~133 | 0.73(s,3H), 0.98(s,3H), 1.07~3.00(m,7H), 2.25(s,3H), 3.72(s,1H), 4.28(s,3H), 6.93(s,4H), 7.83(s,1H), 8.10(s,1H) |
| 26 | CH₃ | CH₃ | 4-CH₃ | CH | B-type | 130~131 | 0.75(s,3H), 1.02(s,3H), 1.02~2.42(m,8H), 2.27(s,3H), 3.93(s,2H), 6.98(s,4H), 7.02(s,2H), 7.58(s,1H) |
| 27 | CH₃ | CH₃ | 2-F,4-Cl | N | A-type | 129~130 | 0.83(s,3H), 1.07(s,3H), 1.17~3.07(m,8H), 2.27(s,3H), 4.07(s,2H), 6.77~7.20(m,2H), 6.95(s,4H), 7.62(s,1H) |
| 28 | CH₃ | CH₃ | 2-F,4-Cl | CH | A-type | 152~154 | 0.62(s,3H), 1.02(s,3H), 1.13~2.67(m,7H), 3.82(s,1H), 4.21(s,2H), 6.23~7.23(m,3H), 7.89(s,1H), 8.11(s,1H) |
| 29 | C₂H₅ | H | 4-Cl | N | A-type | 82~84 | 0.78(s,3H), 1.02(s,3H), 1.10~2.80(m,8H), 3.98(s,2H), 6.68~7.20(m,5H), 7.57(s,1H) |
| 30 | H | C₂H₅ | 4-Cl | N | A-type | 93~95 | 0.67~2.23(m,11H), 2.43(d,1H,J=7), 2.93(s,1H), 4.20(s,2H), 6.93~7.33(m,4H), 7.93(s,1H), 8.07(s,1H) |
| 31 | H | C₂H₅ | 4-Cl | N | B-type | 76~78 | 0.70~2.13(m,11H), 2.13~2.47(m,2H), 3.83(s,1H), 4.00(d,1H,J=14), 4.30(d,1H,J=14), 6.88(d,2H,J=8), 7.18(d,2H,J=8), 7.93(s,1H), 8.17(s,1H) |
| 32 | C₂H₅ | H | 4-Cl | N | B-type | 110~112 | 0.67~3.33(m,13H), 3.07(d,1H,J=14), 4.13(d,1H,J=14), 4.40(d,1H,J=14), 7.03(d,2H,J=8), 7.23(d,2H,J=8), 7.97(s,1H), 8.18(s,1H) |
| 33 | C₂H₅ | H | 4-Cl | N | A-type | 124~126 | 0.67~2.20(m,12H), 2.73(d,1H,J=10), 4.15(s,1H), 4.30(s,2H), 6.95(d,2H,J=8), 7.20(d,2H,J=8), 7.97(s,1H), 8.25(s,1H) |
| 34 | C₂H₅ | C₂H₅ | 4-Cl | N | B-type | 143~145 | 0.67~1.07(m,6H), 1.07~2.40(m,11H), 3.52(s,1H), 4.30(s,2H), 6.87(d,2H,J=9), 7.18(d,2H,J=9), 7.93(s,1H), 8.18(s,1H) |
| 35 | C₂H₅ | C₂H₅ | 4-Cl | CH | A-type | Oily material | 0.87(t,6H,J=6), 1.10~1.97(m,8H), 1.97~2.54(m,2H), 2.73(d,1H,J=9), 3.33~3.70(b,1H), 4.43(s,2H), 6.92(d,2H,J=9), 7.20(d,2H,J=9), 7.97(s,1H), 8.27(s,1H) |
| 36 | C₂H₅ | C₂H₅ | 4-Cl | CH | B-type | 143~145 | 0.87(t,6H,J=6), 1.07~2.50(m,11H), 3.33(s,1H), 3.90(d,1H,J=14), 4.18(d,1H,J=14), 6.70~7.23(m,6H), 7.67(s,1H), 0.87(t,6H,J=6), 1.10~2.33(m,10H), 2.53~2.88(m,2H), 4.13(s,2H) |

TABLE 1-continued

Azole derivatives

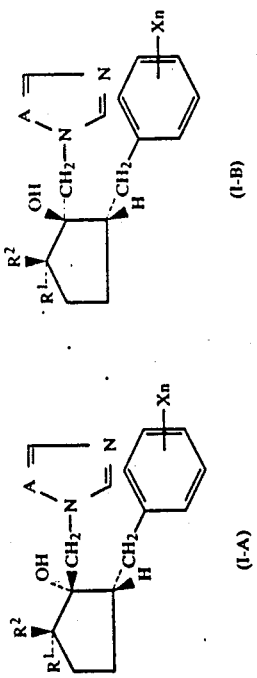

(I-A)                (I-B)

| Compound No. | Indication in Formulation (I) | | | | Indication of Stereo-isomer | Melting point (°C.) | NMR Spectral data (CDCl₃, δppm) |
|---|---|---|---|---|---|---|---|
| | R¹ | R² | Xₙ | A | | | |
| 37 | n-C₃H₇ | H | 4-Cl | N | A-type | 83~85 | 6.75~7.35(m,6H), 7.70(s,1H)<br>0.61~2.26(m,13H), 2.26~2.57(m,2H), 2.51~2.81(b,1H), 4.21(s,2H),<br>7.03(d,2H,J=9), 7.23(d,2H,J=9), 7.96(s,1H), 8.07(s,1H) |
| 38 | H | n-C₃H₇ | 4-Cl | N | A-type | 75~77 | 0.65~1.04(m,3H), 1.04~2.18(m,10H), 1.04~2.48(m,2H), 3.70(bs,1H), 3.98(d,1H,J=14),<br>4.29(d,1H,J=14), 6.86(d,2H,J=8.4), 7.16(d,2H,J=8.4), 7.94(s,1H), 8.12(s,1H) |
| 39 | n-C₃H₇ | H | 4-Cl | CH | A-type | 115~117 | 0.57~1.04(m,3H), 1.04~2.24(m,10H), 2.43(bs,2H), 2.55(bs,1H), 3.96(s,2H),<br>6.99(d,2H,J=8.4), 7.02(bs,2H), 7.20(d,2H,J=6), 3.10(s,1H), 4.23(s,2H) |
| 40 | C₂H₅ | H | 2,4-Cl₂ | N | A-type | 124~127 | 0.63~2.40(m,11H), 2.68(d,2H,J=6), 3.10(s,1H), 8.10(s,1H)<br>7.13(bs,2H), 7.30(bs,1H), 7.93(s,1H), 8.10(s,1H) |
| 41 | C₂H₅ | H | 2,4-Cl₂ | CH | A-type | 111~113 | 0.67~2.27(m,11H), 2.50(d,2H,J=7), 2.63(bs,1H), 3.98(s,2H),<br>6.90(bs,2H), 6.97(bs,2H), 7.37(bs,1H), 7.50(s,1H) |
| 42 | C₂H₅ | H | 4-F | N | A-type | 73~74 | 0.62~2.19(m,11H), 2.30~2.51(m,2H), 2.62(s,1H), 4.15(s,2H),<br>6.64~7.23(m,4H), 7.88(s,1H), 7.99(s,1H) |
| 43 | C₂H₅ | H | 4-F | CH | A-type | 111~113 | 0.66~2.07(m,11H), 2.19(s,1H), 2.35~2.60(m,2H),<br>3.93(s,2H), 6.63~7.20(m,6H), 7.41(bs,1H) |
| 44 | C₂H₅ | H | 4-Br | N | A-type | 80~82 | 0.68~2.25(m,11H), 2.43(d,2H,J=7), 2.85(s,1H), 4.22(s,2H),<br>7.02(d,2H,J=8), 7.37(d,2H,J=7), 7.93(s,1H), 8.08(s,1H) |
| 45 | C₂H₅ | H | 4-Br | CH | A-type | 117~119 | 0.60~2.50(m,11H), 2.33~3.02(m,2H), 3.18(s,1H), 4.00(s,2H),<br>6.88~7.02(m,2H), 7.03~7.35(m,3H), 7.48(bs,1H) |
| 46 | C₂H₅ | H | 4-C₆H₅ | N | A-type | 107~109 | 0.56~2.34(m,11H), 2.40~2.60(m,2H), 2.65(s,1H), 4.20(s,2H),<br>7.05~7.70(m,9H), 7.95(s,1H), 8.05(s,1H) |
| 47 | C₂H₅ | H | 4-C₆H₅ | CH | A-type | 169~170 | 0.66~2.28(m,11H), 2.01(s,1H), 2.45~2.72(m,2H),<br>3.96(s,2H), 6.85~7.63(m,12H) |
| 48 | C₂H₅ | H | 4-t-C₄H₉ | N | A-type | Oily material | 0.85(t,3H,J=7), 1.29(s,9H), 0.90~1.90(m,8H), 2.41(dd,1H,J=14,10),<br>2.49(dd,1H,J=14.5), 4.23(s,2H), 7.07(d,2H,J=8.3), 7.28(d,2H,J=8.3),<br>7.96(s,1H), 8.01(s,1H) |
| 49 | C₂H₅ | H | 4-t-C₄H₉ | CH | A-type | 132~133 | 0.67~2.83(m,14H), 1.32(s,9H), 4.08(s,2H)<br>6.97~7.53(m,6H), 7.58(s,1H) |
| 50 | i-C₃H₇ | H | 4-Cl | N | A-type | 91~92 | 0.95(d,3H,J=7), 0.97(d,3H,J=7), 1.17~2.93(m,10H), 4.12(d,1H,J=14),<br>4.41(d,1H,J=14), 6.87~7.44(m,4H), 7.97(s,1H), 8.13(s,1H) |
| 51 | n-C₅H₁₁ | H | 4-Cl | N | A-type | Oily material | 0.86(t,3H,J=6.8), 0.90~1.9M(m,14H), 2.38(dd,1H,J=13.4,9.3),<br>2.46(dd,1H,J=13.4,5.4), 2.57(s,1H), 4.23(s,2H), 7.08(d,2H,J=8.3),<br>7.22(d,2H,J=8.3), 7.97(s,1H), 8.08(s,1H) |
| 52 | n-C₅H₁₁ | H | 4-Cl | CH | A-type | 92~95 | 0.87(t,3H,J=6.8), 1.05~1.95(m,14H), 2.43(dd,1H,1.=13.7,10.3),<br>2.56(dd,1H,J=13.7,4.4), 3.47(s,1H), 3.99(s,2H), 6.94(s,1H), 7.05(d,2H,J=8.3),<br>7.06(s,1H), 7.22(d,2H,J=8.3), 7.48(s,1H) |

TABLE 1-continued

Azole derivatives

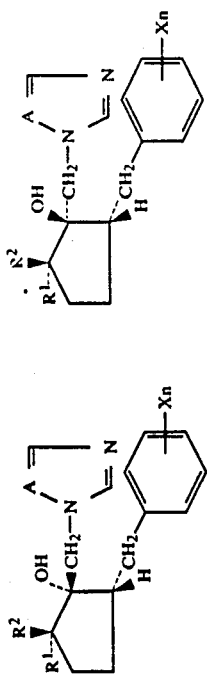

(I-A)

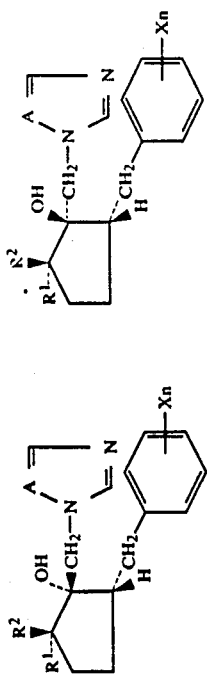

(I-B)

| Compound No. | Indication in Formulation (I) | | | | Indication of Stereo-isomer | Melting point (°C.) | NMR Spectral data (CDCl₃, δppm) |
|---|---|---|---|---|---|---|---|
| | R¹ | R² | Xₙ | A | | | |
| 53 | C₂H₅ | H | 4-Cl | CH | B-type | 138~140 | 0.57~0.98(m,3H), 0.98~2.17(m,9H), 2.73(d,1H,J=10), 3.43(bs,1H), 4.03(s,2H), 6.83~7.03(m,6H), 7.68(bs,1H) |
| 54 | H | n-C₅H₁₁ | 4-Cl | N | A-type | Oily material | 0.88(t,3H,J=6.8), 1.00~1.94(m,14H), 2.31(m,2H), 3.70(bs,1H), 4.05(d,1H,J=13.7), 4.26(d,1H,J=13.7), 6.89(d,2H,J=8.3), 7.17(d,2H,J=8.3), 7.99(s,1H), 8.15(s,1H) |
| 55 | CH₃ | CH₃ | 4-C₄H₉ | N | A-type | 122~124 | 0.63(s,3H), 1.02(s,3H), 1.10~2.13(m,4H), 2.47(bs,3H), 3.62(s,3H), 4.23(s,2H), 7.10~7.73(m,9H), 7.97(s,1H), 8.17(s,1H) |
| 56 | CH₃ | CH₃ | 4-C₄H₉ | N | B-type | 116~118 | 0.77(s,3H), 0.98(s,3H), 1.10~2.80(m,5H), 2.33(d,1H,J=9), 2.98(d,1H,J=9), 3.88(s,1H), 4.33(s,2H), 7.07~7.73(m,9H), 7.97(s,1H), 8.25(s,1H) |
| 57 | CH₃ | CH₃ | 4-C₄H₉ | CH | A-type | 162~163 | 0.80(s,3H), 1.03(s,3H), 1.12~2.08(m,4H), 2.37(bs,3H), 2.43(s,1H), 4.00(s,2H), 6.88~7.78(m,12H) |
| 58 | CH₃ | CH₃ | 4-C₄H₉ | CH | B-type | 165~167 | 0.85(s,3H), 1.03(s,3H), 1.13~2.77(m,5H), 2.30(d,1H,J=9), 2.95(d,1H,J=9), 3.60(s,1H), 4.13(s,2H), 6.90~7.87(m,12H) |
| 59 | i-C₃H₇ | H | 4-Cl | CH | A-type | Oily material | 0.97(d,3H,J=7), 1.00(d,3H,J=7), 1.23~2.53(m,10H), 3.90(d,1H,J=14), 4.17(d,1H,J=14), 6.90~7.43(m,6H), 7.53(bs,1H) |
| 60 | CH₃ | CH₃ | 4-Cl | N | A-type | 107~108 | 0.62(s,3H), 1.01(s,3H), 1.27(s,9H), 1.17~2.00(m,5H), 2.17~2.67(m,2H), 3.50(s,1H), 4.22(s,2H), 7.00(d,2H,J=8.4), 7.25(d,2H,J=8.4), 7.92(s,1H), 8.12(s,1H) |
| 61 | CH₃ | CH₃ | 4-t-C₄H₉ | CH | A-type | 167~168 | 0.78(s,1H), 1.02(s,3H), 1.29(s,9H), 1.14~2.10(m,5H), 2.14~2.57(m,2H), 2.40(s,1H), 3.97(s,2H), 6.96(d,2H,J=8.4), 7.03(bs,2H), 7.23(d,2H,J=8.4), 7.59(bs,1H) |
| 62 | H | i-C₃H₇ | 4-Cl | N | B-type | Oily material | 0.60~3.17(m,15H), 3.43(bs,1H), 4.20(s,2H), 6.92(d,2H,J=8), 7.15(d,2H,J=8), 7.87(s,1H), 8.07(s,1H) |
| 63 | H | i-C₃H₇ | 4-Cl | N | A-type | 102~103 | 0.70~2.33(m,15H), 3.47(bs,1H), 3.97(d,1H,J=14), 4.38(d,1H,J=14), 6.73(d,2H,J=8), 7.10(d,2H,J=8), 7.93(s,1H), 8.10(s,1H) |
| 64 | H | i-C₃H₇ | 4-Cl | CH | A-type | 146~147 | 0.83~2.43(m,16H), 3.73(d,1H,J=14), 4.22(d,1H,J=14), 6.60~7.27(m,6H), 7.53(s,1H) |
| 65 | i-C₃H₇ | H | 4-Cl | N | B-type | 120~121 | 0.70~2.63(m,15H), 3.70(bs,1H), 4.33(s,2H), 7.00(d,2H,J=8), 7.27(d,2H,J=8), 8.07(s,1H), 8.40(s,1H) |
| 66 | n-C₄H₉ | H | 4-Cl | CH | A-type | Oily material | 0.57~2.67(m,17H), 3.05(s,1H), 3.95(s,2H), 6.68~7.25(m,6H), 7.38(bs,1H) |
| 67 | H | n-C₄H₉ | 4-Cl | N | A-type | 94~95 | 0.63~2.43(m,17H), 3.67(s,1H), 3.95(d,1H,J=14), 4.25(d,1H,J=14), 6.77(d,2H,J=8), 7.07(d,2H,J=8), 7.83(s,1H), 8.02(s,1H) |
| 68 | H | n-C₄H₉ | 4-Cl | N | B-type | Oily material | 0.60~2.33(m,16H), 2.90~3.20(m,1H), 3.30(s,1H), 4.22(s,2H), 6.88(d,2H,J=8), 7.12(d,2H,J=8), 7.83(s,1H), 8.02(s,1H) |
| 69 | i-C₄H₉ | H | 4-Cl | N | A-type | Oily material | 0.78(d,3H,J=6), 0.88(d,3H,J=6), 1.07~2.27(m,9H), 2.33~2.67(m,3H), 4.22(s,2H), 7.00(d,2H,J=9), 7.2(d,2H,J=9), 7.93(s,1H), 8.05(s,1H) |
| 70 | i-C₄H₉ | H | 4-Cl | CH | A-type | Oily | 0.81(d,3H,J=6), 0.88(d,3H,J=6), 1.03~2.10(m,9H), 2.26~2.70(m,2H), |

TABLE 1-continued

Azole derivatives

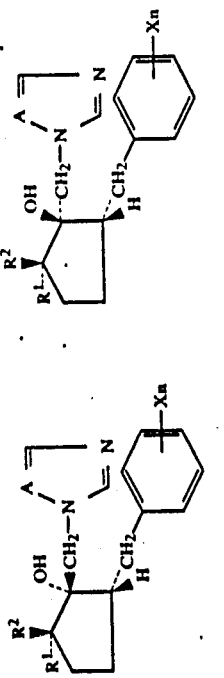

(I-A)    (I-B)

| Compound No. | Indication in Formulation (I) | | | | Indication of Stereo-isomer | Melting point (°C) | NMR Spectral data (CDCl₃, δppm) |
|---|---|---|---|---|---|---|---|
| | R¹ | R² | Xₙ | A | | | |
| 71 | n-C₄H₉ | H | 4-Cl | N | A-type | Oily material | 3.88(s,1H), 4.00(s,2H), 6.70–7.30(m,6H), 7.46(s,1H) 0.60–2.63(m,17H), 2.80(s,1H), 4.23(s,2H), 7.07(d,2H,J=8), 7.27(d,2H,J=8), 8.00(s,1H), 8.13(s,1H) |
| 72 Isomer a | CH₃ | C₂H₅ | 4-Cl | N | A-type | Mixture of 72-a & 72-b | 0.57–1.02(m,6H), 1.12–2.55(m,9H), 3.55, 3.67(2s,1H), 4.20(bs,2H), 6.95(d,2H,J=9), 7.18(d,2H,J=9) |
| Isomer b | C₂H₅ | CH₃ | 4-Cl | N | A-type | 98–101 | 7.92(s,1H), 8.12(s,1H) |
| 73 Isomer a | CH₃ | C₂H₅ | 4-Cl | N | B-type | Mixture of 73-a & 73-b | 0.67–1.05(m,6H), 1.05–3.12(m,9H), 3.77, 3.92(2s,1H), 4.35(s,2H), 6.95(d,2H,J=8), 7.18(d,2H,J=8), 7.90(s,1H), 8.15, 8.15(2s,1H) |
| Isomer b | C₂H₅ | CH₃ | 4-Cl | N | B-type | 117–119 | |
| 74 Isomer a | CH₃ | C₂H₅ | 4-Cl | CH | B-type | Mixture of 74-a & 74-b | 0.63–1.08(m,6H), 1.08–3.07(m,9H), 3.33(s,1H), 4.12(bs,2H), 6.80–7.30(m,6H), 7.70(bs,1H) |
| Isomer b | C₂H₅ | CH₃ | 4-Cl | CH | B-type | 122–127 | |
| 75 | CH₃ | CH₃ | 4-t-C₄H₉ | N | B-type | Oily material | 0.77(s,3H), 1.01(s,3H), 1.28(s,9H), 1.39–2.11(m,5H), 2.12–2.54(m,2H), 3.78(bs,1H), 4.34(s,2H), 6.95(d,2H,J=8.4), 7.20(d,2H,J=8.4), 7.88(s,1H), 8.14(s,1H) |
| 76 | CH₃ | CH₃ | 4-t-C₄H₉ | CH | B-type | 132–133 | 0.84(s,3H), 1.06(s,3H), 1.30(s,9H), 1.43–3.10(m,8H), 4.13(s,2H), 6.87(bs,1H), 7.01(d,2H,J=8.4), 7.19(bs,1H), 7.29(d,2H,J=8.4), 7.73(bs,1H) |

TABLE 2

Oxirane Derivative

Structures (II-A) and (II-B): cyclopentane with R¹, R² substituents bearing an epoxide-CH₂-phenyl-Xn group, differing in stereochemistry.

| Compound No. | R¹ | R² | Xn | Indication of Stereo-isomer | Physical property | NMR Spectral data (CDCl₃, δppm) |
|---|---|---|---|---|---|---|
| 77 | CH₃ | CH₃ | 4-Cl | A-type | Oily material | 0.83(s,3H), 0.95(s,3H), 1.33~1.73(m,4H), 2.33~2.53(m,3H), 2.52(d,1H,J=4), 2.67(d,1H,J=4), 7.03(d,2H,J=8), 7.23(d,2H,J=8) |
| 78 | CH₃ | CH₃ | 4-Cl | B-type | Oily material | 0.87(s,3H), 0.93(s,3H), 1.45~1.73(m,4H), 2.13~2.70(m,3H), 2.60(d,1H,J=4), 2.83(d,1H,J=4), 7.02(d,2H,J=8), 7.23(d,2H,J=8) |
| 79 | CH₃ | CH₃ | 4-Br | A-type | Oily material | 0.83(s,3H), 0.93(s,3H), 1.17~1.73(m,4H), 2.17~2.67(m,3H), 2.50(d,1H,J=4), 2.60(s,1H,J=4), 6.80~7.33(m,4H) |
| 80 | CH₃ | CH₃ | 4-Br | B-type | Oily material | 0.87(s,3H), 0.93(s,3H), 1.20~2.73(m,7H), 2.60(d,1H,J=4), 2.80(d,1H,J=4), 6.80~7.47(m,4H) |
| 81 | CH₃ | CH₃ | 4-F | A-type | Oily material | 0.80(s,3H), 0.90(s,3H), 1.00~2.00(m,4H), 2.00~2.67(m,5H), 6.70~7.23(m,4H) |
| 82 | CH₃ | CH₃ | 4-F | B-type | Oily material | 0.88(s,3H), 0.93(s,3H), 1.03~2.00(m,4H), 2.00~2.93(m,5H), 6.70~7.27(m,4H) |
| 83 | CH₃ | CH₃ | 2,4-Cl₂ | A-type | Oily material | 0.85(s,3H), 0.92(s,3H), 1.27~1.82(m,4H), 2.28~2.78(m,5H), 6.92~7.28(m,3H) |
| 84 | CH₃ | CH₃ | 2,4-Cl₂ | B-type | Oily material | 0.87(s,3H), 0.97(s,3H), 1.48~1.72(m,4H), 2.33~2.77(m,3H), 2.62(d,1H,J=4), 2.85(d,1H,J=4), 7.05~7.37(m,3H) |
| 85 | CH₃ | H | 4-Cl | A-type | Oily material | 0.80(d,3H,J=6), 1.14~2.51(m,6H), 2.31~2.51(b,2H), 2.63(s,2H), 7.00(d,2H,J=9), 7.19(d,2H,J=9) |
| 86 | H | CH₃ | 4-Cl | A-type | Oily material | 0.89(d,3H,J=6), 0.85~2.68(m,6H), 2.32~2.42(b,2H, 2.47(d,1H,J=4.6), 2.78(d,1H,J=4.6), 6.75~7.28(m,4H) |
| 87 | H | CH₃ | 4-Cl | B-type | Oily material | 0.81(d,3H,J=6), 0.93~3.00(m,8H), 2.54(d,1H,J=4.6), 2.79(d,1H,J=4.6), 6.80~7.33(m,4H) |
| 88 | CH₃ | H | 4-Cl | B-type | Oily material | 1.09(d,3H,J=6), 0.83~3.26(m,10H), 6.95(d,2H,J=9), 7.14(d,2H,J=9) |
| 89 | CH₃ | CH₃ | H | A-type | Oily material | 0.73~2.07(m,5H), 0.87(s,3H), 0.97(s,3H), 2.27~2.77(m,2H), 2.55(d,1H,J=4), 2.67(d,1H,J=4), 7.23(s,5H) |
| 90 | CH₃ | CH₃ | 4-CH₃ | A-type | Oily material | 0.83(s,3H), 0.97(s,3H), 1.17~1.97(m,5H), 2.17~2.77(m,2H), 2.27(s,3H), 2.55(d,1H,J=4), 2.65(d,1H,J=4), 7.00(s,4H) |
| 91 | CH₃ | CH₃ | 4-CH₃ | B-type | Oily material | 0.87(s,3H), 0.93(s,3H), 1.47~1.77(m,5H), 2.17~2.97(m,2H), 2.30(s,3H), 2.65(d,1H,J=4), 2.87(d,1H,J=4), 7.07(s,4H) |
| 92 | CH₃ | CH₃ | 2-F-4-Cl | A-type | Oily material | 0.83(s,3H), 0.93(s,3H), 1.09~2.79(m,9H), 6.83~7.15(m,3H) |
| 93 | C₂H₅ | H | 4-Cl | A-type | Oily material | 0.60~2.83(m,11H), 2.43(bs,2H), 2.65(s,2H), 6.92~7.33(m,4H) |
| 94 | H | C₂H₅ | 4-Cl | A-type | Oily material | 0.67~2.77(m,11H), 2.37(bs,2H), 2.53(d,1H,J=4), 2.85(d,1H,J=4), 6.87~7.33(m,4H) |
| 95 | H | C₂H₅ | 4-Cl | B-type | Oily material | 0.60~2.92(m,13H), 2.57(d,1H,J=4), 2.82(d,1H,J=4), 6.87~7.30(m,4H) |
| 96 | C₂H₅ | H | 4-Cl | B-type | Oily material | 0.67~2.85(m,13H), 2.75(s,2H), 6.88~7.33(m,4H) |
| 97 | C₂H₅ | C₂H₅ | 4-Cl | A-type | Oily material | 0.57~1.03(m,6H), 1.03~2.05(m,9H), 2.38(bs,2H), 2.57(d,1H,J=4), 2.67(d,1H,J=4), 6.90~7.30(m,4H) |
| 98 | C₂H₅ | C₂H₅ | 4-Cl | B-type | Oily material | 0.63~1.03(m,6H), 1.03~1.90(m,9H), 2.07~2.50(m,2H), 2.62(d,1H,J=4), 2.75(d,1H,J=4), 6.83~7.23(m,4H) |
| 99 | n-C₃H₇ | H | 4-Cl | A-type | Oily material | 0.59~1.02(m,3H), 1.02~2.29(m,10H), 2.29~2.52(m,2H), 2.68(s,2H), 7.05(d,2H,J=9), 7.25(d,2H,J=9) |
| 100 | H | n-C₃H₇ | 4-Cl | A-type | Oily material | 0.62~1.03(m,3H), 1.03~2.32(m,10H), 2.32~2.48(b,2H), 2.53(d,1H,J=4.4), 2.86(d,1H,J=4.4), 7.03(d,2H,J=9), 7.22(d,2H,J=9) |
| 101 | C₂H₅ | H | 2,4-Cl₂ | A-type | Oily material | 0.67~3.10(m,13H), 2.70(s,2H), 7.10(m,2H), 7.28(m,1H) |
| 102 | C₂H₅ | H | 4-F | A-type | Oily material | 0.65~2.50(m,13H), 2.62(s,2H), 6.60~7.24(m,4H) |
| 103 | C₂H₅ | H | 4-Br | A-type | Oily material | 0.67~2.13(m,11H), 2.42(m,2H), 2.65(s,2H), 6.98(d,2H,J=8), 7.35(d,2H,J=8) |
| 104 | C₂H₅ | H | 4-C₆H₅ | A-type | Solid mp: 69~71°C. | 0.63~2.58(m,13H), 2.66(s,2H), 7.04~7.68(m,9H) |
| 105 | C₂H₅ | H | 4-t-C₄H₉ | A-type | Oily material | 0.69~2.55(m,13H), 1.27(s,9H), 2.65(s,2H), 6.93~7.42(m,4H) |
| 106 | i-C₃H₇ | H | 4-Cl | A-type | Oily material | 0.85(d,5H,J=7), 1.00~2.83(m,9H), 2.63(s,2H), 6.90~7.33(m,4H) |
| 107 | n-C₅H₁₁ | H | 4-Cl | A-type | Oily material | 0.87(t,3H,J=6.8), 1.00~2.56(m,16H), 2.67(d,1H,J=4.4), 2.71(d,1H,J=4.4), 7.08(d,2H,J=8.3), 7.22(d,2H,J=8.3) |
| 108 | H | n-C₅H₁₁ | 4-Cl | A-type | Oily | 0.87(t,3H,J=6.8), 1.00~2.54(m,16H), 2.56(d,1H,J=4.4), |

TABLE 2-continued

Oxirane Derivative

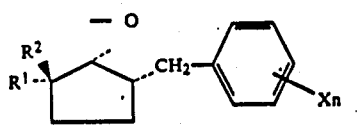 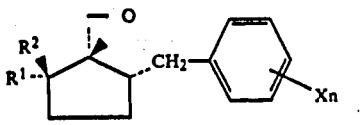

(II-A)      (II-B)

| Compound No. | Indication in formula (II) R¹ | R² | $X_n$ | Indication of Stereo-isomer | Physical property | NMR Spectral data (CDCl₃, δppm) |
|---|---|---|---|---|---|---|
| 109 | CH₃ | CH₃ | 4-t-C₄H₉ | A-type | Oily material | 2.88(d,1H,J=4.4), 7.09(d,2H,J=8.3), 7.23(d,2H,J=8.3) 0.80(s,3H), 0.94(s,3H), 1.28(s,9H), 1.41~1.96(m,4H), 2.18~ 2.48(b,3H), 2.55(d,1H,J=4.4), 2.64(d,1H,J=4.4), 7.02(d,2H,J=8), 7.18(d,2H,J=8) |
| 110 | CH₃ | CH₃ | 4-t-C₄H₉ | B-type | Oily material | 0.87(s,3H), 0.94(s,3H), 1.28(s,9H), 1.40~1.93(m,4H), 2.20~ 2.76(m,3H), 2.60(d,1H,J=4.4), 2.84(d,1H,J=4.4), 7.02(d,2H,J=8), 7.27(d,2H,J=8) |
| 111 | CH₃ | CH₃ | 4-C₆H₅ | A-type | Oily material | 0.83(s,3H), 0.92(s,3H), 1.10~2.18(m,4H), 2.47(bs,3H), 2.50(d,1H,J=4), 2.63(d,1H,J=4), 6.97~7.63(m,9H) |
| 112 | CH₃ | CH₃ | 4-C₆H₅ | B-type | Oily material | 0.85(s,3H), 0.93(s,3H), 1.20~1.97(m,4H), 1.97~2.90(m,3H), 2.57(d,1H,J=4), 2.82(d,1H,J=4), 6.97~7.58(m,9H) |
| 113 | H | i-C₃H₇ | 4-Cl | A-type | Oily material | 0.82(d,3H,J=6), 0.85(d,3H,J=6), 0.97~2.73(m,9H), 2.60(d,1H,J=4), 2.88(d,1H,J=4), 6.93~7.37(m,4H) |
| 114 | H | i-C₃H₇ | 4-Cl | B-type | Oily material | 0.67~1.03(m,6H), 1.03~2.77(m,9H), 2.50(d,1H,J=4), 2.83(d,1H,J=4), 6.90~7.33(m,4H) |
| 115 | i-C₃H₇ | H | 4-Cl | B-type | Oily material | 0.87(d,3H,J=6), 0.90(d,3H,J=6), 1.10~3.20(m,9H), 2.87(s,2H), 6.90~7.40(m,4H) |
| 116 | n-C₄H₉ | H | 4-Cl | A-type | Oily material | 0.63~2.80(m,17H), 2.67(s,2H), 6.93~7.37(m,4H) |
| 117 | H | n-C₄H₉ | 4-Cl | A-type | Oily material | 0.50~2.70(m,17H), 2.50(d,1H,J=4), 2.83(d,1H,J=4), 6.90~7:30(m,4H) |
| 118 | H | n-C₄H₉ | 4-Cl | B-type | Oily material | 0.63~2.73(m,17H), 2.53(d,1H,J=4), 2.77(d,1H,J=4), 6.80~7.23(m,4H) |
| 119 | i-C₄H₉ | H | 4-Cl | A-type | Oily material | 0.78(d,3H,J=7), 0.88(d,3H,J=7), 1.00~2.27(m,9H), 2.27~2.50(m,2H), 2.63(s,2H), 6.87~7.33(m,4H) |
| 120 Isomer a | CH₃ | C₂H₅ | 4-Cl | A-type | Mixture of 120a & 120b Oily material | 0.68~0.97(m,6H), 0.97~1.85(m,6H), 2.15~2.75(m,5H), 7.00(d,2H,J=8) 7.17(d,2H,J=8) |
| Isomer b | C₂H₅ | CH₃ | 4-Cl | A-type | | |
| 121 Isomer a | CH₃ | C₂H₅ | 4-Cl | B-type | Mixture of 121a & 121b Oily material | 0.67~1.00(m,6H), 1.00~1.90(m,6H), 2.13~2.90(m,5H), 6.97(d,2H,J=8), 7.17(d,2H,J=8) |
| Isomer b | C₂H₅ | CH₃ | 4-Cl | B-type | | |

TABLE 3

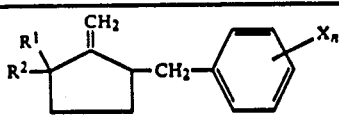

(III) (Methylenecyclopentane Derivatives)

| Compound No. | Indication in Formula (III) R¹ | R² | $X_n$ | Physical property | NMR Spectral Data (CDCl₃, δppm) |
|---|---|---|---|---|---|
| 122 | CH₃ | CH₃ | 4-Cl | Oily material | 1.03(s,3H), 1.08(s,3H), 1.28~1.85(m,4H), 2.35~3.12(m,3H), 4.75~4.95(m,2H), 7.07(d,2H,J=8), 7.27(d,2H,J=8) |
| 123 | CH₃ | CH₃ | 4-Br | Oily material | 1.00(s,3H), 1.03(s,3H), 1.13~1.77(m,5H), 2.30~3.10(m,2H), 4.63~4.08(m,2H), 6.83~7.40(m,4H) |
| 124 | CH₃ | CH₃ | 4-F | Oily material | 1.00(s,3H), 1.07(s,3H), 1.13~2.00(m,4H), 2.00~3.13(m,3H), 4.72~4.90(m,2H), 6.70~7.28(m,4H) |
| 125 | CH₃ | CH₃ | 2,4-Cl₂ | Oily material | 1.07(s, 3H × 2), 1.27~1.80(m,4H), 2.43~3.18(m,3H), 4.72~4.88(m,2H), 7.05~7.37(m,3H) |
| 126 | CH₃ | CH₃ | 4-CH₃ | Oily material | 1.03(s,3H), 1.07(s,3H), 0.66~1.90(m,5H), 2.17~3.13(m,2H), 4.83(bs,2H), 7.07(s,4H) |
| 127 | CH₃ | CH₃ | 4-t-C₄H₉ | Oily material | 1.03(s,3H), 1.08(s,3H), 1.30(s,9H), 1.36~1.86(m,4H), 2.20~3.13(m,3H), 4.76~4.93(bs,2H), 7.07(d,2H,J=8), 7.27(d,2H,J=8) |
| 128 | CH₃ | CH₃ | 4-C₆H₅ | Oily material | 1.03(s,3H), 1.10(s,3H), 1.10~1.92(m,4H), 2.17~3.17(m,3H), 4.83(bs,2H), 7.08~7.70(m,9H) |
| 129 | C₂H₅ | H | 4-Cl | Oily material | 0.93(t,3H,J=7), 1.08~3.08(m,10H), 4.76~4.93(m,2H), 6.97~7.37(m,4H) |
| 130 | i-C₃H₇ | H | 4-Cl | Oily material | 0.60(d,3H,J=8), 0.70(d,3H,J=8), 0.87~2.97(m,9H), 4.57~4.83(m,2H), 6.77~7.20(m,4H) |
| 131 | C₂H₅ | C₂H₅ | 4-Cl | Oily | 0.63~1.05(m,6H), 1.05~1.93(m,8H), 2.13~3.13(m,3H), |

TABLE 3-continued (III) (Methylenecyclopentane Derivatives)

| Compound No. | Indication in Formula (III) R¹ | R² | X$_n$ | Physical property | NMR Spectral Data (CDCl$_3$, δppm) |
|---|---|---|---|---|---|
| 132 | CH$_3$ | C$_2$H$_5$ | 4-Cl | Oily material | 4.80(dd,2H,J=12,2), 6.95~7.33(m,4H) 0.63~1.10(m,6H), 1.10~1.80(m,6H), 2.23~3.13(m,3H) 4.67~4.87(m,2H), 7.03(d,2H,J=9), 7.23(d,2H,J=9) |

TABLE 4

(IV) (Cyclopentanone Derivatives)

| Compound No. | Indication in Formula (IV) R¹ | R² | X$_n$ | Physical property | NMR Spectral Data (CDCl$_3$, δppm) |
|---|---|---|---|---|---|
| 133 | CH$_3$ | CH$_3$ | 4-Cl | Oily material BP 124° C. (1 mm Hg) | 0.83(s,3H), 1.05(s,3H), 1.52~1.83(m,4H), 2.25~3.17(m,3H), 6.97(d,2H,J=8), 7.17(d,2H,J=8) |
| 134 | CH$_3$ | CH$_3$ | 4-Br | Oily material BP 131~2° C. (0.7 mm Hg) | 0.87(s,3H), 1.07(s,3H), 1.17~3.27(m,7H), 6.83~7.53(m,4H) |
| 135 | CH$_3$ | CH$_3$ | 4-F | Oily material BP 95~8° C. (0.7 mm Hg) | 0.85(s,3H), 1.07(s,3H), 1.20~3.23(m,7H), 6.73~7.27(m,4H) |
| 136 | CH$_3$ | CH$_3$ | 2,4-Cl$_2$ | Oily material BP 142~6° C. (1.5 mm Hg) | 0.90(s,3H), 1.05(s,3H), 1.3~2.07(m,4H), 2.23~3.40(m,3H), 7.0~7.32(m,3H) |
| 137 | CH$_3$ | H | 4-Cl | Oily material BP 120~145° C. (3 mm Hg) | 0.97, 1.08(2d,3H,J=7,J=6), 1.20~3.27(m,8H), 7.03(d,2H,J=7), 7.19(d,2H,J=7) |
| 138 | CH$_3$ | CH$_3$ | H | Oily material BP 93~94° C. (0.3 mm Hg) | 0.87(s,3H), 1.03(s,3H), 0.83~3.23(m,7H), 7.07(s,5H) |
| 139 | CH$_3$ | CH$_3$ | 4-CH$_3$ | Oily material | 0.87(s,3H), 1.07(s,3H), 1.20~3.20(m,7H), 2.27(s,3H), 7.70(s,4H) |
| 140 | CH$_3$ | CH$_3$ | 2-F-4-Cl | Oily material BP 102~104° C. (0.3 mm Hg) | 0.89(s,3H), 1.05(s,3H), 1.32~3.49(m,7H), 6.83~7.21(m,3H) |
| 141 | CH$_3$ | CH$_3$ | 4-t-C$_4$H$_9$ | Oily material BP 132~140° C. (1.0 mm Hg) | 0.86(s,3H), 1.04(s,3H), 1.26(s,9H), 1.37~3.21(m,7H), 6.95(d,2H,J=8.4), 7.18(d,2H,J=8.4) |
| 142 | CH$_3$ | CH$_3$ | 4-C$_6$H$_5$ | Solid MP 63~66° C. | 0.87(s,3H), 1.03(s,3H), 1.17~3.40(m,7H), 7.00~7.67(m,9H) |
| 143 | C$_2$H$_5$ | H | 4-Cl | Oily material BP 135~145° C. (0.65 mm Hg) | 0.89(t,3H,J=7), 1.10~3.28(m,10H), 7.05(d,2H,J=9), 7.27(d,2H,J=9) |
| 144 | C$_2$H$_5$ | H | 4-F | Oily material BP 102~108° C. (0.2 mm Hg) | 0.70~1.10(m,3H), 1.20~3.28(m,10H), 6.70~7.25(m,4H) |
| 145 | C$_2$H$_5$ | H | 4-Br | Oily material BP 126~128° C. (0.5 mm Hg) | 0.87(t,3H,J=7), 1.10~3.40(m,10H), 6.97(d,2H,J=8), 7.32(d,2H,J=8) |
| 146 | C$_2$H$_5$ | H | 2,4-Cl$_2$ | Oily material BP 178~179° C. (4 mm Hg) | 0.90(t,3H,J=7), 1.10~3.60(m,10H), 7.13~7.30(m,3H) |
| 147 | C$_2$H$_5$ | H | 4-t-C$_4$H$_9$ | Oily material BP 132° C. (0.5 mm Hg) | 0.87(t,3H,J=7), 1.00~3.30(m,10H), 6.87~7.43(m,4H) |
| 148 | C$_2$H$_5$ | H | 4-C$_6$H$_5$ | Solid MP 72~75° C. | 0.70~1.07(m,3H), 1.13~3.30(m,10H), 6.98~7.65(m,9H) |
| 149 | n-C$_3$H$_7$ | H | 4-Cl | Oily material BP 150~160° C. (3 mm Hg) | 0.66~1.08(m,3H), 1.08~3.26(m,12H), 7.04(d,2H,J=9), 7.24(d,2H,J=9) |
| 150 | i-C$_3$H$_7$ | H | 4-Cl | Oily material BP 143~149° C. (1.2 mm Hg) | 0.60~1.07(m,6H), 1.07~3.27(m,9H), 6.83~7.27(m,4H) |
| 151 | n-C$_4$H$_9$ | H | 4-Cl | Oily material BP 146~149° C. (0.6 mm Hg) | 0.87(t,3H,J=7.0), 1.03~3.28(m,14H), 7.02(d,2H,J=9.0), 7.25(d,2H,J=9.0) |
| 152 | n-C$_5$H$_{11}$ | H | 4-Cl | Oily material BP 135~137° C. (0.06 mm Hg) | 0.87(t,3H,J=7.0), 1.10~2.50(m,14H), 2.53~3.10(m,2H), 7.08(d,2H,J=8.3), 7.24(d,2H,J=8.3) |
| 153 | C$_2$H$_5$ | C$_2$H$_5$ | 4-Cl | Oily material | 0.57~1.07(m,6H), 1.07~3.27(m,11H), 6.95~7.37(m,4H) |

TABLE 4-continued

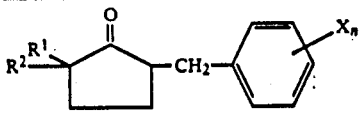

(IV) (Cyclopentanone Derivatives)

| Compound No. | Indication in Formula (IV) | | | Physical property | NMR Spectral Data (CDCl₃, δppm) |
|---|---|---|---|---|---|
| | R¹ | R² | Xₙ | | |
| 154 | i-C₄H₉ | H | 4-Cl | Oily material BP 130~136° C. (0.3 mm Hg) | 0.85(d,3H,J=6), 0.90(d,3H,J=6), 1.10~3.33(m,11H), 7.00(d,2H,J=9), 7.21(d,2H,J=9) |
| 155 | CH₃ | C₂H₅ | 4-Cl | Oily material BP 123~130° C. (0.2 mm Hg) | 0.57~1.07(m,6H), 1.17~3.23(m,9H), 7.00(d,2H,J=9), 7.20(d,2H,J=9) |

TABLE 5

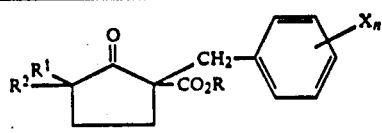

(IV) (Ester Derivatives of Cyclopentanecarboxylic acid)

| Compound No. | Indication in Formula (V) | | | | Physical property | NMR Spectral Data (CDCl₃, δppm) |
|---|---|---|---|---|---|---|
| | R¹ | R² | Xₙ | R | | |
| 156 | CH₃ | CH₃ | 4-Cl | CH₃ | Oily material BP 142~143° C. (0.7 mm Hg) | 0.72(s,3H), 1.05(s,3H), 1.37~2.40(m,4H), 3.13(s,2H), 3.70(s,3H), 7.07(d,2H,J=9), 7.27(d,2H,J=9) |
| 157 | CH₃ | CH₃ | 4-Br | CH₃ | Oily material | 0.70(s,3H), 1.03(s,3H), 1.25~2.43(m,4H), 3.07(s,2H), 3.63(s,3H), 6.80~7.53(m,4H) |
| 158 | CH₃ | CH₃ | 4-F | CH₃ | Oily material | 0.70(s,3H), 1.08(s,3H), 1.20~2.57(m,4H), 3.13(s,2H), 3.67(s,3H), 6.73~7.37(m,4H) |
| 159 | CH₃ | CH₃ | 2,4-Cl₂ | CH₃ | Oily material BP 130~133° C. (0.60 mm Hg) | 0.70(s,3H), 1.05(s,3H), 1.20~2.45(m,4H), 3.10(s,2H), 3.65(s,3H), 7.05~7.30(m,3H) |
| 160 | CH₃ | H | 4-Cl | CH₃ | Oily material BP 142~145° C. (0.1 mm Hg) | 0.83~1.12(m,3H), 1.40~2.63(m,5H), 3.12, 3.15(2s,2H), 3.70(s,3H), 7.07(d,2H,J=8), 7.27(d,2H,J=8) |
| 161 | CH₃ | CH₃ | H | CH₃ | Oily material | 0.67(s,3H), 1.03(s,3H), 0.77~3.23(m,4H), 3.10(s,2H), 3.63(s,3H), 7.07(s,5H) |
| 162 | CH₃ | CH₃ | 4-CH₃ | CH₃ | Oily material | 0.70(s,3H), 1.03(s,3H), 1.13~2.40(m,4H), 2.27(s,3H), 3.07(s,2H), 3.67(s,3H), 6.97(s,4H) |
| 163 | CH₃ | CH₃ | 2-F-4-Cl | CH₃ | Oily material | 0.79(s,3H), 1.09(s,3H), 1.18~2.61(m,4H), 3.00(d,1H,J=14), 3.33(d,1H,J=14), 3.70(s,3H), 6.89~7.32(m,3H) |
| 164 | CH₃ | CH₃ | 4-t-C₄H₉ | CH₃ | Oily material | 0.68(s,3H), 1.05(s,3H), 1.26(s,9H), 1.32~2.62(m,4H), 3.10(bs,2H), 3.68(s,3H), 7.01(d,2H,J=8.6), 7.26(d,2H,J=8.6) |
| 165 | CH₃ | CH₃ | 4-C₆H₅ | CH₃ | Solid mp. 95~98° C. | 0.75(s,3H), 1.05(s,3H), 1.13~2.88(m,4H), 3.13(s,2H), 3.62(s,3H), 6.95~7.62(m,9H) |
| 166 | C₂H₅ | H | 4-Cl | C₂H₅ | Oily material BP 152~160° C. (0.45 mm Hg) | 0.67~1.03(m,3H), 1.20(t,3H,J=7), 1.45~2.53(m,9H), 3.03, 3.08(2s,2H), 4.10(q,2H,J=7), 6.98(d,2H,J=9), 7.20(d,2H,J=7) |
| 167 | C₂H₅ | H | 4-F | CH₃ | Oily material BP 144~154° C. (3.0 mm Hg) | 0.63~1.10(m,3H), 1.21~2.68(m,7H), 3.07, 3.11(2s,2H), 3.66(s,3H), 6.70~7.22(m,4H) |
| 168 | C₂H₅ | H | 4-Br | CH₃ | Oily material BP 149~151° C. (0.5 mm Hg) | 0.60~2.90(m,10H), 3.07, 3.12(2s,2H), 3.67(s,3H), 7.06(d,2H,J=8.0), 7.42(d,2H,J=8.0) |
| 169 | C₂H₅ | H | 2,4-Cl₂ | CH₃ | Oily material BP 143° C. (0.5 mm Hg) | 0.67~2.82(m,10H), 3.10(d,0.4H,J=14), 3.15(d,0.6H,J=16), 3.45(d,0.4H,J=14), 3.50(d,0.6H,J=14), 3.68(s,3H), 7.08(m,2H), 7.30(m,1H) |
| 170 | C₂H₅ | H | 4-t-C₄H₉ | CH₃ | Oily material BP 152~156° C. (0.2 mm Hg) | 0.72~2.52(m,10H), 1.27(s,9H), 3.09(bs,2H), 3.65(s,3H), 6.79~7.39(m,4H) |
| 171 | C₂H₅ | H | 4-C₆H₅ | CH₃ | Solid mp. 52~54° C. | 0.61~1.10(m,3H), 1.45~2.50(m,7H), 3.11, 3.16(2s,2H), 3.66(s,3H), 6.96~7.61(m,9H) |
| 172 | n-C₃H₇ | H | 4-Cl | C₂H₅ | Oily material | 0.54~1.08(m,3H), 1.22(t,3H,J=7.4), 1.08~2.61(m,9H), 3.08, 3.13(2s,2H), 4.15(q,2H,J=7.4), 7.06(d,2H,J=9.8), 7.27(d,2H,J=9.8) |
| 173 | n-C₄H₉ | H | 4-Cl | CH₃ | Oily material BP 160~172° C. (0.3 mm Hg) | 0.85(t,3H), 0.97~2.12(m,11H), 3.03, 3.03, 3.08(2s,2H), 3.62(s,3H), 6.92(d,2H,J=8), 7.13(d,2H,J=8) |
| 174 | n-C₅H₁₁ | H | 4-Cl | CH₃ | Oily material BP 185~186° C. (0.25 mm Hg) | 0.86(t,3H), 0.98~2.32(m,13H), 3.05~3.16(m,2H), 3.69, 3.71(2s,2H), 7.04(d,2H,J=8.3), 7.22(d,2H,J=8.3) |
| 175 | C₂H₅ | C₂H₅ | 4-Cl | CH₃ | Oily material | 0.50~2.63(m,14H), 2.90(d,1H,J=14), 3.27(d,1H,J=14), 3.67(s,3H), 6.93~7.37(m,4H) |
| 176 | i-C₃H₇ | H | 4-Cl | CH₃ | Oily material | 0.58~1.10(m,6H), 1.10~3.01(m,6H), 3.08, 3.12(2s,2H), 3.71(s,3H), |

TABLE 5-continued

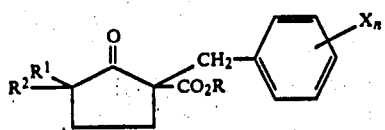

(IV) (Ester Derivatives of Cyclopentanecarboxylic acid)

| Compound No. | Indication in Formula (V) | | | | Physical property | NMR Spectral Data (CDCl$_3$, δppm) |
|---|---|---|---|---|---|---|
| | R$^1$ | R$^2$ | X$_n$ | R | | |
| 177 | i-C$_4$H$_9$ | H | 4-Cl | CH$_3$ | Oily material | 6.84~7.30(m,4H)<br>0.82(d,3H,J=6), 0.89(d,3H,J=6),<br>1.04~3.00(m,8H), 3.07, 3.11(2s,2H), 3.69(s,3H), |
| 178 | CH$_3$ | C$_2$H$_5$ | 4-Cl | CH$_3$ | Oily material<br>BP 145~155° C.<br>(0.6 mm Hg) | 6.77~7.30(m,4H)<br>0.58~1.17(m,6H), 1.17~2.87(m,6H),<br>3.05, 3.12(2s,2H), 3.70(s,3H),<br>7.03(d,2H,J=9), 7.25(d,2H,J=9) |

The NMR spectra of compounds in the Table 1 to 5 are measured by using TMS as internal standard. The notations are as follows.
s—singlet,
d—doublet,
t—triplet,
q—quartet,
m—multiplet,
b—broad line,
j—coupling constant (unit, Hz).

Figure 76:
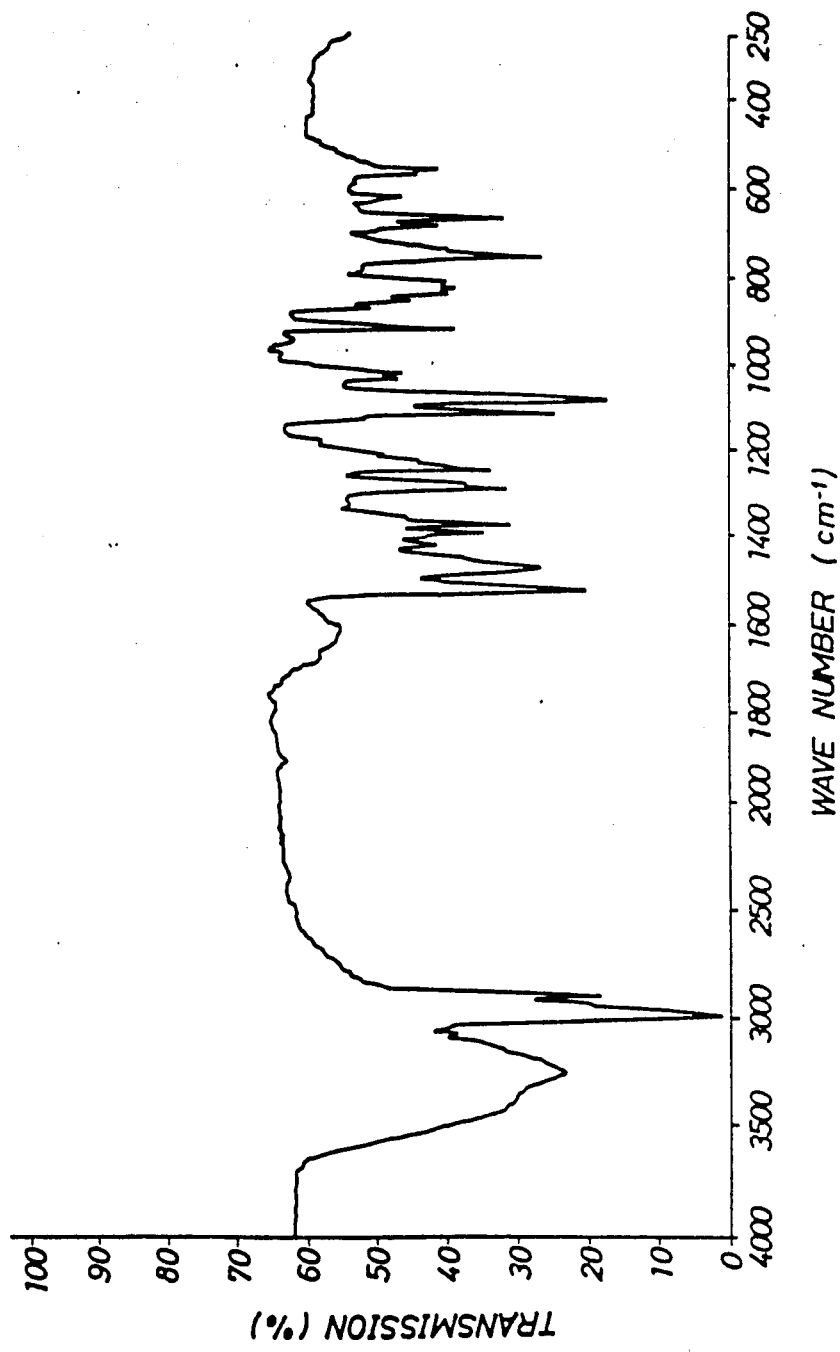

The infrared absorption spectrum of each of the azole derivatives exemplified in Table 1 is shown in each of the attached FIGS. 1 to 76.

In the azole derivative represented by the formula (I), according to the view points of the plant diseases controlling activity and the plant growth regulating activity, an azole derivative wherein R$^1$ is a hydrogen atom or a (C$_1$-C$_4$)alkyl; R$^2$ is a hydrogen atom or a (C$_1$-C$_3$)alkyl (both R$^1$ and R$^2$ do not represent hydrogen atoms at the same time); X is a halogen atom substituting the 4-position of the benzene ring; n is 1 and A is represented by a nitrogen atom or a CH is preferable, and furthermore, an azole derivative wherein R$^1$ and R$^2$ respectively represent a hydrogen atom or a (C$_1$-C$_3$)alkyl group (both R$^1$ and R$^2$ do not represent hydrogen atoms at the same time); X represents a halogen atom substituting the 4-position of the benzene ring; n is represented by 1 and A is represented by a nitrogen atom is particularly preferable.

Of the compounds exemplified in Table 1, those azole derivatives of Compound Nos. 1-3, 5, 9-11, 16, 18, 29-32, 37, 38, 42-45, 50, 59, 62, 63, 65 and 69 are preferable.

The azole derivative according to the present invention is produced by the following process.

The objective azole derivative represented by the formula (I) can be obtained by reacting the oxirane derivative represented by the formula (II) with a 1,2,4-triazole or imidazole represented by the following formula (VI) in the presence of a diluent:

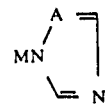

(VI)

wherein M represents a hydrogen atom or an alkali metal atom and A represents a nitrogen atom or a CH.

The oxirane derivative represented by the formula (II), which is used as the starting substance can be obtained by the following process.

Namely, by reacting the cyclopentanone represented by the formula (IV) with sulfonium ylide or oxosulfonium ylide, for instance, dimethyloxosulfonium methylide or dimethylsulfonium methylide in the presence of a diluent while following the methods described in Org. Syn. 49, 78 (1968) and in J. Amer. Chem. Soc., (1965) 1353, the oxirane derivative represented by the formula (II) is obtained (this method is referred to as A-method).

Still more, as a different method (referred to as B-method), there is a method by which a methylenecyclopentane represented by the formula (III) is obtained from a cyclopentanone represented by the formula (IV) through the Wittig reaction [refer to Org. Syn. 40, 66 (1966) and J. Org. Chem. 28, 1128 (1963)], and then the oxirane derivative represented by the formula (II) can be obtained from the thus prepared compound by the epoxidation [refer to Org. Syn. Coll. vol., 4, 552 (1963), 49, 62 (1969)].

The reaction formulae according to the abovementioned A-method and B-method are shown below.

Methods for producing the oxirane derivative represented by the formula (II)

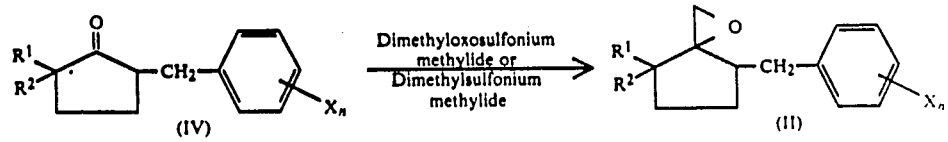

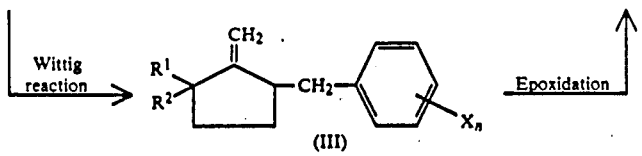

Still more, the cyclopentanone derivative represented by the formula (IV) can be obtained by the following method:

Namely, in the case where both $R^1$ and $R^2$ of the formula (IV) are the same $(C_1-C_5)$alkyl groups, a cyclopentanone compound represented by the formula (VII) is subjected to dialkylation, thereby converting into the ester derivative of cyclopentanecarboxylic acid represented by the formula (V) and the ester derivative represented by the formula (V) is subjected to hydrolysis and decarboxylation, and in the case where any one of $R^1$ and $R^2$ is a $(C_1-C_5)$alkyl group and the other one is a hydrogen atom, a desired benzyl group is introduced into the alkylcyclopentane carboxylate derivative represented by the formula (VIII) to obtain the ester derivative of cyclopentanecarboxylic acid represented by the formula (V) and then the thus obtained ester derivative is subjected to hydrolysis and decarboxylation. By doing so, the cyclopentanone derivative represented by the formula (IV) can be obtained.

Further, in the case where $R^1$ and $R^2$ of the formula (IV) are the mutually different $(C_1-C_5)$alkyl groups, after introducing a different $(C_1-C_5)$alkyl group into an ester derivative of cyclopentanecarboxylic acid represented by formula (V) in which either of $R^1$ or $R^2$ is a $(C_1-C_5)$alkyl group and the other (remainder) is a hydrogen atom, the obtained ester derivative is subjected to hydrolysis and decarboxylation, thereby obtaining the desired derivative represented by the formula (IV).

The reaction form of the above-mentioned cyclopentanone is shown below.

Synthetic route of cyclopentanone of the formula (IV)

bons such as benzene, toluene, xylene, etc.; halogenohydrocarbons such as methylene chloride, chloroform, carbon tetrachloride, etc.; alcohols such as methanol, ethanol, etc.; ethers such as diethyl ether, diisopropyl ether, tetrahydrofurane, dioxane, etc. and as the others, acetonitrile, acetone, dimethylformamide, dimethylsulfoxide, etc. may be exemplified.

Still more, in the process for producing the azole derivative according to the present invention, the reaction is carried out in the coexistence of a base or an acid in addition to the above-mentioned diluent. As the base used herein, alkali metal carbonates such as sodium carbonate, potassium carbonate, etc.; alkali metal hydroxides such as sodium hydroxide, potassium hydroxide, etc.; alkali metal alcoholates such as sodium methylate, sodium ethylate, potassium tertiarybutylate, etc.; alkali metal hydrides such as sodium hydride, potassium hydride, etc.; alkyl compounds of an alkali metal such as n-butyl lithium, etc. and as the others, triethylamine, pyridine may be exemplified.

As the acid, inorganic acids such as hydrochloric acid, hydrobromic acid, hydroiodic acid, sulfuric acid, etc. and organic acids such as formic acid, acetic acid, butyric acid, p-toluenesulfonic acid, etc. may be exemplified.

In order to enforce the process for production of the azole derivative according to the present invention, for instance, in the case of obtaining the ester derivative of cyclopentanecarboxylic acid represented by the formula (V), it is preferable to react a halogenated alkyl or a substituted benzyl halide with the compound represented by the formula (VII) or the formula (VIII) which has been dissolved in the diluent, in the presence of the base as occasion demands. The reaction temperature

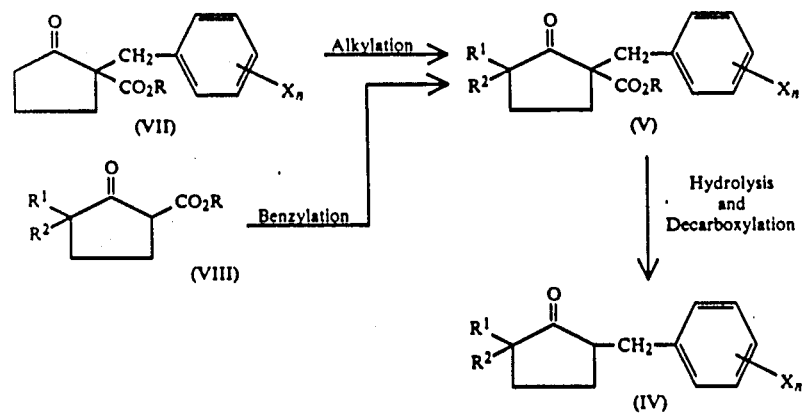

By the way, the compounds shown in the formulae (VII) and (VIII) are known and can be obtained from an alkyl ester of 2-oxocyclopentanecarboxylic acid by the method described in *Org. Syn.* 45, 7 (1965) and *J. Org. Chem.* 29, 2781 (1964).

As the diluent used in reactions in the process of producing the azole derivative represented by the formula (I) according to the present invention, hydrocarmay be selected optionally in the range of from the solidifying temperature of the diluent as the solvent to the boiling point thereof, preferably from 0 to 100° C.

The derivative represented by the formula (IV) can be obtained by subjecting the ester derivative of cyclopentanecarboxylic acid represented by the formula (V) to decarboxylation at a temperature of from 80 to 150° C. with the inorganic acid or organic acid for from 2 to 24 hours, preferably under agitation.

In order to produce the oxirane derivative represented by the formula (II), in the case of applying the A-method, it is preferable to add a solution prepared by dissolving a ketone represented by the formula (IV) in the diluent (particularly, dimethylsulfoxide is preferable) to dimethyloxosulfonium methylide or dimethylsulfonium methylide prepared by equivalently mixing the base (for instance, sodium hydride) and trimethyloxosulfonium iodide or trimethylsulfonium iodide, and to react the two compounds.

In this case, the reaction amount of dimethyloxosulfonium methylide or dimethylsulfonium methylide is preferably from 1.0 to 2.0 equivalent amount of the cyclopentanone derivative represented by the formula (IV). The reaction is preferably carried out at a temperature in the range of from 25 to 100° C. for from 1 to 40 hours.

On the other hand, in the case where the production is carried out by the B-method, the cyclopentanone derivative represented by the formula (IV) is added to triphenylphosphine methylide (Wittig reagent) prepared by equivalently mixing the base (for instance, sodium hydride), and methyltriphenylphosphonium halide in the diluent (particularly, dimethylsulfoxide is preferable), and to react the two compounds for from 2 to 10 hours at a temperature of from 0 to 100° C. The thus formed methylenecyclopentanone derivative represented by the formula (III) is isolated, dissolved in the diluent and reacted at a temperature of from −10° C. to the boiling point of the diluent, preferably from −10 to 80° C. after adding hydrogen peroxide or an organic per- acid such as peracetic acid, perbenzoic acid, m-chloroperbenzoic acid, The oxirane compound (II) obtained from the cyclopentanone derivative represented by the formula (IV) by the A-method or B-method takes the following stereoisomeric structures concerning the conformation of the oxirane group at the 3-position and the substituted benzyl group at the 7-position in the 1-oxaspiro[2,4]heptane of the oxirane compound represented by the formula (II):

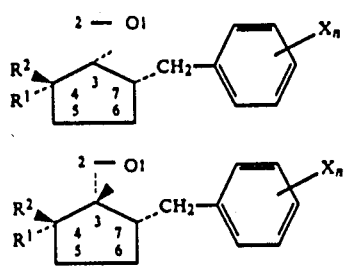

The separation of these stereoisomers represented by the formulae (II-A) and (II-B) can be carried out by, for instance, chromatography (thin-layer chromatography, column chromatography, high performance liquid chromatography, etc.). The characteristics of the structure of these stereoisomers can be found by, for instance, NMR spectrum.

In order to obtain the azole derivative represented by the formula (I), the oxirane compound represented by the formula (II) is added in the presence of the base as occasion demands, to a solution prepared by dissolving the azole compound represented by the formula (VI) into the diluent, or conversely, an alkali metal salt of the azole compound is added to a solution prepared by dissolving the oxirane compound in the diluent, to react the two compounds. The reaction temperature may be selected optionally in the range of from the solidifying point to the boiling point of the diluent, however, practically, it is preferable to carry out the reaction at a temperature of from 0 to 120° C., more preferably from 60 to 120° C. for from one to 10 hours under agitation.

After finishing the reaction, the thus obtained reaction mixture is cooled and extracted by an organic solvent such as ethyl acetate, chloroform, methylene chloride, benzene, etc. in a iced water. After separating the organic layer, washing it with water and drying the washed layer, the solvent is distilled off under a reduced pressure from the organic layer. By subjecting the thus obtained residue to purification treatment, the objective compound can be obtained. The purification treatment can be carried out by subjecting the residue to recrystallization, silica gel-chromatography, etc.

Because of the existence of the two isomers represented by the formulae (II-A) and (II-B) in the oxirane compound which is the starting compound of the azole derivative represented by the formula (I), there are the following stereoisomers in the objective azole derivative represented by the formula (I) which is obtained by the reaction of the oxirane compound represented by the formula (II) and 1,2,4-triazole or imidazole represented by the formula (VI):

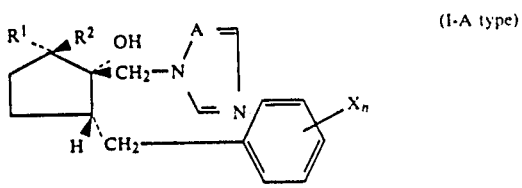

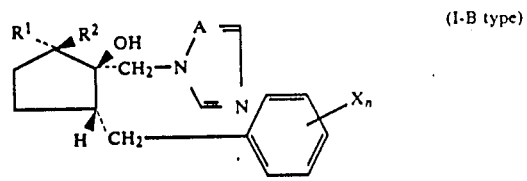

- - - - - - - = in the back of the depicted plane,
─────── = on the depicted plane, ━━━━━ = in front of the depicted plane.

Of course, the separation of the isomers represented by the formulae (I-A) and (I-B) can be carried out by, for instance, chromatography.

The utility of the azole derivative (azolylcyclopentanol derivative) represented by the formula (I) according to the present invention as an active ingredient of the agricultural and horticultural composition will be explained.

(1) Fungicidal action to plant disease fungi

The azole derivative according to the present invention shows the controlling effect against the following plant diseases in a broad range.
Pyricularia oryzae on rice plant,
Cochliobolus miyabeanus on rice plant,
Xanthomonas oryzae on rice plant,
Rhizoctonia solani on rice plant,
Helminthosporium sigmoideum on rice plant,

*Gibberella fujikuroi* on rice plant,
*Podosphaera leucotricha* on apple,
*Venturia inaequalis* on apple,
*Sclerotinia mali* on apple,
*Alternaria mali* on apple,
*Valsa mali* on apple,
*Alternaria kikuchiana* on pear,
*Phyllactinia pyri* on pear,
*Gymnosoorangium haraeonum* on pear,
*Venturia nashicola* on pear,
*Unccinula necator* on grape,
*Phakospora ampelopsidis* on grape,
*Glomerella cingulata* on grape,
*Erysiphe graminis* f. sp. *hordei* on barley,
*Rhynchosporium secalis* on barley,
*Puccinia graminis* on barley,
*Puccinia triformis* on barley,
*Puccinia recondita* on wheat,
*Septoria tritici* on wheat,
*Puccinia triformis* on wheat,
*Erysiphe graminis* f. sp. *tritici* on wheat,
*Sphaerotheca fuliginea* on melons,
*Colletotrichum lagenarium* on melons,
*Fusarium oxysporum* on watermelon,
*Fusarium oxysporum* f. *cucumerinum* on cucumber,
*Fusarium oxysporum* f. *raphani* on Japanese radish,
*Erysiphe cichoracearum* on tomato,
*Alternaria solani* on tomato,
*Erysiphe cichoracearum* on egg plant,
*Sephaerotheca humuli* on strawberry,
*Erysiphe cichoracearum* on tobacco,
*Alternaria longipes* on tobacco,
*Cercospora beticola* on sugar beet,
*Alternaria solani* on potato,
*Septoria glycines* on soybean,
*Cercospora kikuchii* on soybean,
*Sclerotinia cinerea* on stone fruit trees,
*Botrytis cinerea* on various crops,
*Sclerotinia sclerotiorum*, etc.

Furthermore, the azole derivative according to the present invention takes not only the prophylactic controlling effect but also the therapeutic effect on a few diseases among the plant diseases.

(2) Plant growth regulating action

Accompanying with the elucidation of the mechanism of the plant growth regulation by plant hormones, the chemicals which are called as the plant growth regulating agent have come to be used in the production field of agriculture and horticulture in recent years.

For instance, production of seedless grapes by gibberellin, promotion of rooting of cuttings by α-naphthaleneacetic acid and utilization of 2-chloroethyltrimethylammonium chloride (trade name of CCC) as a growth retardant for wheat have been known.

Besides, the application of the regulating technique of the plant life circle by using the plant growth regulating agent has been enlarged not only to crop plants such as cereals, vegetables, fruit trees, etc. but also to horticultural plants such as flowers, etc. and further to trees as the plants in a broad range, and the function of the plant growth regulating agent has a possibility of cover the promotion of rooting, control of blooming, fruit bearing, enlargement of fruits, growth promotion, growth control and control of metabolism.

Accordingly, both the kinds and the amount of use of the plant growth regulating agent have shown the increasing tendency in recent years, however, it is the actual state that the practical use of the plant growth regulating agent has not been promoted so much as is expected.

The azole derivative (azolylcyclopentanol derivative) according to the present invention has a specific property of showing the diverse plant growth regulating activity on plants in a broad range, which will be exemplified as follows.

i) Inhibition of vegetative grow of plants, particularly the growth inhibition of the height of plants, ii) Increasing activity of the content of the useful component of plants, and iii) Controlling activity of the ripe timing and the flowering timing of plants.

As the example of utilizing the growth inhibiting activity of i), the growth inhibition of weeds (herbicidal function) and turf; the prevention of falling-down of the easily falling plants such as rice plant, barley, wheat, etc.; the application of the mechanical-yield method of soybean and cotton flower by inhibiting the height thereof; the inhibition of the germination of auxillary buds for the growth promotion of the leaves of tobacco; the alleviation of the pruning operation by the growth inhibition of hedges; the improvement of the commercial value of the appreciation plants by growth retardation thereof, etc. may be mentioned.

As the example of utilizing the increasing activity of the content of the useful component of plants of ii), the improvement of the quality of sugar beet, sugar cane and citrus fruits by the increase of sugar; the improvement of the quality of cereals and soybean by the increase of protein, etc. may be mentioned, and further, as the example of utilizing the controlling activity concerning the ripe timing of the fruits and flowering timing of iii), the appropriation of the shipment of the fresh fruits and live flowers while complying with the demanding season, etc. may be mentioned.

In order to apply the azole derivative represented by the formula (I) as the fungicide and plant growth regulating agent, the derivative itself or a mixture of the derivative and a carrier (diluent) is processed into powders, wettable powders, granules, emulsifiable concentrate, liquid preparations, etc. and the thus prepared preparations can be advantageously used.

Still more, it is also possible, of course, to make sure of the effect by adding adjuvants such as spreaders, emulsifiers, wetting agents, sticking agents other than the carrier as occasion demands.

By the way, since the azole derivative represented by the formula (I) contains a 1,2,4-triazole ring or an imidazole ring, the azole derivative can be used as the form of an acid addition salt with an inorganic acid or organic acid, or as the form of a metal complex.

Still more, since in the azole derivative represented by the formula (I) according to the present invention, an azolylmethyl group, a ($C_1$–$C_5$)alkyl group and a substituted benzyl group are respectively contained at the 1-position, the 2-position and the 5-position of the cyclopentane ring, the stereoisomers such as geometrical isomers of cis and trans and optical isomers can exist, and the present invention includes each of the isomers and the mixtures of each isomer in an optional ratio.

Accordingly, it is to be recognized that the agricultural and horticultural composition according to the present invention includes those containing the single isomer or the mixture of the isomers as the active ingredient.

The azole derivative represented by the formula (I) according to the present invention is excellent the plant diseases controlling activity and the plant growth regulating activity, and is a useful compound as the active ingredient of the agricultural and horticultural composition.

The effectiveness of the present invention will be explained while showing the concrete examples of the agricultural and horticultural composition utilizing the azole derivative according to the present invention as the active ingredient, however, the present invention is not limited to the following examples so far as not coming over the essential features thereof.

[I] The examples of production of the azole derivative represented by the formula (I) and of each of the intermediates for producing the azole derivative represented by the formula (I).

EXAMPLE 1

Production of methyl 1-(4-chlorobenzyl)-3,3-dimethyl-2-oxocyclopentanecarboxylate (the intermediate compound No. 156 shown in Table 5)

Into 150 ml of anhydrous benzene, 5.0 g of sodium hydride (prepared by washing 60 % oily sodium hydride with anhydrous benzene) were added while stirring under a helium atmosphere, and 50 g of methyl 1-(4-chlorobenzyl)-2-oxocylopentanecarboxylate were added to the mixture, and the whole mixture was stirred for 40 min at 80° C. After cooling the reaction mixture to room temperature, 29.4 g of methyl iodide were dropped into the reaction mixture and the thus formed mixture was stirred for 2 hours at 80° C. After cooling the reaction mixture to room temperature, 5.0 g of sodium hydride (one equivalent) were added to the reaction mixture and the reaction mixture was stirred for 30 min at 80° C. After cooling the reaction mixture again to room temperature, 29.4 g of methyl iodide (one equivalent) were added to the reaction mixture and the reaction mixture was stirred for 8 hours at 80° C.

After leaving the thus obtained reaction mixture to cooling, the reaction mixture was poured into a mixture of acetic acid and iced water, and the whole mixture was extracted by ethyl acetate to obtain an organic layer. After washing the thus obtained organic layer with an aqueous solution of sodium hydrogen carbonate and then with a saline solution, the thus washed organic layer was dried on anhydrous sodium sulfate and the solvent in the organic layer was distilled off under a reduced pressure.

By subjecting the thus obtained residue to distillation under a reduced pressure and to purification, 44.8 g of the objective compound [boiling point: 142–143° C. (0.7 mmHg)] were obtained.

EXAMPLE 2

Production of 5-(4-chlorobenzyl)-2,2-dimethyl-1-cyclopentanone(the intermediate compound No. 133 shown in Table 4

Into 120 ml of 47 % hydrobromic acid, 44.8 g of methyl 1-(4-chlorobenzyl)-3,3-dimethyl-2-oxocyclopentanecarboxylate (the compound No. 156 shown in Table 5) were added, and the thus formed mixture was vigorously stirred for 12 hours at 100° C.

After leaving the thus obtained reaction mixture to cooling, the reaction mixture was poured into iced water and the mixture was extracted with ethyl acetate to obtain an organic layer. After washing the organic layer with an aqueous solution of sodium hydrogen carbonate and then with an aqueous saline solution, the organic layer was dried on anhydrous sodium sulfate. By distilling the solvent off from the organic layer under a reduced pressure, a residue was obtained. By subjecting the thus obtained residue to distillation under a reduced pressure and to purification, 31 g of the objective compound [boiling point: 124° C. (1 mmHg)] were obtained.

EXAMPLE 3

Production of 5-(4-chlorobenzyl)-2,2-dimethyl-1-methylenecyclopentane (the intermediate compound No. 122 shown in Table 3

Into 50 ml of anhydrous dimethylsulfoxide, 3.6 g of sodium hydride (prepared by washing 60 % oily sodium hydride with anhydrous benzene) were added under a helium atmosphere, and the thus formed mixture was stirred for 30 min at 70° C. After cooling the reaction mixture with iced water, 53.6 g of methyltriphenyl phosphonium bromide were added to the reaction mixture, and the thus formed mixture was stirred for 30 min under cooling with iced water and then, the thus cooled mixture was stirred for 10 min at room temperature. Then, 23.6 g of 5-(4-chlorobenzyl)-2,2-dimethyl-1-cyclopentanone (the compound No. 133 shown in Table 4) were added to the mixture, and the whole mixture was stirred for one hour at room temperature and then for 30 min at 70° C. to complete the reaction.

After leaving the reaction mixture to cooling, the reaction mixture was poured into iced water and was extracted with ethyl acetate to obtain an organic layer. After washing the thus obtained organic layer with an aqueous saline solution, the thus washed organic layer was dried on anhydrous sodium sulfate, and the solvent was distilled off from the thus dried organic layer under a reduced pressure.

From the thus obtained mixture of an oily material and a solid material, the oily material was extracted with n-hexane, and the thus obtained n-hexane extract was purified by subjecting the extract to silica gel column chromatography to obtain 22.1 g of the objective compound.

EXAMPLE 4

Production of 7-(4-chlorobenzyl)-4,4-dimethyl-1-oxaspiro[2.4]heptane (the intermediate compounds No. 77 and No. 78 shown in Table 2 by the A-method)

Into 70 ml of anhydrous dimethylsulfoxide, 3 g of sodium hydride (prepared by washing 60 % oily sodium hydride with anhydrous benzene) were added while stirring dimethylsulfoxide under a helium atmosphere, and then 27.5 g of trimethyloxosulfonium iodide were added to the thus formed mixture. After stirring the whole mixture for 30 min at room temperature, a solution of 23.6 g of 5-(4-chlorobenzyl)-2,2-di-methyl-1-cyclopentanone (the compound No. 133 shown in Table 4) in 20 ml of anhydrous dimethylsulfoxide was added within 30 min to the mixture, and the whole mixture was stirred for 2 hours at 90° C.

After leaving the thus obtained reaction mixture to cooling, it was poured into iced water and the thus obtained mixture was extracted with ethyl acetate to obtain an organic layer. After washing the organic layer with an aqueous saline solution, the layer was dried on anhydrous sodium sulfate and the solvent was distilled off from the thus dried organic layer under a reduced pressure. The thus obtained residue was subjected to silica gel column chromatography to obtain 13.95 g the objective compound No. 77 and 1.05 g of the objective compound No. 78.

EXAMPLE 5

Production of 7-(4-fluorobenzyl)-4,4-dimethyl-1-oxaspiro[2.4]heptane (the intermediate compounds No. 81 and No. 82 shown in Table 2 according to the B-method)

Into 170 ml of chloroform, 17 g of 5-[4-fluorobenzyl)-2,2-dimethyl-1-methylenecyclopentane (the compound No. shown in Table 3) were dissolved, and then, 27.1 g of m-chloroperbenzoic acid were added to the mixture within 10 min, and the thus obtained mixture was stirred for 2 hours at room temperature. In the next place, 25.4 g of calcium hydroxide were added to the mixture within 10 min, and the mixture was stirred for 30 min at room temperature.

After filtering the separated solid material, the chloroform layer of the filtrate was condensed to obtain a colourless oily material. The thus remained oily material was subjected to silica gel column chromatography to be purified, thereby obtaining 4.5 g of the objective compound No. 81 and 8.6 g of the objective compound No. 82.

EXAMPLE 6

Production of C-5-(2,4-dichlorobenzyl)-2,2-dimethyl-1-(1H-imidazol-1-ylmethyl)-r-1-cyclopentanol(the compound No. 15 shown in Table 1)

Into 18 ml of anhydrous dimethylformamide, 996 mg of sodium hydride (prepared by washing 60 % oily sodium hydride with anhydrous benzene) were added in a helium atmosphere while stirring. In the next place, 2.83 g of 1H-imidazole were added to the thus formed mixture and the whole mixture was stirred at room temperature until the bubbling stopped. To the thus obtained solution, a solution prepared by dissolving 5.93 g of 7-(2,4-dichlorobenzyl)-4,4-dimethyl-1-oxaspiro[2.4]heptane (the compound No. 83 shown in Table 2) into 10 ml of anhydrous dimethylformamide was dropped, and the thus obtained mixture was stirred for 2 hours at 80° C.

After leaving the thus obtained reaction mixture to cooling, it was poured into iced water, and the thus obtained mixture was extracted with ethyl acetate to obtain an organic layer.

After washing the organic layer with water, the organic layer was dried with anhydrous sodium sulfate and the solvent was distilled off from the organic layer under a reduced pressure.

The thus obtained residue was subjected to purification by silica gel column chromatography, and further to recrystallization with a mixture of n-hexane and ethyl acetate. As a result, 2.7 g of the objective compound were obtained.

EXAMPLE 7

Production of t-5-(4-chlorobenzyl)-2,2-dimethyl-1-(1H-1,2,4-triazol-1-ylmethyl)-r-1-cyclopentanol (the compound No. 2 of Table 1)

Into 30 ml of anhydrous dimethylformamide, 5.0 g of 7-(4-chlorobenzyl)-4,4-dimethyl-1-oxaspiro[2.4]heptane (the compound No. 78 of Table 2) were added and dissolved while stirring under a helium atmosphere, and 2.2 g of sodium salt of 1H-1,2,4-triazole (purity: 90 %, commerciallized, made by Aldrich Co.) were slowly added to the thus formed solution. Then the mixture was stirred for 2 hours at 70° C.

After leaving the thus obtained reaction mixture to cooling, it was poured into iced water and the whole mixture was extracted with ethyl acetate to obtain an organic layer. After washing the organic layer with water, the organic layer was dried on anhydrous sodium sulfate, and the solvent was distilled off from the dried organic layer under a reduced pressure.

The thus obtained residue was purified by subjecting the residue to silica gel column chromatography to obtain 3.1 g of the objective compound.

EXAMPLE 8

Production of 2-(4-chlorobenzyl)-5-methyl-1-cyclopentanone (the intermediate compound No. 137 of Table 4)

Into 126 ml of anhydrous benzene, 3.04 g of sodium hydride (prepared by washing 60 % oily sodium hydride with anhydrous benzene) were added, and then 18 g of methyl 3-methyl-2-oxocyclopentanecarboxylate were added to the thus formed mixture. After stirring the whole mixture for one hour at room temperature, 21.5 g of 4-chlorobenzyl chloride were added to the mixture and the thus obtained mixture was refluxed for 6 hours in an oil bath at 90° C.

After leaving the reaction mixture to cooling, it was extracted with benzene and the benzene layer was washed with an aqueous saline solution. After drying the benzene layer on anhydrous sodium sulfate, the solvent was distilled off from the dried benzene layer under a reduced pressure to obtained 33.6 g of a yellowish brown oily material of methyl 1-(4-chlorobenzyl)-3-methyl-2-oxocyclopentanecarboxylate (the intermediate compound No. 160 of Table 5).

Without purifying the thus obtained ester, 100 ml of 47 % hydrobromic acid were added to the ester, and the thus formed mixture was vigorously stirred for 18 hours at 110° C. After leaving the reaction mixture to cooling, it was extracted with methylene chloride and the organic layer was washed with an aqueous solution of sodium carbonate and then with an aqueous saline solution. The thus washed organic layer was dried on anhydrous sodium sulfate, and the solvent was distilled off from the organic layer under a reduced pressure.

The thus obtained residue was purified by distillation under a reduced pressure to obtain 17.4 g of the objective compound.

EXAMPLE 9

Production of methyl 1-(4-chlorobenzyl)-3-ethyl-3-methyl-2-oxocyclopentanecarboxylate (the intermediate compound No. 178 shown in Table 5)

Into 80 ml of anhydrous tetrahydrofurane, 1.7 g of sodium hydride (prepared by washing 60 % oily sodium hydride with anhydrous benzene) were added while stirring under a helium atmosphere, and then, 18.2 g of methyl 1-(4-chlorobenzyl)-3-methyl-2-oxocyclopentanecarboxylate (the intermediate compound No. 160 shown in Table 5) were added to the thus formed mixture and the whole mixture was stirred for 2 hours at a room temperature.

In the next place, 11.1 g of ethyl iodide were dropped into the mixture while maintaining the mixture at a temperature of from 20 to 30° C., and then the whole mixture was stirred for one hour at a temperature of from 20 to 30° C. and successively for one hour at a temperature of 60° C.

After leaving the reaction mixture to cooling, it was poured into a mixture of acetic acid and iced water and the whole mixture was extracted with ethyl acetate to obtain an organic layer. After washing the organic layer with an aqueous solution of sodium hydrogen carbonate then, with an aqueous saline solution, the thus washed organic layer was dried on anhydrous sodium sulfate and the solvent was distilled off from the dried organic layer under a reduced pressure.

The thus obtained residue was purified by distillation under a reduced pressure to obtain 15 g of the objective compound.

EXAMPLE 10

Production of 4-(4-chlorobenzyl)-7-methyl-1-oxaspiro[2.4]heptane [the intermediate compound No. 85 in Table 2)

Into 37 ml of anhydrous dimethylsulfoxide, 1.44 g of sodium hydride [prepared by washing 60 % oily sodium hydride with anhydrous benzene) were added while stirring under a helium atmosphere, and then 13.2 g of trimethyloxosulfonium iodide were added to the thus formed mixture and the whole mixture was stirred for 30 min at room temperature. In the next place, a solution of 12.2 g of 2-(4-chlorobenzyl)-5-methyl-1-cyclopentanone (the compound No. 137 of Table 4) in 12 ml of anhydrous dimethylsulfoxide was added to the mixture within 10 min, and the whole mixture was stirred for 4 hours at room temperature.

The thus obtained reaction liquid was poured into iced water, and the thus formed mixture was extracted with methylene chloride to obtain an organic layer. After washing the organic layer with an aqueous saline solution, the organic layer was dried on anhydrous sodium sulfate, and the solvent was distilled off from the organic layer under a reduced pressure.

The thus obtained residue was purified by subjecting the residue to silica gel column chromatography to obtain 6.67 g of the objective compound.

Still more, other than the objective compound, three kinds of isomers of the objective compound were isolated.

Namely, 0.15 g of the intermediate compound No. 86; 0.16 g of the intermediate compound No. 87 and 0.16 g of the intermediate compound No. 88 of Table 2 were obtained.

EXAMPLE 11

Production of 4-(4-chlorobenzyl)-7-ethyl-1-oxaspiro[2.4]heptane the intermediate compounds Nos. 93, 94, 95 and 96 in Table 2)

Into 100 ml of chloroform, 8.0 g of 2-(4-chlorobenzyl)-5-ethyl-1-methylenecyclopentane (the compound No. 129 shown in Table 3) were dissolved, and then 11.6 g of m-chloroperbenzoic acid were added to the thus formed mixture within 5 min, and the whole mixture was stirred for 2 hours at room temperature. In the next place, 11 g of calcium hydroxide were added to the mixture under cooling with iced water, and the whole mixture was stirred for 30 min at room temperature.

The thus separated solid material was filtered off, and the chloroform layer of the filtrate was condensed to obtain a colourless oily material. The oily material was purified by subjecting it to silica gel column chromatography to obtain 0.7 g of the compound No. 93; 2.4 g of the compound No. 94; 2.2 g of the compound No. 95 and 2.6 g of the comPound No. 96 of the entitled compound.

EXAMPLE 12

Production of C-2-(4-chlorobenzyl)-5-methyl-1-(1H-1,2,4-triazol-1-ylmethyl)-r-1-cyclopentanol (the compound No. 16 of Table 1)

Into 10 ml of anhydrous dimethylformamide, 630 mg of sodium hydride (prepared by washing 60 % oily sodium hydride with anhydrous benzene) were added and then, 1.8 g of 1H-1,2,4-triazole were added to the mixture and the whole mixture was stirred at room temperature until the bubbling was settled.

Into the thus obtained reaction mixture, a solution of 3.1 g of 4-(4-chlorobenzyl)-7-methyl-1-oxaspiro[2·4·]heptane (the compound No. 85 in Table 2) in 6.2 ml of anhydrous dimethylformamide was added, and the thus formed mixture was stirred for one hour at 80° C.

After leaving the thus obtained reaction liquid to cooling, it was poured into iced water, and the thus obtained mixture was extracted with methylene chloride to obtain an organic layer.

After washing the organic layer with an aqueous saline solution, the organic layer was dried on anhydrous sodium sulfate and the solvent was distilled off from the organic layer under a reduced pressure.

The thus obtained residue was purified by subjecting the residue to silica gel column chromatography, and was further recrystallized from a mixture of n-hexane and ethyl acetate to obtain 2.83 g of the objective compound.

EXAMPLE 13

Production of C-2(4-chlorobenzyl)-5-methyl-1-(1H-imidazol-1-ylmethyl)-r-1-cyclopentanol (the compound No. 17 of Table 1)

Into 10 ml of anhydrous dimethylformamide, 670 mg of sodium hydride (prepared by washing 60 % oily sodium hydride) were added and then, 1.9 g of 1H-imidazole were added to the thus formed mixture and the whole mixture was stirred at room temperature until the bubbling was settled.

In the next place, a solution of 3.3 g of 4-4-chlorobenzyl)-7-methyl-1-oxaspiro[2.4]heptane (the compound No. 85 of Table 2) in 6.6 ml of anhydrous dimethylformamide was added to the mixture, and the whole mixture was stirred for one hour at 80° C.

After leaving the thus obtained reaction liquid to cooling, it was poured into iced water and the thus formed mixture was extracted with methylene chloride to obtain an organic layer.

After washing the organic layer with an aqueous saline solution, the organic layer was dried on anhydrous sodium sulfate and the solvent was distilled off from the organic layer under a reduced pressure.

The thus obtained residue was purified by subjecting the residue to silica gel column chromatography and was further recrystallized from a mixture of n-hexane and ethyl acetate to obtain 3.16 g of the objective compound.

[II] THE EXAMPLES OF PREPARING THE AGRICULTURAL AND HORTICULTURAL FUNGICIDE COMPOSITIONS.

EXAMPLE 14

Dust (powder)

Three parts by weight of the azole derivative according to the present invention [the compound No. 3), 40 Parts by weight of clay and 57 parts by weight of talc were mixture and pulverized to prepare an agricultural and horticultural fungicide composition of dust form.

The thus prepared composition is used by scattering.

EXAMPLE 15

Wettable powder

Fifty parts by weight of the azole derivative according to the present invention (the compound No. 1), 5 parts by weight of a salt of ligninsulfonic acid, 3 parts by weight of a salt of alkylsulfonic acid and 42 parts by weight of diatomaceous earth were mixed and pulverized to prepare a wettable powder.

The thus prepared composition was used as a wettable powder after diluting with water.

EXAMPLE 16

Granule

Five parts by weight of the azole derivative according to the present invention (the compound No. 16), 43 parts by weight of bentonite, 45 parts by weight of clay and 7 parts by weight of a salt of ligninsulfonic acid were uniformly mixed, and after adding water to the mixture, the whole materials were kneaded together, processed into granular form by an extruding granulator and dried to obtain the composition of granular form.

EXAMPLE 17

Emulsifiable concentrate

Twenty parts by weight of the azole derivative according to the present invention [the compound No. 13), 10 parts by weight of a polyoxyethylene alkyl aryl ether, 3 parts by weight of a polyoxyethylene sorbitan monolaurate and 67 parts by weight of xylene were uniformly mixed together to prepare the composition of emulsifiable concentrate form.

[III] THE EXAMPLES OF APPLICATION OF THE AGRICULTURAL AND HORTICULTURAL FUNGICIDE COMPOSITION ACCORDING TO THE PRESENT INVENTION TO PLANT DISEASES.

EXAMPLE 18

Test for controlling effect against *Erysiphe graminis* f. sp. *tritici* on wheat Onto the young seedlings of wheat of the secondleaf stage (variety: NORIN No. 64, 16 seedlings per pot and 3 pots being used in the treated plot), which had been cultured while using unglazed pots, of 10 cm in diameter, 5 ml. per pot of an aqueous suspension of the wettable powder prepared in Example 15 (diluted with water to a predetermined concentration) were applied. After air drying the applied dilution, a suspension of the summer spores of *Erysiphe graminis* f. sp. *tritici*, which had been collected from the attacked leaf of wheat was sprayed onto the seedlings in the pots, the pots were maintained at from 20 to 24° C. for 24 hours under a highly humid condition and then the pots were left in a glass room. On the day after 9 to 11 days of the inoculation, the extent of the disease on the seedlings was investigated according to the following investigation standards and the control value of the fungicide composition was calculated according to the following formula.

| (Investigation standards) ||
| Degree of disease | Extent of disease |
| --- | --- |
| 0 | not attacked |
| 0.5 | The rate of area of the disease spots is below 10% |
| 1 | The rate of area of the disease spots is not less than 10% and below 20% |
| 2 | The rate of area of the disease spots is not less than 20% and below 40% |
| 3 | The rate of area of the disease spots is not less than 40% and below 60% |
| 4 | The rate of area of the disease spots is not less than 60% and below 80% |
| 5 | The rate of area of the disease spots is not less than 80%. |

$$\text{Control value} = \left(1 - \frac{\text{Degree of disease on treated plot}}{\text{Degree of disease on control plot}}\right) \times 100 \, (\%)$$

The results of the test are shown in Table 6.

TABLE 6

| Compound tested (No. in Table 1) | Concentration of spray (ppm) | Control value (%) |
| --- | --- | --- |
| 1 | 125 | 100 |
| 2 | 125 | 100 |
| 3 | 125 | 95 |
| 4 | 125 | 100 |
| 5 | 125 | 100 |
| 6 | 125 | 100 |
| 7 | 125 | 95 |
| 8 | 125 | 95 |
| 9 | 125 | 100 |
| 10 | 125 | 100 |
| 11 | 125 | 100 |
| 12 | 125 | 90 |
| 13 | 125 | 100 |
| 14 | 125 | 100 |
| 15 | 125 | 95 |

TABLE 6-continued

| Compound tested (No. in Table 1) | Concentration of spray (ppm) | Control value (%) |
| --- | --- | --- |
| 16 | 125 | 100 |
| 17 | 125 | 95 |
| 18 | 125 | 100 |
| 19 | 125 | 100 |
| 20 | 125 | 50 |
| 21 | 125 | 100 |
| 22 | 125 | 100 |
| 23 | 125 | 100 |
| 24 | 125 | 100 |
| 25 | 125 | 100 |
| 26 | 125 | 100 |
| 27 | 125 | 100 |
| 28 | 125 | 100 |
| 29 | 125 | 100 |
| 30 | 125 | 100 |
| 31 | 125 | 100 |
| 32 | 125 | 100 |
| 33 | 125 | 100 |
| 34 | 125 | 100 |
| 35 | 125 | 100 |
| 36 | 125 | 100 |
| 37 | 125 | 100 |
| 38 | 125 | 100 |
| 39 | 125 | 100 |
| 40 | 125 | 100 |
| 41 | 125 | 100 |
| 42 | 125 | 100 |
| 43 | 125 | 95 |
| 44 | 125 | 100 |
| 45 | 125 | 100 |
| 46 | 125 | 95 |
| 47 | 125 | 100 |
| 48 | 125 | 100 |
| 49 | 125 | 100 |
| 50 | 125 | 100 |
| 51 | 125 | 100 |
| 52 | 125 | 100 |
| 53 | 125 | 75 |
| 54 | 125 | 100 |
| 55 | 125 | 100 |
| 56 | 125 | 100 |
| 57 | 125 | 100 |
| 58 | 125 | 100 |
| 59 | 125 | 100 |
| 60 | 125 | 100 |
| 61 | 125 | 100 |
| 62 | 125 | 100 |
| 63 | 125 | 100 |
| 64 | 125 | 100 |
| 65 | 125 | 100 |
| 66 | 125 | 100 |
| 67 | 125 | 100 |
| 68 | 125 | 100 |
| 69 | 125 | 100 |
| 70 | 125 | 100 |
| 71 | 125 | 100 |
| 72 | 125 | 100 |
| 73 | 125 | 100 |
| 74 | 125 | 100 |
| 75 | 125 | 100 |
| 76 | 125 | 100 |
| Commerciallized material Triadimephon* | 125 | 100 |
| Control (not treated) | | 0 |

(Note)
*Triadimephon of the commerciallized material has the compound represented by the following formula as the active ingredient.

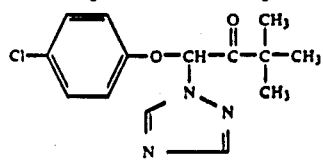

EXAMPLE 19

Test for controlling effect against *Sphaerotheca fuliginea* on cucumber

Onto the cucumber plants of the second-leaf stage (variety: SAGAMI HAMPAKU, one plant per pot and 3 pots being used in the treated plot), which had been cultured while using unglazed pots of 10 cm in diameter, 5 ml per pot of an aqueous suspension of the wettable powder prepared in Example 15 (diluted with water to a predetermined concentration) were applied. After air-drying the applied leaves, the spores of *Sphaerotheca fuliginea* were sprinkled with a brush from the diseased leaf of cucumber to inoculate the cucumber plants and the disease was caused on the plants in a glass room.

On the day after from 9 to 11 days of the inoculation, the degree of disease on the cucumber plants was investigated according to the following investigation standards and the control value of the fungicide composition was calculated according to the following formula:

(Investigation standards)

| Degree of disease | Extent of disease |
| --- | --- |
| 0 | not attacked |
| 0.5 | The rate of area of the disease spots is below 10% |
| 1 | The rate of area of the disease spots is not less than 10% and below 20% |
| 2 | The rate of area of the disease spots is not less than 20% and below 40% |
| 3 | The rate of area of the disease spots is not less than 40% and below 60% |
| 4 | The rate of area of the disease spots is not less than 60% and below 80% |
| 5 | The rate of area of the disease spots is not less than 80% |

$$\text{Control value} = \left(1 - \frac{\text{Degree of disease on treated plot}}{\text{Degree of disease on control plot}}\right) \times 100\,(\%)$$

The results are shown in Table 7.

TABLE 7

| Compound tested (No. in Table 1) | Concentration of spray (ppm) | Control value (%) |
| --- | --- | --- |
| 1 | 125 | 100 |
| 2 | 125 | 100 |
| 3 | 125 | 100 |
| 4 | 125 | 100 |
| 5 | 125 | 100 |
| 6 | 125 | 100 |
| 7 | 125 | 100 |
| 8 | 125 | 100 |
| 9 | 125 | 100 |
| 10 | 125 | 100 |
| 11 | 125 | 100 |
| 12 | 125 | 100 |
| 13 | 125 | 100 |
| 14 | 125 | 100 |
| 15 | 125 | 100 |
| 16 | 125 | 100 |
| 17 | 125 | 100 |
| Commerciallized material Triadimephon* | 125 | 100 |
| Control (not treated) | | 0 |

EXAMPLE 20

Test for controlling effect against *Puccinia recondita* on wheat

Onto the young seedlings of wheat of the secondleaf stage (variety: NORIN No. 64, 16 seedlings per pot and 3 pots being used in the treated plot), which had been cultured while using unglazed pots of 10 cm in diameter, 5 ml per pot of an aqueous suspension of the wettable powder prepared in Example 15 (diluted with water to a predetermined concentration) were applied by spraying.

After air-drying the applied dilution, a suspension of the summer spores of *Puccinia recondita*, which had been collected from the contracted leaf of wheat, was sprayed onto the seedlings in the pots, the pots were maintained at from 20 to 23° C. for 24 hours under a highly humid condition and then the pots were left in a glass room. On the day after 7 to 10 days of the inoculation, the extent of the disease on ten seedlings was investigated according to the following investigation standards and the control value of the fungicide composition was calculated according to the following formula from the mean degree of disease per leaf.

(Investigation standards)

| Degree of disease | Extent of disease |
| --- | --- |
| 0 | not attacked |
| 0.5 | The rate of area of the disease spots is below 10% |
| 1 | The rate of area of the disease spots is not less than 10% and below 20% |
| 2 | The rate of area of the disease spots is not less than 20% and below 40% |
| 3 | The rate of area of the disease spots is not less than 40% and below 60% |
| 4 | The rate of area of the disease spots is not less than 60% and below 80% |
| 5 | The rate of area of the disease spots is not less than 80%. |

$$\text{Control value} = \left(1 - \frac{\text{Degree of disease on treated plot}}{\text{Degree of disease on control plot}}\right) \times 100 \, (\%)$$

The results are shown in Table 8.

TABLE 8

| Compound tested (No. in Table 1) | Concentration of spray (ppm) | Control value (%) |
| --- | --- | --- |
| 1 | 125 | 100 |
| 2 | 125 | 95 |
| 3 | 125 | 100 |
| 4 | 125 | 95 |
| 5 | 125 | 100 |
| 6 | 125 | 100 |
| 7 | 125 | 100 |
| 8 | 125 | 95 |
| 9 | 125 | 100 |
| 10 | 125 | 100 |
| 11 | 125 | 100 |
| 12 | 125 | 95 |
| 13 | 125 | 100 |
| 14 | 125 | 100 |
| 15 | 125 | 100 |
| 16 | 125 | 100 |
| 17 | 125 | 95 |
| 18 | 125 | 100 |
| 19 | 125 | 100 |
| 20 | 125 | 100 |
| 21 | 125 | 100 |
| 22 | 125 | 100 |
| 23 | 125 | 100 |
| 24 | 125 | 70 |
| 25 | 125 | 100 |
| 26 | 125 | 95 |
| 27 | 125 | 100 |
| 28 | 125 | 100 |
| 29 | 125 | 100 |
| 30 | 125 | 100 |
| 31 | 125 | 100 |
| 32 | 125 | 100 |
| 33 | 125 | 100 |
| 34 | 125 | 100 |
| 35 | 125 | 100 |
| 36 | 125 | 100 |
| 37 | 125 | 100 |
| 38 | 125 | 100 |
| 39 | 125 | 100 |
| 40 | 125 | 100 |
| 41 | 125 | 100 |
| 42 | 125 | 100 |
| 43 | 125 | 100 |
| 44 | 125 | 100 |
| 45 | 125 | 100 |
| 46 | 125 | 100 |
| 47 | 125 | 100 |
| 48 | 125 | 100 |
| 49 | 125 | 90 |
| 50 | 125 | 100 |
| 51 | 125 | 100 |
| 53 | 125 | 95 |
| 54 | 125 | 100 |
| 55 | 125 | 100 |
| 56 | 125 | 100 |
| 57 | 125 | 100 |
| 58 | 125 | 90 |
| 59 | 125 | 100 |
| 60 | 125 | 90 |
| 61 | 125 | 90 |
| 62 | 125 | 100 |
| 63 | 125 | 100 |
| 64 | 125 | 100 |
| 65 | 125 | 100 |
| 66 | 125 | 100 |
| 67 | 125 | 100 |
| 68 | 125 | 100 |
| 69 | 125 | 100 |
| 70 | 125 | 100 |
| 71 | 125 | 100 |
| 72 | 125 | 100 |
| 73 | 125 | 100 |
| 74 | 125 | 100 |
| 75 | 125 | 90 |
| 76 | 125 | 90 |
| Commercialized material Triadimephon* | 125 | 95 |
| Control (not treated) | | 0 |

EXAMPLE 21

Test for controlling effect against *Botrytis cinerea* on kidney bean

Onto the leaves of kidney bean plants at the first true-leaf stage (variety: HONKINTOKI), which had been cultured while using unglazed pots of, 10 cm in diameter, 5 ml per pot of an aqueous suspension of the wettable powder prepared in Example 15 (diluted with water to a predetermined concentration) were applied by spraying.

After air-drying the thus applied leaves, a circular cutting of agar of a diameter of 4 mm containing the fungi of *Botrytis cinerea*, which had been preliminarily cultured for 3 days at 20° C. while using a sugar-added agar medium containing potato soup, was directly adhered to the center part of the leaf of kidney bean plants, and the plants were maintained at a temperature of from 20 to 22° C. under a highly humid condition. On the 3rd day of the inoculation, the area of disease spot of the thus treated plot was compared with that of the control(untreated) plot to investigate the degree of disease according to the following investigation standards and the control value of the fungicide composition was calculated according to the following formula.

| (Investigation standards) | |
|---|---|
| Degree of disease | Extent of attack |
| 0 | not attacked |
| 0.5 | Only attacked the part just below the inoculated fungi-containing agar and the peripheral parts thereof. |
| 1 | The rate of area of the disease spots is below 20% |
| 2 | The rate of area of the disease spots is not less than 20% and below 40% |
| 3 | The rate of area of the disease spots is not less than 40% and below 60% |
| 4 | The rate of area of the disease spots is not less than 60% and below 80% |
| 5 | The rate of area of the disease spots is not less than 80%. |

Control value $= \left(1 - \frac{\text{Degree of disease on treated plot}}{\text{Degree of disease on control plot}}\right) \times 100\ (\%)$ The results are shown in Table 9.

TABLE 9

| Compound tested (No. in Table 1) | Concentration of spray (ppm) | Control value (%) |
|---|---|---|
| 1 | 500 | 100 |
| 2 | 500 | 100 |
| 3 | 500 | 90 |
| 4 | 500 | 80 |
| 5 | 500 | 100 |
| 6 | 500 | 100 |
| 7 | 500 | 70 |
| 8 | 500 | 70 |
| 9 | 500 | 100 |
| 10 | 500 | 100 |
| 11 | 500 | 85 |
| 12 | 500 | 80 |
| 13 | 500 | 100 |
| 14 | 500 | 100 |
| 15 | 500 | 90 |
| 16 | 500 | 100 |
| 17 | 500 | 80 |
| 18 | 500 | 100 |
| 19 | 500 | 100 |
| 21 | 500 | 100 |
| 22 | 500 | 65 |
| 23 | 500 | 100 |
| 24 | 500 | 90 |
| 25 | 500 | 85 |
| 27 | 500 | 100 |
| 28 | 500 | 90 |
| 29 | 500 | 100 |
| 30 | 500 | 100 |
| 31 | 500 | 60 |
| 32 | 500 | 100 |
| 33 | 500 | 85 |
| 37 | 500 | 100 |
| 38 | 500 | 100 |
| 39 | 500 | 75 |
| 41 | 500 | 100 |
| 42 | 500 | 100 |
| 44 | 500 | 100 |

TABLE 9-continued

| Compound tested (No. in Table 1) | Concentration of spray (ppm) | Control value (%) |
|---|---|---|
| 45 | 500 | 100 |
| 46 | 500 | 70 |
| 47 | 500 | 60 |
| 48 | 500 | 100 |
| 49 | 500 | 100 |
| 50 | 500 | 100 |
| 54 | 500 | 100 |
| 55 | 500 | 100 |
| 56 | 500 | 95 |
| 57 | 500 | 70 |
| 58 | 500 | 70 |
| 59 | 500 | 80 |
| 60 | 500 | 80 |
| 61 | 500 | 85 |
| 62 | 500 | 100 |
| 63 | 500 | 100 |
| 64 | 500 | 80 |
| 65 | 500 | 100 |
| 66 | 500 | 60 |
| 67 | 500 | 100 |
| 68 | 500 | 60 |
| 69 | 500 | 100 |
| 70 | 500 | 65 |
| 71 | 500 | 100 |
| 72 | 500 | 100 |
| 73 | 500 | 80 |
| 74 | 500 | 60 |
| 75 | 500 | 85 |
| 76 | 500 | 60 |
| Commerciallized material Rovral* | 500 | 100 |

(Note)
*The commerciallized material (Rovral) contains the compound represented by the following formula as an active ingredient.

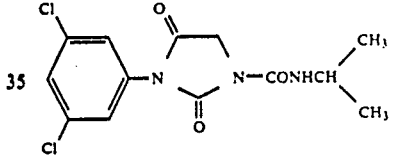

EXAMPLE 22

Test for controlling effect against *Cochliobolus miyabeanus* on rice plant

In each of unglazed pots of 10 cm in diameter, 16 seeds of rice plate (variety: SASANISHIKI) were sown, and at the time when the rice seedlings became the 4–5 leaf-stage, an aqueous suspension of the wettable powder prepared in Example 15 (diluted to a predetermined concentration with water) was sprinkled onto the seedlings.

After air-drying the thus treated leaves, 5 ml per pot of a suspension of the spores of *Cochliobolus miyabeanus*, which had been preliminarily cultured, were applied by spraying to the thus treated seedlings. Under the microscope of magnifications, 15 spores of the fungus in the suspension were found in the field.

Just after finishing the inoculation, the thus treated pots were introduced into an inoculation room at 25° C. and at a saturated humidity and after keeping the pots therein for 2 days, the pots were introduced into a glass house to be attacked. On the 5th day of the inoculation, the number of disease spots on 10 leaves per pot was counted, and the control value of the fungicidal composition was calculated according to the following formula:

Control value =

$$1 - \frac{\text{Number of disease spots on the treated plot}}{\text{Number of disease spots on the contol (untreated) plot}} \times 100\,(\%)$$

The results are shown in Table 10.

TABLE 10

| Compound tested (No. in Table 1) | Concentration of spray (ppm) | Control value (%) |
| --- | --- | --- |
| 1 | 125 | 100 |
| 2 | 125 | 100 |
| 3 | 125 | 100 |
| 4 | 125 | 100 |
| 5 | 125 | 100 |
| 6 | 125 | 100 |
| 7 | 125 | 100 |
| 8 | 125 | 100 |
| 9 | 125 | 100 |
| 10 | 125 | 100 |
| 11 | 125 | 100 |
| 12 | 125 | 100 |
| 13 | 125 | 100 |
| 14 | 125 | 95 |
| 15 | 125 | 90 |
| 16 | 125 | 100 |
| 17 | 125 | 100 |
| Commerciallized material: Rovral | 125 | 85 |
| Control (not treated) | | 0 |

EXAMPLE 23

Antifungal test against several pathogenic fungi

The present example shows the results of the antifungal property of the azole derivative according to the present invention against various plant-pathogenic fungi.

Test method

The compound according to the present invention is dissolved into dimethyl sulfoxide so as to give a solution of the predetermined concentration and 0.6 ml of the thus Prepared solution is well mixed with 60 ml of the PAS culture medium of about 60° C. in a conical flask of 100 ml in capacity. The thus formed mixture is poured into a glass dish and is solidified to be a flat culture medium containing the compound.

On the other hand, the test fungus, which has been preliminarily cultured in a flat culture medium, is striked by a cork borer of 4 mm in diameter and the thus striked piece of the culture medium containing the test fungus is inoculated on the flat culture medium containing the compound. After inoculation, the thus prepared culture medium containing the compound and the fungus is cultured for from 1 to 3 days at an appropriate temperature for growing each of the fungi, and the growth of the fungus is measured by the diameter of the fungal colony. By comparing the growth of the fungus in the thus prepared culture medium with that in the untreated plot (the culture medium not containing the compound), the rate of inhibiting the mycelial growth of the fungus is obtained according to the following formula:

$$R = (dc - dt)\,100/dc$$

wherein R is the rate of inhibiting the mycelial growth; dc is the diameter of fungal colony on the flat medium not containing the compound and dt is the diameter of fungal colony on the flat medium containing the compound.

The results are evaluated into 5 stages according to the following standards and shown in Table 11. Rate of inhibiting the mycelial growth:

5: The rate of inhibiting the growth is not smaller than 90–100 %
4: The rate of inhibiting the growth is not smaller than 70 % and below 90 %
3: The rate of inhibiting the growth is not smaller than 40 % and below 70 %
2: The rate of inhibiting the growth is not smaller than 20 % and below 40 %
1: The rate of inhibiting the growth is below 20 %

TABLE 11

| No. of compound tested (No. in Table 1) | Concentration of Compound (µg/ml) | Fungus Tested | | | | | | | | | | | | | | | |
| --- | --- | --- | --- | --- | --- | --- | --- | --- | --- | --- | --- | --- | --- | --- | --- | --- | --- |
| | | P.o. | C.m. | G.f. | H.s. | R.s. | Bo.c. | S.s. | F.n. | F.c. | F.r. | C.l. | C.b. | S.c. | V.m. | A.k. | A.m. | G.c. |
| 1 | 100 | 5 | 5 | 5 | 5 | 5 | 5 | 5 | 5 | 5 | 5 | 5 | 5 | 5 | 5 | 5 | 5 | 5 |
| 2 | 100 | 5 | 5 | 5 | 5 | 5 | 5 | 5 | 5 | 5 | 5 | 5 | 5 | 5 | 5 | 5 | 5 | 5 |
| 3 | 100 | 5 | 5 | 5 | 5 | 5 | 5 | 5 | 5 | 5 | 5 | 5 | 5 | 5 | 5 | 5 | 5 | 5 |
| 4 | 100 | 5 | 5 | 5 | 5 | 5 | 5 | 5 | 5 | 5 | 5 | 5 | 5 | 5 | 5 | 5 | 5 | 5 |
| 5 | 100 | 5 | 5 | 5 | 5 | 5 | 5 | 5 | 5 | 5 | 5 | 5 | 5 | 5 | 4 | 5 | 5 | 5 |
| 6 | 100 | 5 | 5 | 5 | 5 | 5 | 5 | 5 | 5 | 5 | 5 | 5 | 5 | 5 | 5 | 5 | 5 | 5 |
| 7 | 100 | 5 | 5 | 5 | 5 | 5 | 5 | 5 | 5 | 5 | 5 | 5 | 5 | 5 | 5 | 5 | 5 | 5 |
| 8 | 100 | 5 | 5 | 5 | 5 | 5 | 5 | 5 | 5 | 5 | 5 | 5 | 5 | 5 | 5 | 5 | 5 | 5 |
| 9 | 100 | 5 | 5 | 5 | 5 | 4 | 5 | 5 | 5 | 5 | 5 | 5 | 5 | 5 | 5 | 4 | 5 | 5 |
| 10 | 100 | 5 | 5 | 5 | 5 | 5 | 5 | 5 | 5 | 5 | 5 | 5 | 5 | 5 | 5 | 5 | 5 | 5 |
| 11 | 100 | 5 | 5 | 5 | 5 | 4 | 5 | 5 | 5 | 5 | 5 | 5 | 5 | 5 | 5 | 5 | 5 | 5 |
| 12 | 100 | 5 | 5 | 5 | 5 | 4 | 5 | 5 | 5 | 5 | 5 | 5 | 5 | 5 | 5 | 5 | 5 | 5 |
| 13 | 100 | 5 | 5 | 5 | 5 | 5 | 5 | 5 | 5 | 5 | 5 | 5 | 5 | 5 | 4 | 4 | 5 | 5 |
| 14 | 100 | 5 | 5 | 5 | 5 | 5 | 5 | 5 | 5 | 5 | 5 | 5 | 5 | 5 | 4 | 4 | 5 | 5 |
| 15 | 100 | 5 | 5 | 5 | 5 | 5 | 5 | 5 | 5 | 5 | 5 | 5 | 5 | 5 | 5 | 5 | 5 | 5 |
| 16 | 100 | 5 | 5 | 5 | 5 | 4 | 5 | 5 | 5 | 5 | 5 | 5 | 5 | 5 | 5 | 5 | 5 | 5 |
| 17 | 100 | 5 | 5 | 5 | 5 | 5 | 5 | 5 | 5 | 5 | 5 | 5 | 5 | 5 | 5 | 5 | 5 | 5 |
| 18 | 100 | 5 | 5 | 5 | 5 | 5 | 5 | 5 | 5 | 5 | 5 | 5 | 5 | 5 | 5 | 5 | 5 | 5 |
| 19 | 100 | 5 | 5 | 5 | 4 | 4 | 5 | 4 | 5 | 5 | 5 | 5 | 5 | 5 | 4 | 4 | 5 | 5 |
| 20 | 100 | 5 | 5 | 5 | 5 | 4 | 5 | 5 | 5 | 5 | 5 | 5 | 5 | 5 | 5 | 5 | 5 | 5 |
| 21 | 100 | 5 | 5 | 5 | 5 | 5 | 5 | 5 | 5 | 5 | 5 | 5 | 5 | 5 | 5 | 5 | 5 | 5 |
| 22 | 100 | 5 | 5 | 5 | 5 | 5 | 5 | 5 | 5 | 5 | 5 | 5 | 5 | 5 | 5 | 5 | 5 | 5 |
| 23 | 100 | 5 | 5 | 5 | 5 | 5 | 5 | 5 | 5 | 5 | 5 | 5 | 5 | 5 | 5 | 5 | 5 | 5 |
| 24 | 100 | 5 | 5 | 5 | 5 | 4 | 5 | 5 | 5 | 5 | 5 | 5 | 5 | 5 | 5 | 5 | 5 | 5 |

TABLE 11-continued

| No. of compound tested (No. in Table 1) | Concentration of Compound (μg/ml) | P.o. | C.m. | G.f. | H.s. | R.s. | Bo.c. | S.s. | F.n. | F.c. | F.r. | C.l. | C.b. | S.c. | V.m. | A.k. | A.m. | G.c. |
|---|---|---|---|---|---|---|---|---|---|---|---|---|---|---|---|---|---|---|
| 25 | 100 | 5 | 5 | 5 | 5 | 5 | 5 | 5 | 5 | 5 | 5 | 5 | 4 | 5 | 5 | 5 | 5 | 5 |
| 26 | 100 | 5 | 5 | 5 | 5 | 4 | 5 | 5 | 5 | 5 | 5 | 5 | 5 | 5 | 5 | 5 | 5 | 5 |
| 27 | 100 | 5 | 5 | 5 | 5 | 5 | 5 | 5 | 5 | 5 | 5 | 5 | 5 | 5 | 5 | 5 | 5 | 5 |
| 28 | 100 | 5 | 5 | 5 | 5 | 5 | 5 | 5 | 5 | 5 | 5 | 5 | 5 | 5 | 5 | 5 | 5 | 5 |
| 29 | 100 | 5 | 5 | 5 | 5 | 5 | 5 | 5 | 5 | 5 | 5 | 5 | 5 | 5 | 5 | 5 | 5 | 5 |
| 30 | 100 | 5 | 5 | 5 | 5 | 5 | 5 | 5 | 5 | 5 | 5 | 5 | 5 | 5 | 5 | 5 | 5 | 5 |
| 31 | 100 | 5 | 5 | 5 | 5 | 4 | 5 | 5 | 5 | 5 | 5 | 5 | 5 | 5 | 5 | 4 | 4 | 5 |
| 32 | 100 | 5 | 5 | 5 | 5 | 5 | 5 | 5 | 5 | 5 | 5 | 5 | 5 | 5 | 5 | 5 | 5 | 5 |
| 33 | 100 | 5 | 5 | 5 | 5 | 5 | 5 | 5 | 5 | 5 | 5 | 5 | 5 | 5 | 5 | 5 | 5 | 5 |
| 34 | 100 | 5 | 5 | 5 | 5 | 5 | 5 | 5 | 5 | 5 | 5 | 5 | 5 | 5 | 5 | 5 | 5 | 5 |
| 35 | 100 | 5 | 5 | 5 | 5 | 5 | 5 | 5 | 5 | 5 | 5 | 5 | 3 | 5 | 5 | 5 | 5 | 5 |
| 36 | 100 | 3 | 5 | 5 | 5 | 5 | 5 | 5 | 5 | 5 | 5 | 5 | 3 | 5 | 5 | 5 | 5 | 5 |
| 37 | 100 | 5 | 5 | 5 | 5 | 5 | 5 | 5 | 5 | 5 | 5 | 5 | 5 | 5 | 5 | 5 | 5 | 5 |
| 38 | 100 | 5 | 5 | 5 | 5 | 5 | 5 | 5 | 5 | 5 | 5 | 5 | 5 | 5 | 5 | 5 | 5 | 5 |
| 39 | 100 | 5 | 5 | 5 | 5 | 5 | 5 | 5 | 5 | 5 | 5 | 5 | 5 | 5 | 5 | 5 | 5 | 5 |
| 40 | 100 | 5 | 5 | 4 | 5 | 5 | 5 | 4 | 4 | 4 | 4 | 5 | 3 | 5 | 5 | 4 | 5 | 5 |
| 41 | 100 | 5 | 5 | 5 | 5 | 5 | 5 | 5 | 5 | 5 | 5 | 5 | 3 | 5 | 5 | 5 | 5 | 5 |
| 42 | 100 | 5 | 5 | 5 | 5 | 3 | 5 | 5 | 5 | 5 | 5 | 5 | 5 | 5 | 5 | 5 | 5 | 5 |
| 43 | 100 | 5 | 5 | 5 | 5 | 4 | 5 | 5 | 5 | 5 | 5 | 5 | 5 | 5 | 5 | 5 | 5 | 5 |
| 44 | 100 | 5 | 5 | 5 | 5 | 5 | 5 | 5 | 5 | 5 | 5 | 5 | 5 | 5 | 5 | 5 | 5 | 5 |
| 45 | 100 | 5 | 5 | 5 | 5 | 5 | 5 | 5 | 5 | 5 | 5 | 5 | 5 | 5 | 5 | 5 | 5 | 5 |
| 46 | 100 | 5 | 4 | 5 | 5 | 3 | 5 | 5 | 4 | 4 | 4 | 5 | 5 | 5 | 5 | 4 | 4 | 5 |
| 47 | 100 | 5 | 5 | 5 | 5 | 5 | 5 | 5 | 5 | 5 | 5 | 5 | 5 | 5 | 5 | 4 | 5 | 5 |
| 48 | 100 | 5 | 5 | 4 | 5 | 5 | 4 | 4 | 4 | 4 | 4 | 5 | 5 | 5 | 5 | 4 | 5 | 5 |
| 49 | 100 | 5 | 5 | 5 | 5 | 5 | 5 | 5 | 5 | 5 | 5 | 5 | 5 | 5 | 5 | 5 | 5 | 5 |
| 50 | 100 | 5 | 5 | 5 | 5 | 5 | 5 | 5 | 5 | 5 | 5 | 5 | 5 | 5 | 5 | 5 | 5 | 5 |
| 51 | 100 | 5 | 4 | 5 | 5 | 4 | 5 | 5 | 4 | 4 | 4 | 5 | 4 | 5 | 5 | 4 | 4 | 5 |
| 52 | 100 | 5 | 5 | 5 | 5 | 5 | 5 | 5 | 5 | 5 | 5 | 5 | 5 | 5 | 5 | 5 | 5 | 5 |
| 53 | 100 | 5 | 5 | 5 | 5 | 5 | 5 | 5 | 5 | 5 | 5 | 5 | 5 | 5 | 5 | 5 | 5 | 5 |
| 54 | 100 | 5 | 5 | 5 | 5 | 4 | 5 | 5 | 5 | 5 | 5 | 5 | 4 | 5 | 5 | 4 | 4 | 5 |
| 55 | 100 | 5 | 4 | 5 | 5 | 5 | 5 | 5 | 5 | 5 | 5 | 5 | 4 | 5 | 5 | 4 | 4 | 5 |
| 56 | 100 | 5 | 4 | 5 | 5 | 4 | 5 | 5 | 4 | 4 | 4 | 5 | 3 | 5 | 5 | 3 | 3 | 5 |
| 57 | 100 | 5 | 4 | 5 | 5 | 4 | 5 | 5 | 5 | 5 | 5 | 5 | 4 | 5 | 5 | 4 | 4 | 5 |
| 58 | 100 | 5 | 4 | 5 | 5 | 5 | 5 | 5 | 5 | 5 | 5 | 5 | 3 | 5 | 5 | 3 | 3 | 5 |
| 59 | 100 | 5 | 5 | 5 | 5 | 5 | 5 | 5 | 5 | 5 | 5 | 5 | 5 | 5 | 5 | 5 | 5 | 5 |
| 60 | 100 | 5 | 5 | 5 | 5 | 5 | 5 | 5 | 5 | 5 | 5 | 5 | 4 | 5 | 5 | 5 | 4 | 5 |
| 61 | 100 | 5 | 5 | 5 | 5 | 5 | 5 | 5 | 5 | 5 | 5 | 5 | 4 | 5 | 5 | 5 | 4 | 5 |
| 62 | 100 | 5 | 5 | 5 | 5 | 5 | 5 | 5 | 5 | 5 | 5 | 5 | 5 | 5 | 5 | 5 | 5 | 5 |
| 63 | 100 | 5 | 5 | 5 | 5 | 5 | 5 | 5 | 5 | 5 | 5 | 5 | 5 | 5 | 5 | 5 | 5 | 5 |
| 64 | 100 | 5 | 5 | 5 | 5 | 5 | 5 | 5 | 5 | 5 | 5 | 5 | 5 | 5 | 5 | 5 | 5 | 5 |
| 65 | 100 | 5 | 5 | 5 | 5 | 5 | 5 | 5 | 5 | 5 | 5 | 5 | 5 | 5 | 5 | 5 | 5 | 5 |
| 66 | 100 | 5 | 5 | 5 | 5 | 3 | 5 | 5 | 5 | 5 | 5 | 5 | 5 | 5 | 5 | 5 | 5 | 5 |
| 67 | 100 | 5 | 5 | 5 | 5 | 4 | 5 | 5 | 5 | 5 | 5 | 5 | 5 | 5 | 5 | 5 | 5 | 5 |
| 68 | 100 | 5 | 5 | 5 | 5 | 3 | 5 | 5 | 4 | 4 | 4 | 5 | 5 | 5 | 5 | 4 | 4 | 5 |
| 69 | 100 | 5 | 5 | 5 | 5 | 5 | 5 | 5 | 5 | 5 | 5 | 5 | 5 | 5 | 5 | 5 | 5 | 5 |
| 70 | 100 | 5 | 5 | 5 | 5 | 5 | 5 | 5 | 5 | 5 | 5 | 5 | 5 | 5 | 5 | 5 | 5 | 5 |
| 71 | 100 | 5 | 5 | 5 | 5 | 4 | 5 | 5 | 5 | 5 | 5 | 5 | 5 | 5 | 5 | 5 | 5 | 5 |
| 75 | 100 | 5 | 5 | 5 | 5 | 5 | 5 | 5 | 5 | 5 | 5 | 5 | 4 | 5 | 5 | 5 | 4 | 5 |
| 76 | 100 | 5 | 5 | 5 | 5 | 3 | 5 | 5 | 5 | 5 | 5 | 5 | 4 | 5 | 5 | 5 | 4 | 5 |

The abbreviation in Table 11 shows each of the following fungi:
P.o. : *Pyricularia oryzae* on rice plant
C.m. : *Cochliobolus miyabeanus* on rice plant
G.f. : *Gibberella fujikuroi* on rice plant
H.s. : *Helminthosporium sigmoideum* on rice plant
R.s. : *Rhizoctonia solani* on rice plant
Bo.c.: *Botrytis cinerea*
S.s. : *Sclerotinia sclerotirum*
F.n. : *Fusarium oxysporum* f. *niveum* on water melon
F.c. : *Fusarium oxysporum* f. *cucumerinum* on cucumber
F.r. : *Fusarium oxysporum* f. *raphani* on Japanese radish
C.l. : *Colletotrichum lagenarium* on melons
C.b. : *Cercospola beticola* on sugar beet
S.c. : *Sclerotinia cinerea* on peach
V.m. : *Valsa mali* on apple
A.m. : *Alternaria mali* on apple
A.k. : *Alternaria alternata (kikuchiana)* on pear
G.c. : *Glomerella cingulata* on grape

[IV] The examples of the agricultural and horticultural plant growth regulating agent containing the azole derivative according to the present invention as an active ingredient.

EXAMPLE 24

Form of wettable powder

Fifty parts by weight of the azole derivative according to the present invention (the compound No. 3 in Table 1), 5 parts by weight of a salt of ligninsulfonic acid, 3 parts by weight of a salt of alkylsulfonic acid and 42 parts by weight of diatomaceous earth were mixed and pulverized to obtain a composition of the form of wettable powder. The composition is used after diluting with water.

EXAMPLE 25

Form of emulsifiable concentrate

Twenty five parts by weight of the azole derivative according to the present invention (the compound No. 20 in Table 1), 65 parts by weight of xylene and 10 parts by weight of polyoxyethylene alkyl aryl ether were uniformly mixed together to obtain a composition of the form of emulsifiable concentrate. The composition is used after diluting with water.

EXAMPLE 26

Form of dust(powder)

Eight parts by weight of the azole derivative according to the present invention (the compound No. 11 in Table 1), 40 parts by weight of bentonite, 45 parts by weight of clay and 7 parts by weight of a salt of ligninsulfonic acid were mixed uniformly, and after adding water to the thus formed mixture, the whole mixture was kneaded together and processed into granular form by an extruding granulator and the granular material was dried to be the composition of the form of dust.

EXAMPLE 27

Plant height-restraining effect on rice plant

Into each of the glass dishes of 8.5 cm in diameter, 10 ml of a solution containing each of the compounds according to the present invention at a concentration of 10 ppm were introduced, and 10 seed of rice plant variety: SASANISHIKI) were sown in the glass dish. The dishes were kept in a room at 27° C. for 7 days to germinate the seeds, and then the height of the seedlings were measured to obtain the data shown in Table 12.

As are seen in Table 12, every one of the tested azole derivatives according to the present invention showed the growth-restraining effect without giving any phytotoxicity.

TABLE 12

| No. of compound (No. in Table 1) | Rate of restraining the height (%) | Phytotoxicity |
|---|---|---|
| 1 | 84.2 | none |
| 2 | 63.8 | none |
| 3 | 71.8 | none |
| 4 | 70.0 | none |
| 5 | 70.0 | none |
| 6 | 74.6 | none |
| 7 | 85.9 | none |
| 8 | 72.3 | none |
| 9 | 75.7 | none |
| 10 | 79.7 | none |
| 11 | 76.8 | none |
| 12 | 67.2 | none |
| 13 | 87.0 | none |
| 14 | 76.8 | none |
| 15 | 77.4 | none |
| 16 | 84.2 | none |
| 17 | 76.8 | none |

What is claimed is:

1. An azole compound represented by the formula (I):

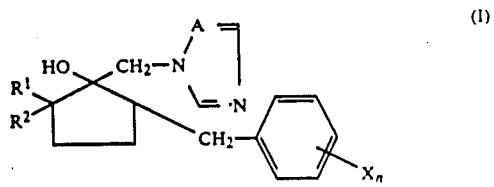

wherein $R^1$ and $R^2$ respectively represent a $C_1$-$C_5$ alkyl group or a hydrogen atom; X represents a halogen atom, a $C_1$-$C_5$ alkyl group or a phenyl group; n represents an integer from 0 to 2 and A represents a CH group, provided that $R^1$ is not a hydrogen atom when $R^2$ is a hydrogen atom.

2. The azole compound according to claim 12, wherein $R^1$ is a hydrogen atom or a $C_1$-$C_4$ alkyl group; $R^2$ is a hydrogen atom or a $C_1$-$C_3$ alkyl group; X is a halogen atom at the 4-position of the benzene ring; and n is 1.

3. An agricultural and horticultural composition having fungicidal and plant growth regulating activities, which comprises a fungicidal and plant growth regulating effective amount of an azole compound, as an active ingredient. represented by the formula (I):

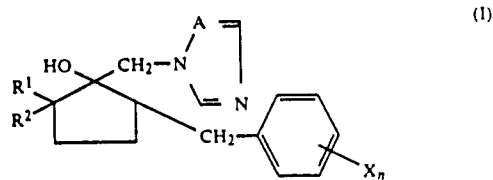

wherein $R^1$ and $R^2$ respectively represent a $C_1$-$C_5$ alkyl group or a hydrogen atom; X represents a halogen atom, a $C_1$-$C_5$ alkyl group or a phenyl group; n represents an integer of from 0 to 2, and A represents a CH group, provided that $R^1$ is not a hydrogen atom when $R^2$ is a hydrogen atom together with a suitable carrier or diluent.

4. The agricultural and horticultural composition according to claim 3, wherein $R^1$ is a hydrogen atom or a $C_1$-$C_4$ alkyl group; $R^2$ is a hydrogen atom or a $C_1$-$C_4$ alkyl group; $R^2$ is a hydrogen atom or a $C_1$-$C_3$ alkyl group; X is a halogen atom at the 4-position of the benzene ring; and n is 1.

* * * * *

UNITED STATES PATENT AND TRADEMARK OFFICE
CERTIFICATE OF CORRECTION

PATENT NO. : 5,028,254
DATED : July 2, 1991
INVENTOR(S) : KUMAZAWA et al

It is certified that error appears in the above-identified patent and that said Letters Patent is hereby corrected as shown below:

```
On Title Page: Column 1, item [30], last line
"62-271227" should be --62-271277--.
```

Signed and Sealed this

First Day of June, 1993

Attest:

MICHAEL K. KIRK

Attesting Officer

Acting Commissioner of Patents and Trademarks